US010723728B2

(12) United States Patent
Blumberg et al.

(10) Patent No.: US 10,723,728 B2
(45) Date of Patent: Jul. 28, 2020

(54) PRODRUGS OF NH-ACIDIC COMPOUNDS

(71) Applicant: ALKERMES PHARMA IRELAND LIMITED, Dublin (IE)

(72) Inventors: Laura Cook Blumberg, Lincoln, MA (US); Julius F. Remenar, Framingham, MA (US); Orn Almarsson, Shrewsbury, MA (US); Tarek A. Zeidan, Lexington, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

(21) Appl. No.: 16/540,802

(22) Filed: Aug. 14, 2019

(65) Prior Publication Data

US 2019/0367501 A1    Dec. 5, 2019

Related U.S. Application Data

(60) Continuation of application No. 16/023,887, filed on Jun. 29, 2018, now Pat. No. 10,428,058, which is a continuation of application No. 15/227,117, filed on Aug. 3, 2016, now Pat. No. 10,040,787, which is a division of application No. 14/755,412, filed on Jun. 30, 2015, now abandoned, which is a division of application No. 14/172,391, filed on Feb. 4, 2014, now Pat. No. 9,102,618, which is a continuation of application No. 12/823,102, filed on Jun. 24, 2010, now Pat. No. 8,686,009.

(60) Provisional application No. 61/293,133, filed on Jan. 7, 2010, provisional application No. 61/293,087, filed on Jan. 7, 2010, provisional application No. 61/220,480, filed on Jun. 25, 2009.

(51) Int. Cl.
| | |
|---|---|
| C07D 417/12 | (2006.01) |
| C07D 215/22 | (2006.01) |
| C07D 263/58 | (2006.01) |
| C07D 401/12 | (2006.01) |
| C07D 471/14 | (2006.01) |
| C07F 9/6558 | (2006.01) |
| A61K 31/496 | (2006.01) |
| A61K 31/554 | (2006.01) |
| C07D 471/04 | (2006.01) |
| C07D 215/14 | (2006.01) |
| C07D 401/04 | (2006.01) |
| C07D 401/14 | (2006.01) |
| C07D 239/553 | (2006.01) |
| C07D 239/56 | (2006.01) |
| C07H 19/06 | (2006.01) |
| C07D 215/00 | (2006.01) |

(52) U.S. Cl.
CPC .......... *C07D 417/12* (2013.01); *A61K 31/496* (2013.01); *A61K 31/554* (2013.01); *C07D 215/00* (2013.01); *C07D 215/14* (2013.01); *C07D 215/22* (2013.01); *C07D 239/553* (2013.01); *C07D 239/56* (2013.01); *C07D 263/58* (2013.01); *C07D 401/04* (2013.01); *C07D 401/12* (2013.01); *C07D 401/14* (2013.01); *C07D 471/04* (2013.01); *C07D 471/14* (2013.01); *C07F 9/65583* (2013.01); *C07H 19/06* (2013.01)

(58) Field of Classification Search
CPC .................................................. C07D 417/12
USPC ......................................................... 514/334
See application file for complete search history.

(56) References Cited

U.S. PATENT DOCUMENTS

| | | | |
|---|---|---|---|
| 404,065 | A | 5/1889 | Woolridge |
| 2,418,499 | A | 4/1947 | Burke |
| 3,266,984 | A | 8/1966 | Kenzo et al. |
| 3,523,121 | A | 8/1970 | Lewis et al. |
| 3,573,308 | A | 3/1971 | Ning et al. |
| 3,798,219 | A | 3/1974 | von Strandtmann et al. |
| 3,957,808 | A | 5/1976 | Miller et al. |
| 4,160,099 | A | 7/1979 | Bodor |
| 4,260,769 | A | 4/1981 | Stella et al. |
| 4,267,326 | A | 5/1981 | Ozaki et al. |
| 4,428,935 | A | 1/1984 | Myers |
| 4,443,464 | A | 4/1984 | Biedemann et al. |
| 4,448,906 | A | 5/1984 | Deinet et al. |
| 4,500,708 | A | 2/1985 | Chorvat et al. |

(Continued)

FOREIGN PATENT DOCUMENTS

| | | |
|---|---|---|
| CA | 1157677 A | 11/1983 |
| DE | 1273533 B | 7/1968 |

(Continued)

OTHER PUBLICATIONS

U.S. Appl. No. 12/823,102, filed Jun. 24, 2010, Blumberg.
U.S. Appl. No. 14/172,391, filed Feb. 4, 2014, Blumberg.
U.S. Appl. No. 14/755,412, filed Jun. 30, 2015, Blumberg.
U.S. Appl. No. 15/277,117, filed Aug. 3, 2016, Blumberg.
U.S. Appl. No. 16/023,887, filed Jun. 29, 2018, Blumberg.
U.S. Appl. No. 16/540,802, filed Aug. 14, 2019, Blumberg.

(Continued)

*Primary Examiner* — Kahsay Habte
(74) *Attorney, Agent, or Firm* — Brian C. Trinque; Lathrop GPM, LLP

(57) ABSTRACT

The invention provides a method of sustained delivery of a lactam, imide, amide, sulfonamide, carbamate or urea containing parent drug by administering to a patient an effective amount of a prodrug compound of the invention wherein upon administration to the patient, release of the parent drug from the prodrug is sustained release. Prodrug compounds suitable for use in the methods of the invention are labile conjugates of parent drugs that are derivatized through carbonyl linked prodrug moieties. The prodrug compounds of the invention can be used to treat any condition for which the lactam, imide, amide, sulfonamide, carbamate or urea containing parent drug is useful as a treatment.

5 Claims, 10 Drawing Sheets

(56) References Cited

U.S. PATENT DOCUMENTS

| | | | |
|---|---|---|---|
| 4,594,190 A | 6/1986 | Giani et al. | |
| 4,694,006 A | 9/1987 | Bundgaard et al. | |
| 4,727,151 A | 2/1988 | Bodor | |
| 4,760,057 A | 7/1988 | Alexander | |
| 4,837,337 A | 6/1989 | Murao et al. | |
| 4,914,094 A | 4/1990 | Oshiro et al. | |
| 5,006,528 A | 4/1991 | Oshiro et al. | |
| 5,206,386 A | 4/1993 | Narayanan et al. | |
| 5,350,747 A | 9/1994 | Howard | |
| 5,462,934 A | 10/1995 | Goto et al. | |
| 5,700,946 A | 12/1997 | Shimasaki et al. | |
| 5,719,303 A | 2/1998 | Yoshida et al. | |
| 5,783,589 A | 7/1998 | Hamilton et al. | |
| 5,985,856 A | 11/1999 | Stella et al. | |
| 6,127,357 A | 10/2000 | Cliffe et al. | |
| 6,133,248 A | 10/2000 | Stella | |
| 6,150,366 A | 11/2000 | Arenson et al. | |
| 6,180,095 B1 | 1/2001 | Greenwald et al. | |
| 6,608,084 B1 | 8/2003 | Bourzat et al. | |
| 6,653,312 B1 | 11/2003 | Auvin et al. | |
| 7,115,587 B2 | 10/2006 | Nerurkar et al. | |
| 7,160,888 B2 | 1/2007 | Johnson et al. | |
| 7,538,121 B2 | 5/2009 | MacDonald et al. | |
| 8,431,576 B2 | 4/2013 | Remenar et al. | |
| 8,686,009 B2* | 4/2014 | Blumberg | C07D 401/14 514/369 |
| 9,102,618 B2* | 8/2015 | Blumberg | C07D 215/14 |
| 10,040,787 B2* | 8/2018 | Blumberg | C07D 471/04 |
| 10,428,058 B2* | 10/2019 | Blumberg | C07D 215/00 |
| 2002/0176841 A1 | 11/2002 | Barker et al. | |
| 2004/0254182 A1 | 12/2004 | Mulvihill et al. | |
| 2005/0203089 A1 | 9/2005 | Starrett et al. | |
| 2006/0040932 A1 | 2/2006 | Eijgendaal et al. | |
| 2006/0142333 A1 | 6/2006 | MacDonald et al. | |
| 2006/0293217 A1 | 12/2006 | Barker et al. | |
| 2007/0031513 A1 | 2/2007 | Kikuchi et al. | |
| 2007/0191611 A1 | 8/2007 | Rao et al. | |
| 2007/0213300 A1 | 9/2007 | Liu et al. | |
| 2008/0085888 A1 | 4/2008 | Breining et al. | |
| 2008/0143403 A1 | 6/2008 | Huang et al. | |
| 2008/0186971 A1 | 8/2008 | Carmichael et al. | |
| 2008/0261954 A1 | 10/2008 | Maelicke | |
| 2008/0312199 A1 | 12/2008 | Glinsky | |
| 2008/0318905 A1 | 12/2008 | Muhammad et al. | |
| 2009/0053329 A1 | 2/2009 | Peters et al. | |
| 2009/0068290 A1 | 3/2009 | Bourin et al. | |
| 2009/0069419 A1 | 3/2009 | Jandeleit et al. | |
| 2009/0143403 A1 | 6/2009 | Brown | |
| 2009/0163545 A1 | 6/2009 | Goldfarb | |
| 2010/0098641 A1 | 4/2010 | Baker et al. | |
| 2010/0286136 A1 | 11/2010 | Jones | |
| 2010/0292316 A1 | 11/2010 | Sanders et al. | |
| 2011/0003828 A1 | 1/2011 | Blumberg | |
| 2011/0015156 A1 | 1/2011 | Remenar et al. | |
| 2011/0166128 A1 | 7/2011 | Remenar et al. | |
| 2011/0166156 A1 | 7/2011 | Blumberg et al. | |
| 2011/0166194 A1 | 7/2011 | Blumberg et al. | |
| 2011/0178068 A1 | 7/2011 | Almarsson et al. | |
| 2011/0275803 A1 | 11/2011 | Remenar et al. | |
| 2011/0319422 A1 | 12/2011 | Blumberg et al. | |
| 2012/0015866 A1 | 1/2012 | Blumberg et al. | |
| 2014/0221653 A1 | 8/2014 | Blumberg | |
| 2015/0376143 A1 | 12/2015 | Blumberg | |
| 2017/0015659 A1 | 1/2017 | Blumberg | |
| 2019/0031648 A1 | 1/2019 | Blumberg | |

FOREIGN PATENT DOCUMENTS

| | | |
|---|---|---|
| DE | 104526 A1 | 3/1974 |
| EP | 0207581 A2 | 1/1987 |
| EP | 0590793 A1 | 4/1994 |
| EP | 1891956 A1 | 2/2008 |
| GB | 849541 A | 9/1960 |
| JP | 61-267580 A | 11/1986 |
| JP | 63284165 A | 11/1988 |
| JP | 02-191256 A | 7/1990 |
| JP | 05-194517 A | 8/1993 |
| WO | WO 1990014080 A1 | 11/1990 |
| WO | WO 9100863 A1 | 1/1991 |
| WO | WO 9115488 A1 | 10/1991 |
| WO | WO 9206089 A1 | 4/1992 |
| WO | WO 9325197 A1 | 12/1993 |
| WO | WO 9612725 A1 | 5/1996 |
| WO | WO 96026929 A1 | 9/1996 |
| WO | WO 9743284 A1 | 11/1997 |
| WO | WO 9933846 A2 | 7/1999 |
| WO | WO 0050417 A1 | 8/2000 |
| WO | WO 02096351 A2 | 12/2002 |
| WO | WO 02100861 A1 | 12/2002 |
| WO | WO 2003084572 A1 | 10/2003 |
| WO | WO 2004026864 A1 | 4/2004 |
| WO | WO 2004029054 A1 | 4/2004 |
| WO | WO 2004067546 A1 | 8/2004 |
| WO | WO 2004089925 A1 | 10/2004 |
| WO | WO 2005019215 A1 | 3/2005 |
| WO | WO 2005066165 A1 | 7/2005 |
| WO | WO 2005120577 A2 | 12/2005 |
| WO | WO 2006037090 A2 | 4/2006 |
| WO | WO 2006085219 A2 | 8/2006 |
| WO | WO 2006090273 A2 | 8/2006 |
| WO | WO 2007059111 A2 | 5/2007 |
| WO | WO 2009052467 A1 | 4/2009 |
| WO | WO 2011084848 A2 | 7/2011 |
| WO | WO 2011160084 A1 | 12/2011 |

OTHER PUBLICATIONS

Alvarez, F.J., et al., "Pancreatic Lipase-Catalyzed Hydrolysis of Esters of Hydroxymethyl Phenytoin Dissolved in Various Metabolizable Vehicles, Dispersed in Micellar Systems, and in Aqueous Suspensions," Pharmaceutical Research 6, pp. 555-563 (1989).

Bender, et. al., "Cyclopropanecarboxylic Acid Esters as Potential Prodrugs with Enhanced Hydrolytic Stability," Org. Lett. vol. 10(3): 509-511 (2008).

Boehme, H., et al., "Zur Kenntnis der N-[-Alkoxy-alkyl]-carbonsaureamide and der durch ihre thermische Spaltung entstehenden Enamide," Chem. Ber., 99(7): pp. 2127-2135 (1966).

CAS RN 1001254-47-2, STN Entry Date Feb. 1, 2008.

CAS RN 441314-50-7, STN Entry Date Jul. 31, 2002.

CAS RN 52598-34-2, STN Entry Date Nov. 16, 1984.

CAS RN 66395-34-4, STN Entry Date Nov. 16, 1984.

CAS RN 760152-91-8 STN Entry Date Oct. 11, 2004.

CAS RN 91305-39-4, STN Entry Date Nov. 16, 1984.

Dezi, Modeling of 5-HT2A and 5-HT2C Receptors and of Their Complexes with Actual and Potential Antipsychotic PhD Thesis, Pompeu Fabra Univerisity, Barcelona, pp. 1-239 (2007).

Doshi, A., et al., "In Vivo Pharmacokinetic Studies of Prodrugs of Ibuprofen," Indian Journal of Pharmaceutical 69(6): 824-827 (Nov.-Dec. 2007).

Hartung, R., et al., "A Simple and Efficient Preparation of Novel Formaldehyde Derivatives," Synthesis, No. 3, pgs. (Jan. 2009).

Iley et al. "Acyloxymethyl as a Drug Protecting Group: Part 4. The Hydrolysis of Tertiary Amidomethyl Ester Prodrugs of Carboxylic Acid Agents," Pharmaceutical Research. 14(11):1634-1639 (1997).

Kearney, A.S., "Prodrugs and Targeted Drug Delivery," Advanced Drug Delivery Reviews, 19, pp. 225-239 (1996).

Kim, C., et al., "A new class of acyclic phosphonate nucleotide analogs: Phosphonate isosteres of acyclovir and ganciclovir monophosphates as antiviral agents," Journal of Medicinal Chemistry 34(7):2286-2294 (1991).

Krise, J.P., et al. Novel Prodrug Approach for Tertiary Amines Synthesis and Preliminary Evaluation of N- Phosphonooxymethyl Prodrugs, J. Med. Chem 42, pp. 3094-3100 (1999).

Link, J T., et al., "First Total Synthesis of Staurosporine and ent-Staurosporine," J. Am. Chem. Soc. 117, pp. 552-553 (1995).

Lopes et al. Journal of the Chemical Society, Perkin Transactions 2: Physical Organic Chemistry (3):431-439 (1999).

(56) References Cited

OTHER PUBLICATIONS

McCaron, P.A., et al., Incorporation of novel 1-alkylcarbonyloxymethyl Prodrugs of 5-Fluorouracil into Poly(lactide-co glycolide) Nanoparticles, International Journal of Pharmaceutics 348, pp. 115-124 (2008).

Miao, et al., "Characterization of a Novel Metabolite Intermediate of Ziprasidone in Hepatic Cytosolic Fractions of Rat, Dog, and Human by ESI-MS/MS, Hydrogen/Deuterium Exchange, and Chemical Derivatization." Drug Metabolism and Disposition, 33(7):879-883 (2005).

Nielsen, A.B., et al.. "Bioreversible quaternary N-acyloxymethyl derivatives of the tertiary amines bupivacaine and lidocaine synthesis, aqueous solubility and stability in buffer, human plasma and simulated intestinal fluid," European Journal of Pharmaceutical Sciences 24:433-440 (2005).

Nomura, et al., "(3-Substituted benzyl)thiazolidine-2,4-diones as structurally new antihyperglycemic agents," Bioorg Med Chem Lett. 9(4):533-538 (1999).

Palin, R., et al., "Structure-activity relationships and CoMFA of N-3 substituted phenoxypropyl piperidine benzimidazol-2-one analogues as NOP receptor agonists with analgesic properties," Bioorganic & Medicinal Chemistry vol. 16, pp. 2829-2851 (2008).

Rautio, J., et. al., "Prodrugs: design and clinical applications," Nature Reviews, 7:255-270 (2008).

Redden, P.R., et al., "Acyloxymethyl Acidic Drug Derivatives: In Vitro Hydrolytic Reactivity," International Journal of Pharmaceutics, 180, pp. 151-160 (1999).

Robinson, R., et al., "Discovery of the Hemifumarate and {alpha-L-Alanyloxy)methyl Ether as Prodrugs of Antirheumatic Oxindole: Prodrugs for the Enolic OH Group," J. Med. Chem, 39:10-18 (1996).

Simplicio, A.L., "Beta-Aminoketones as Prodrugs with pH-Controlled Activation," International Journal of Pharmaceutics 336(2):208-214 (2007).

Simplicio, A.L., et al., "Prodrugs for Amines," molecules, 13: 519-547 (2008).

Skinner, W.A., "Topical Mosquito Repellents: X: 2-Oxazolidones," J. Pharmaceutical Sci., 66(4); 587-589.

Stella, V., et al., "Aqueous solubility and dissolution rate does not adequately predict in vivo performance: A probe utilizing some N-acyloxymethyl phenytoin prodrugs," Journal of Pharmaceutical Sciences, 88(8): 775-779 (1999).

Varma et al., (1968) "Synthesis and Antibacterial Activity of Certain 3-Substituted Benzoxazolines," Journal of Pharmaceutical Sciences, 57(1):39-44.

Weiler, E.D., et al., Isothiazoles VII: N-Hydroxyalkylation and Mannich Reaction of 4-Isothiazolin-3-one, J. Chem., 13(5): 1097-1098 (1976).

Weitzel, G., et al., Weitere Tumorhemmende Verbindungsklassen, I Cytostatische Effekte von N-and S-Hydroxymethyl-Verbindungen, Hoppe-Seyler's Zeitschrift Fur Physiologische Chemie, 334 (1): 1-25 (1963).

White, H.S., et al., "Correlation between Anticonvulsant Activity and Inhibitory Action of Glial y-Aminobutyric Acid Uptake of the Highly Selective Mouse y-aminobutyric Acid Transporter 1 Inhibitor 3-Hydroxy-4-amino-4, 5, 6, 7—and Its n-aikylated Analogs," The Journal of Pharmacology and Experimental Terapeutics, 302(2): 636-644 (2002).

Yoda, et al., "SmI2-mediated hetero-coupling reaction of lactams with aldehydes: synthesis of indolizidine alkaloids, (-)-delta-coniceine, (+)-5-epiinodolizidine 167B and (+)-lentiginosine," Tetrahedron Letters, 42(13): 2509-2512, Abstract Only, pp. 1-2 (2001).

Zinner et al., "Benzazole, IV. Mitteil.: Mannich-Basen des Benzoxazolons", Chemisch Bericthe, 1956, vol. 89, pp. 2131-6.

\* cited by examiner

PRODRUGS OF NH-ACIDIC COMPOUNDS

RELATED APPLICATIONS

This application is a divisional of U.S. application Ser. No. 14/755,412, filed Jun. 30, 2015, which is a divisional of U.S. application Ser. No. 14/172,391, filed on Feb. 4, 2014, now U.S. Pat. No. 9,102,618, which is a continuation of U.S. application Ser. No. 12/823,102, filed on Jun. 24, 2010, now U.S. Pat. No. 8,686,009, which claims the benefit of U.S. Provisional Application No. 61/220,480, filed on Jun. 25, 2009; 61/293,087, filed on Jan. 7, 2010; and 61/293,133, filed on Jan. 7, 2010. The entire teachings of the above applications are incorporated herein by reference.

BACKGROUND OF THE INVENTION

(i) Field of the Invention

The present invention relates to prodrugs of lactam, amide, imide, sulfonamide, carbamate, urea, benzamide, and acylaniline containing pharmacophores.

(ii) Background of the Invention

Drug delivery systems are often critical for the safe and effective administration of a biologically active agent. Perhaps the importance of these systems is best realized when patient compliance and consistent dosing are taken under consideration. For instance, reducing the dosing requirement for a drug from four-times-a-day to a single dose per day would have significant value in terms of ensuring patient compliance and optimizing therapy.

Optimization of a drug's bioavailability has many potential benefits. For patient convenience and enhanced compliance it is generally recognized that less frequent dosing is desirable. By extending the period through which the drug is released, a longer duration of action per dose is expected. This will then lead to an overall improvement of dosing parameters such as taking a drug once a day where it has previously required four doses per day or dosing once a week or even less frequently when daily dosing was previously required. Many drugs are presently dosed once per day, but not all of these drugs have pharmacokinetic properties that are suitable for dosing intervals of exactly twenty-four hours. Extending the period through which these drugs are released would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is so narrow that dosage formulation becomes critical.

In an attempt to address the need for improved bioavailability, several drug release modulation technologies have been developed. For example, poorly soluble 5,5 diphenylimidazolidine-2,4-diones have been derivatized into phosphate ester prodrugs to improve solubility. (Stella et. al., U.S. Pat. No. 4,260,769, 1981). Enteric coatings have been used as a protector of pharmaceuticals in the stomach and microencapsulating active agents using proteinaceous microspheres, liposomes or polysaccharides have been effective in abating enzymatic degradation of the active agent. Enzyme inhibiting adjuvants have also been used to prevent enzymatic degradation.

A wide range of pharmaceutical formulations provide sustained release through microencapsulation of the active agent in amides of dicarboxylic acids, modified amino acids or thermally condensed amino acids. Slow release rendering additives can also be intermixed with a large array of active agents in tablet formulations.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix or degradation of the matrix, or both, which is highly dependent on the chemical properties and water solubility of the active agent. Conversely, water-soluble microspheres swell by an infinite degree and, unfortunately, may release the active agent in bursts with limited active agent available for sustained release. Furthermore, in some technologies, control of the degradation process required for active agent release is unreliable. For example, because an enterically coated active agent depends on pH to release the active agent and pH and residence time varies, the release rate is difficult to control.

Several implantable drug delivery systems have utilized polypeptide attachment to drugs. Additionally, other large polymeric carriers incorporating drugs into their matrices are used as implants for the gradual release of drug. Yet another technology combines the advantages of covalent drug attachment with liposome formation where the active ingredient is attached to highly ordered lipid films.

However, there is still a need for an active agent delivery system that is able to deliver certain active agents which have been heretofore not formulated or difficult to formulate in a sustained release formulation for release over a sustained period of time and which is convenient for patient dosing.

There is a generally recognized need for sustained delivery of drugs that reduces the daily dosing requirement and allows for controlled and sustained release of the parent drug and also avoids irregularities of release and cumbersome formulations encountered with typical dissolution controlled sustained release methods.

SUMMARY OF THE INVENTION

The present invention accomplishes this by extending the period during which a lactam, amide, imide, sulfonamide, carbamate, urea, benzamide, acylaniline, and cyclic amide containing parent drug is released and absorbed after administration to the patient and providing a longer duration of action per dose than the parent drug itself. In one embodiment, the compounds suitable for use in the methods of the invention are derivatives of lactam-, amide-, imide-, sulfonamide-, carbamate-, urea-, benzamide-, acylaniline-, and cyclic amide-containing parent drugs that are substituted at the amide nitrogen or oxygen atom with labile aldehyde-linked prodrug moieties. Preferably, the prodrug moieties are hydrophobic and reduce the polarity and solubility of the parent drug under physiological conditions.

In one embodiment, the invention provides a prodrug compound of Formula I, II or III:

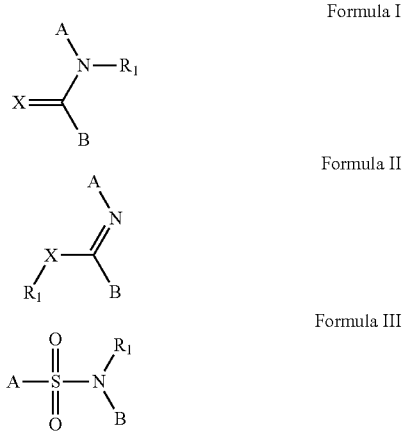

Formula I

Formula II

Formula III and the geometric isomers, enantiomers, diastereomers, racemates, pharmaceutically acceptable salts and solvates thereof;

wherein A and B together with the —N(C=X)— or —N=C—X— or —S(O)$_2$—N— group to which they are attached form a parent drug;

X is —S— or —O—;

$R_1$ is selected from —C($R_A$)($R_B$)—OR$_{20}$, —C($R_A$)($R_B$)—OC(O)OR$_{20}$, —C($R_A$)($R_B$)—OC(O)R$_{20}$, —C($R_A$)($R_B$)—OC(O)NR$_{20}$R$_{21}$, —(C($R_A$)($R_B$))—OPO$_3$MY, —(C($R_A$)($R_B$))—OP(O)(OR$_{20}$)(OR$_{21}$), —[C($R_A$)($R_B$)O]$_z$—R$_{20}$, —[C($R_A$)($R_B$)O]$_z$—C(O)OR$_{20}$, —[C($R_A$)($R_B$)O]$_z$—C(O)R$_{20}$, —[C($R_A$)($R_B$)O]$_z$—C(O)NR$_{20}$R$_{21}$, —[C($R_A$)($R_B$)O]$_z$—OPO$_3$MY, —[C($R_A$)($R_B$)O]$_z$—P(O)$_2$(OR$_{20}$)M and —[C($R_A$)($R_B$)]$_z$—P(O)(OR$_{20}$)(OR$_{21}$);

wherein z is 2 or 3;

wherein each $R_A$ and $R_B$ is independently selected from hydrogen, halogen, aliphatic, substituted aliphatic, aryl or substituted aryl;

each $R_{20}$ and $R_{21}$ is independently selected from hydrogen, aliphatic, substituted aliphatic, aryl or substituted aryl;

Y and M are the same or different and each is a monovalent cation; or M and Y together is a divalent cation, and, wherein when said parent drug contains a 5,5 diphenylimidazolidine-2,4-dione moiety of formula I, $R_1$ is other than —CH($R_A$)OPO$_3$MY, CH($R_A$)OP(O)(OH)$_2$, or —CH($R_A$)OC(O)R$_{20}$.

The invention further provides a method for sustained delivery of a parent drug by the administration of a conjugate of the parent drug with a labile moiety, wherein the conjugate is represented by formula I, II or III.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
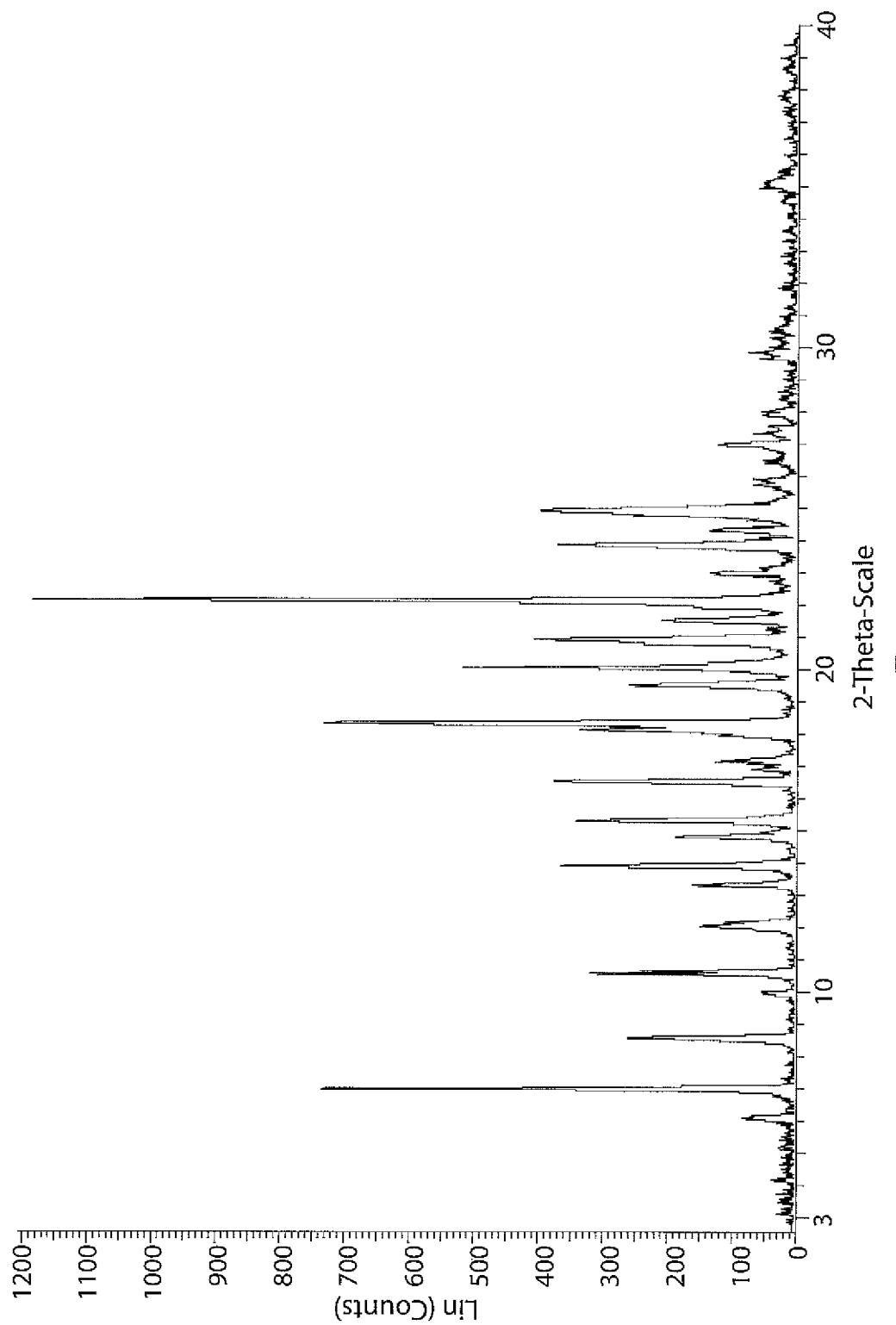
FIG. 1: PXRD spectrum of Compound-7
Figure 2:
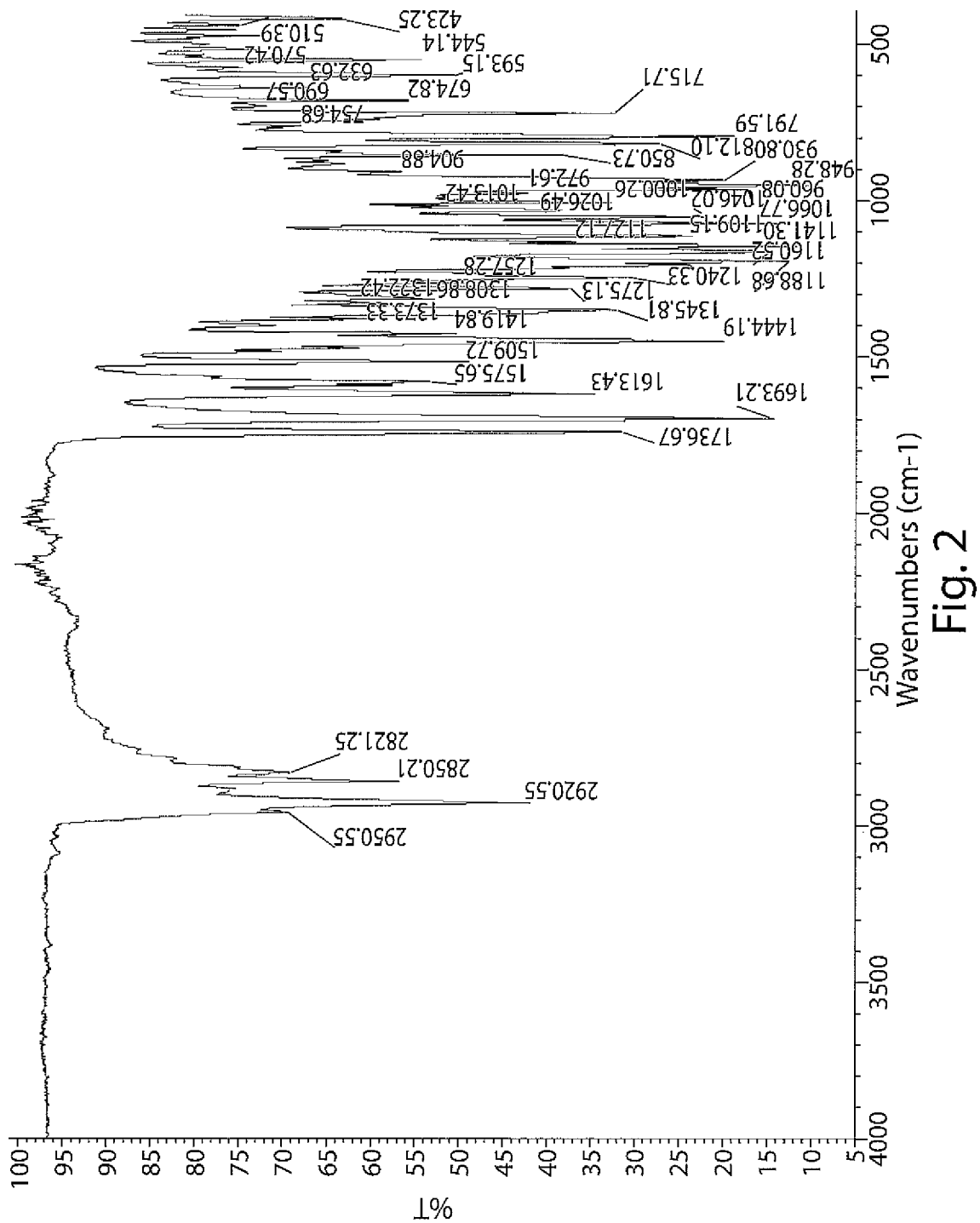
FIG. 2: IR Spectrum of Compound-7
Figure 3:
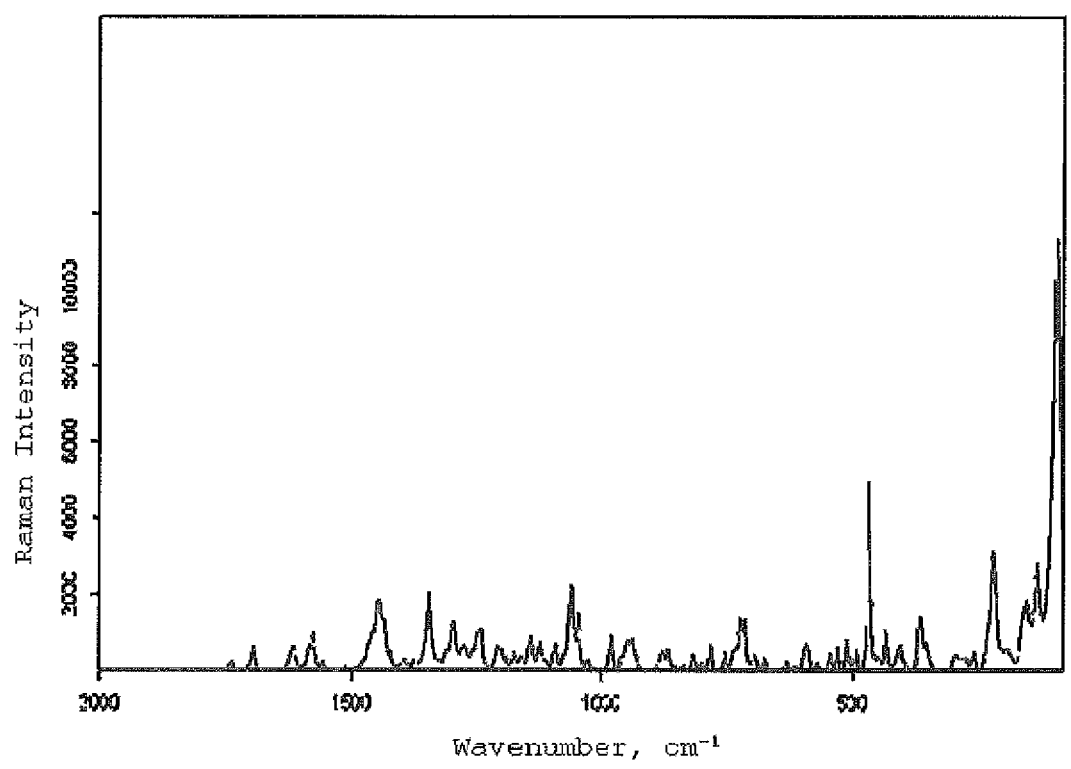
FIG. 3: Raman spectrum of Compound-7
Figure 4:
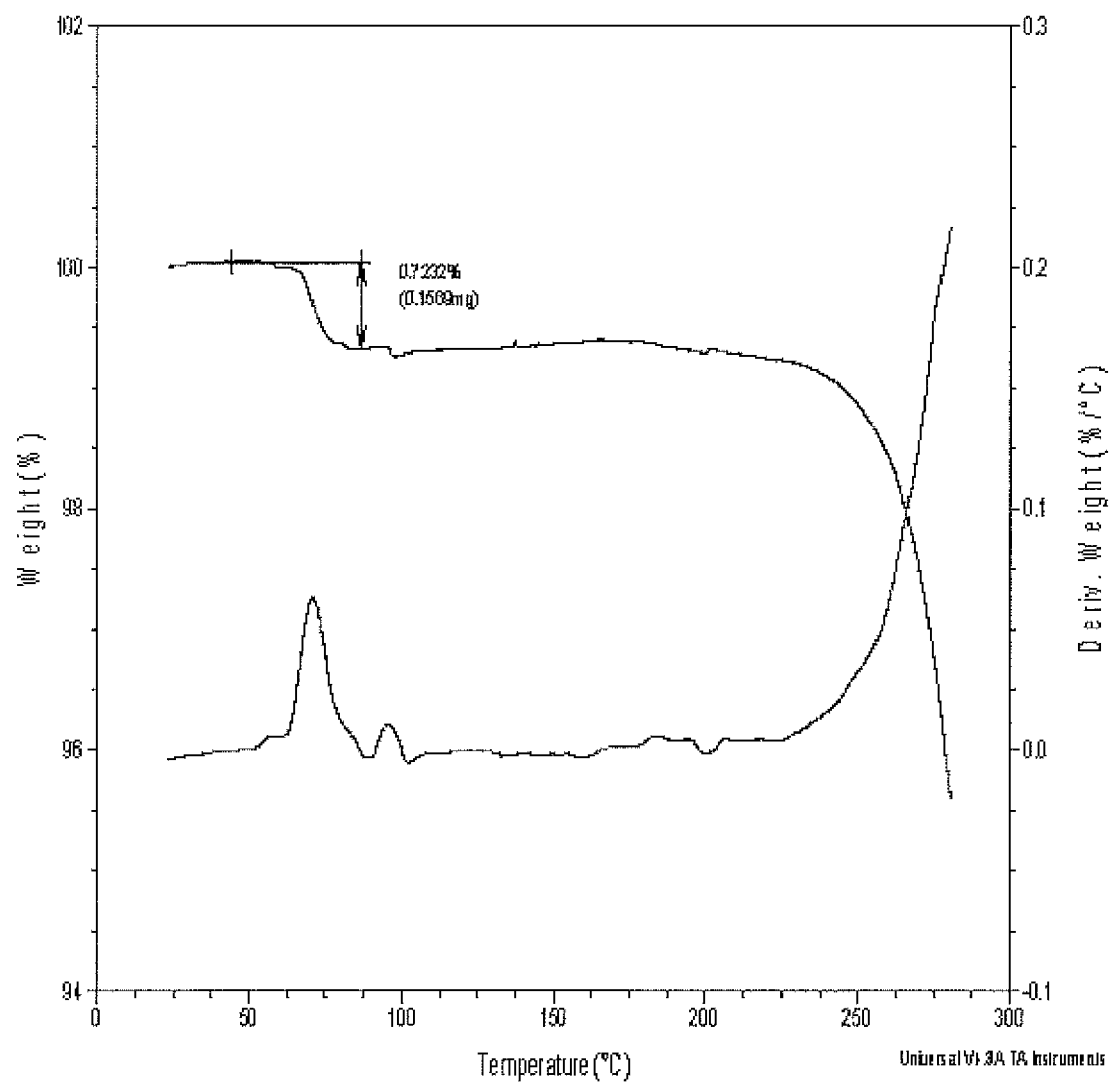
FIG. 4: TGA thermogram of Compound-7
Figure 5:
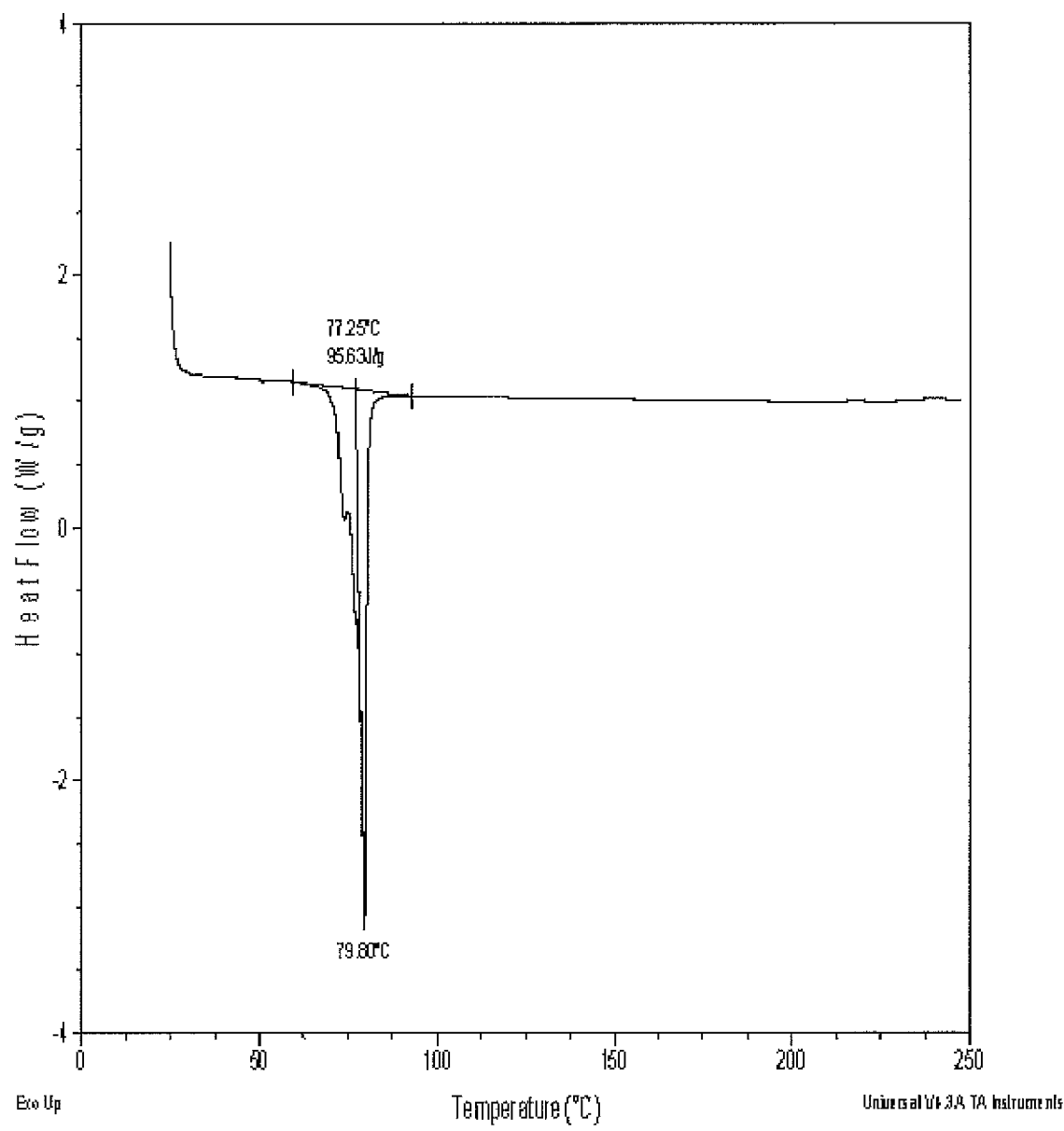
FIG. 5: DSC thermogram of Compound-7

One aspect of the present invention provides a compound having the general formula I, II or III:

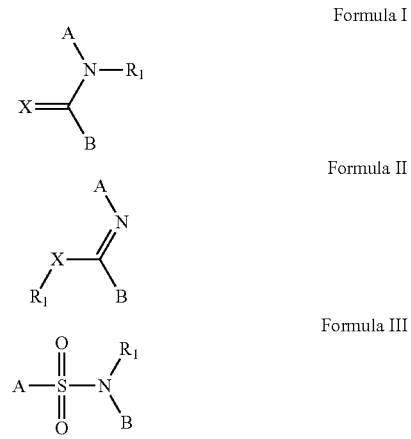

Formula I

Formula II

Formula III or its geometric isomers, enantiomers, diastereomers, racemates, pharmaceutically acceptable salts and solvates thereof;

wherein A and B together with the —N(C=X)— or —N=C—X— or —S(O)$_2$—N— they are attached forms a parent drug;

X is —S— or —O—;

$R_1$ is selected from —C($R_A$)($R_B$)—OR$_{20}$, —C($R_A$)($R_B$)—OC(O)OR$_{20}$, —C($R_A$)($R_B$)—OC(O)R$_{20}$, —C($R_A$)($R_B$)—OC(O)NR$_2$OR$_{21}$, —(C($R_A$)($R_B$)—OPO$_3$MY, —(C($R_A$)($R_B$))—OP(O)(OR$_{20}$)(OR$_{21}$), —[C($R_A$)($R_B$)O]$_z$—R$_{20}$, —[C($R_A$)($R_B$)O]$_z$—C(O)OR$_{20}$, —[C($R_A$)($R_B$)O]$_z$—C(O)R$_{20}$, —[C($R_A$)($R_B$)O]$_z$—C(O)NR$_{20}$R$_{21}$, —[C($R_A$)($R_B$)O]$_z$—OPO$_3$MY, —[C($R_A$)($R_B$)O]$_z$—P(O)$_2$(OR$_{20}$)M and —[C($R_A$)($R_B$)O]$_z$—P(O)(OR$_{20}$)(OR$_{21}$);

wherein each $R_A$ and $R_B$ is independently selected from hydrogen, halogen, aliphatic, substituted aliphatic, aryl or substituted aryl;

each $R_{20}$ and $R_{21}$ is independently selected from hydrogen, aliphatic, substituted aliphatic, aryl or substituted aryl;

Y and M are the same or different and each is a monovalent cation; or M and Y together is a divalent cation; and, wherein when said parent drug contains a 5,5 diphenylimidazolidine-2,4-dione moiety of formula I, $R_1$ is other than —CH($R_A$)OPO$_3$MY, CH($R_A$)OP(O)(OH)$_2$, or —CH($R_A$)OC(O)R$_{20}$.

In one embodiment, the compounds of the invention having Formulas I, II and III are less soluble, and are preferably at least an order of magnitude less soluble, as compared to the parent drug from which they were derived. In one embodiment, the prodrugs of Formulas I, II and III have an aqueous solubility of less than about 0.5 mg/ml, preferably less than about 0.1 mg/mL, preferably less than about 0.01 mg/mL, preferably less than about 0.001 mg/mL, preferably less than about 0.0001 mg/mL and even more preferably less than about 0.00001 mg/ml when solubility is measured in a phosphate buffer (pH 7.4) at room temperature.

In a preferred embodiment, a compound of the invention provides sustained delivery of the parent drug over hours, days, weeks or months when administered, for example, orally or parenterally, to a subject. For example, the compounds can provide sustained delivery of the parent drug for at least 8, 12, 24, 36 or 48 hours or at least 4, 7, 15, 30, 60, 75 or 90 days or longer. Without being bound by a theory, it is believed that the compounds of the invention form an insoluble depot upon parenteral administration, for example subcutaneous, intramuscular or intraperitoneal injection. In one embodiment a prodrug of the invention may further comprise a sustained release delivery system for providing additional protection of the prodrug from enzymatic or chemical degradation.

In another embodiment, the invention provides a method for sustained delivery of a parent lactam, amide, imide, sulfonamide, carbamate, urea, benzamide, or acylaniline containing drug to a subject in need thereof. Each of these groups comprises an amidic N—H group. The method comprises administering to the subject an effective amount of a prodrug formed by substituting on the NH group a labile, hydrophobic aldehyde-linked prodrug moiety wherein the prodrug has reduced solubility under physiological conditions compared to the parent drug and provides for longer sustained therapeutic levels of the parent drug following administration than observed levels following administration of the parent drug. In a preferred embodiment, the amidic N—H group has a pKa of about 5 to about 22, preferably about 5 to about 21, and preferably about 5 to about 20.

In a preferred embodiment, $R_1$ is selected from Table-1.

TABLE 1

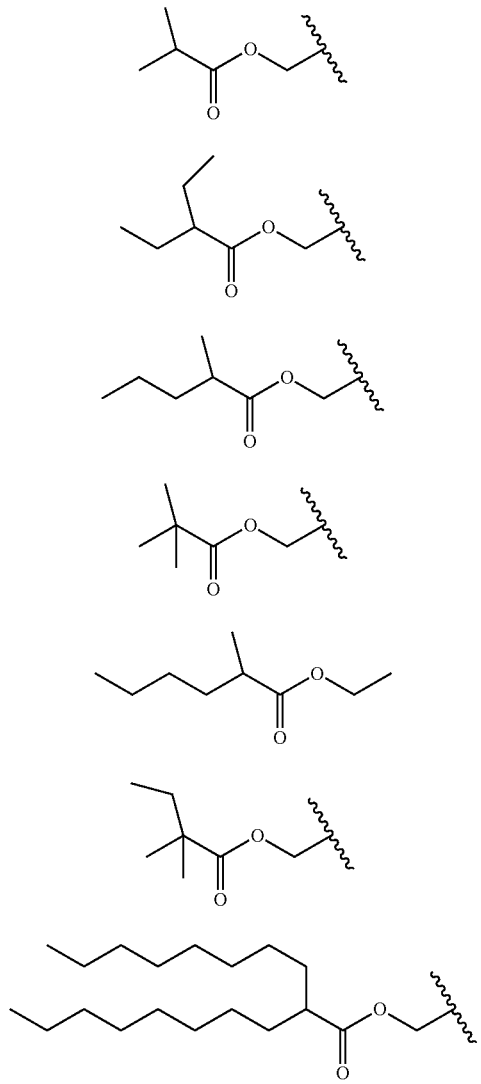

TABLE 1-continued
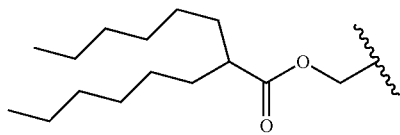 [SMILES: *COC(=O)C(CCCCCC)CCCCCC]
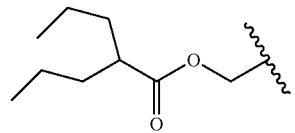 [SMILES: *COC(=O)C(CCC)CCC]
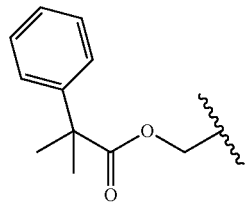 [SMILES: *COC(=O)C(C)(C)c1ccccc1]
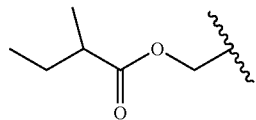 [SMILES: *COC(=O)C(C)CC]
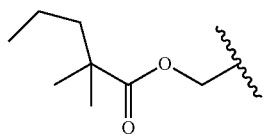
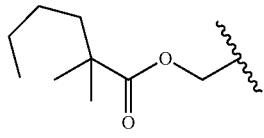 [SMILES: *COC(=O)C(C)(C)CCCC]
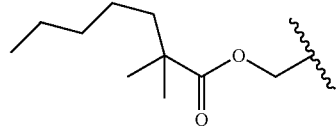 [SMILES: *COC(=O)C(C)(C)CCCCC]
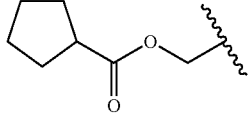 [SMILES: *COC(=O)C1CCCC1]
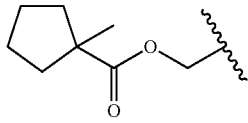 [SMILES: *COC(=O)C1(C)CCCC1]
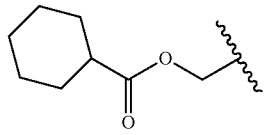 [SMILES: *COC(=O)C1CCCCC1]
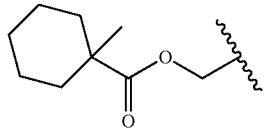 [SMILES: *COC(=O)C1(C)CCCCC1]

TABLE 1-continued
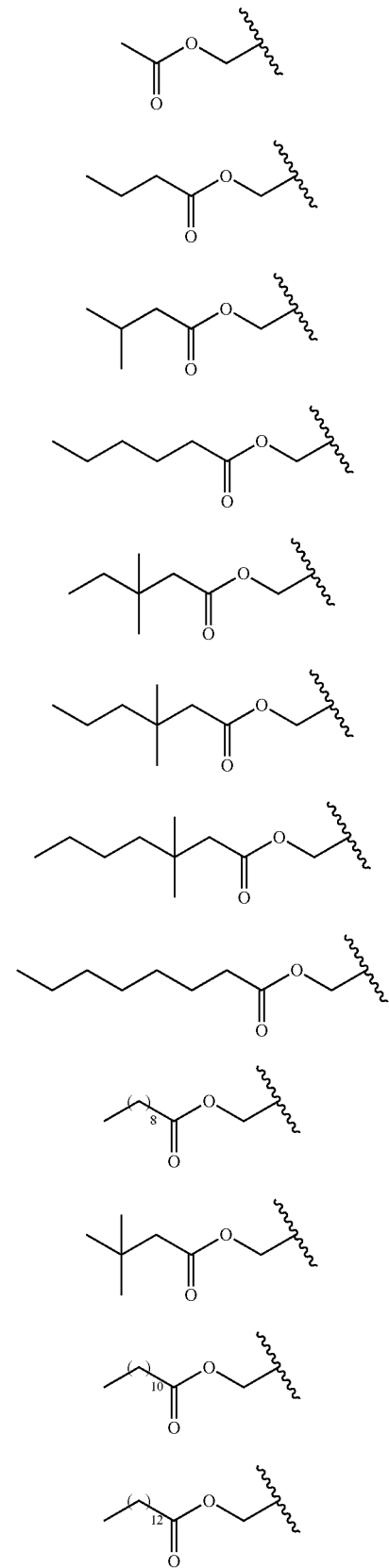

TABLE 1-continued
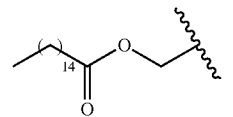
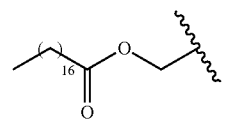
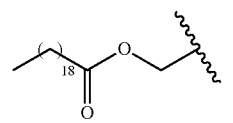
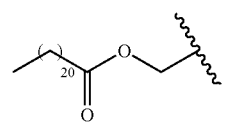
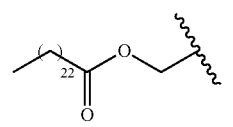
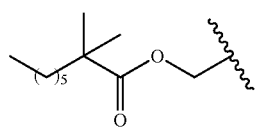
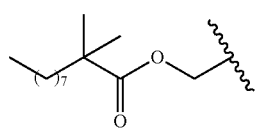
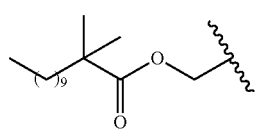
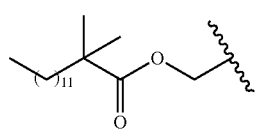
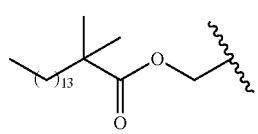
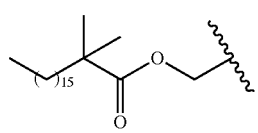

TABLE 1-continued
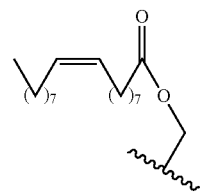
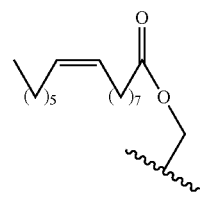
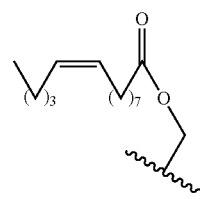
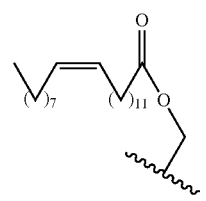
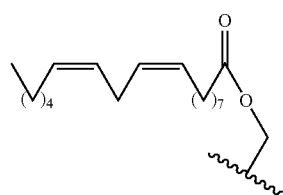
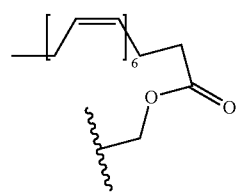
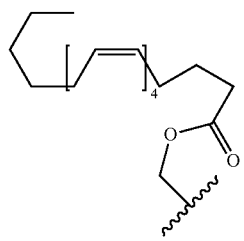

TABLE 1-continued
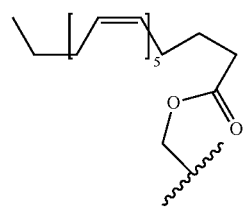
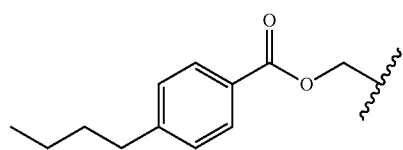 [SMILES: *COC(=O)c1ccc(CCCC)cc1]
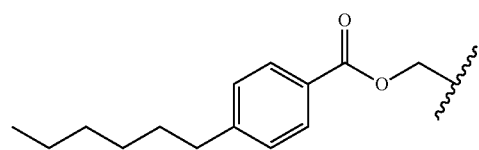 [SMILES: *COC(=O)c1ccc(CCCCCC)cc1]
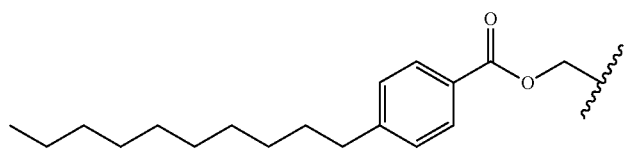 [SMILES: *COC(=O)c1ccc(CCCCCCCCCC)cc1]
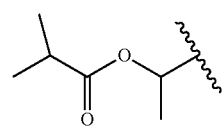 [SMILES: *C(C)OC(=O)C(C)C]
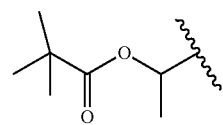 [SMILES: *C(C)OC(=O)C(C)(C)C]
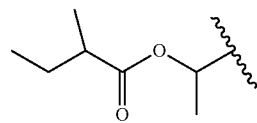 [SMILES: *C(C)OC(=O)C(C)CC]
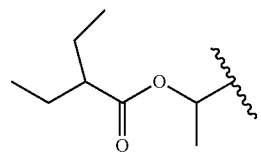 [SMILES: *C(C)OC(=O)C(CC)CC]
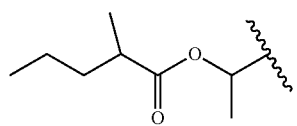 [SMILES: *C(C)OC(=O)C(C)CCC]
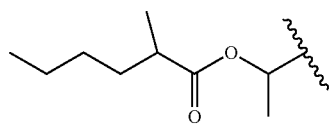 [SMILES: *C(C)OC(=O)C(C)CCCC]

TABLE 1-continued
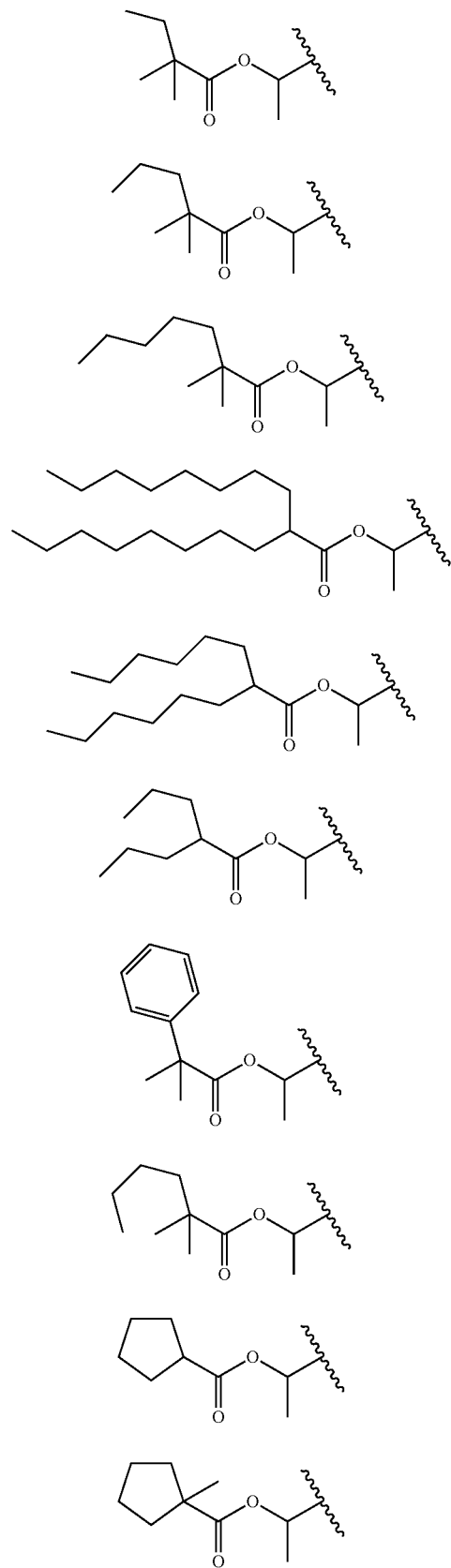

TABLE 1-continued
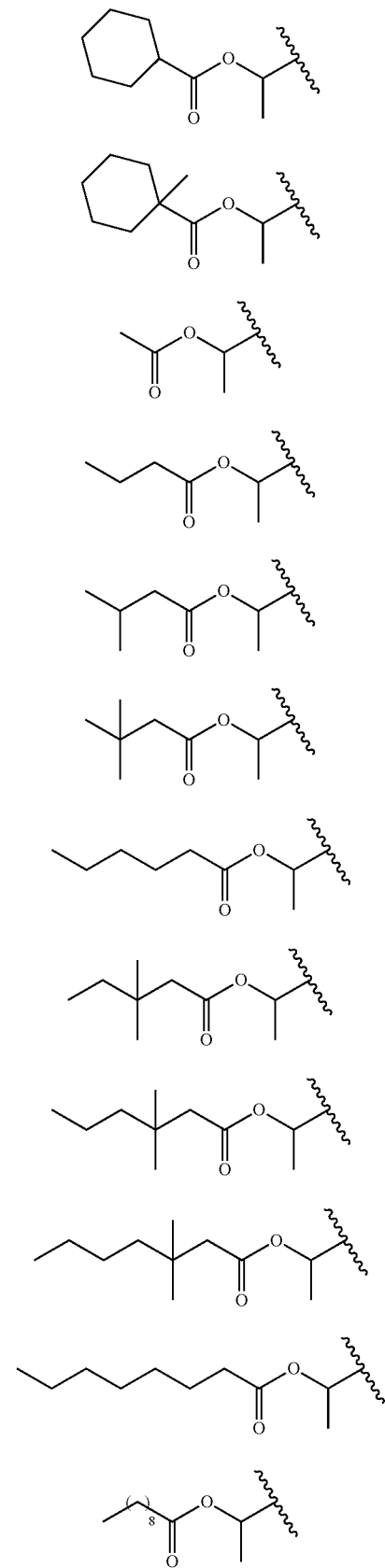

TABLE 1-continued
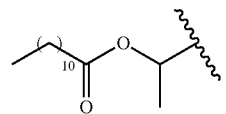
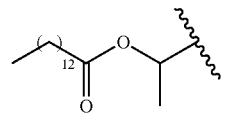
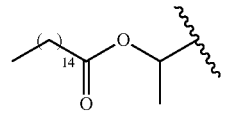
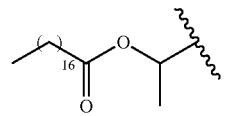
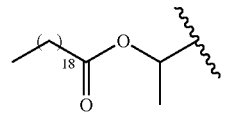
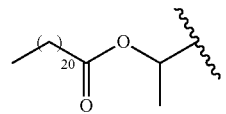
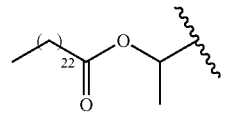
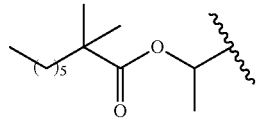
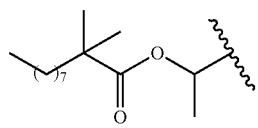
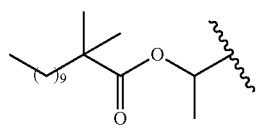
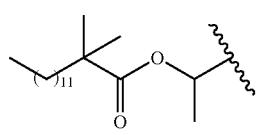
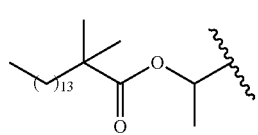

TABLE 1-continued
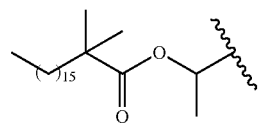
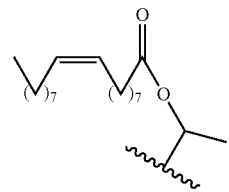
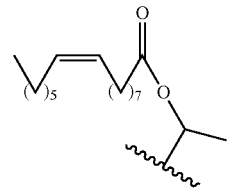
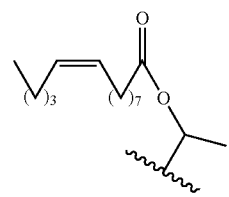
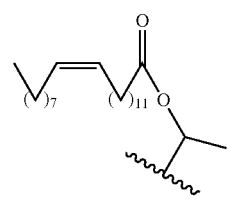
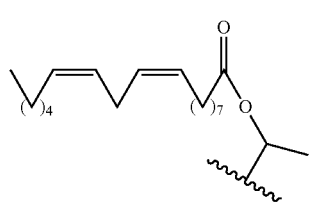
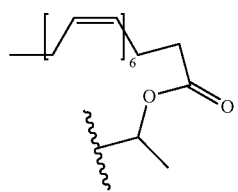
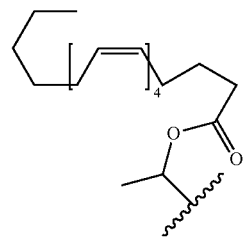

TABLE 1-continued
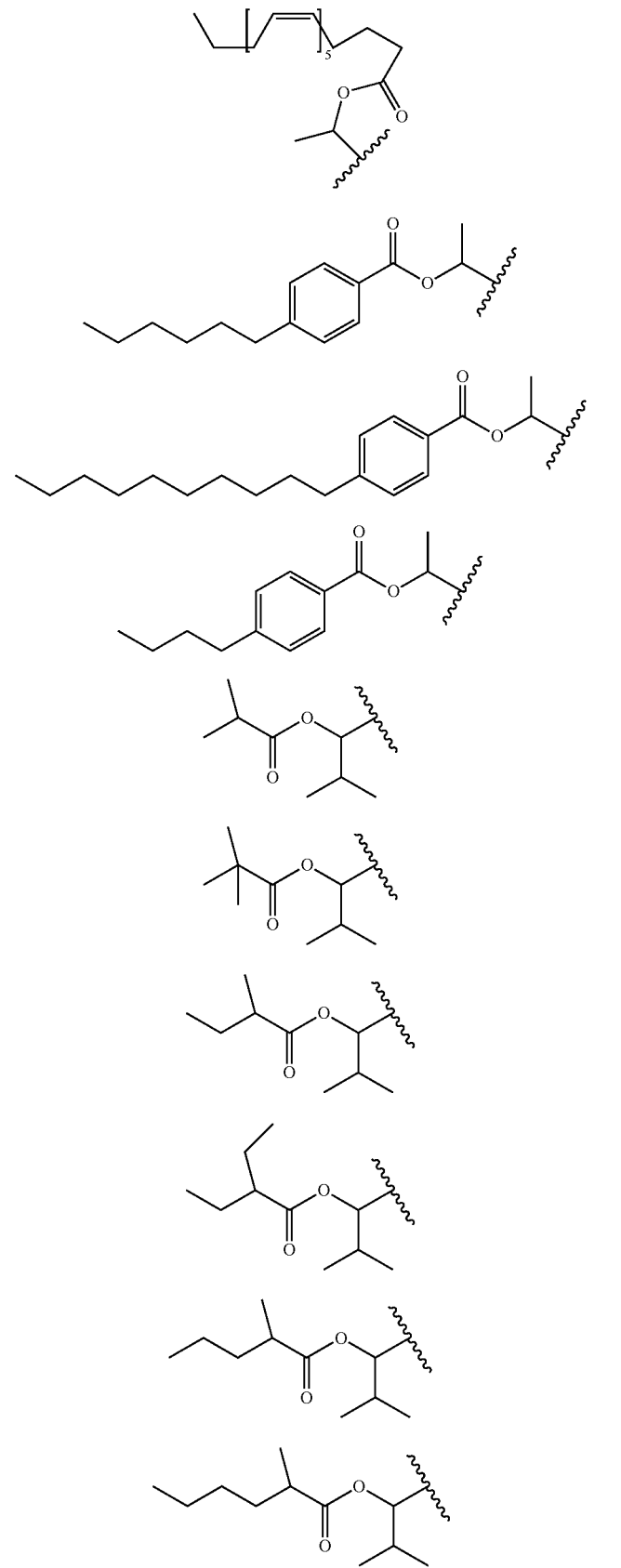

TABLE 1-continued
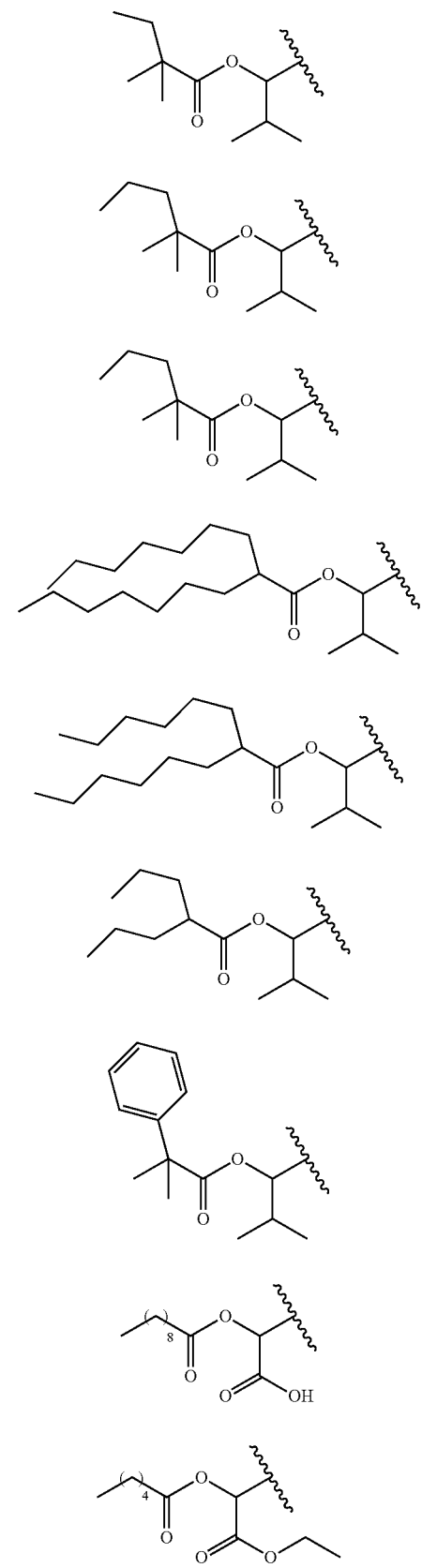

TABLE 1-continued
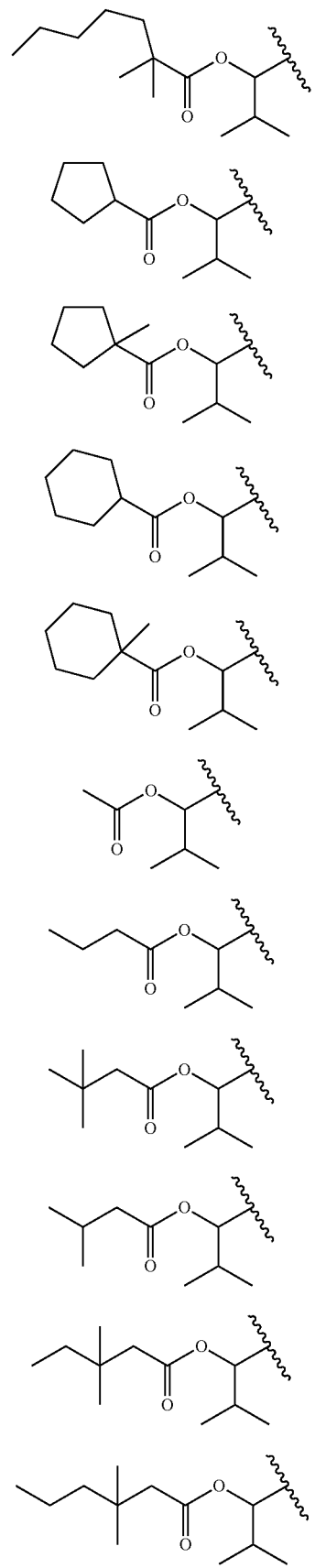

TABLE 1-continued
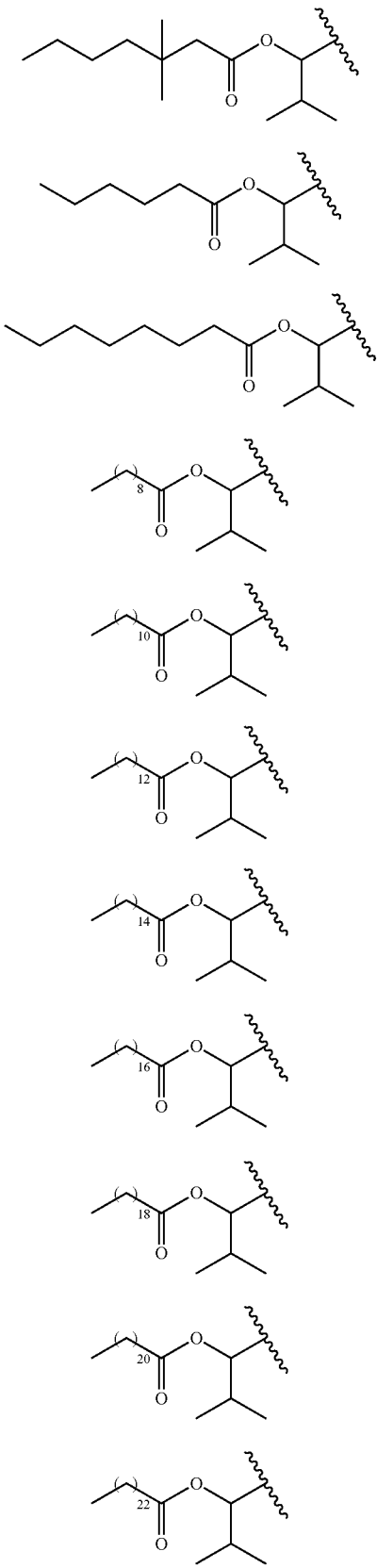

TABLE 1-continued
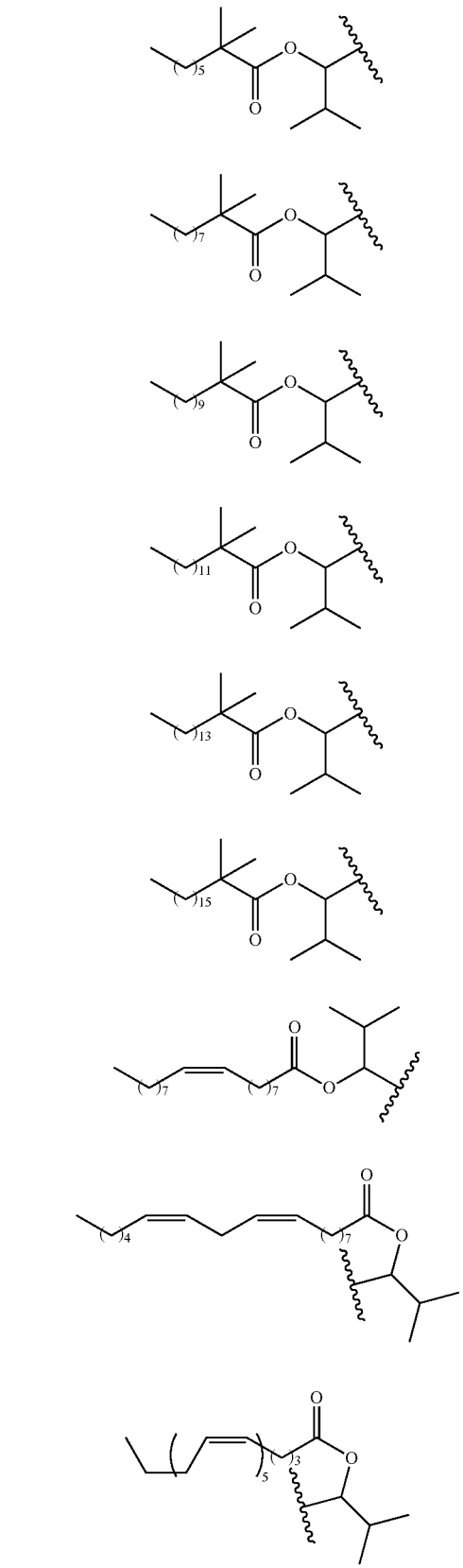

TABLE 1-continued
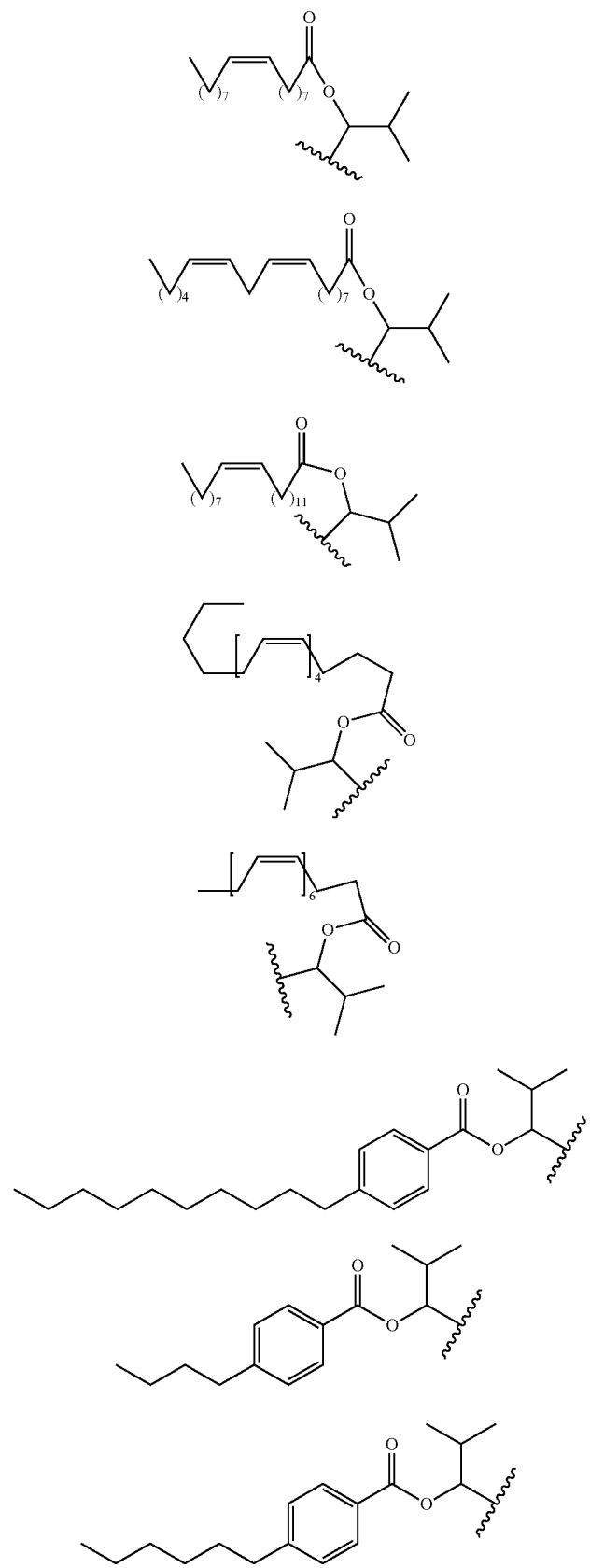

TABLE 1-continued
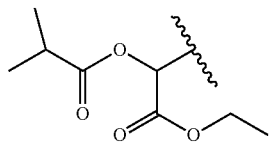 [SMILES: *C(OC(=O)C(C)C)C(=O)OCC]
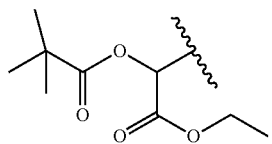 [SMILES: *C(OC(=O)C(C)(C)C)C(=O)OCC]
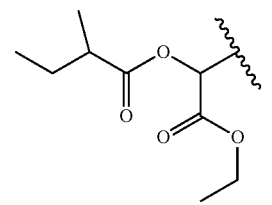 [SMILES: *C(OC(=O)C(C)CC)C(=O)OCC]
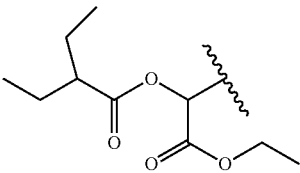 [SMILES: *C(OC(=O)C(CC)CC)C(=O)OCC]
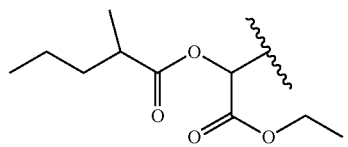 [SMILES: *C(OC(=O)C(C)CCC)C(=O)OCC]
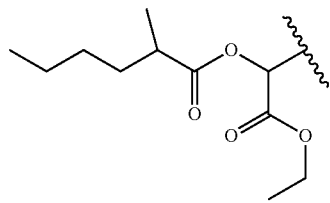 [SMILES: *C(OC(=O)C(C)CCCC)C(=O)OCC]
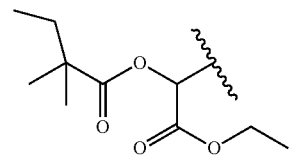 [SMILES: *C(OC(=O)C(C)(C)CC)C(=O)OCC]
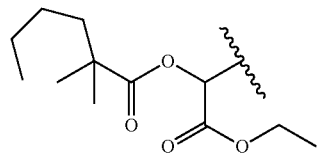 [SMILES: *C(OC(=O)C(C)(C)CCCC)C(=O)OCC]
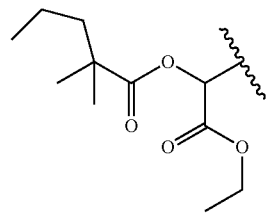 [SMILES: *C(OC(=O)C(C)(C)CCC)C(=O)OCC]

TABLE 1-continued
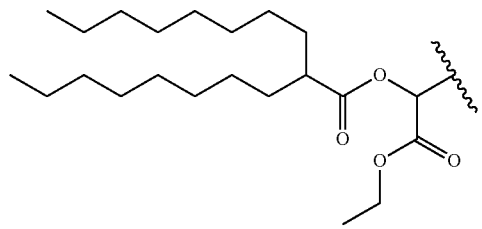 [SMILES: *C(OC(=O)C(CCCCCCCC)CCCCCCCC)C(=O)OCC]
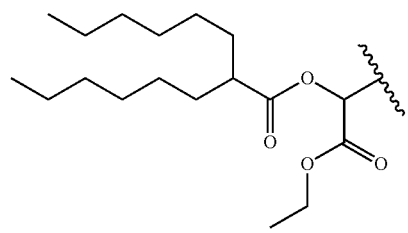 [SMILES: *C(OC(=O)C(CCCCCC)CCCCCC)C(=O)OCC]
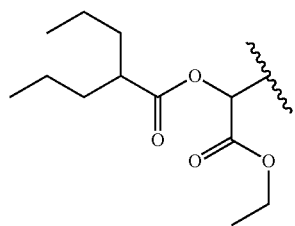 [SMILES: *C(OC(=O)C(CCC)CCC)C(=O)OCC]
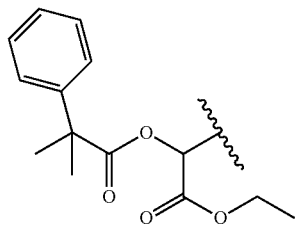 [SMILES: *C(OC(=O)C(C)(C)c1ccccc1)C(=O)OCC]
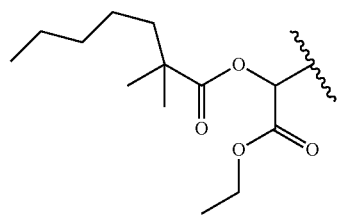 [SMILES: *C(OC(=O)C(C)(C)CCCCC)C(=O)OCC]
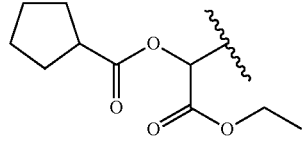 [SMILES: *C(OC(=O)C1CCCC1)C(=O)OCC]
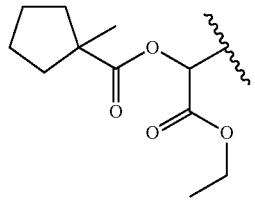 [SMILES: *C(OC(=O)C1(C)CCCC1)C(=O)OCC]

TABLE 1-continued
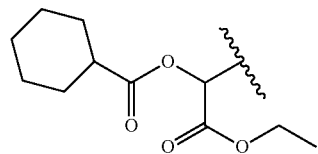 [SMILES: *C(OC(=O)C1CCCCC1)C(=O)OCC]
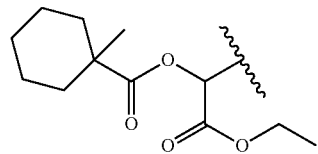 [SMILES: *C(OC(=O)C1(C)CCCCC1)C(=O)OCC]
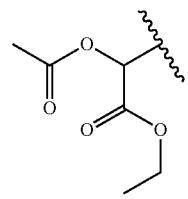 [SMILES: *C(OC(C)=O)C(=O)OCC]
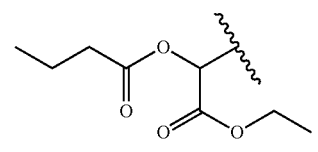 [SMILES: *C(OC(=O)CCC)C(=O)OCC]
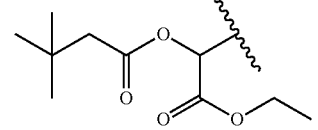 [SMILES: *C(OC(=O)CC(C)(C)C)C(=O)OCC]
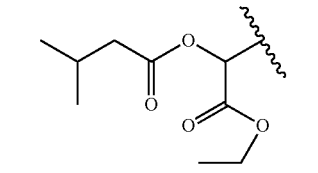 [SMILES: *C(OC(=O)CC(C)C)C(=O)OCC]
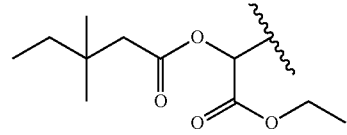 [SMILES: *C(OC(=O)CC(C)(C)CC)C(=O)OCC]
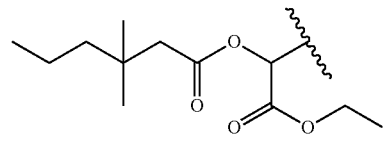 [SMILES: *C(OC(=O)CC(C)(C)CCC)C(=O)OCC]
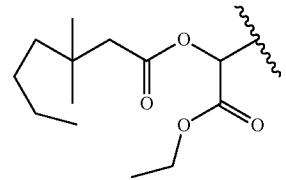 [SMILES: *C(OC(=O)CC(C)(C)CCCC)C(=O)OCC]

TABLE 1-continued
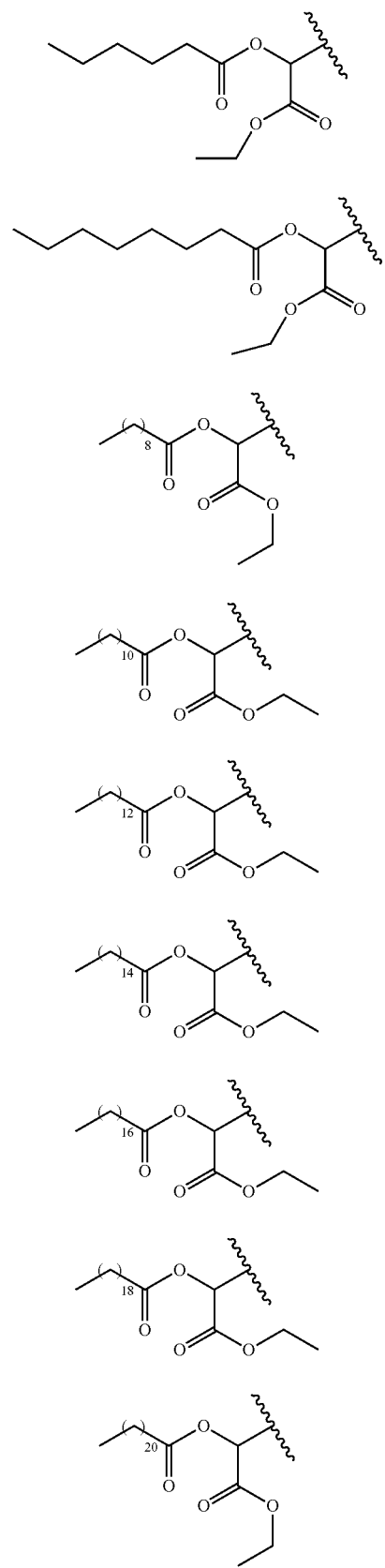

TABLE 1-continued
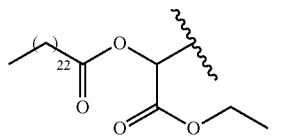
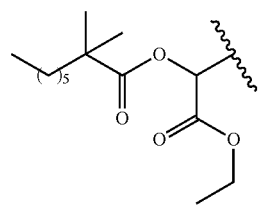
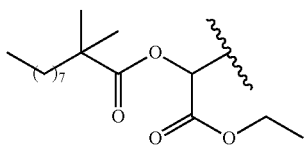
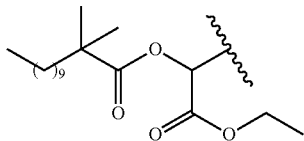
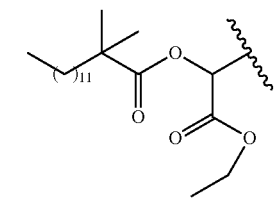
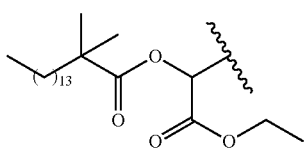
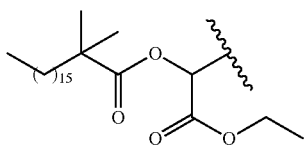
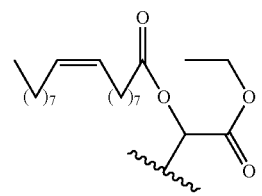
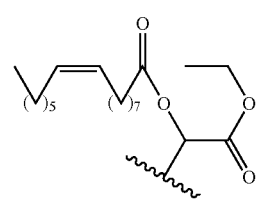

TABLE 1-continued
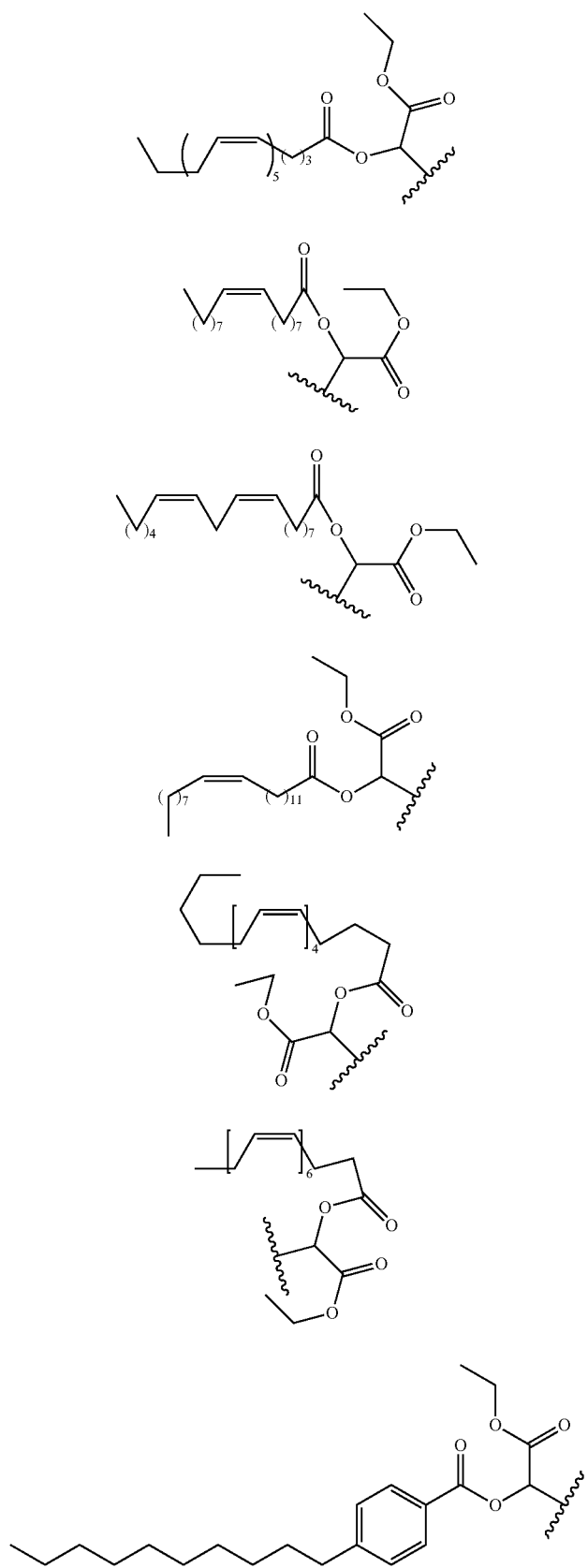

TABLE 1-continued
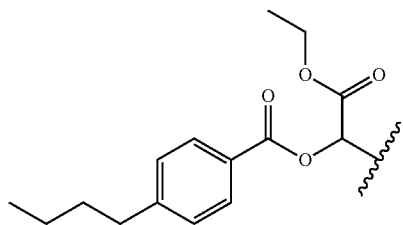 [SMILES: *C(OC(=O)c1ccc(CCCC)cc1)C(=O)OCC]
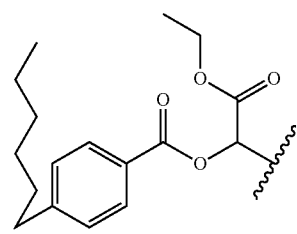 [SMILES: *C(OC(=O)c1ccc(CCCCCC)cc1)C(=O)OCC]
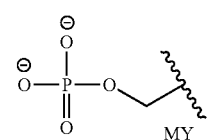
MY
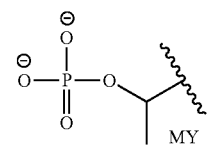
MY
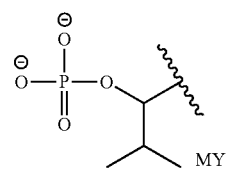
MY
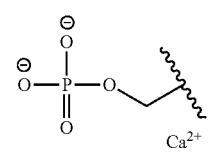 [SMILES: *COP(=O)([O-])[O-] ; [Ca+2]]
Ca²⁺
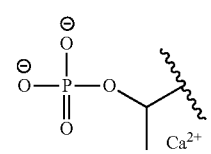
Ca²⁺
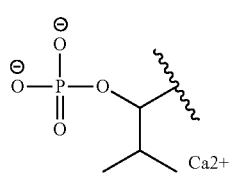
Ca2+
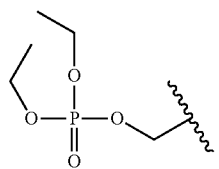 [SMILES: *COP(=O)(OCC)OCC]

TABLE 1-continued
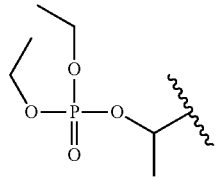 [SMILES: *C(C)OP(=O)(OCC)OCC]
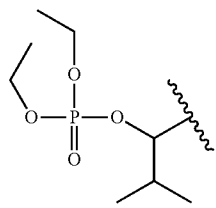 [SMILES: *C(OP(=O)(OCC)OCC)C(C)C]
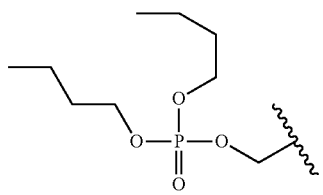 [SMILES: *COP(=O)(OCCCC)OCCCC]
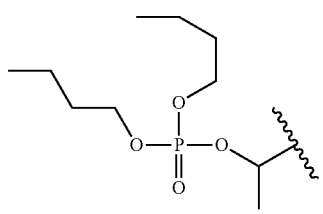 [SMILES: *C(C)OP(=O)(OCCCC)OCCCC]
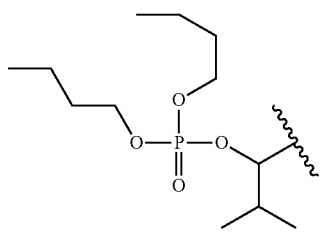 [SMILES: *C(OP(=O)(OCCCC)OCCCC)C(C)C]
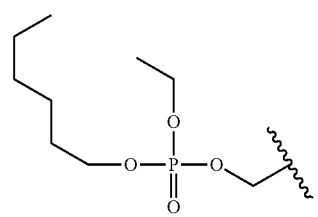 [SMILES: *COP(=O)(OCC)OCCCCCC]
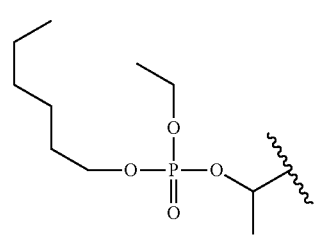 [SMILES: *C(C)OP(=O)(OCC)OCCCCCC]

TABLE 1-continued
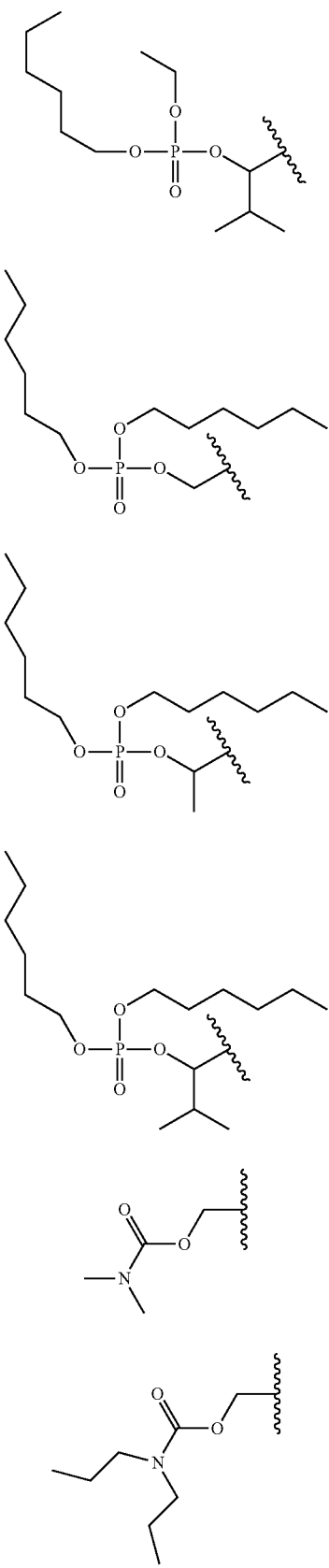

TABLE 1-continued
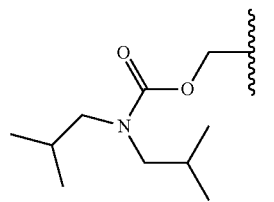 [SMILES: *COC(=O)N(CC(C)C)CC(C)C]
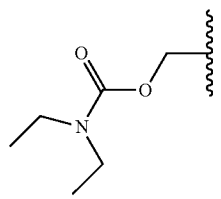 [SMILES: *COC(=O)N(CC)CC]
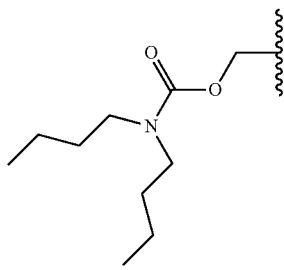 [SMILES: *COC(=O)N(CCCC)CCCC]
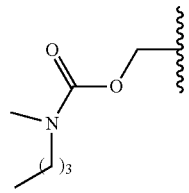
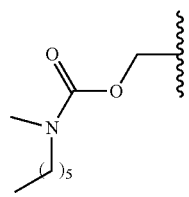
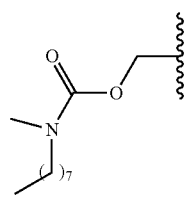
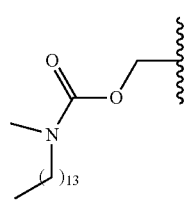

TABLE 1-continued
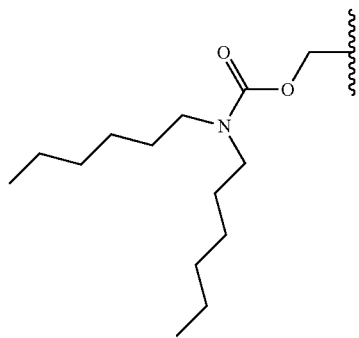 [SMILES: *COC(=O)N(CCCCCC)CCCCCC]
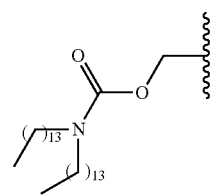
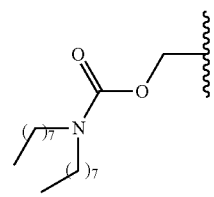
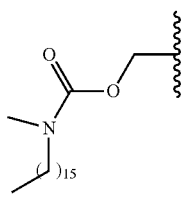
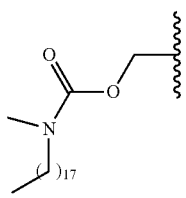
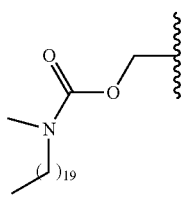
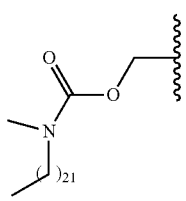

TABLE 1-continued
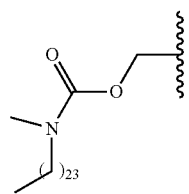
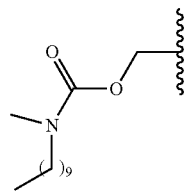
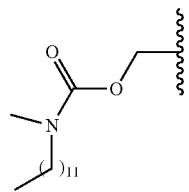
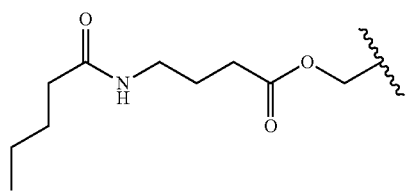 [SMILES: *COC(=O)CCCNC(=O)CCCC]
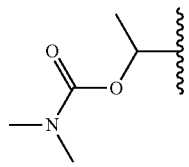 [SMILES: *C(C)OC(=O)N(C)C]
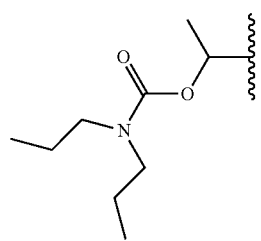 [SMILES: *C(C)OC(=O)N(CCC)CCC]
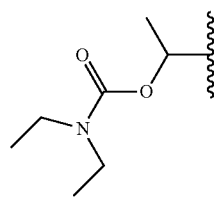 [SMILES: *C(C)OC(=O)N(CC)CC]

TABLE 1-continued
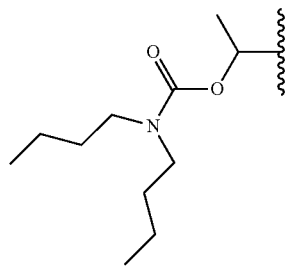 [SMILES: *C(C)OC(=O)N(CCCC)CCCC]
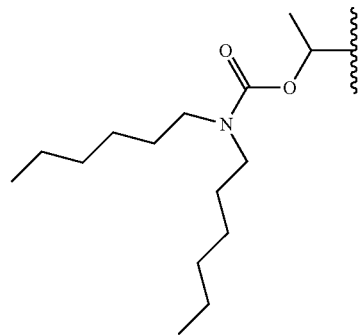 [SMILES: *C(C)OC(=O)N(CCCCCC)CCCCCC]
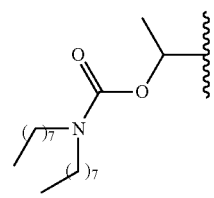
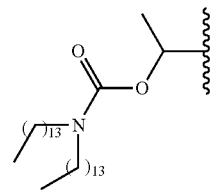
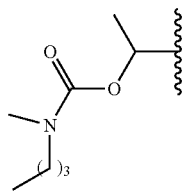
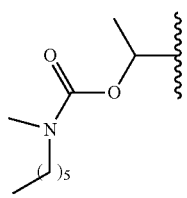
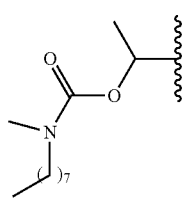

TABLE 1-continued
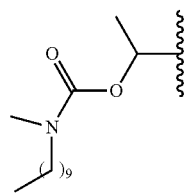
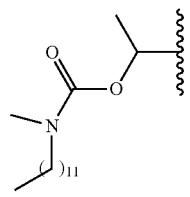
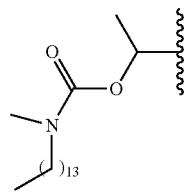
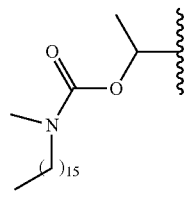
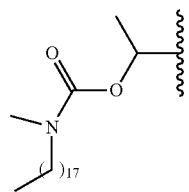
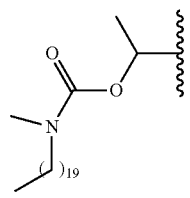
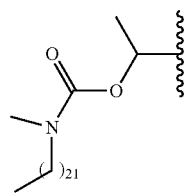
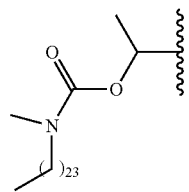

TABLE 1-continued
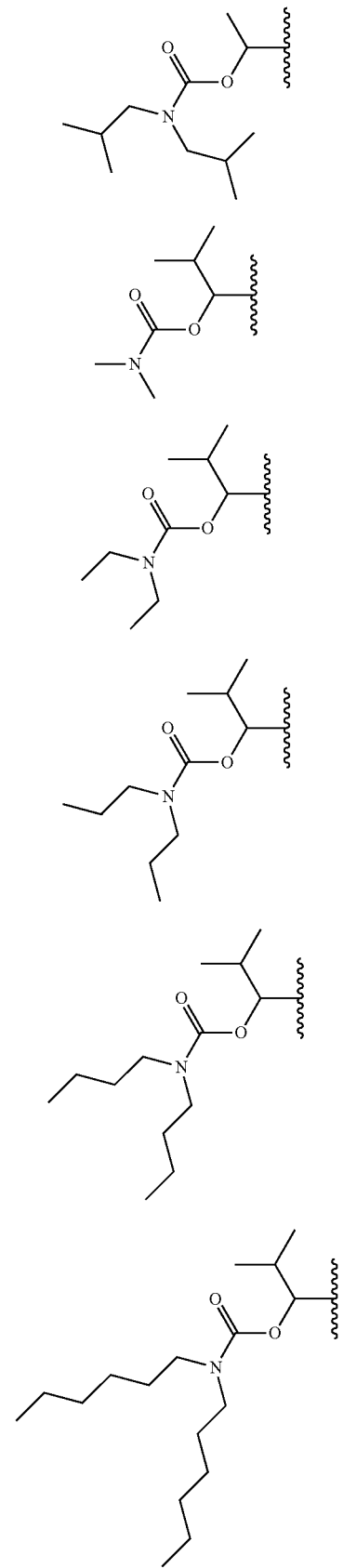

TABLE 1-continued
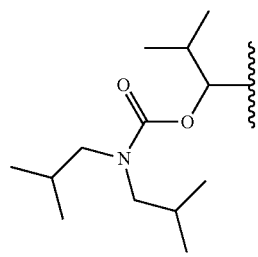 [SMILES: *C(OC(=O)N(CC(C)C)CC(C)C)C(C)C]
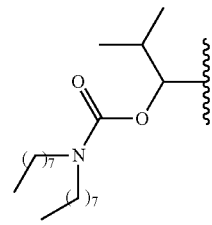
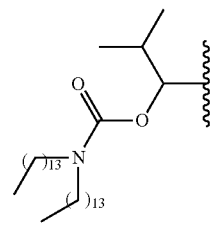
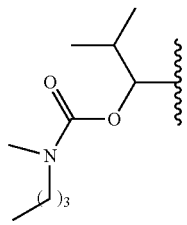
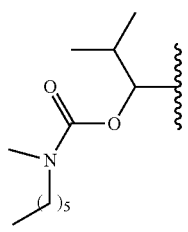
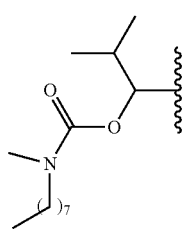
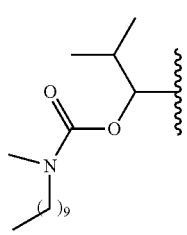

TABLE 1-continued
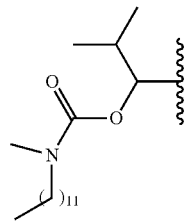
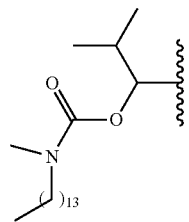
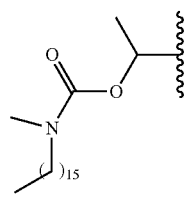
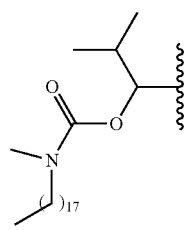
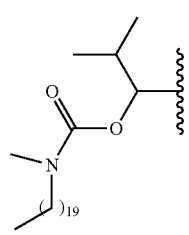
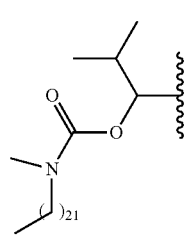
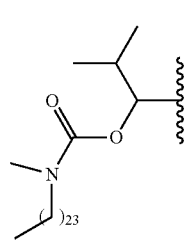

TABLE 1-continued
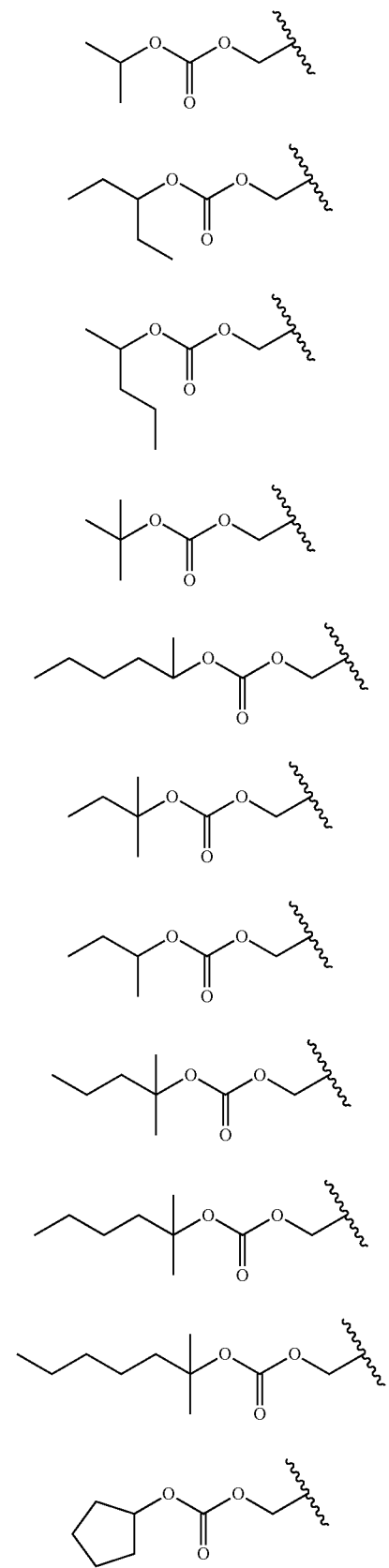

TABLE 1-continued
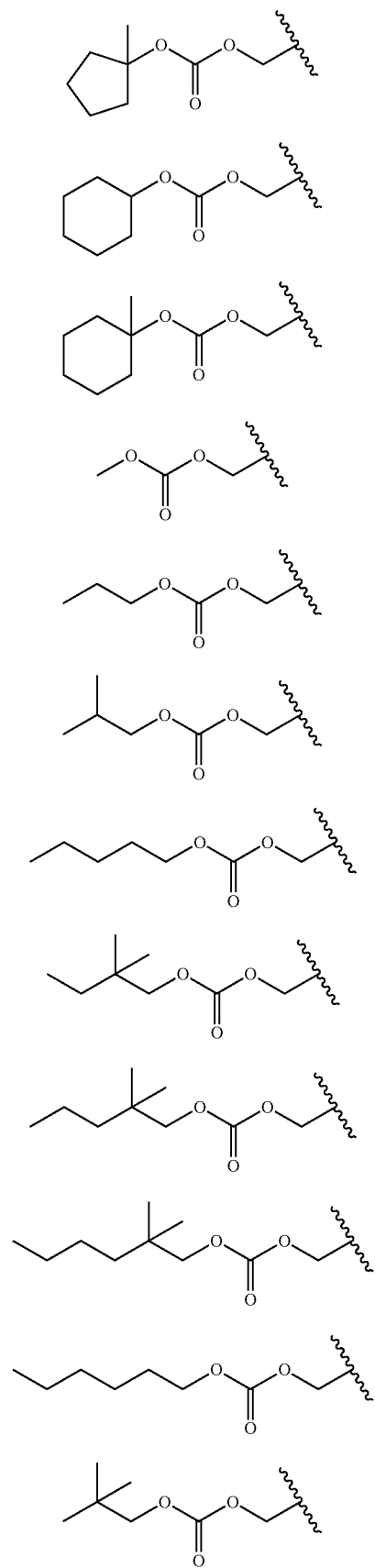

TABLE 1-continued
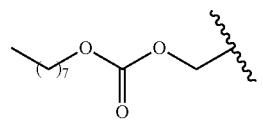
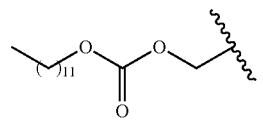
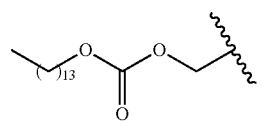
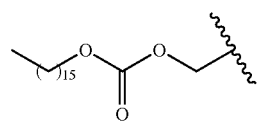
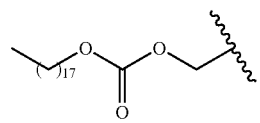
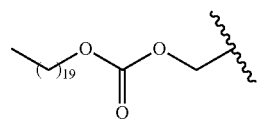
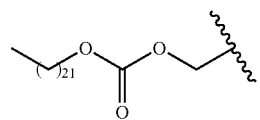
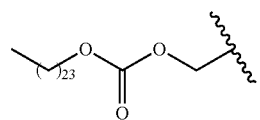
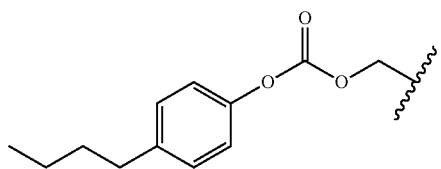 [SMILES: *COC(=O)Oc1ccc(CCCC)cc1]

TABLE 1-continued
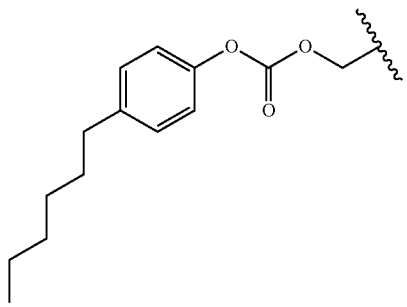 [SMILES: *COC(=O)Oc1ccc(CCCCCC)cc1]
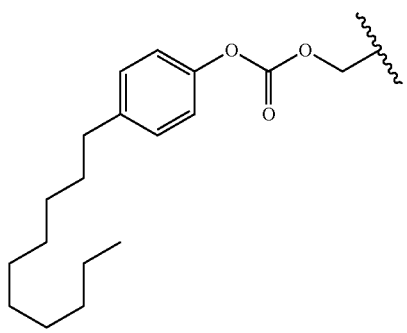 [SMILES: *COC(=O)Oc1ccc(CCCCCCCCCC)cc1]
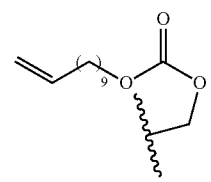
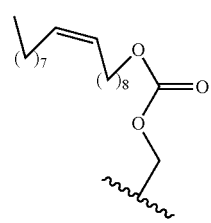
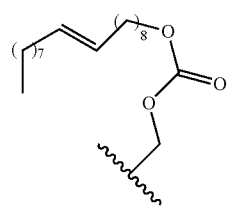
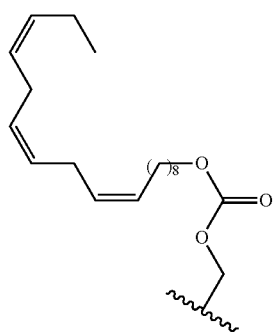

TABLE 1-continued
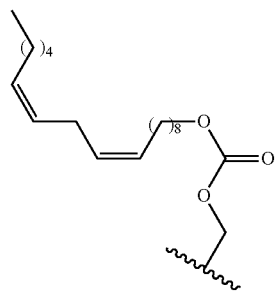
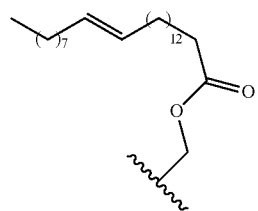
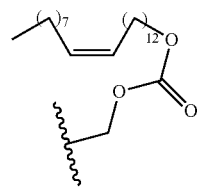
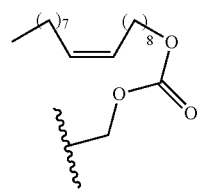
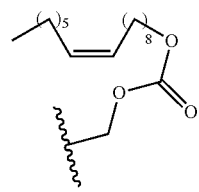
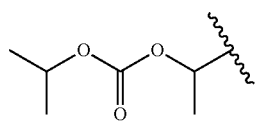 [SMILES: *C(C)OC(=O)OC(C)C]
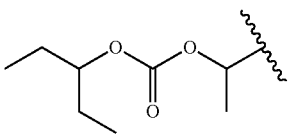 [SMILES: *C(C)OC(=O)OC(CC)CC]
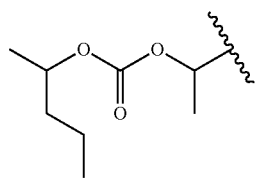 [SMILES: *C(C)OC(=O)OC(C)CCC]

TABLE 1-continued
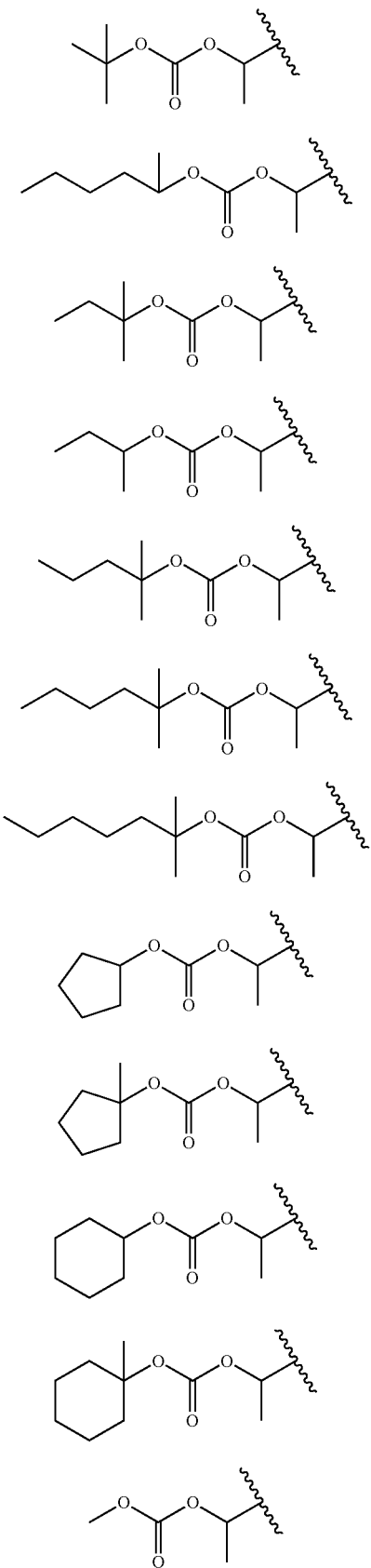

TABLE 1-continued
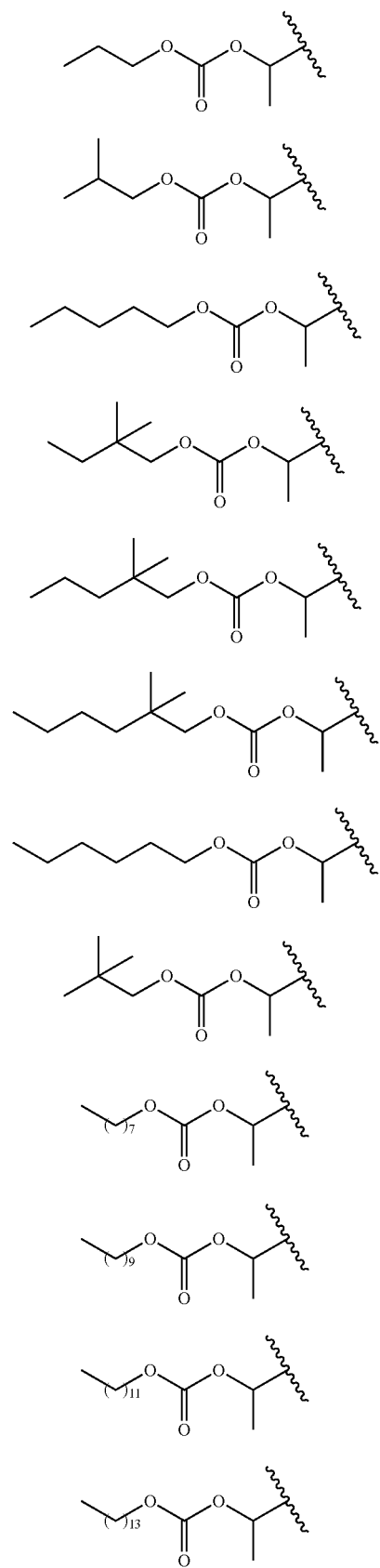

TABLE 1-continued
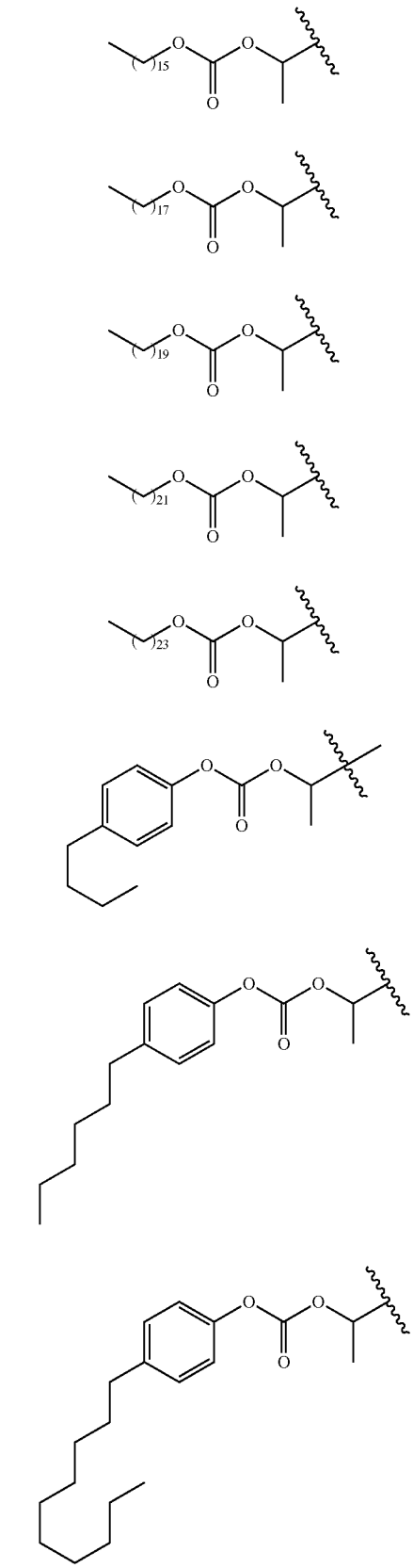

TABLE 1-continued
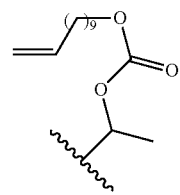
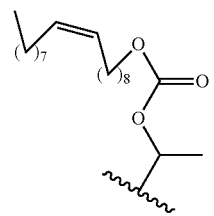
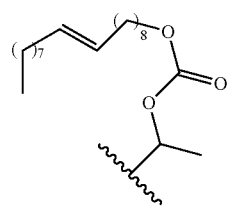
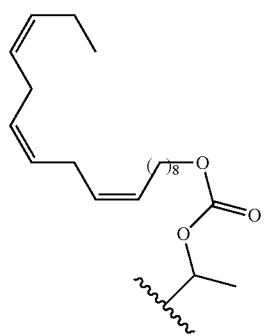
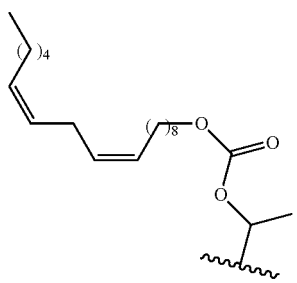
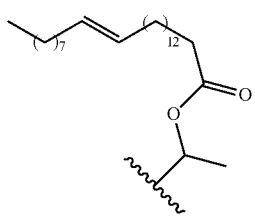

TABLE 1-continued
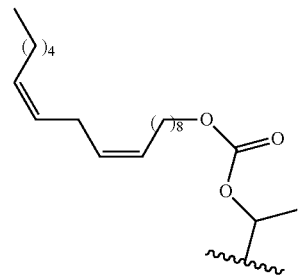
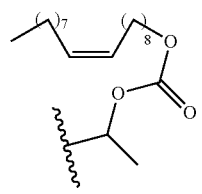
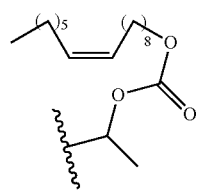
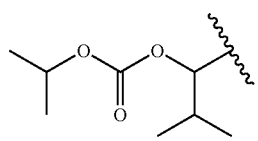 [SMILES: *C(OC(=O)OC(C)C)C(C)C]
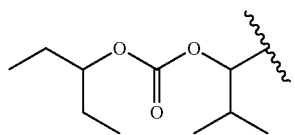 [SMILES: *C(OC(=O)OC(CC)CC)C(C)C]
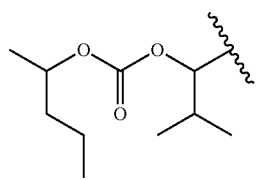 [SMILES: *C(OC(=O)OC(C)CCC)C(C)C]
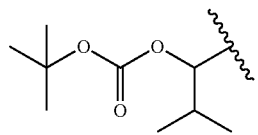
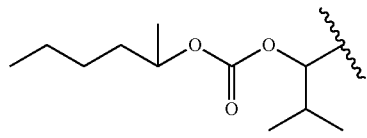 [SMILES: *C(OC(=O)OC(C)CCCC)C(C)C]
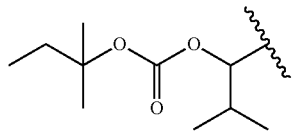 [SMILES: *C(OC(=O)OC(C)(C)CC)C(C)C]

TABLE 1-continued
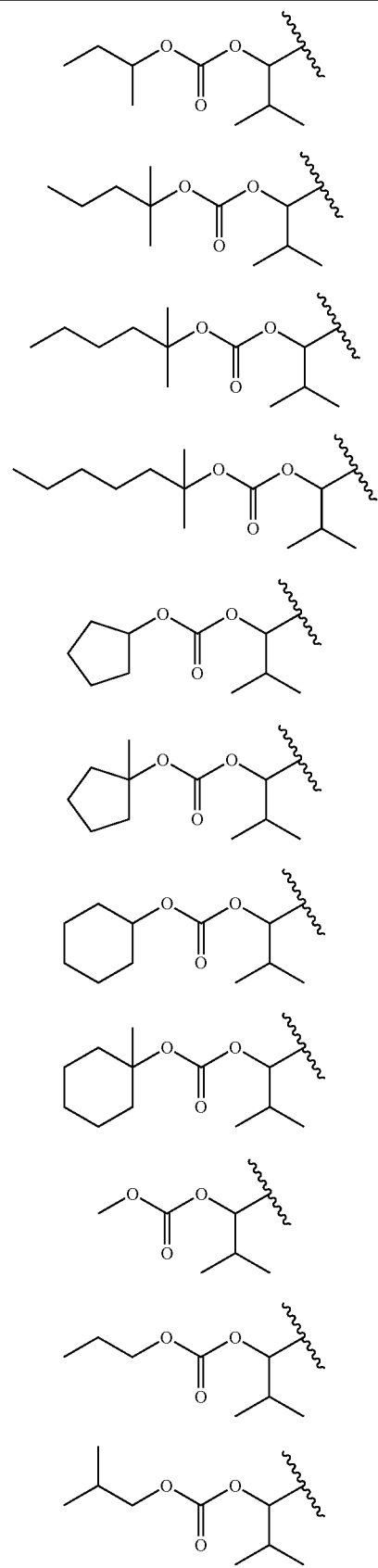

TABLE 1-continued
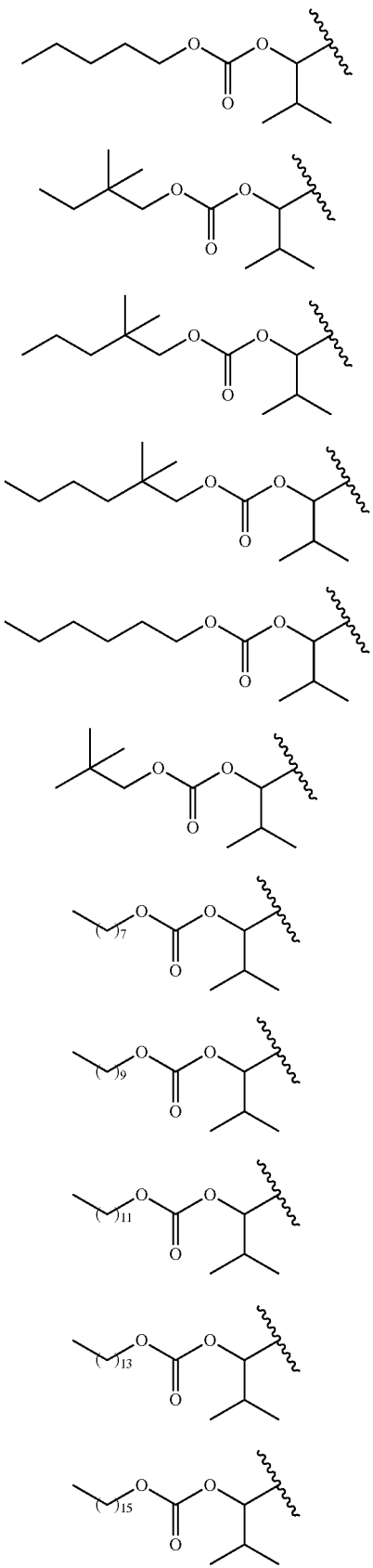

TABLE 1-continued
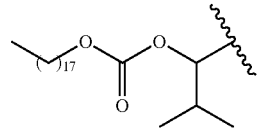
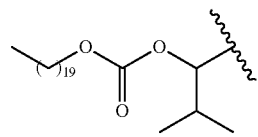
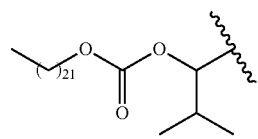
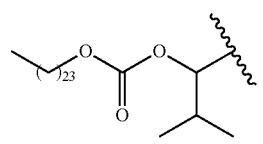
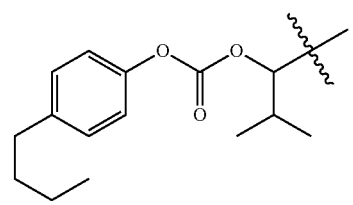 [SMILES: *C(OC(=O)Oc1ccc(CCCC)cc1)C(C)C]
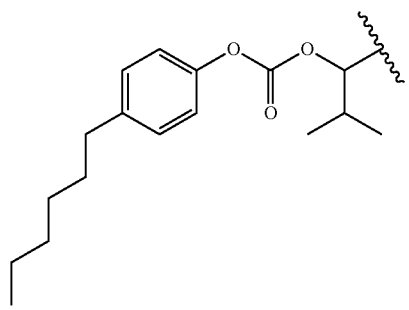 [SMILES: *C(OC(=O)Oc1ccc(CCCCCC)cc1)C(C)C]
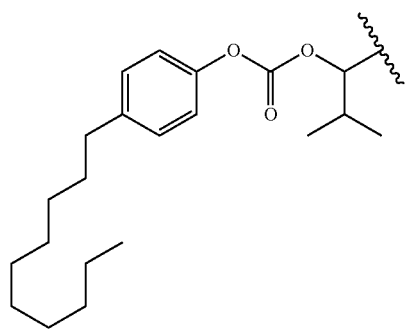 [SMILES: *C(OC(=O)Oc1ccc(CCCCCCCCCC)cc1)C(C)C]
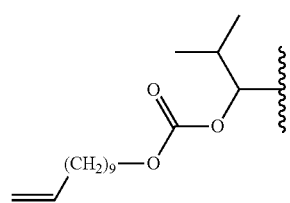

TABLE 1-continued
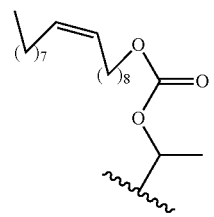
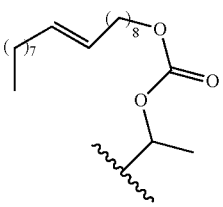
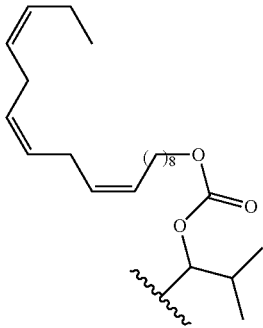
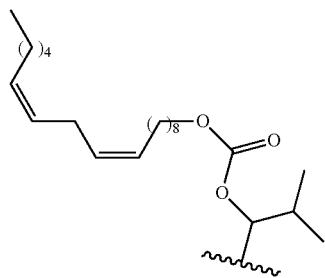
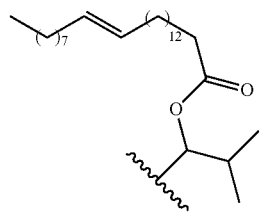
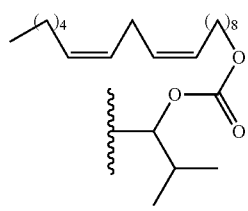

TABLE 1-continued
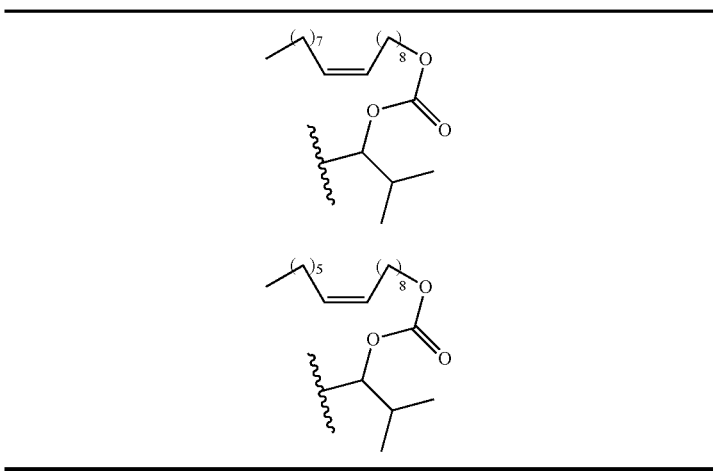
In a more preferred embodiment, R$_1$ is selected from Table 2.
TABLE 2
TABLE 2-continued
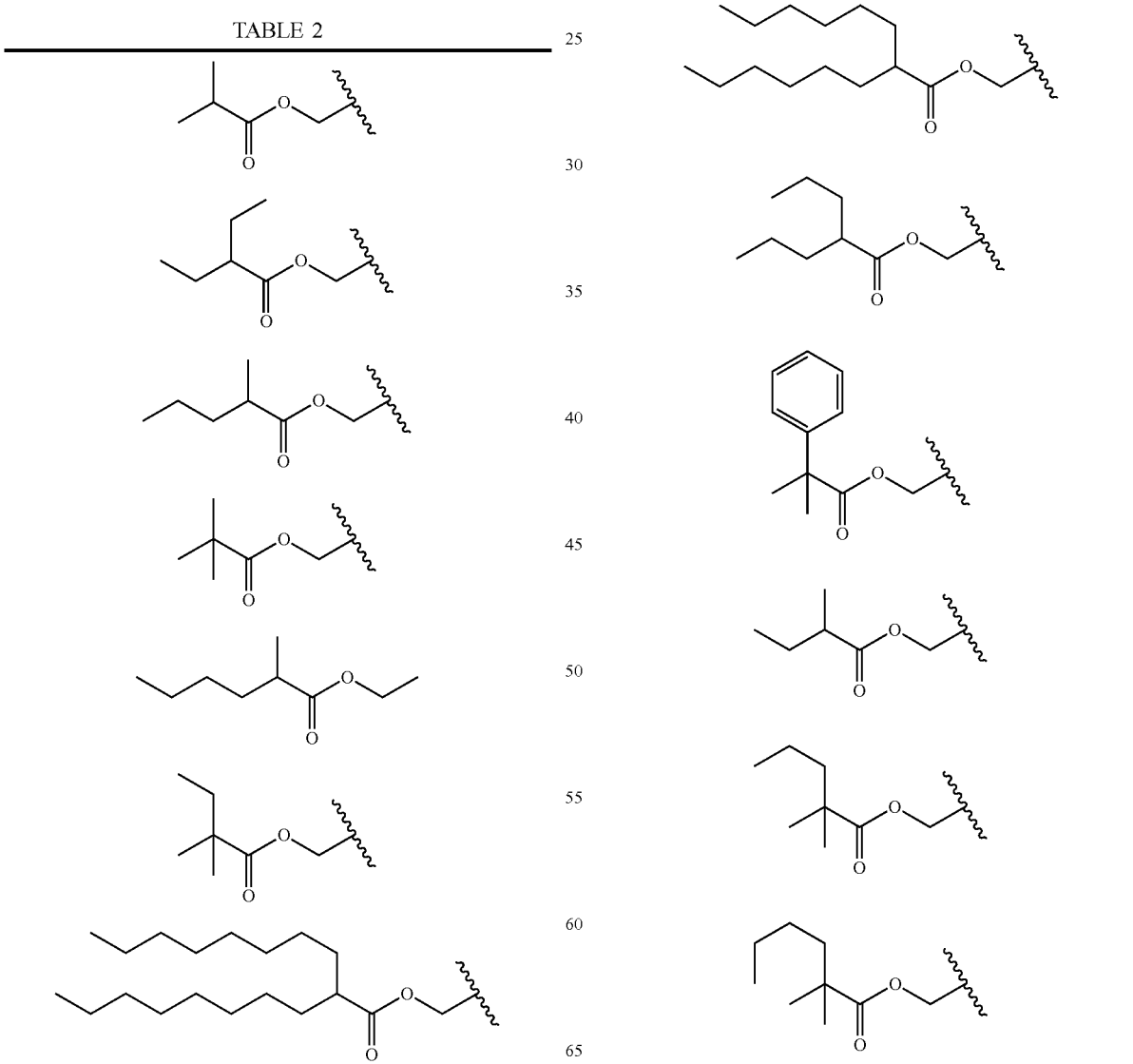

TABLE 2-continued
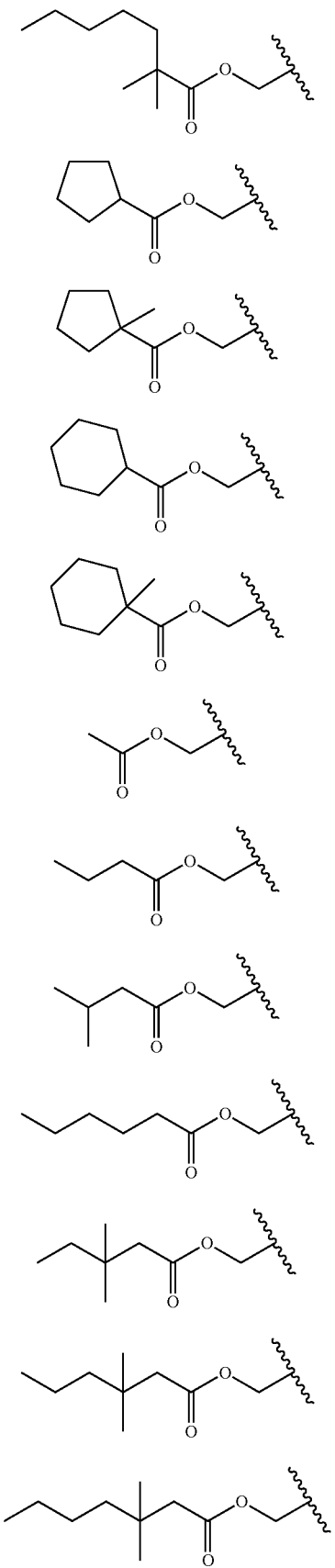
TABLE 2-continued
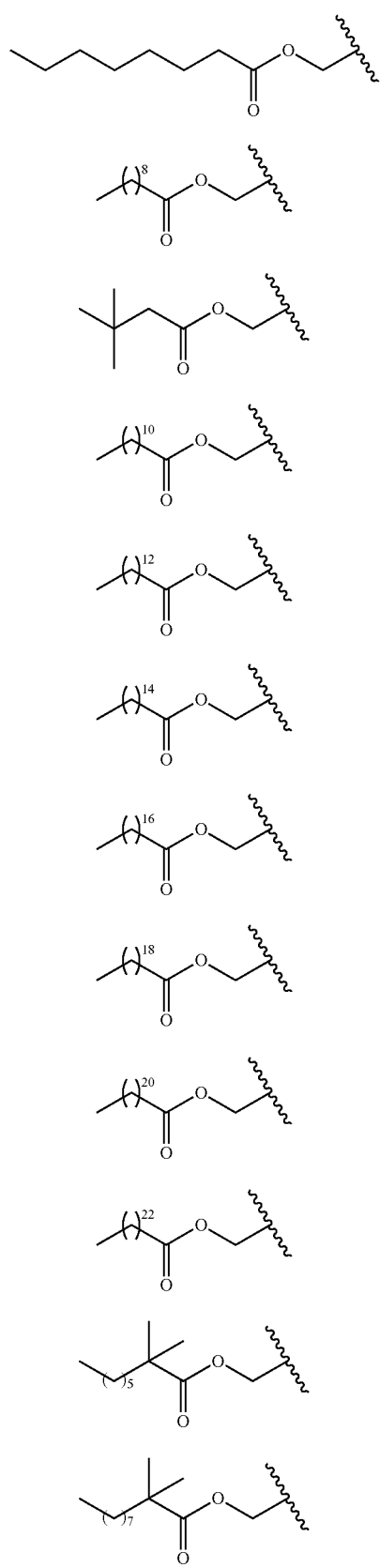

TABLE 2-continued
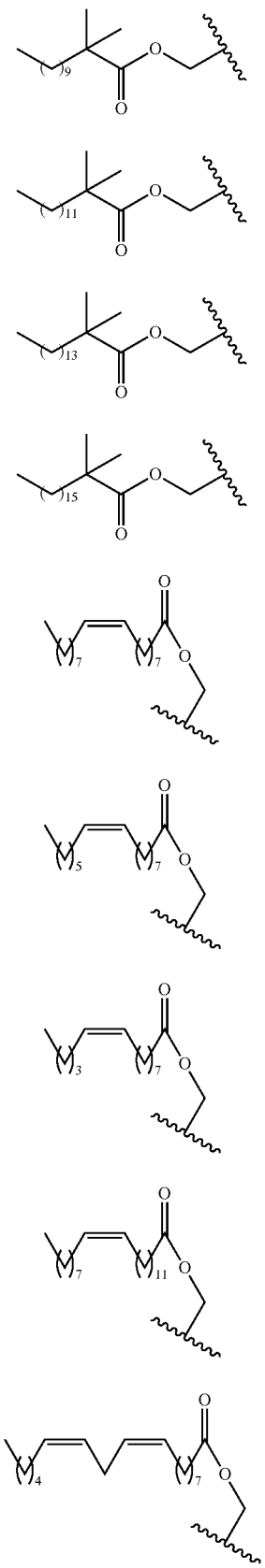
TABLE 2-continued
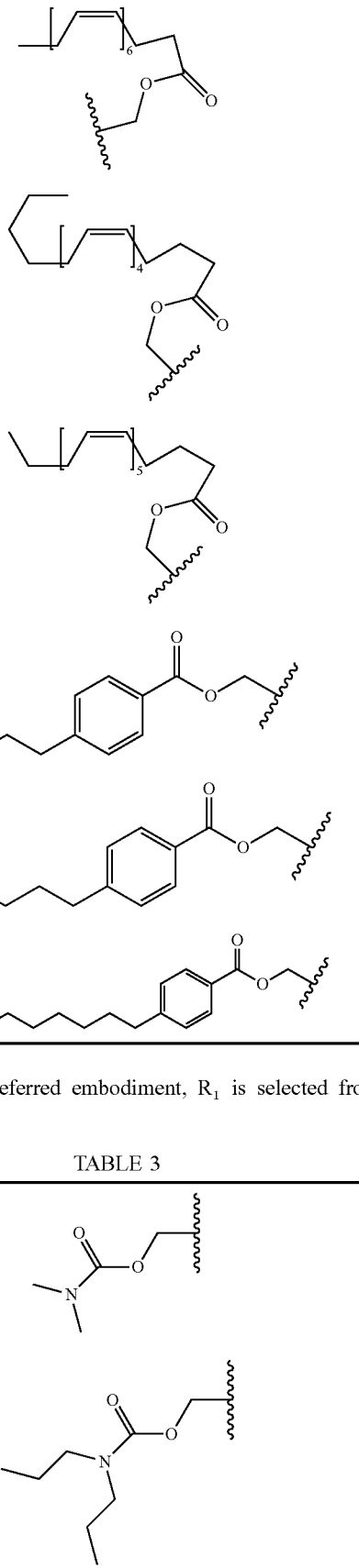
In a more preferred embodiment, $R_1$ is selected from Table 3.
TABLE 3
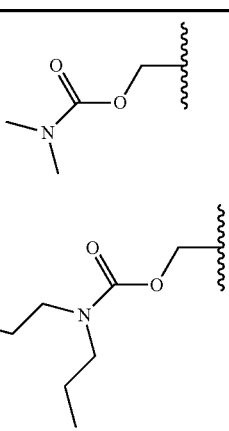

TABLE 3-continued
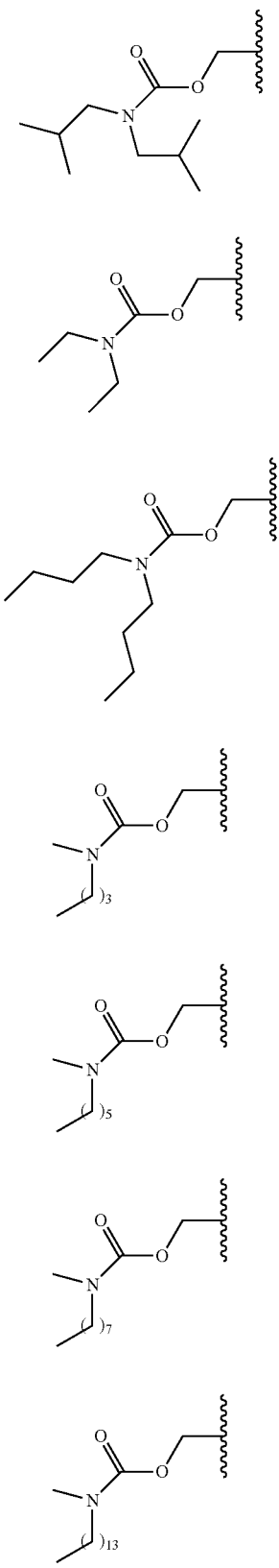
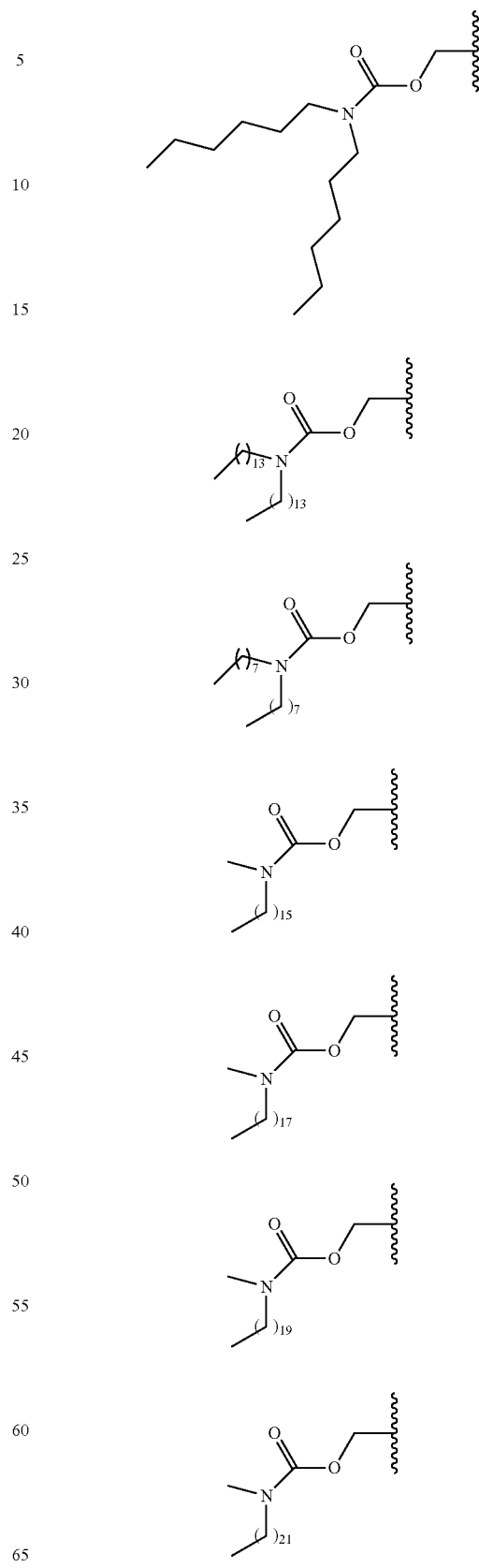

TABLE 3-continued
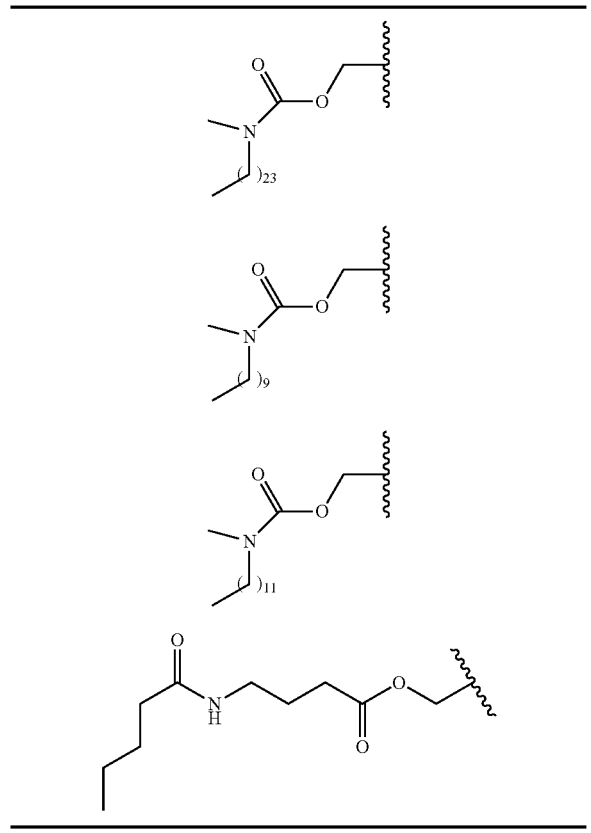
In a more preferred embodiment, $R_1$ is selected from Table 4.
TABLE 4
TABLE 4-continued
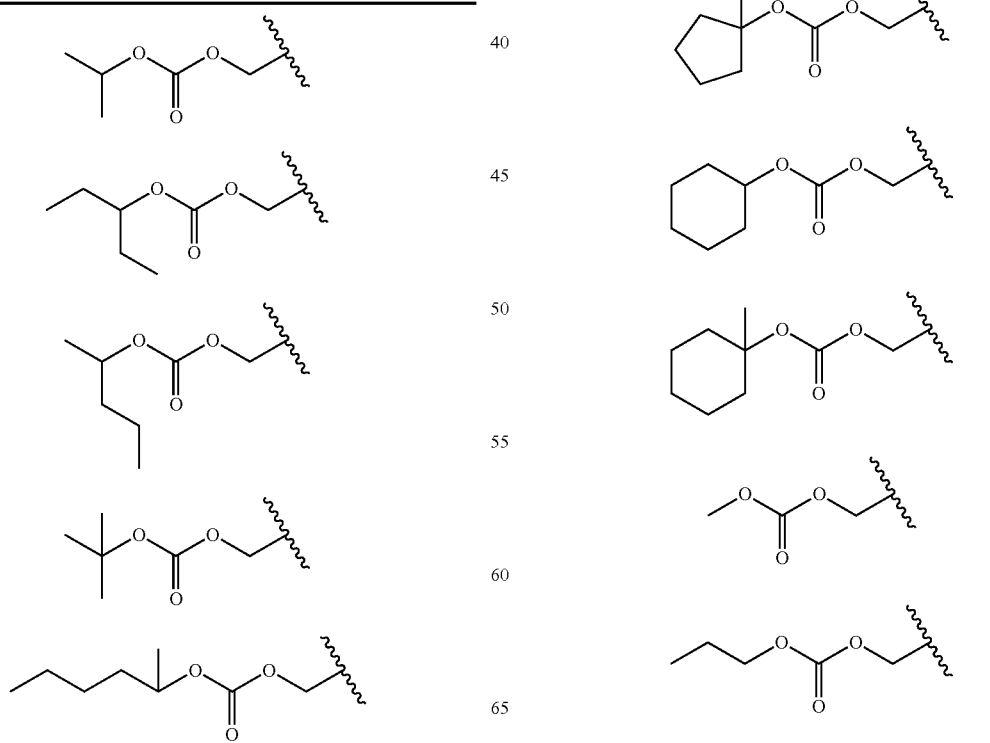

TABLE 4-continued
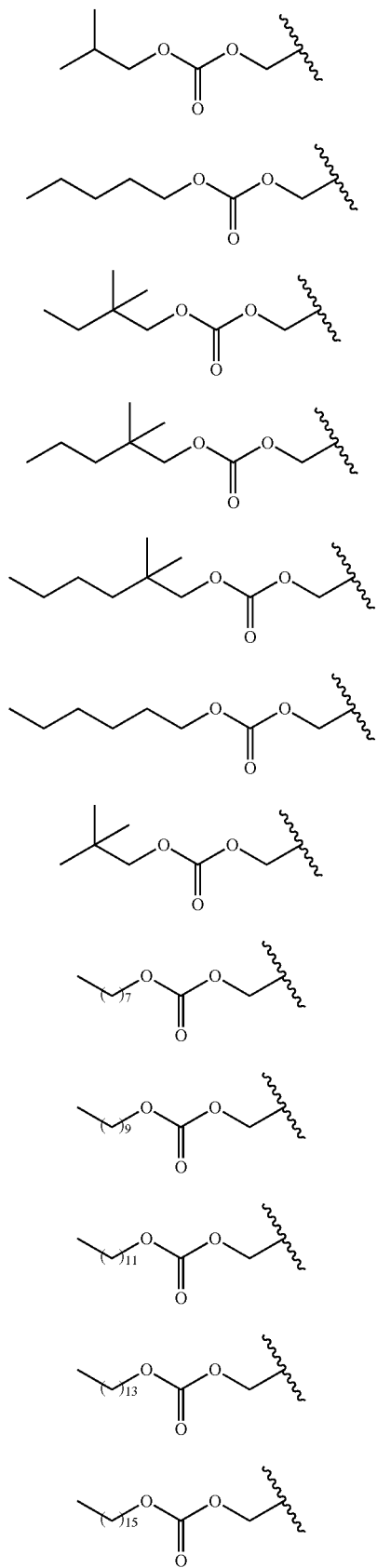
TABLE 4-continued
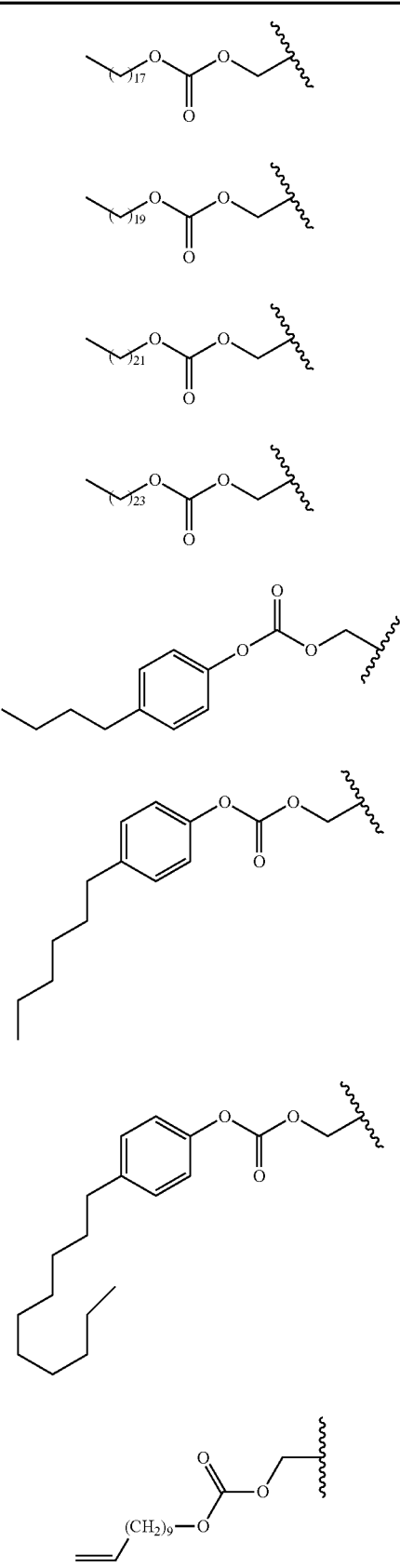

TABLE 4-continued

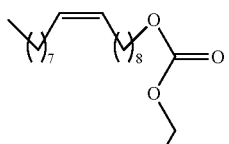
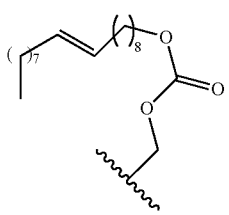
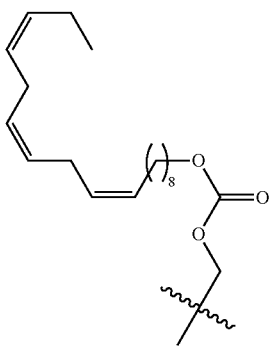
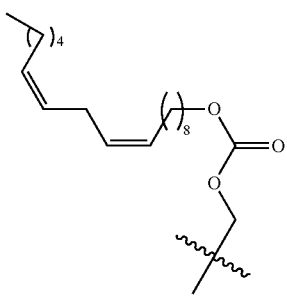
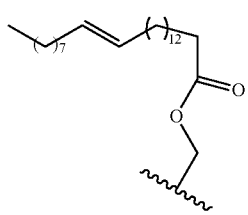
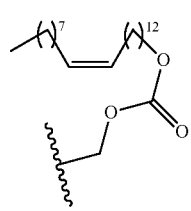

TABLE 4-continued

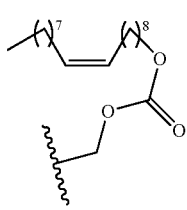
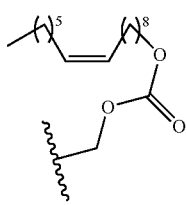

Prodrugs of Lactam, Cyclic Urea, Imide, Carbamate Containing Pharmacophores

In one embodiment, compounds of the present invention are represented by formula IV or V as illustrated below, or its geometric isomers, enantiomers, diastereomers, racemates, pharmaceutically acceptable salts co-crystals and solvates thereof:

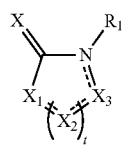

Formula IV

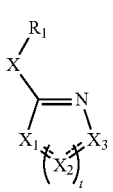

Formula V where ═══ represents a single or double bond;

X and $R_1$ are as defined above;

each $X_1$, $X_2$, and $X_3$ is independently selected from absent, —S—, —O—, —S(O)—, —S(O)$_2$—, —N($R_{10}$)—, —C(O)—, —C(O$R_{10}$)($R_{11}$)—, —[C($R_{10}$)($R_{11}$)]$_v$—, —C($R_{10}$)═C($R_{10}$)—; wherein v is 0, 1, 2, 3, 4, 5, 6, 7, 8, 9 or 10;

wherein each $R_{10}$ and $R_{11}$ is independently absent, hydrogen, halogen, aliphatic, substituted aliphatic, aryl or substituted aryl; alternatively, two $R_{10}$ and $R_{11}$ together with the atoms to which they are attached may form an additional optionally substituted, 3, 4, 5, 6 or 7 membered ring; and t is 0, 1, 2 or 3.

In one embodiment, compounds of the present invention are represented by formula VI or VII as illustrated below, and the geometric isomers, enantiomers, diastereomers, racemates, pharmaceutically acceptable salts and solvates thereof:

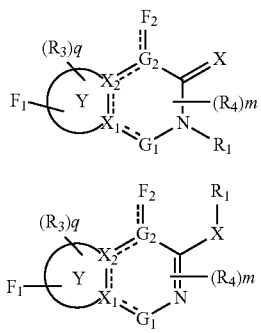

Formula VI

Formula VII wherein ══ represents a single or double bond;
X, $X_1$, $X_2$ and $R_1$ are as defined above;
ring Y is an optionally substituted cycloalkyl, cycloalkenyl, heterocyclyl or aryl containing one, two or three rings;
each $F_1$ and $F_2$ is independently selected from absent and $R_5$-A-$Cy_1$-B-D-;

wherein, A is selected from absent, optionally substituted alkyl, optionally substituted alkenyl, optionally substituted alkynyl, —S—, —O—, —S(O)—, —S(O)$_2$—, —S[C($R_{30}$)($R_{31}$)]$_u$—, —S(O)[C($R_{30}$)($R_{31}$)]$_u$—, —S(O)$_2$[C($R_{30}$)($R_3$)]$_u$—, —O[C($R_{30}$)($R_{31}$)]$_u$—, —N($R_{30}$)—, —N($R_{30}$)[C($R_{31}$)($R_{32}$)]$_u$—, —[C($R_{30}$)($R_{31}$)]$_u$—, —C(O)[C($R_{30}$)($R_{31}$)]$_u$—;

wherein each u is independently 1, 2, 3, 4, 5, 6 or 7;

$Cy_1$ is absent or an optionally substituted cycloalkyl, optionally substituted cycloalkenyl, optionally substituted heterocyclyl, optionally substituted aryl or optionally substituted heteroaryl;

B is absent, or a linker;

D is selected from absent, —O—, —N$R_{33}$, —C($R_{34}$)($R_{35}$)—, —S—, —S(O)—, —S(O)$_2$—, and —C(O)—;

each $G_1$ and $G_2$ is independently selected from absent, —S—, —O—, —S(O)—, —S(O)$_2$—, —SC($R_{40}$)($R_{41}$)—, —S(O) C($R_{40}$)($R_{41}$)—, —S(O)$_2$C($R_{40}$)($R_{41}$)—, —C(O)—, —C(O$R_{40}$)($R_{41}$)—, —OC($R_{40}$)($R_{41}$)—, —N($R_{40}$)—, —C($R_{40}$)═C($R_{41}$)—, —N($R_{40}$)—C($R_{41}$)($R_{42}$)—, and —[C($R_{40}$)($R_{41}$)]$_u$—;

each $R_3$, $R_4$, $R_5$, $R_{30}$, $R_{31}$, $R_{32}$ $R_{33}$, $R_{34}$, $R_{35}$, $R_{40}$, $R_{41}$, and $R_{42}$ is independently selected from absent, hydrogen, halogen, —O$R_{10}$, —S$R_{10}$, —N$R_{10}R_{11}$—, —C(O)$R_{10}$, optionally substituted aliphatic, optionally substituted aryl or optionally substituted heterocyclyl;

alternatively, two $R_3$ groups or two $R_4$ groups or one $R_3$ group with one $R_4$ group together with the atoms to which they are attached and any intervening atoms form an optionally substituted ring;

m and q are independently selected from 0, 1, and 2.

In a preferred embodiment, $G_2$ is selected from —N— or —C($R_{10}$)—.

In a preferred embodiment, the $R_5$ moiety is an aryl or heteroaryl group selected from:

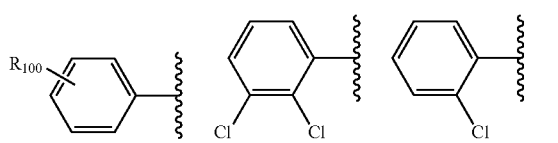

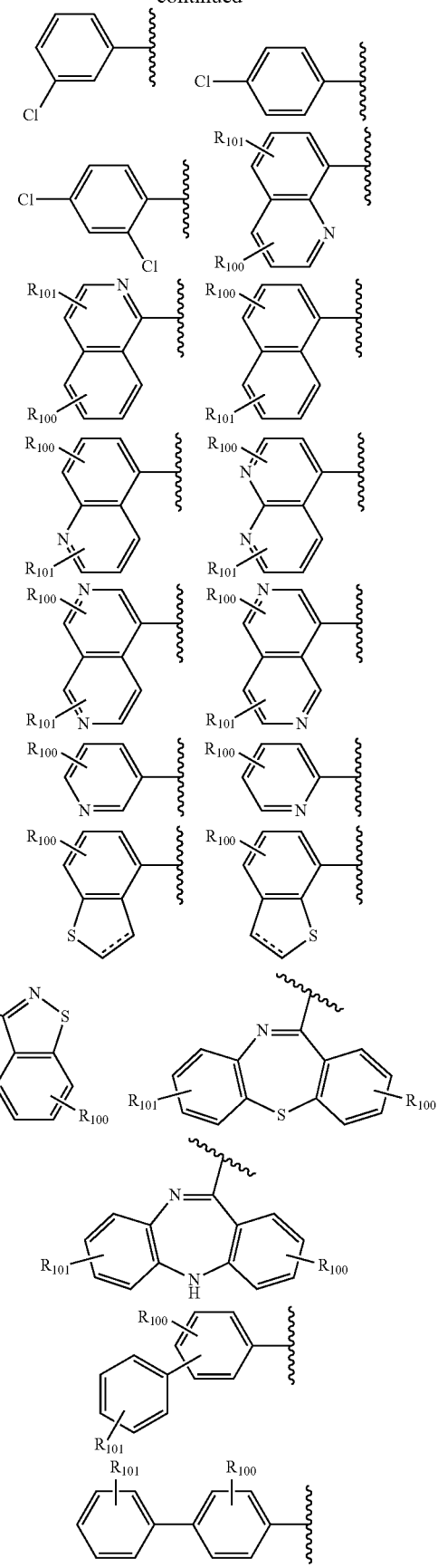

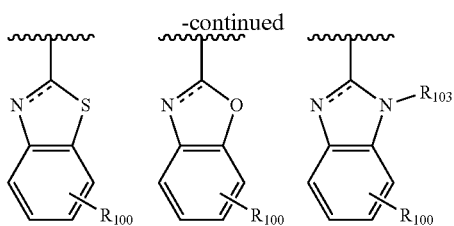

wherein $R_{100}$ and $R_{101}$, each represent 1 to 4 substituents independently selected from hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl; and, $R_{103}$ is selected from hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl.

In a preferred embodiment, $Cy_1$ is selected from:

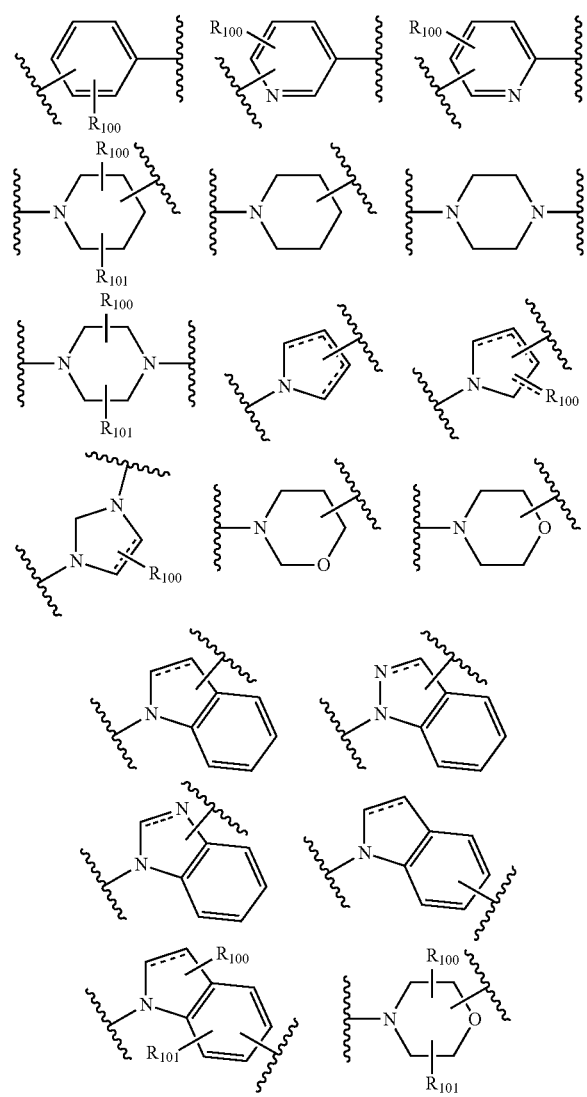

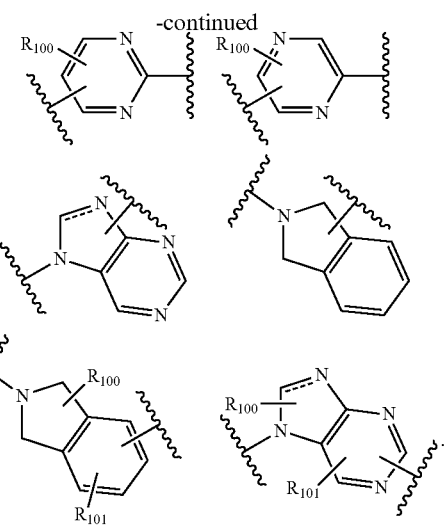

In a preferred embodiment, the bivalent B is a direct bond, a straight chain $C_1$-$C_{10}$ alkyl, $C_1$-$C_{10}$ alkenyl, $C_1$-$C_{10}$ alkynyl, $C_1$-$C_{10}$ alkoxy, alkoxy$C_1$-$C_{10}$alkoxy, $C_1$-$C_{10}$ alkylamino, alkoxy$C_1$-$C_{10}$alkylamino, $C_1$-$C_{10}$ alkylcarbonylamino, $C_1$-$C_{10}$ alkylaminocarbonyl, aryloxy$C_1$-$C_{10}$ alkoxy, aryloxy$C_1$-$C_{10}$alkylamino, aryloxy$C_1$-$C_{10}$ alkylamino carbonyl, $C_1$-$C_{10}$-alkylaminoalkylaminocarbonyl, $C_1$-$C_{10}$ alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxy$C_1$-$C_{10}$alkoxy, alkenylarylamino$C_1$-$C_{10}$alkoxy, alkenylaryllalkylamino$C_1$-$C_{10}$alkoxy, alkenylaryloxy$C_1$-$C_{10}$alkylamino, alkenylaryloxy$C_1$-$C_{10}$alkylaminocarbonyl, piperazinoalkylaryl, heteroaryl$C_1$-$C_{10}$alkyl, heteroaryl$C_2$-$C_{10}$alkenyl, heteroaryl$C_2$-$C_{10}$alkynyl, heteroaryl$C_1$-$C_{10}$alkylamino, heteroaryl$C_1$-$C_{10}$alkoxy, heteroaryloxy$C_1$-$C_{10}$alkyl, heteroaryloxy$C_2$-$C_{10}$alkenyl, heteroaryloxy$C_2$-$C_{10}$alkynyl, heteroaryloxy$C_1$-$C_{10}$alkylamino or heteroaryloxy$C_1$-$C_{10}$alkoxy.

In one embodiment, compounds of the present invention are represented by formula VIII or VIIIA as illustrated below, and the geometric isomers, enantiomers, diastereomers, racemates, pharmaceutically acceptable salts and solvates thereof:

Formula VIII

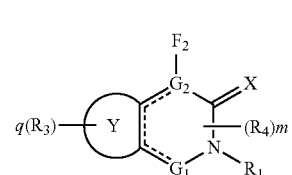

Formula VIIIA

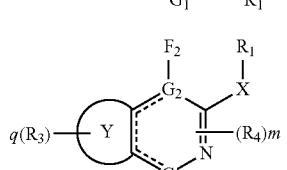

wherein Ring Y, $R_1$, $R_3$, $R_4$, $G_1$, $G_2$, X, $F_2$, m and q are as defined above.

In a more preferred embodiment, compounds of the present invention are represented by formula IX or X as illustrated below, and the geometric isomers, enantiomers, diastereomers, racemates, pharmaceutically acceptable salts and solvates thereof:

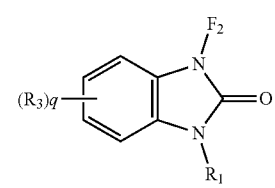

Formula IX

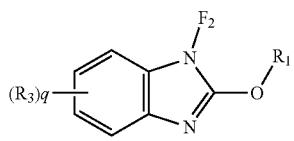

Formula X wherein $R_1$, $R_3$, $F_2$, and q are as defined above.

In a preferred embodiment a compound is selected from Table IX-X. A more preferred embodiment is a compound from Table IX-X wherein $R_1$ is selected from tables 1-4.

TABLE IX-X-continued

| No | Structure |
|----|-----------|
| 14 | 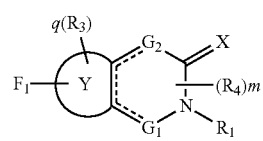 |

In a more preferred embodiment, prodrugs of domperidone are disclosed. (Formula 4 and 11 from Table IX-X). A more preferred embodiment is a compound of Formula 4 from Table IX-X, wherein $R_1$ is selected from table 1. In a more preferred embodiment, a compound of Formula 4 from Table IX-X, wherein $R_1$ is selected from tables 2-4 is disclosed.

In a more preferred embodiment, prodrugs of droperidol are disclosed. (Formula 6 and 13, from Table IX-X). In a more preferred embodiment, a compound of Formula 6 from Table IX-X wherein $R_1$ is selected from table 1 is disclosed. A more preferred embodiment is a compound of Formula 6 from Table IX-X wherein $R_1$ is selected from tables 2-4.

In a more preferred embodiment, prodrugs of pimozide are disclosed. (Formula 7 and 14 from Table IX-X). In a more preferred embodiment, a compound of Formula 7 from Table IX-X wherein $R_1$ is selected from table 1 is disclosed. In a more preferred embodiment, a compound of Formula 7 from Table IX-X wherein $R_1$ is selected from tables 2-4 is disclosed.

In another embodiment, compounds of the present invention are represented by Formula XI or XII as illustrated below, and the geometric isomers, enantiomers, diastereomers, racemates, pharmaceutically acceptable salts and solvates thereof:

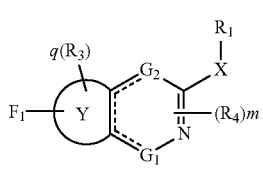

Formula XI

Formula XII wherein Ring Y, $R_1$, $R_3$, R, X, $F_1$, $G_1$, $G_2$, m and q are as defined above.

In another embodiment, compounds of the present invention are represented by Formula XIA or XIIA as illustrated below, and the geometric isomers, enantiomers, diastereomers, racemates, pharmaceutically acceptable salts and solvates thereof:

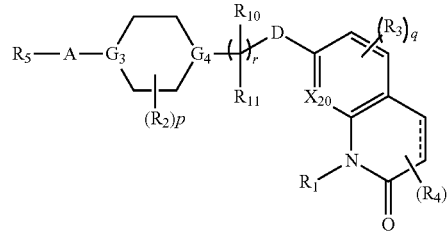

Formula XIA

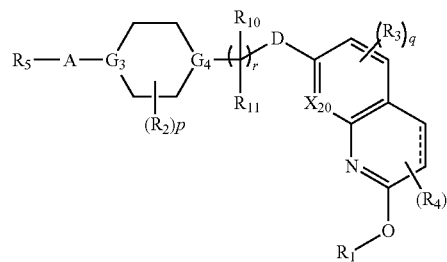

Formula XIIA wherein $R_1$, $R_3$, $R_4$, $R_5$, $R_{10}$, $R_{11}$, A, D, m, and q are as defined above;

$R_2$ is selected from absent, hydrogen, halogen, —$OR_{10}$, —$SR_{10}$, —$NR_{10}R_{11}$—, optionally substituted aliphatic, optionally substituted aryl or aryl or optionally substituted heterocyclyl;

r is 0, 1, 2, 3, 4, 5, 6, 7, 8, 9, 10 or 11;

each $G_3$ and $G_4$ is independently selected from —N—, and —$C(R_{10})$—[$C(R_{10})(R_{11})]_a$—, wherein a is 0, 1 or 2;

$X_{20}$ is —$C(R_{10})$— or —N—; and, p is 0, 1, 2 or 3.

In another embodiment, compounds of the present invention are represented by Formula XIB or XIIB as illustrated below, and the geometric isomers, enantiomers, diastereomers, racemates, pharmaceutically acceptable salts and solvates thereof

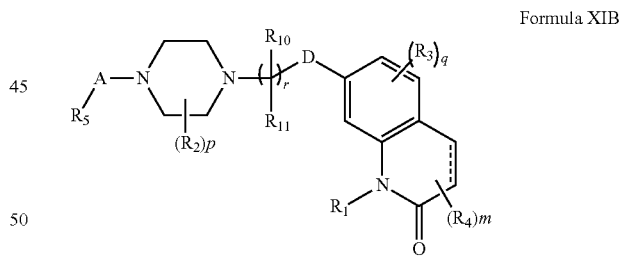

Formula XIB

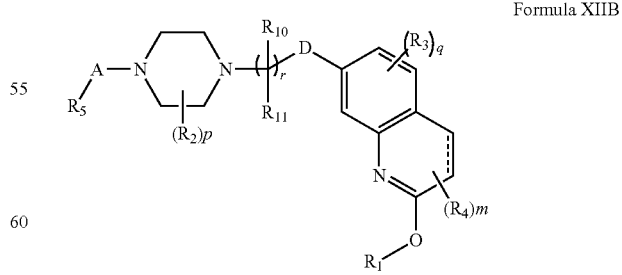

Formula XIIB wherein $R_1$, $R_2$, $R_3$, $R_4$, $R_5$, $R_{10}$, $R_{11}$, A, D, m, p and q are as defined above.

In another embodiment, compounds of the present invention are represented by Formula XIC or XIIC as illustrated below, and the geometric isomers, enantiomers, diastereomers, racemates, pharmaceutically acceptable salts and solvates thereof:

Formula XIC

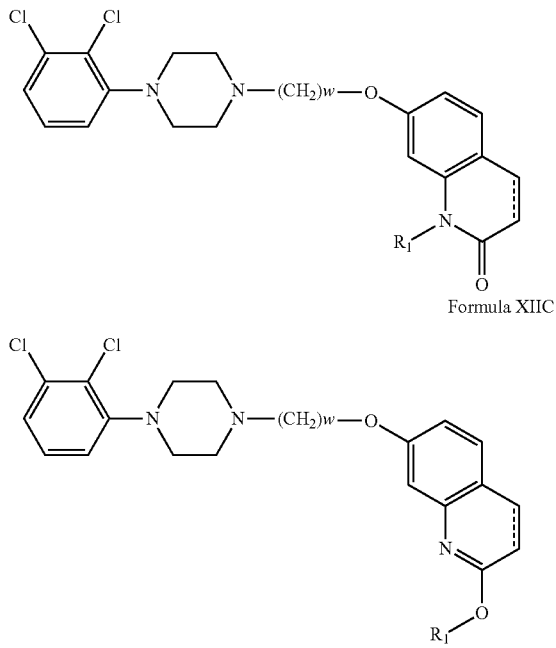

Formula XIIC wherein $R_1$, is as defined above; and, w is 1, 2, 3, 4, 5, 6, 7, 8, 9, 10 or 11.

In another embodiment, compounds of the present invention are represented by Formula XID or XIID as illustrated below, and the geometric isomers, enantiomers, diastereomers, racemates, pharmaceutically acceptable salts and solvates thereof:

Formula XID

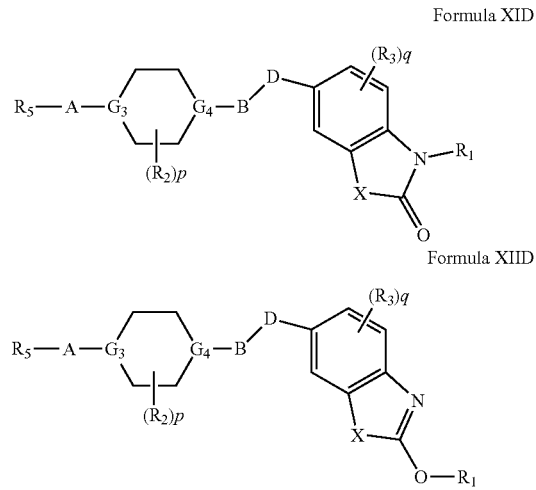

Formula XIID wherein, $X_1$, $R_1$, $R_2$, $R_3$, $R_5$, A, B, D, $G_3$, $G_4$, p, q, $R_{10}$ and $R_{11}$ are as defined above.

In another embodiment, compounds of the present invention are represented by Formula XIE or XIIE as illustrated below, and the geometric isomers, enantiomers, diastereomers, racemates, pharmaceutically acceptable salts and solvates thereof:

Formula XIE

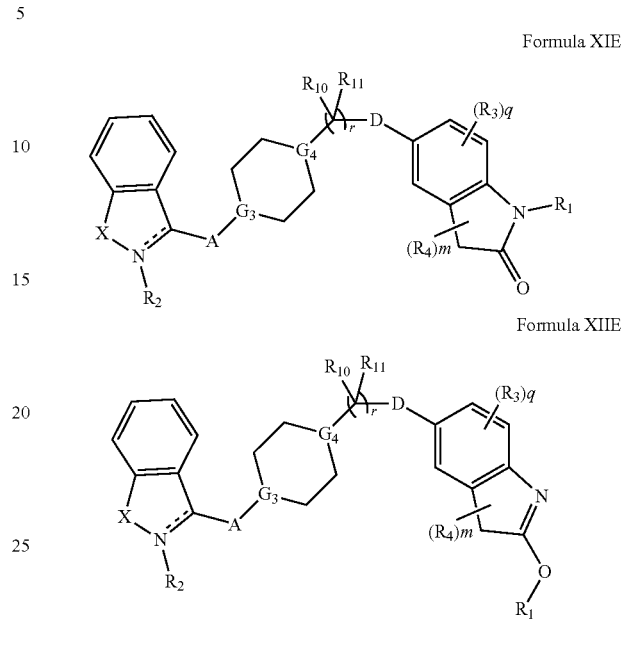

Formula XIIE wherein, X, $R_1$, $R_2$, $R_3$, $R_4$, A, D, $G_3$, $G_4$, m, q, r, $R_{10}$ and $R_{11}$ are as defined above.

In another embodiment, compounds of the present invention are represented by Formula XIF or XIIF as illustrated below, and the geometric isomers, enantiomers, diastereomers, racemates, pharmaceutically acceptable salts and solvates thereof:

Formula XIF

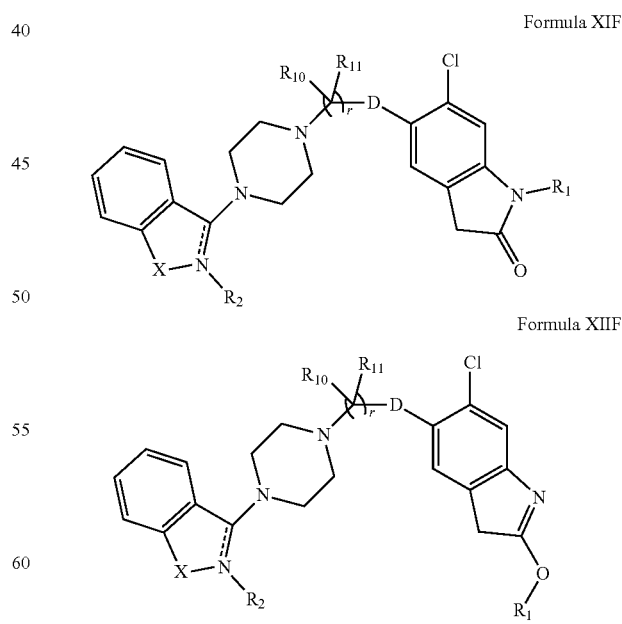

Formula XIIF wherein, X, $R_1$, $R_2$, D, r, $R_{10}$ and $R_{11}$ are as defined above.

In another embodiment, compounds of the present invention are represented by Formula XIG or XIIG as illustrated below, or its geometric isomers, enantiomers, diastereomers, racemates, pharmaceutically acceptable salts and solvates thereof:

Formula XIG

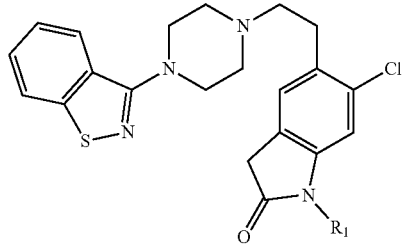

Formula XIIG

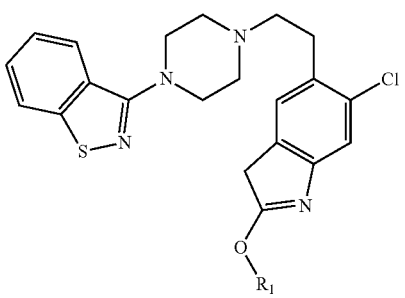

wherein $R_1$, is as defined above.

In another embodiment, compounds of the present invention are represented by Formula XIH or XIIH as illustrated below, and the geometric isomers, enantiomers, diastereomers, racemates, pharmaceutically acceptable salts and solvates thereof:

Formula XIH

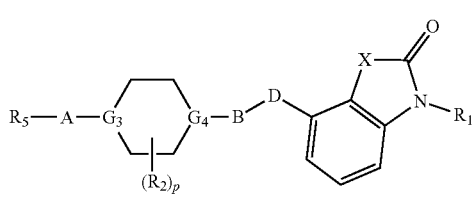

Formula XIIH

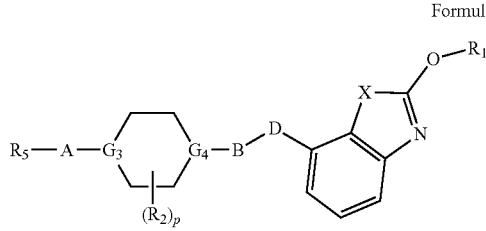

wherein, X, $R_1$, $R_2$, $R_5$, A, D, $G_3$, $G_4$ and p, are as defined above.

In another embodiment, compounds of the present invention are represented by Formula XI-I or XII-I as illustrated below, and the geometric isomers, enantiomers, diastereomers, racemates, pharmaceutically acceptable salts and solvates thereof:

Formula XI-I

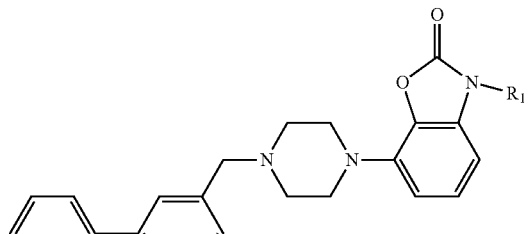

Formula XII-I

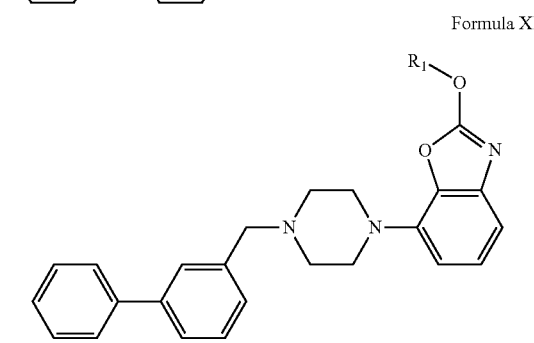

wherein $R_1$, is as defined above.

In another embodiment, compounds of the present invention are represented by Formula XIJ or XIIJ as illustrated below, and the geometric isomers, enantiomers, diastereomers, racemates, pharmaceutically acceptable salts and solvates thereof:

Formula XIJ

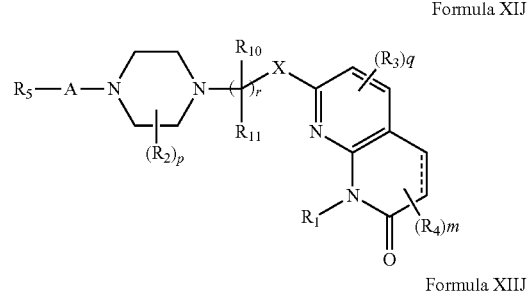

Formula XIIJ

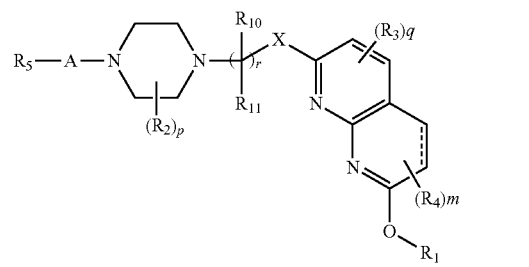

wherein, X, $R_1$, $R_2$, $R_3$, $R_4$, $R_5$, A, D, $G_3$, $G_4$, p, $R_{10}$ and $R_{11}$ are as defined above.

In another embodiment, compounds of the present invention are represented by Formula XIK or XIIK as illustrated below, or its geometric isomers, enantiomers, diastereomers, racemates, pharmaceutically acceptable salts and solvates thereof:

Formula XIK
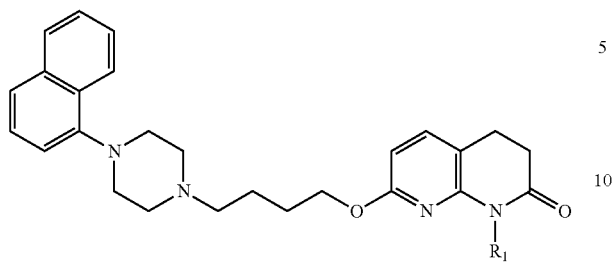
Formula XIIK
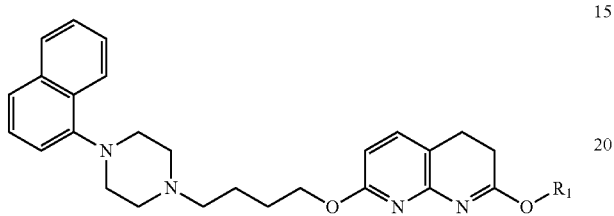
wherein R₁, is as defined above.
In a preferred embodiment a compound is selected from Table XI-XII. A more preferred embodiment is a compound from Table XI-XII wherein R₁ is selected from Table 1-4.
TABLE XI-XII
1 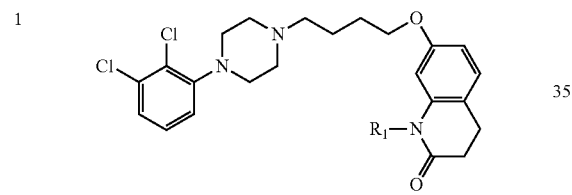
2 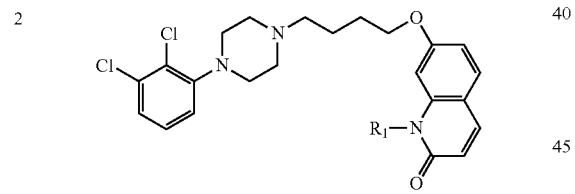
3 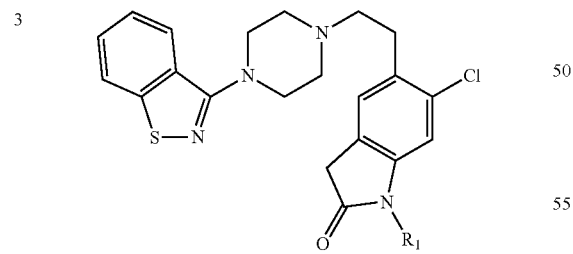
4 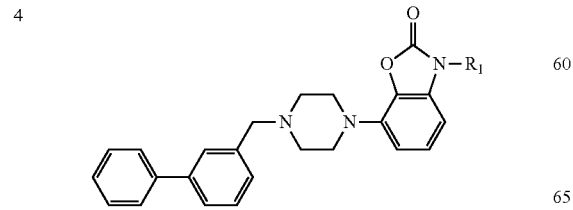
TABLE XI-XII-continued
5 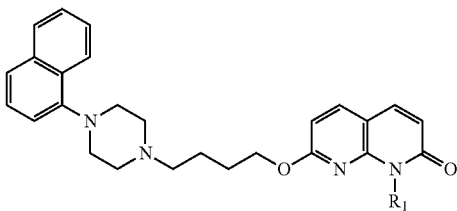
6 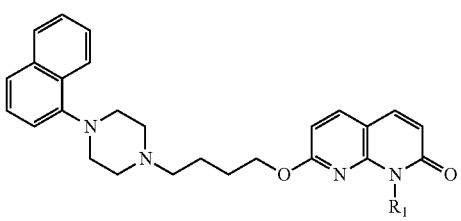
7 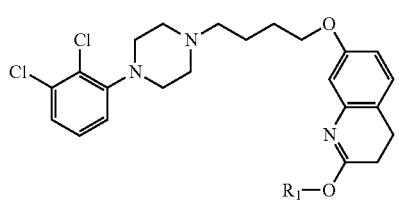
8 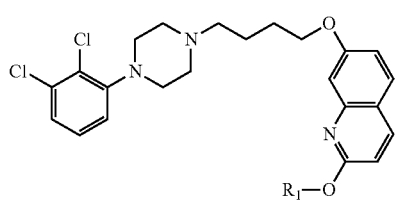
9 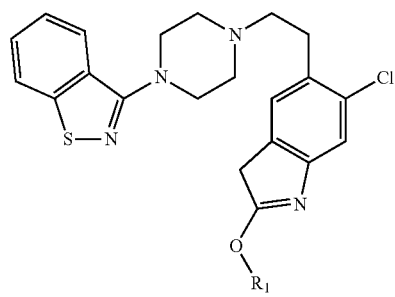
10 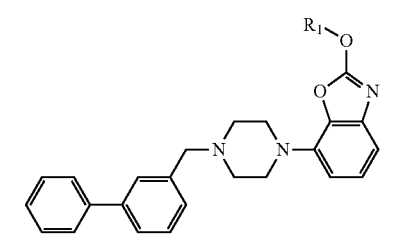
11 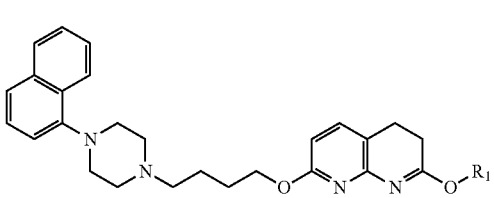

TABLE XI-XII-continued

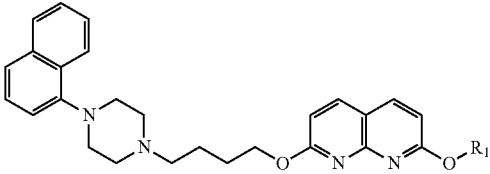

In a more preferred embodiment, prodrugs of aripiprazole are disclosed. (Formula 1 and 7 from Table XI-XII). In a more preferred embodiment, a compound of Formula 1 wherein R₁ is selected from table 1 is disclosed. In a more preferred embodiment, a compound of Formula 1 wherein R₁ is selected from tables 2-4 is disclosed.

In a more preferred embodiment, prodrugs of dehydroaripiprazole are disclosed. (Formula 2 and 8 from Table XI-XII). In a more preferred embodiment, a compound of Formula 2 wherein R₁ is selected from table 1 is disclosed. In a more preferred embodiment, a compound of Formula 2 wherein R₁ is selected from tables 2-4 is disclosed.

In a more preferred embodiment, prodrugs of ziprasidone are disclosed. (Formula 3 and 9 from Table XI-XI). In a more preferred embodiment, a compound of Formula 3 wherein R₁ is selected from table 1 is disclosed. In a more preferred embodiment, a compound of Formula 3 wherein R₁ is selected from tables 2-4 is disclosed.

In a more preferred embodiment, prodrugs of bifeprunox are disclosed. (Formula 4 and 11 from Table XI-XII). In a more preferred embodiment, a compound of Formula 4 wherein R₁ is selected from table 1 is disclosed. In a more preferred embodiment, a compound of Formula 4 wherein R₁ is selected from tables 2-4 is disclosed.

Representative compounds according to the invention are those selected from the Tables A-I below and the geometric isomers, enantiomers, diastereomers, racemates, pharmaceutically acceptable salts and solvates thereof:

TABLE A

| No | Structure |
|---|---|
| 1 | 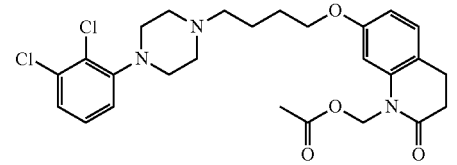 |
| 2 | 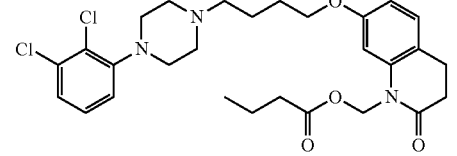 |
| 3 | 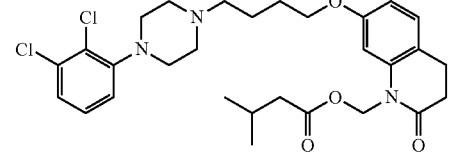 |

TABLE A-continued

| No | Structure |
|---|---|
| 4 | 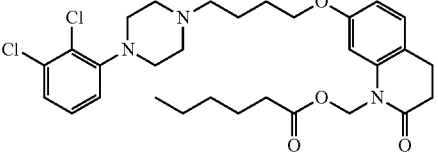 |
| 5 | 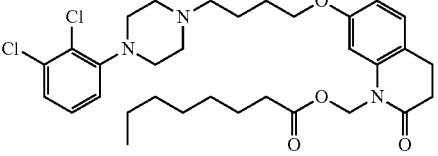 |
| 6 | 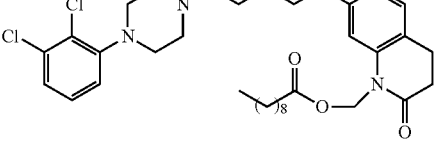 |
| 7 | 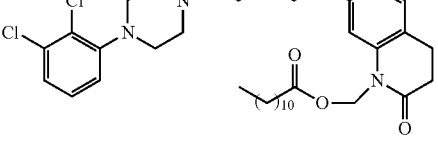 |
| 8 | 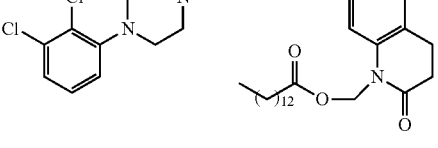 |
| 9 | 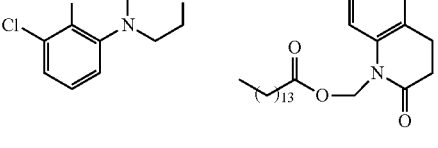 |
| 10 | 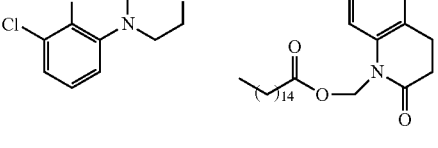 |
| 11 | 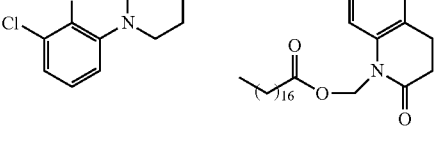 |
| 12 | 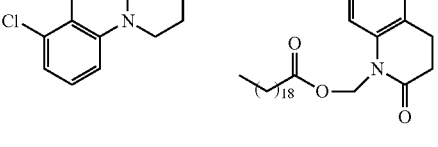 |

TABLE A-continued
| No | Structure |
|---|---|
| 13 | 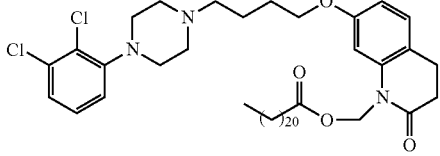 |
| 14 | 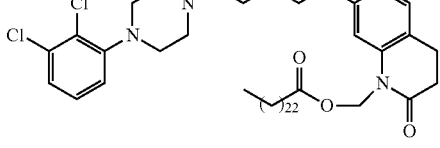 |
| 15 | 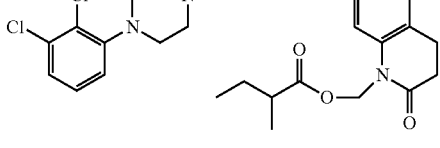 |
| 16 | 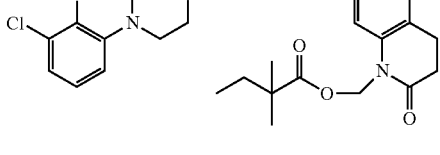 |
| 17 | 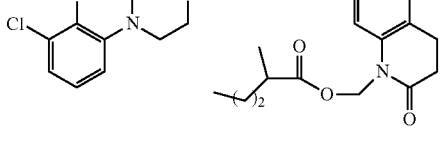 |
| 18 | 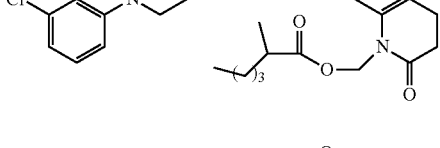 |
| 19 | 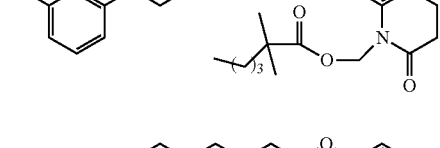 |
| 20 | 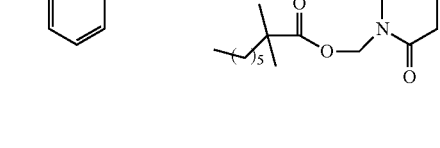 |
| 21 | 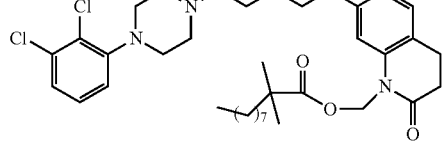 |
| 22 | 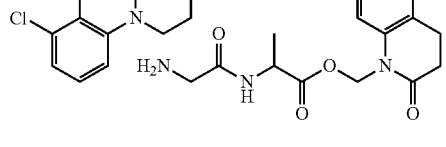 |
| 23 | 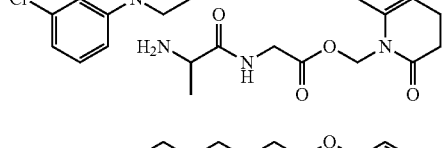 |
| 24 | 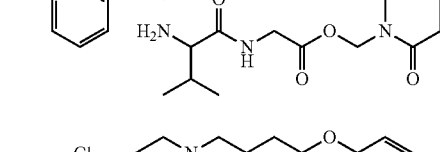 |
| 25 | 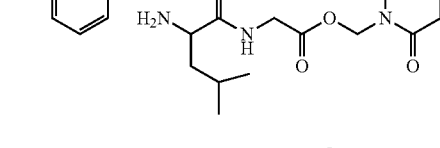 |
| 26 | 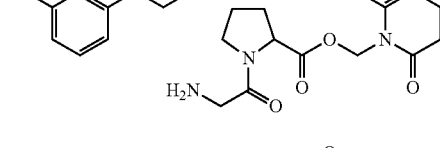 |
| 27 | 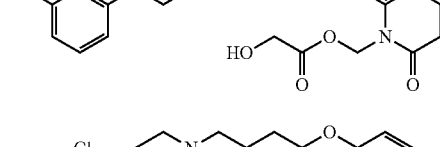 |
| 28 | 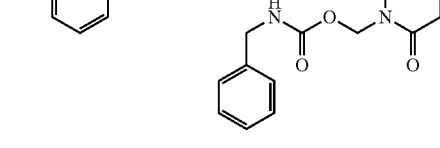 |

TABLE A-continued

| No | Structure |
|---|---|
| 29 | (structure) |
| 30 | (structure) |
| 31 | (structure) |
| 32 | (structure) |
| 33 | (structure) |
| 34 | (structure) |
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) |

TABLE A-continued

| No | Structure |
|----|-----------|
| 44 | (structure) |
| 45 | (structure) |
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |
| 56 | (structure) |
| 57 | (structure) |
| 58 | (structure) |
| 59 | (structure) |

TABLE A-continued
| No | Structure |
|---|---|
| 60 | 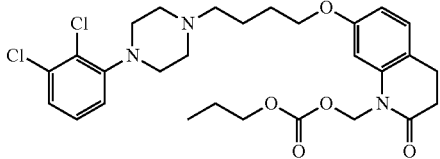 [SMILES: CCCOC(=O)OCN1C(=O)CCc2ccc(OCCCCN3CCN(c4cccc(Cl)c4Cl)CC3)cc21] |
| 61 | 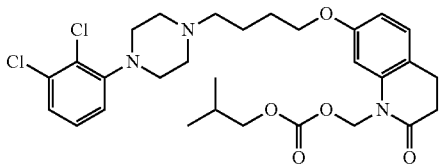 |
| 62 | 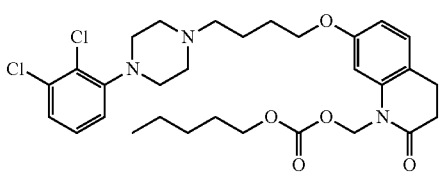 |
| 63 | 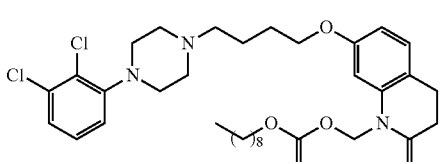 |
| 64 | 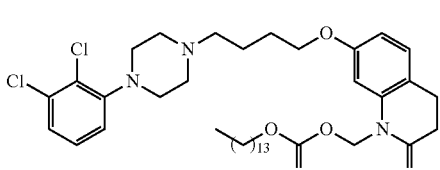 |
| 65 | 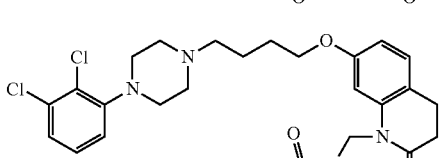 |
| 66 | 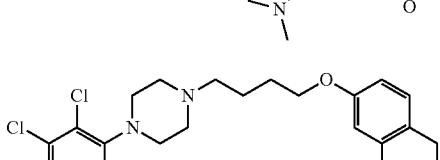 |
| 67 | 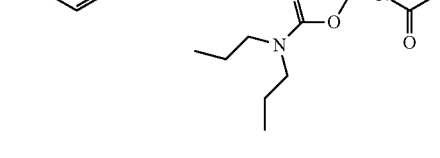 |
| 68 | 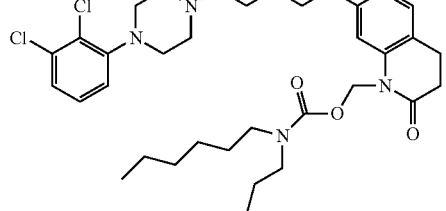 |
| 69 | 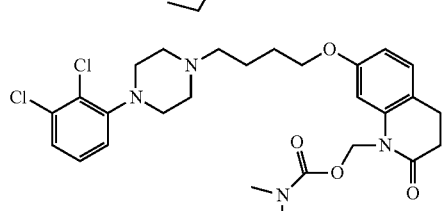 |
| 70 | 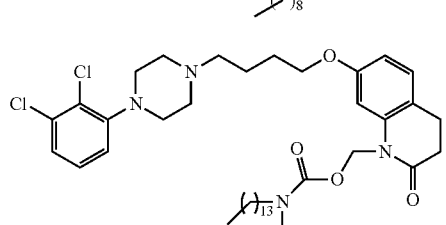 |
| 71 | 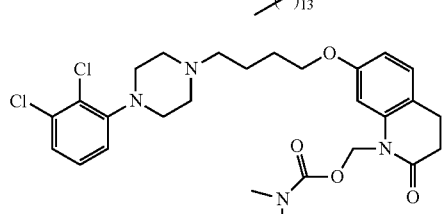 |
| 72 | 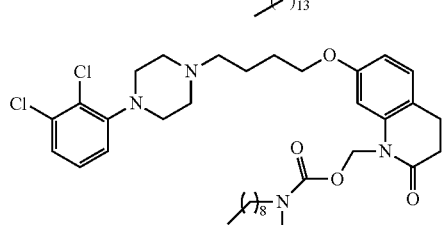 |
| 73 | 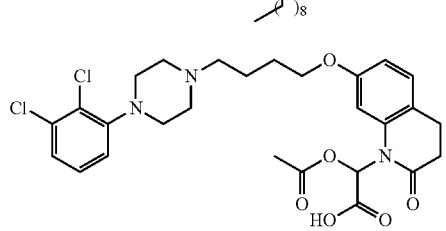 |
| 74 | 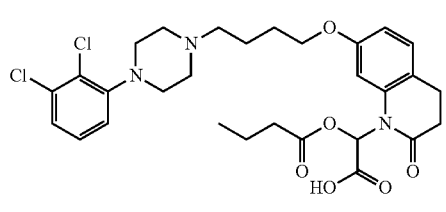 [SMILES: CCCC(=O)OC(C(=O)O)N1C(=O)CCc2ccc(OCCCCN3CCN(c4cccc(Cl)c4Cl)CC3)cc21] |

TABLE A-continued
| No | Structure |
|----|-----------|
| 75 |  |
| 76 | 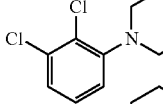 |
| 77 | 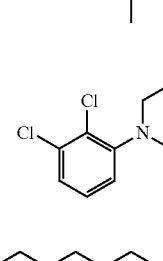 |
| 78 | 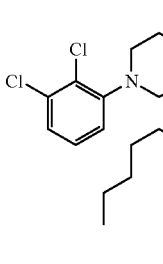 |
| 79 | 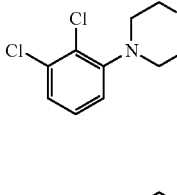 |
| 80 | 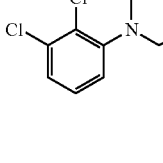 |
| 81 | 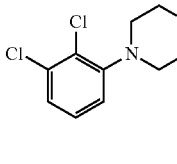 |
| 82 | 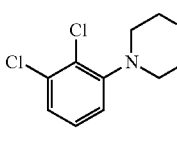 |
| 83 | 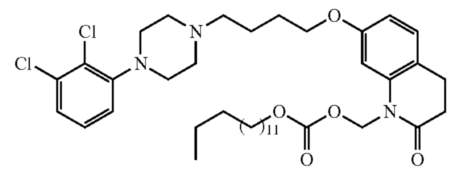 |
| 84 | 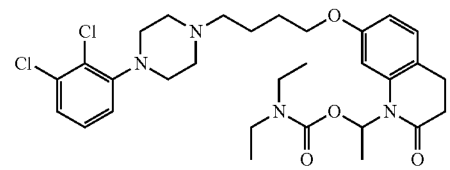 [SMILES: CCN(CC)C(=O)OC(C)N1C(=O)CCc2ccc(OCCCCN3CCN(c4cccc(Cl)c4Cl)CC3)cc21] |
| 85 | 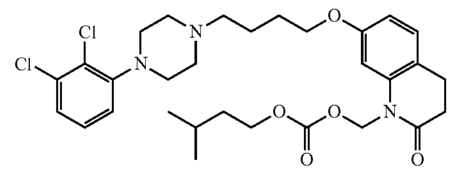 [SMILES: CC(C)CCOC(=O)OCN1C(=O)CCc2ccc(OCCCCN3CCN(c4cccc(Cl)c4Cl)CC3)cc21] |
| 86 | 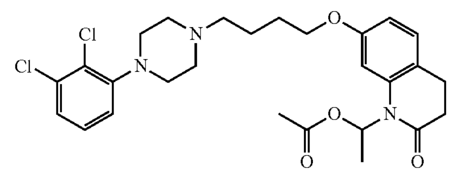 [SMILES: CC(=O)OC(C)N1C(=O)CCc2ccc(OCCCCN3CCN(c4cccc(Cl)c4Cl)CC3)cc21] |
| 87 | 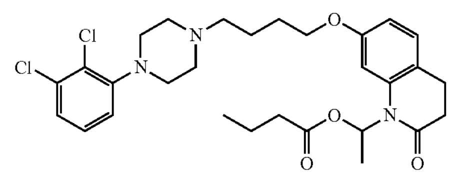 [SMILES: CCCC(=O)OC(C)N1C(=O)CCc2ccc(OCCCCN3CCN(c4cccc(Cl)c4Cl)CC3)cc21] |
| 88 | 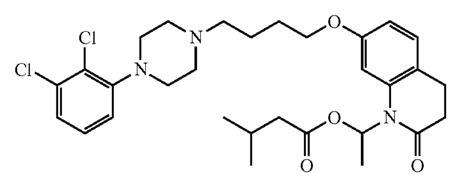 [SMILES: CC(C)CC(=O)OC(C)N1C(=O)CCc2ccc(OCCCCN3CCN(c4cccc(Cl)c4Cl)CC3)cc21] |
| 89 | 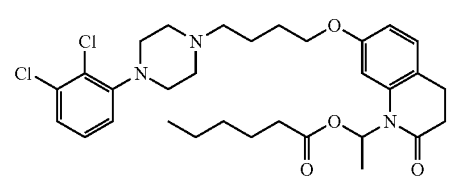 [SMILES: CCCCCC(=O)OC(C)N1C(=O)CCc2ccc(OCCCCN3CCN(c4cccc(Cl)c4Cl)CC3)cc21] |
| 90 | 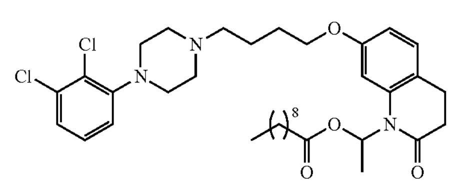 |
| 91 | 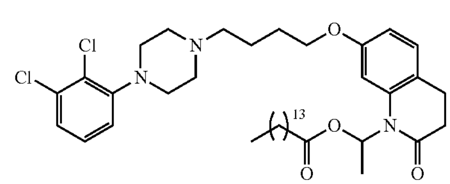 |

TABLE A-continued
| No | Structure |
|----|-----------|
| 92 | 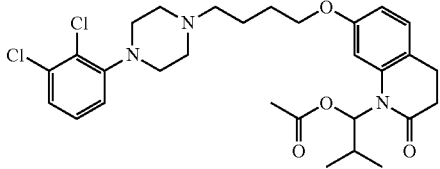 [SMILES: CC(=O)OC(C(C)C)N1C(=O)CCc2ccc(OCCCCN3CCN(c4cccc(Cl)c4Cl)CC3)cc21] |
| 93 | 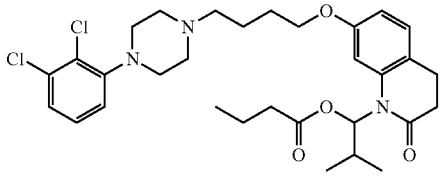 [SMILES: CCCC(=O)OC(C(C)C)N1C(=O)CCc2ccc(OCCCCN3CCN(c4cccc(Cl)c4Cl)CC3)cc21] |
| 94 | 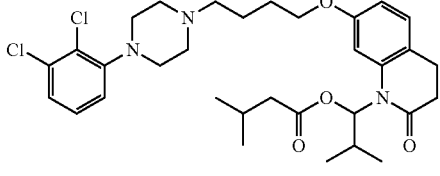 |
| 95 | 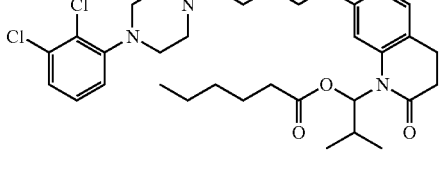 |
| 96 | 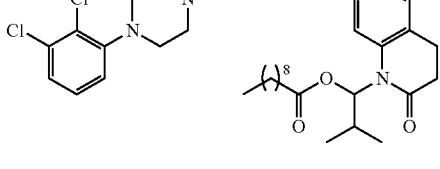 |
| 97 | 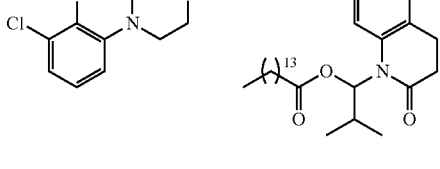 |
| 98 | 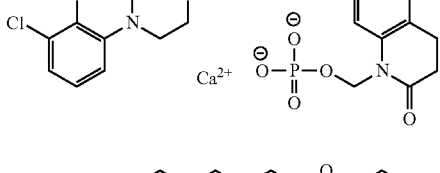 |
| 99 | 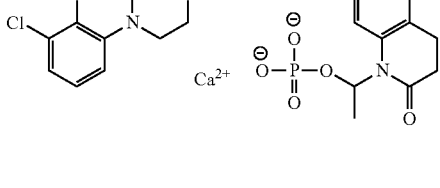 |
| 100 | 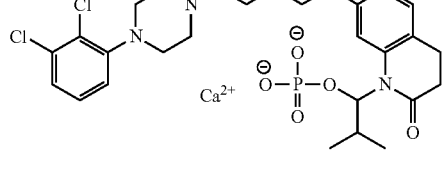 |
| 101 | 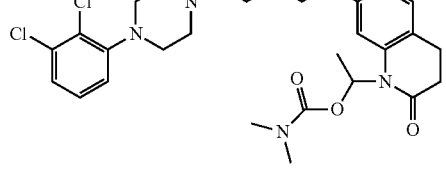 |
| 102 | 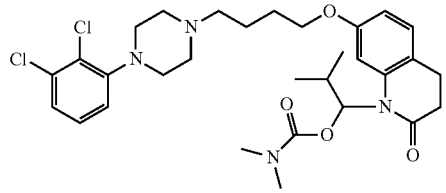 [SMILES: CC(C)C(OC(=O)N(C)C)N1C(=O)CCc2ccc(OCCCCN3CCN(c4cccc(Cl)c4Cl)CC3)cc21] |
| 103 | 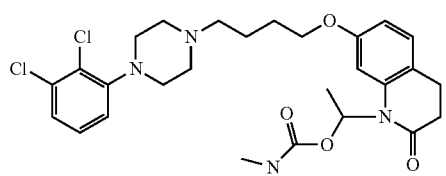 |
| 104 | 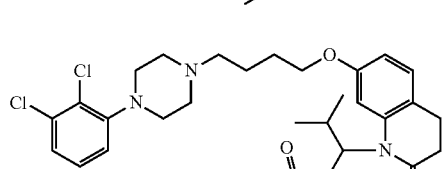 |
| 105 | 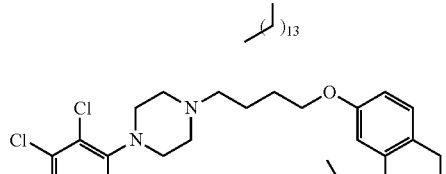 |
| 106 | 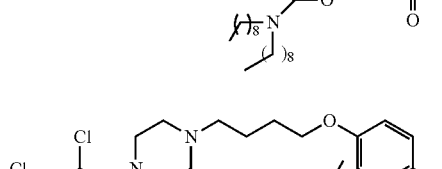 |

TABLE A-continued

| No | Structure |
|---|---|
| 107 | 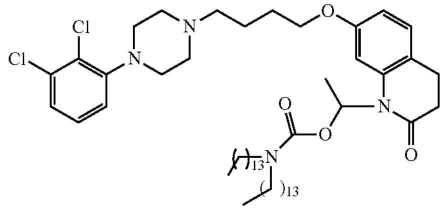 |
| 108 | 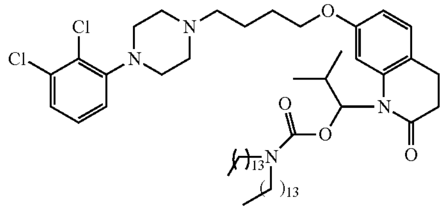 |
| 109 | 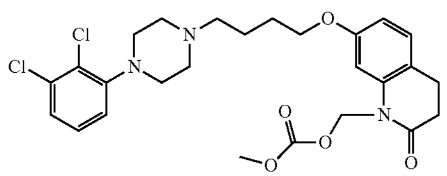 [SMILES: COC(=O)OCN1C(=O)CCc2ccc(OCCCCN3CCN(c4cccc(Cl)c4Cl)CC3)cc21] |
| 110 | 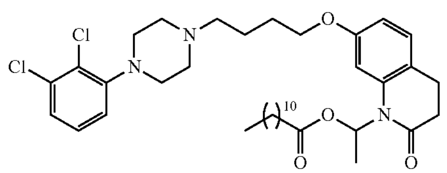 |
| 111 | 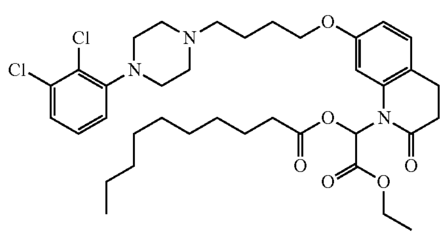 [SMILES: CCCCCCCCCC(=O)OC(C(=O)OCC)N1C(=O)CCc2ccc(OCCCCN3CCN(c4cccc(Cl)c4Cl)CC3)cc21] |
| 112 | 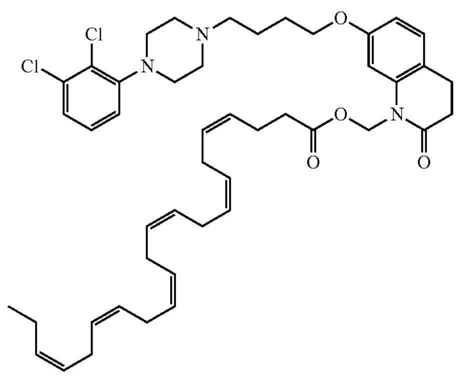 [SMILES: CC/C=C\C/C=C\C/C=C\C/C=C\C/C=C\C/C=C\CCC(=O)OCN1C(=O)CCc2ccc(OCCCCN3CCN(c4cccc(Cl)c4Cl)CC3)cc21] |
| 113 | |
| 114 | |
| 115 | |
| 116 | |
| 117 | |

TABLE A-continued

| No | Structure |
|---|---|
| 118 | (structure) |

TABLE B

| No | Structure |
|---|---|
| 150 | (structure) |
| 151 | (structure) |
| 152 | (structure) |
| 153 | (structure) |
| 154 | (structure) |
| 155 | (structure) |

TABLE B-continued

| No | Structure |
|---|---|
| 156 | (structure) |
| 157 | (structure) |
| 158 | (structure) |
| 159 | (structure) |
| 160 | (structure) |
| 161 | (structure) |
| 162 | (structure) |
| 163 | (structure) |
| 164 | (structure) |

TABLE B-continued
| No | Structure |
|---|---|
| 165 | 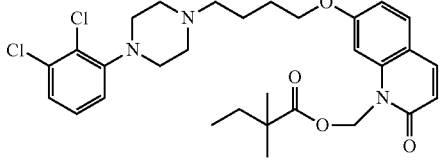 |
| 166 | 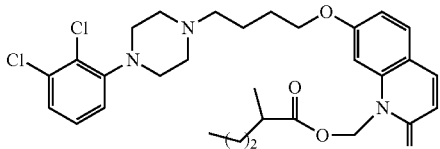 |
| 167 | 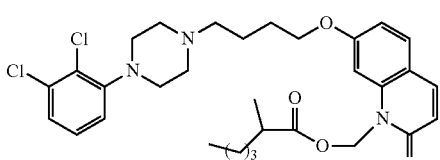 |
| 168 | 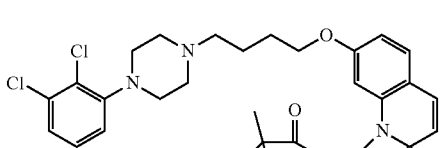 |
| 169 | 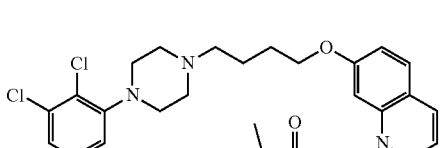 |
| 170 | 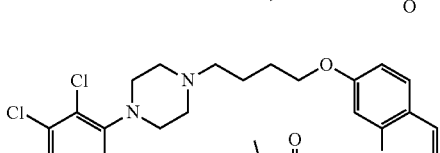 |
| 171 | 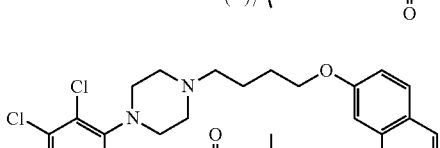 |
| 172 | 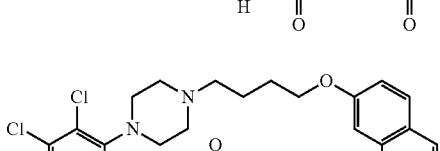 |
| 173 | 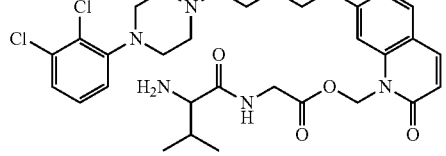 |
| 174 | 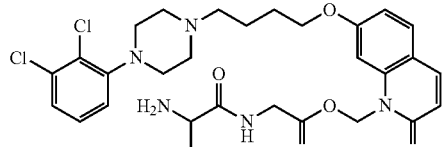 |
| 175 | 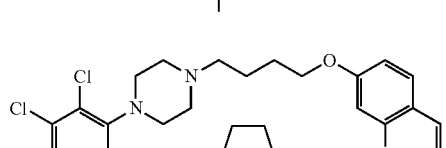 |
| 176 | 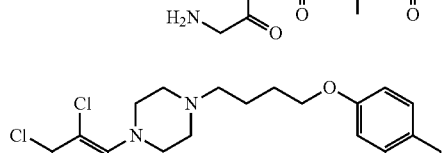 |
| 177 | 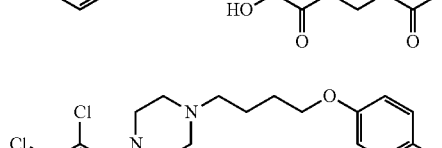 |
| 178 | 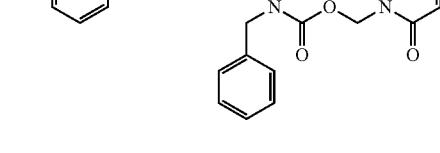 |
| 179 | 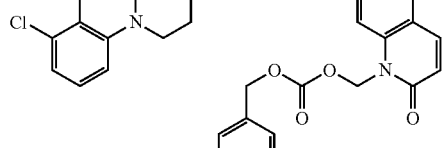 |

TABLE B-continued

| No | Structure |
|---|---|
| 180 | 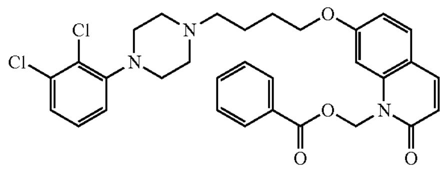 [SMILES: O=C(OCn1c(=O)ccc2ccc(OCCCCN3CCN(c4cccc(Cl)c4Cl)CC3)cc21)c1ccccc1] |
| 181 | 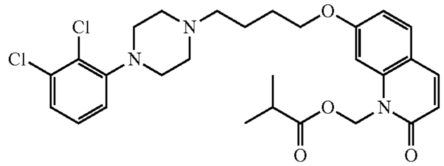 |
| 182 | 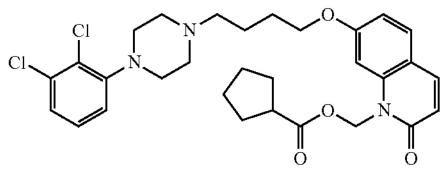 [SMILES: O=C(OCn1c(=O)ccc2ccc(OCCCCN3CCN(c4cccc(Cl)c4Cl)CC3)cc21)C1CCCC1] |
| 183 | 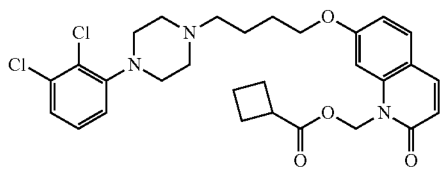 [SMILES: O=C(OCn1c(=O)ccc2ccc(OCCCCN3CCN(c4cccc(Cl)c4Cl)CC3)cc21)C1CCC1] |
| 184 | 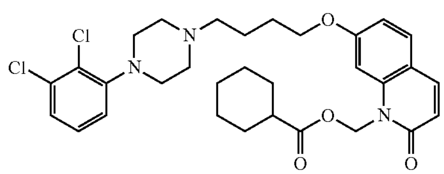 |
| 185 | 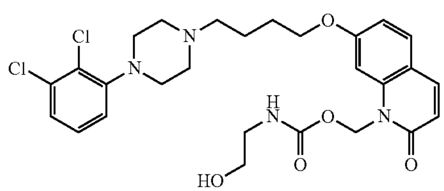 |
| 186 | 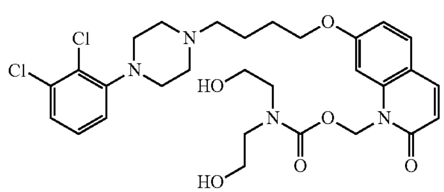 |
| 187 | 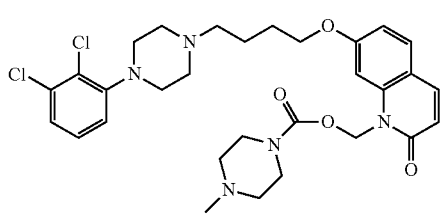 [SMILES: CN1CCN(C(=O)OCn2c(=O)ccc3ccc(OCCCCN4CCN(c5cccc(Cl)c5Cl)CC4)cc32)CC1] |
| 188 | |
| 189 | |
| 190 | |
| 191 | |
| 192 | |
| 193 | |
| 194 | |

TABLE B-continued

| No | Structure |
|---|---|
| 195 | (structure) |
| 196 | (structure) |
| 197 | (structure) |
| 198 | (structure) |
| 199 | (structure) |
| 200 | (structure) |
| 201 | (structure) |
| 202 | (structure) |
| 203 | (structure) |
| 204 | (structure) |
| 205 | (structure) |
| 206 | (structure) |
| 207 | (structure) |
| 209 | (structure) |
| 210 | (structure) |
| 211 | (structure) |
| 212 | (structure) |

TABLE B-continued
| No | Structure |
|----|-----------|
| 213 | 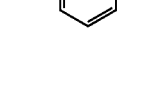 |
| 214 | 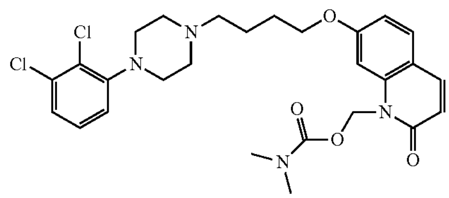 [SMILES: CN(C)C(=O)OCn1c(=O)ccc2ccc(OCCCCN3CCN(c4cccc(Cl)c4Cl)CC3)cc21] |
| 215 | 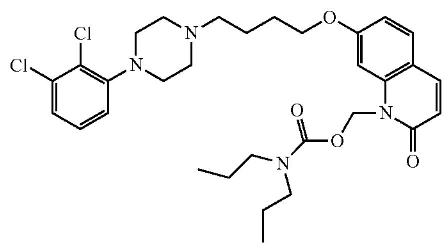 [SMILES: CCCN(CCC)C(=O)OCn1c(=O)ccc2ccc(OCCCCN3CCN(c4cccc(Cl)c4Cl)CC3)cc21] |
| 216 | 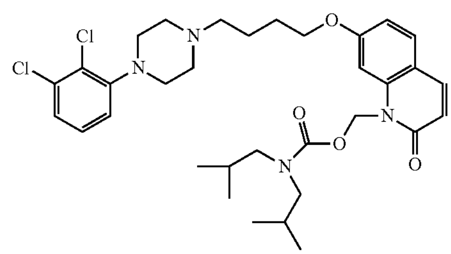 [SMILES: CC(C)CN(CC(C)C)C(=O)OCn1c(=O)ccc2ccc(OCCCCN3CCN(c4cccc(Cl)c4Cl)CC3)cc21] |
| 217 | 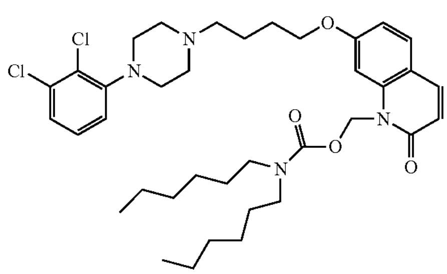 [SMILES: CCCCCCN(CCCCCC)C(=O)OCn1c(=O)ccc2ccc(OCCCCN3CCN(c4cccc(Cl)c4Cl)CC3)cc21] |
| 218 | 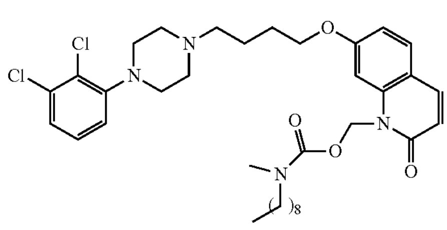 |
TABLE B-continued
| No | Structure |
|----|-----------|
| 219 | 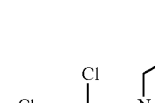 |
| 220 | 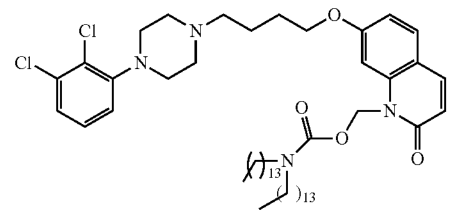 |
| 221 | 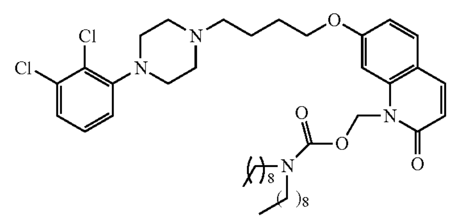 |
| 222 | 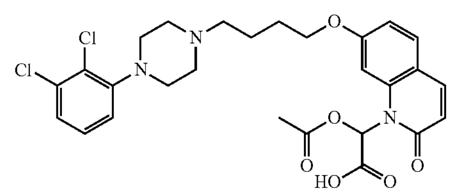 [SMILES: CC(=O)OC(C(=O)O)n1c(=O)ccc2ccc(OCCCCN3CCN(c4cccc(Cl)c4Cl)CC3)cc21] |
| 223 | 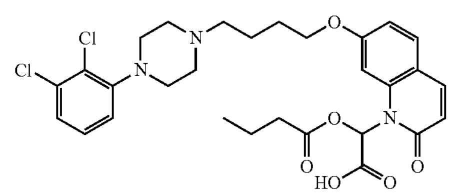 |
| 224 | 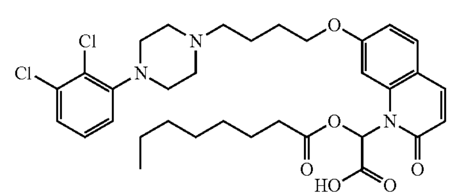 |
| 225 | 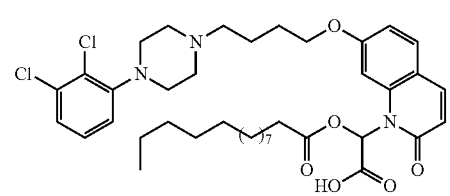 |

TABLE B-continued

| No | Structure |
|---|---|
| 226 | (structure) |
| 227 | (structure) |
| 228 | (structure) |
| 229 | (structure) |
| 230 | (structure) |
| 231 | (structure) |
| 232 | (structure) |
| 233 | (structure) |
| 234 | (structure) |
| 235 | (structure) |
| 236 | (structure) |
| 237 | (structure) |
| 238 | (structure) |
| 239 | (structure) |
| 240 | (structure) |
| 241 | (structure) |

TABLE B-continued
| No | Structure |
|---|---|
| 242 | 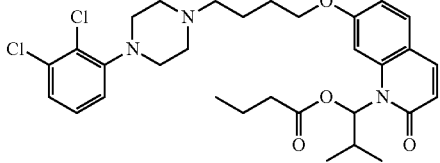 |
| 243 | 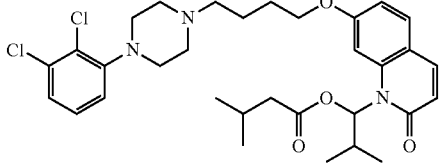 |
| 244 | 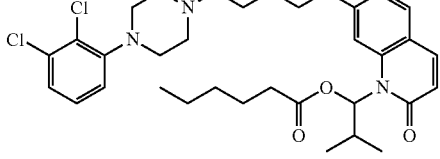 |
| 245 | 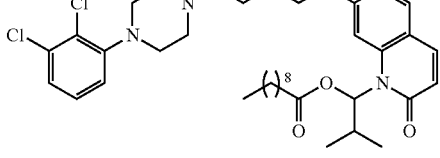 |
| 246 | 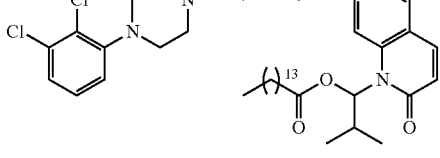 |
| 247 | 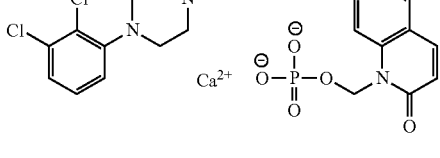 |
| 248 | 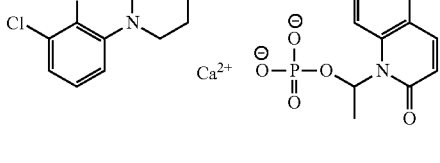 |
| 249 | 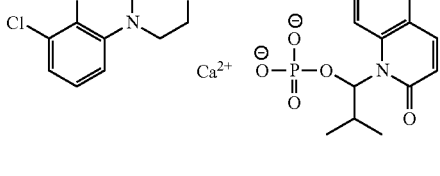 |
| 250 | 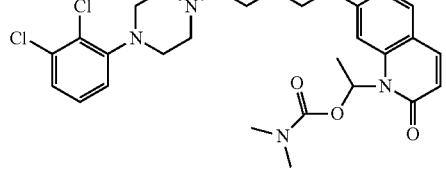 |
| 251 | 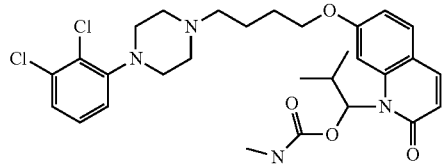 |
| 252 | 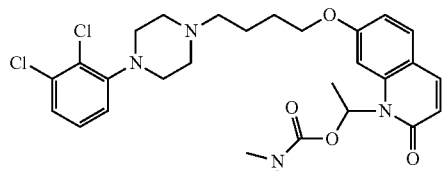 |
| 253 | 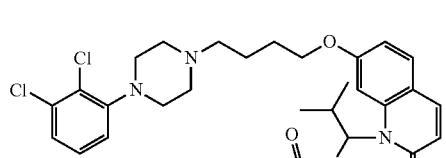 |
| 254 | 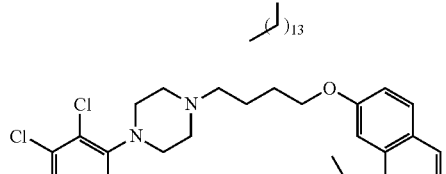 |
| 255 | 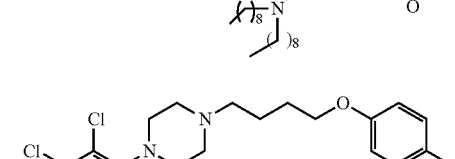 |
| 256 | 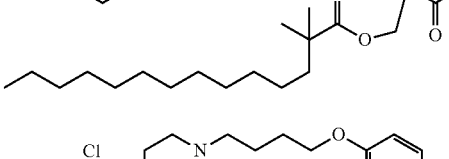 |

TABLE B-continued
| No | Structure |
|----|-----------|
| 257 | 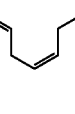 |
| 258 | 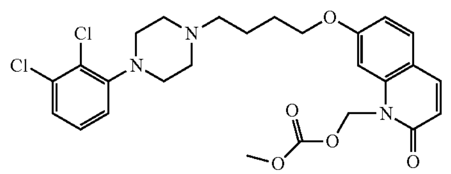 |
| 259 | 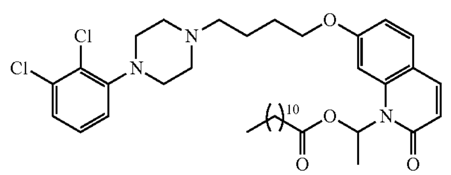 |
| 260 | 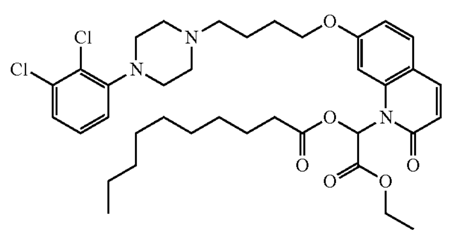 |
| 261 | 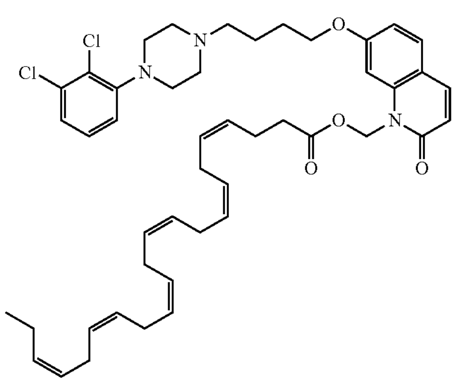 [SMILES: CC/C=C\C/C=C\C/C=C\C/C=C\C/C=C\C/C=C\CCC(=O)OCn1c(=O)ccc2ccc(OCCCCN3CCN(c4cccc(Cl)c4Cl)CC3)cc21] |
| 262 | 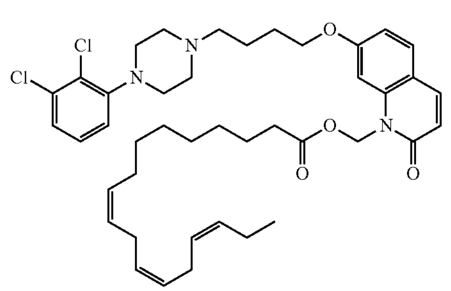 [SMILES: CC/C=C\C/C=C\C/C=C\CCCCCCCC(=O)OCn1c(=O)ccc2ccc(OCCCCN3CCN(c4cccc(Cl)c4Cl)CC3)cc21] |
| 263 | 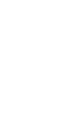 |
| 264 | |
| 265 | |
| 266 | |

TABLE C
| No. | Structure |
|---|---|
| 400 | 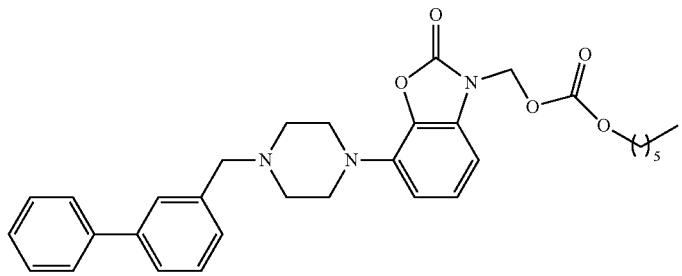 |
| 401 | 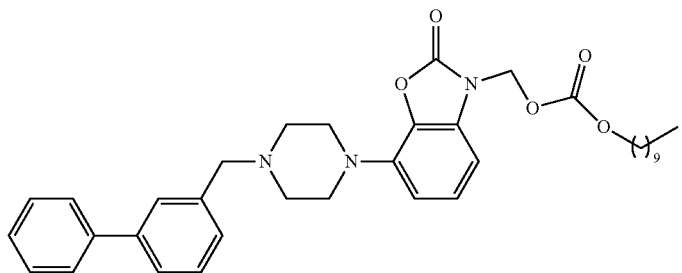 |
| 402 | 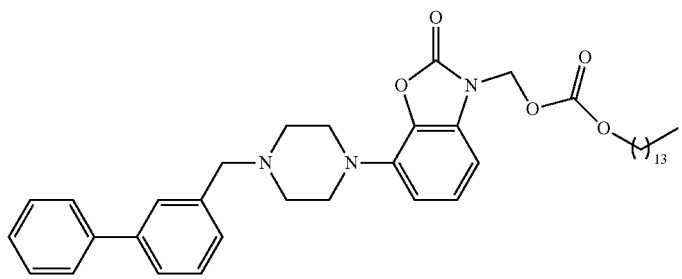 |
| 403 | 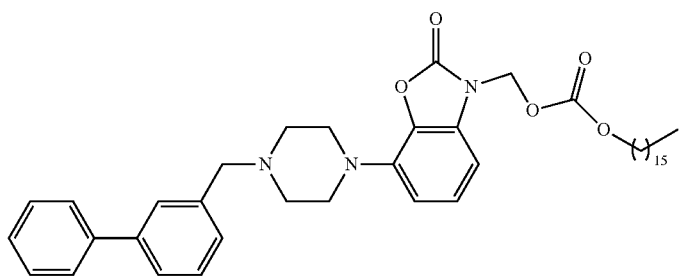 |
| 404 | 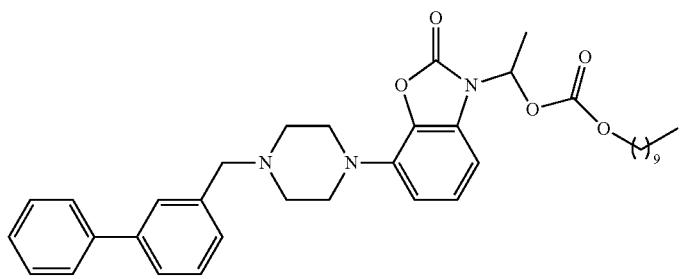 |

TABLE C-continued
| No. | Structure |
|-----|-----------|
| 405 | 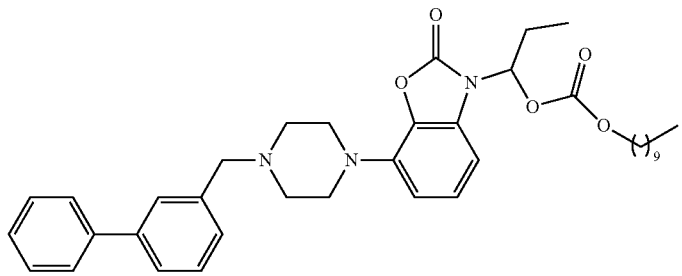 |
| 406 | 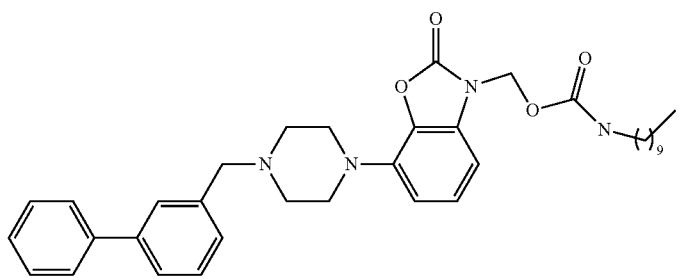 |
| 407 | 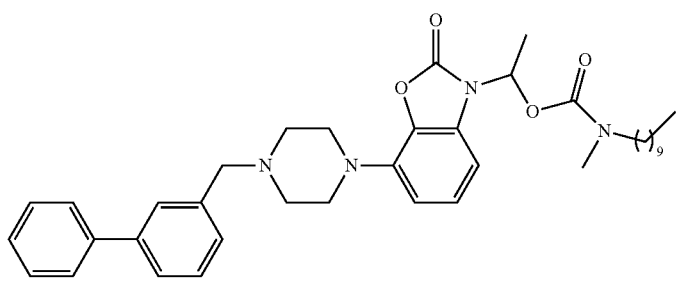 |
| 408 | 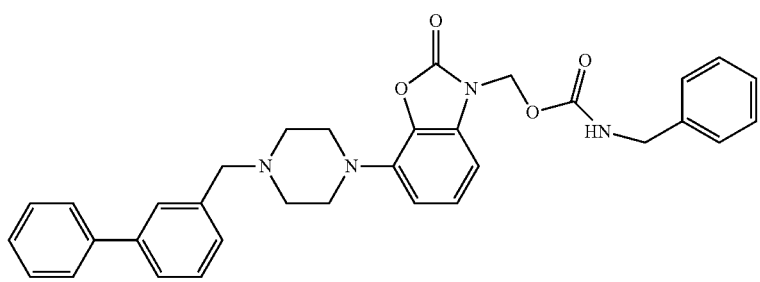 [SMILES: O=C(NCc1ccccc1)OCn1c(=O)oc2c(N3CCN(Cc4cccc(-c5ccccc5)c4)CC3)cccc21] |
| 409 | 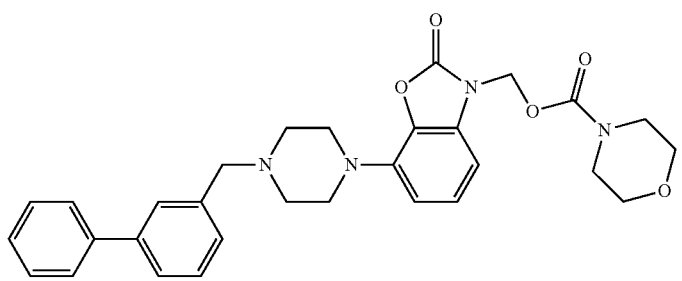 [SMILES: O=C(OCn1c(=O)oc2c(N3CCN(Cc4cccc(-c5ccccc5)c4)CC3)cccc21)N1CCOCC1] |

US 10,723,728 B2
163                                                                                                                                        164
TABLE C-continued
| No. | Structure |
|---|---|
| 410 | 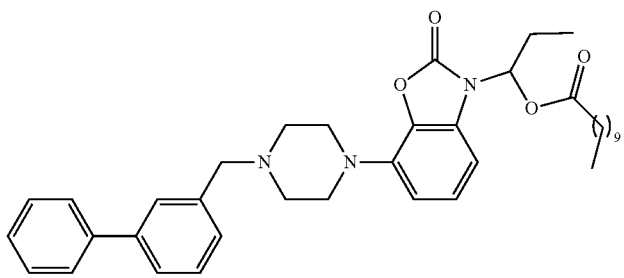 |
| 411 | 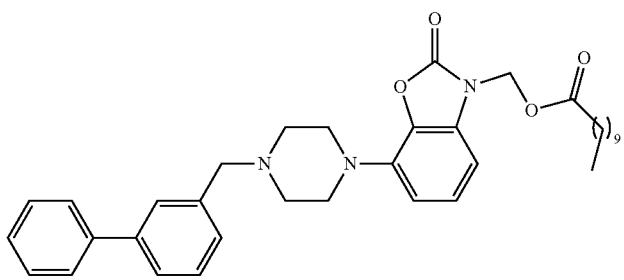 |
| 412 | 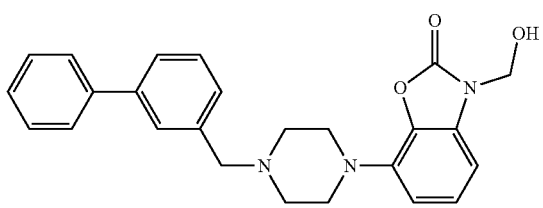 [SMILES: O=c1oc2c(N3CCN(Cc4cccc(-c5ccccc5)c4)CC3)cccc2n1CO] |
| 413 | 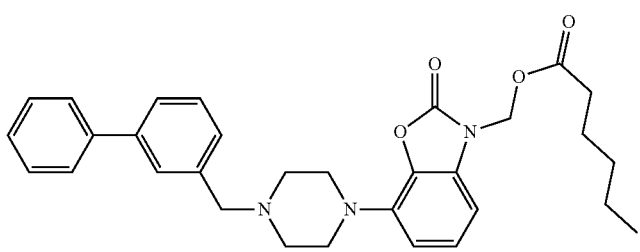 [SMILES: CCCCCC(=O)OCn1c(=O)oc2c(N3CCN(Cc4cccc(-c5ccccc5)c4)CC3)cccc21] |
| 414 | 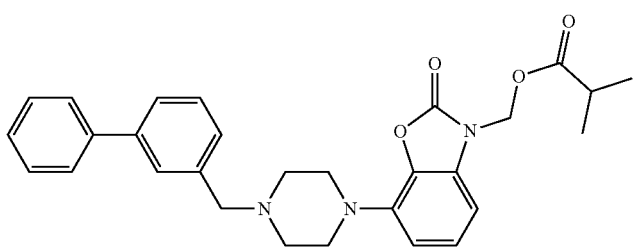 [SMILES: CC(C)C(=O)OCn1c(=O)oc2c(N3CCN(Cc4cccc(-c5ccccc5)c4)CC3)cccc21] |
| 430 | 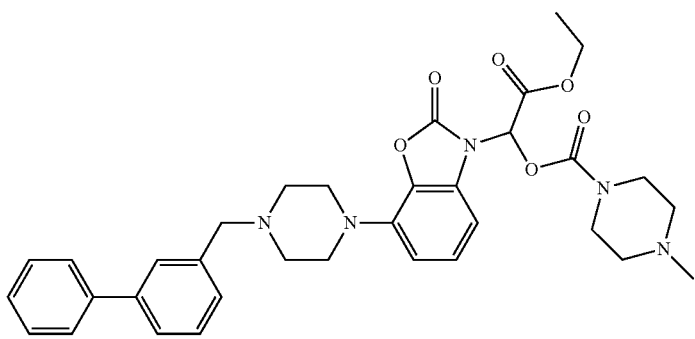 [SMILES: CCOC(=O)C(OC(=O)N1CCN(C)CC1)n1c(=O)oc2c(N3CCN(Cc4cccc(-c5ccccc5)c4)CC3)cccc21] |

TABLE C-continued
| No. | Structure |
|---|---|
| 432 | 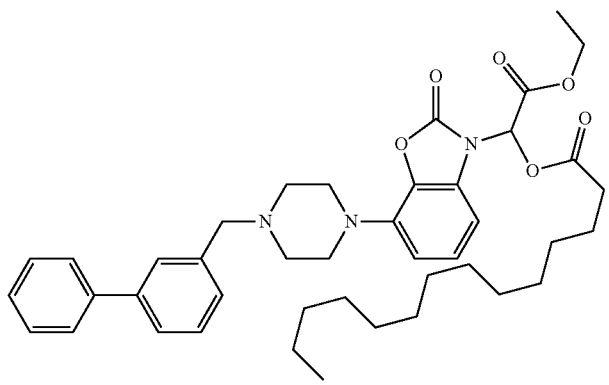 [SMILES: CCCCCCCCCCCCCC(=O)OC(C(=O)OCC)n1c(=O)oc2c(N3CCN(Cc4cccc(-c5ccccc5)c4)CC3)cccc21] |
| 434 | 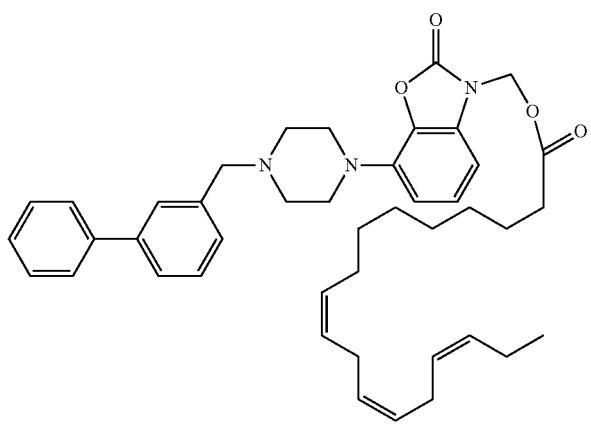 [SMILES: CC/C=C\C/C=C\C/C=C\CCCCCCCC(=O)OCn1c(=O)oc2c(N3CCN(Cc4cccc(-c5ccccc5)c4)CC3)cccc21] |
| 436 | 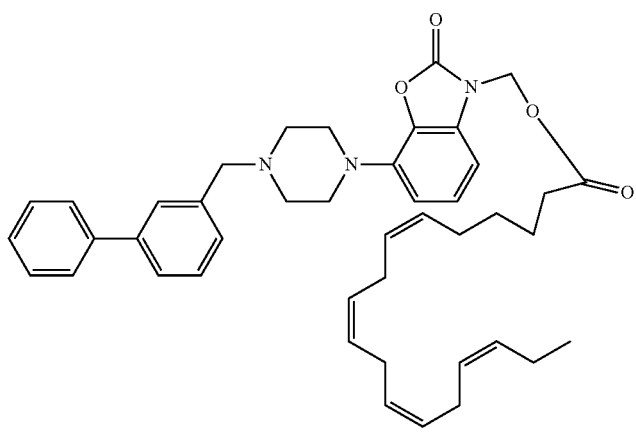 [SMILES: CC/C=C\C/C=C\C/C=C\C/C=C\CCCCC(=O)OCn1c(=O)oc2c(N3CCN(Cc4cccc(-c5ccccc5)c4)CC3)cccc21] |
| 415 | 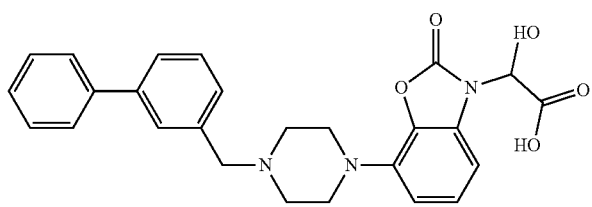 [SMILES: O=C(O)C(O)n1c(=O)oc2c(N3CCN(Cc4cccc(-c5ccccc5)c4)CC3)cccc21] |

TABLE C-continued
| No. | Structure |
|---|---|
| 416 | 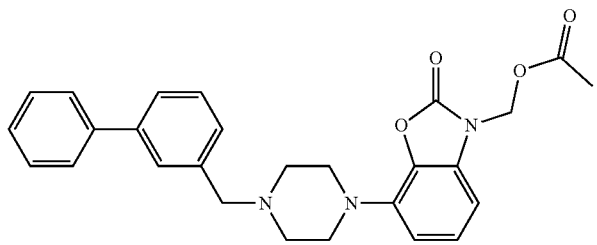 [SMILES: CC(=O)OCn1c(=O)oc2c(N3CCN(Cc4cccc(-c5ccccc5)c4)CC3)cccc21] |
| 417 | 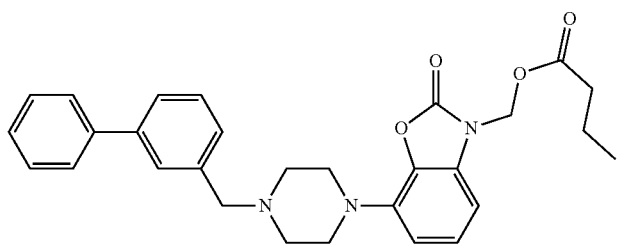 [SMILES: CCCC(=O)OCn1c(=O)oc2c(N3CCN(Cc4cccc(-c5ccccc5)c4)CC3)cccc21] |
| 418 | 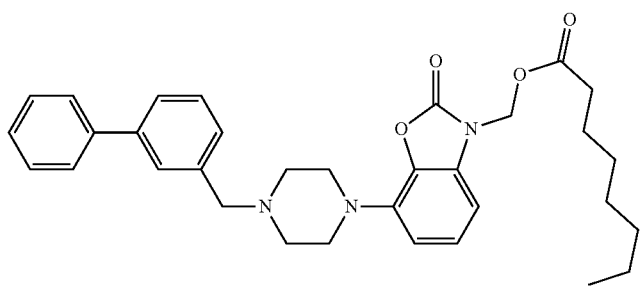 [SMILES: CCCCCCCC(=O)OCn1c(=O)oc2c(N3CCN(Cc4cccc(-c5ccccc5)c4)CC3)cccc21] |
| 419 | 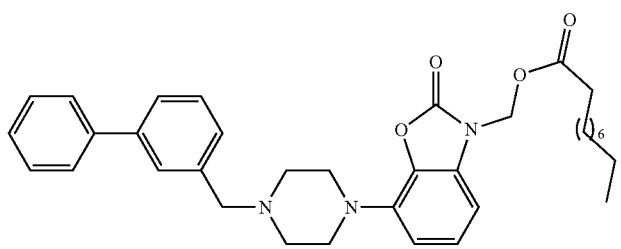 |
| 420 | 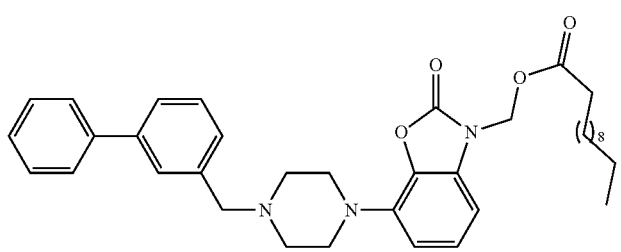 |
| 421 | 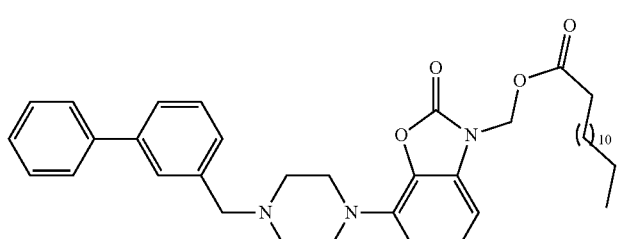 |

TABLE C-continued
| No. | Structure |
|---|---|
| 422 | 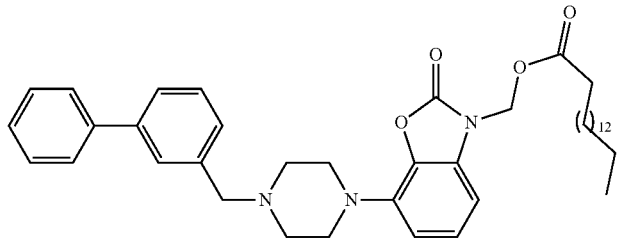 |
| 423 | 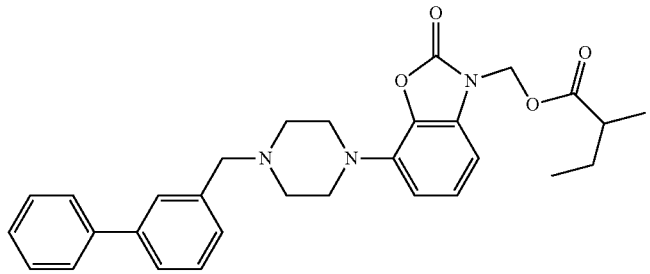 [SMILES: CCC(C)C(=O)OCn1c(=O)oc2c(N3CCN(Cc4cccc(-c5ccccc5)c4)CC3)cccc21] |
| 424 | 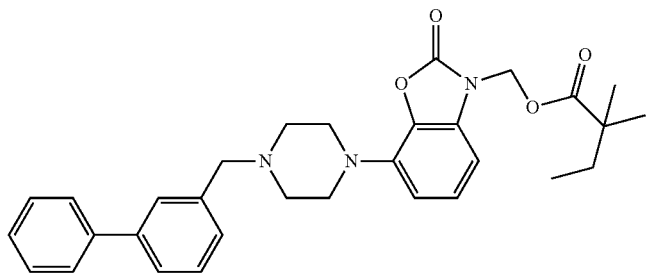 [SMILES: CCC(C)(C)C(=O)OCn1c(=O)oc2c(N3CCN(Cc4cccc(-c5ccccc5)c4)CC3)cccc21] |
| 425 | 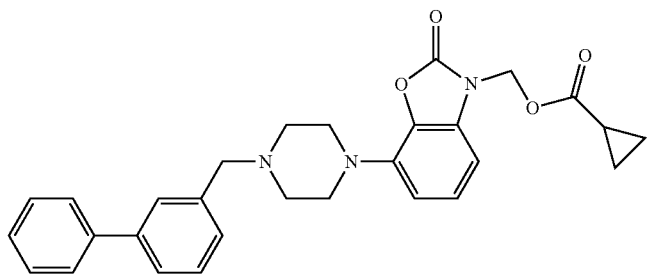 [SMILES: O=C(OCn1c(=O)oc2c(N3CCN(Cc4cccc(-c5ccccc5)c4)CC3)cccc21)C1CC1] |
| 426 | 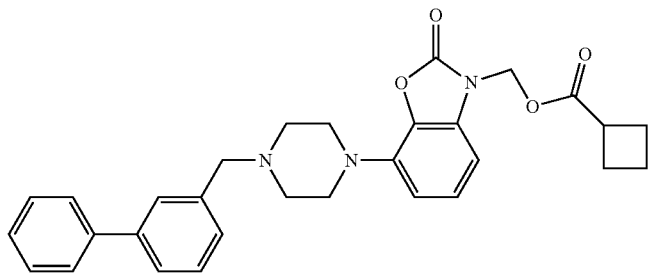 [SMILES: O=C(OCn1c(=O)oc2c(N3CCN(Cc4cccc(-c5ccccc5)c4)CC3)cccc21)C1CCC1] |

TABLE C-continued
| No. | Structure |
|---|---|
| 427 | 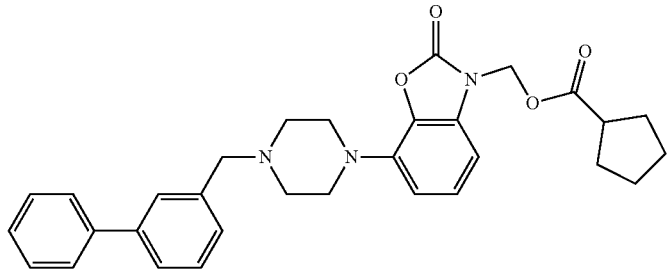 [SMILES: O=C(OCn1c(=O)oc2c(N3CCN(Cc4cccc(-c5ccccc5)c4)CC3)cccc21)C1CCCC1] |
| 428 | 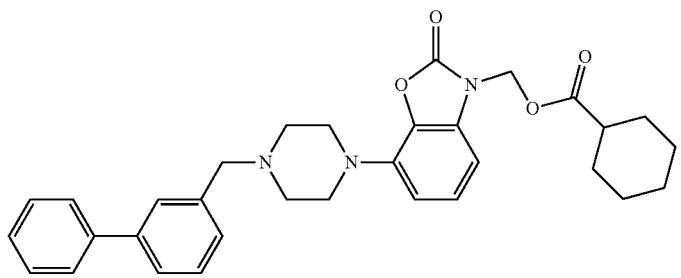 [SMILES: O=C(OCn1c(=O)oc2c(N3CCN(Cc4cccc(-c5ccccc5)c4)CC3)cccc21)C1CCCCC1] |
| 429 | 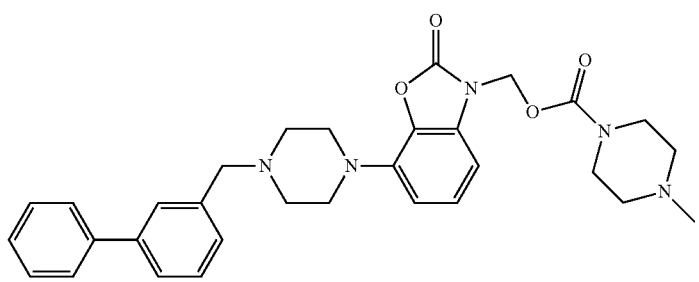 [SMILES: CN1CCN(C(=O)OCn2c(=O)oc3c(N4CCN(Cc5cccc(-c6ccccc6)c5)CC4)cccc32)CC1] |
| 431 | 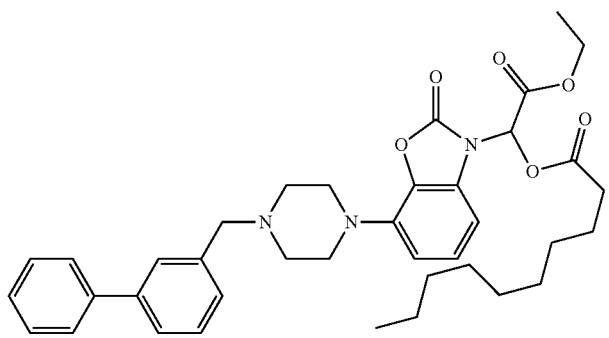 [SMILES: CCCCCCCCCC(=O)OC(C(=O)OCC)n1c(=O)oc2c(N3CCN(Cc4cccc(-c5ccccc5)c4)CC3)cccc21] |

TABLE C-continued
| No. | Structure |
|---|---|
| 433 | 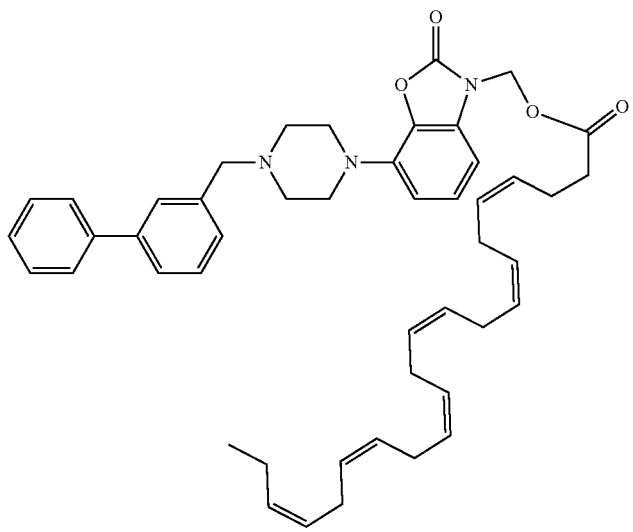 [SMILES: CC/C=C\C/C=C\C/C=C\C/C=C\C/C=C\C/C=C\CCC(=O)OCn1c(=O)oc2c(N3CCN(Cc4cccc(-c5ccccc5)c4)CC3)cccc21] |
| 435 | 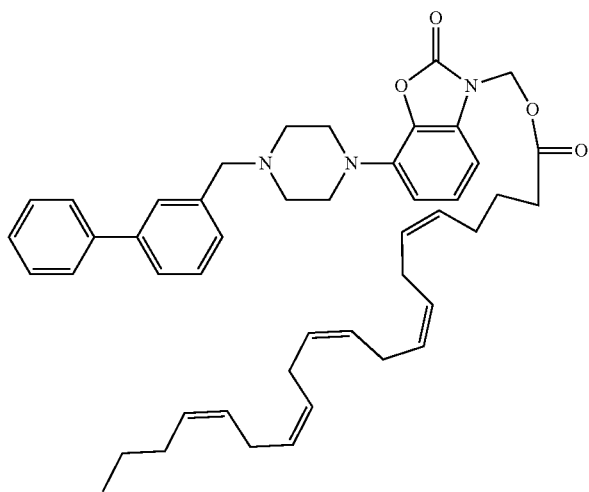 [SMILES: CCC/C=C\C/C=C\C/C=C\C/C=C\C/C=C\CCCC(=O)OCn1c(=O)oc2c(N3CCN(Cc4cccc(-c5ccccc5)c4)CC3)cccc21] |
| 437 | 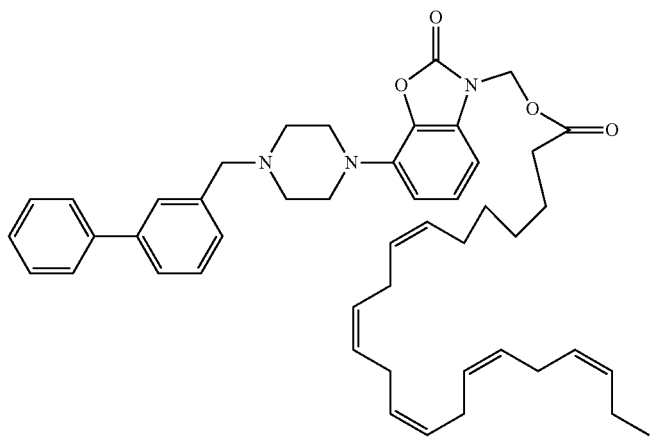 [SMILES: CC/C=C\C/C=C\C/C=C\C/C=C\C/C=C\CCCCCC(=O)OCn1c(=O)oc2c(N3CCN(Cc4cccc(-c5ccccc5)c4)CC3)cccc21] |

TABLE D
| No. | Structure |
|---|---|
| 501 | 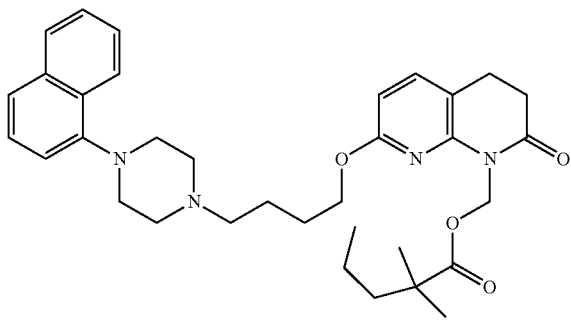 [SMILES: CCCC(C)(C)C(=O)OCN1C(=O)CCc2ccc(OCCCCN3CCN(c4cccc5ccccc45)CC3)nc21] |
| 502 | 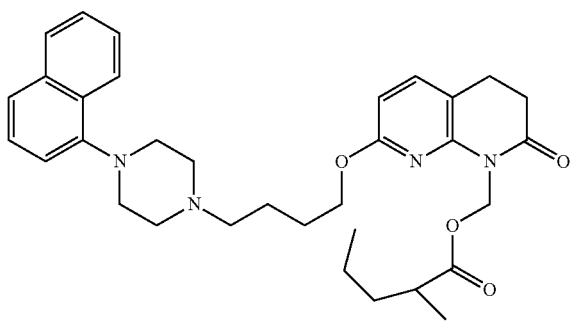 [SMILES: CCCC(C)C(=O)OCN1C(=O)CCc2ccc(OCCCCN3CCN(c4cccc5ccccc45)CC3)nc21] |
| 503 | 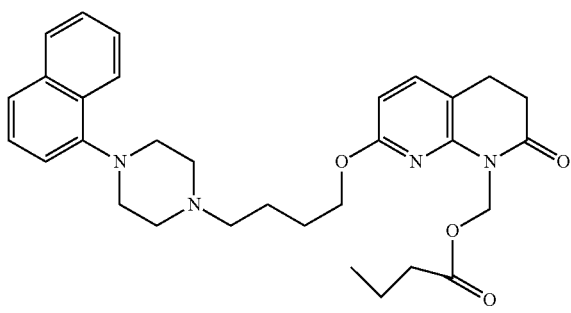 [SMILES: CCCC(=O)OCN1C(=O)CCc2ccc(OCCCCN3CCN(c4cccc5ccccc45)CC3)nc21] |
| 504 | 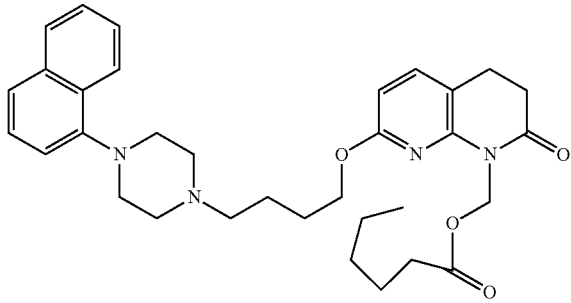 [SMILES: CCCCCC(=O)OCN1C(=O)CCc2ccc(OCCCCN3CCN(c4cccc5ccccc45)CC3)nc21] |
| 505 | 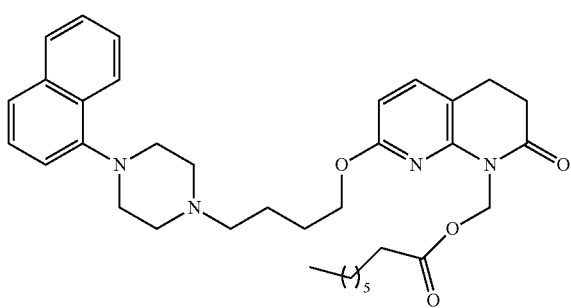 |

TABLE D-continued
| No. | Structure |
|-----|-----------|
| 506 | 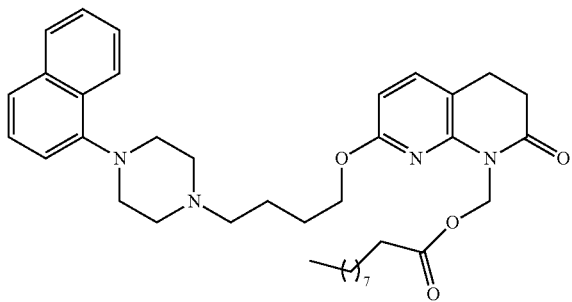 |
| 507 | 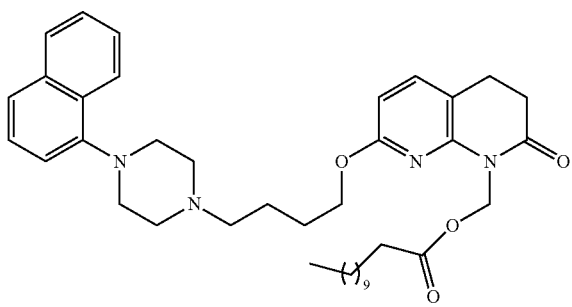 |
| 508 | 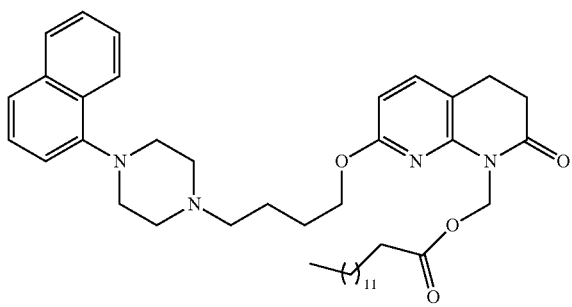 |
| 509 | 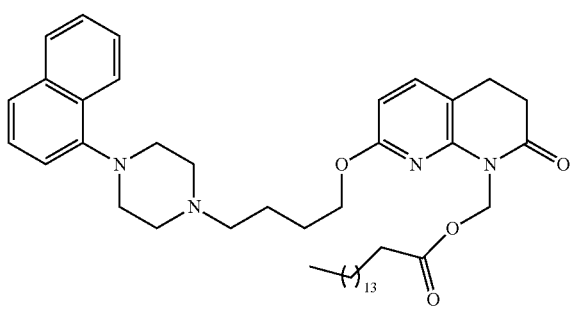 |
| 510 | 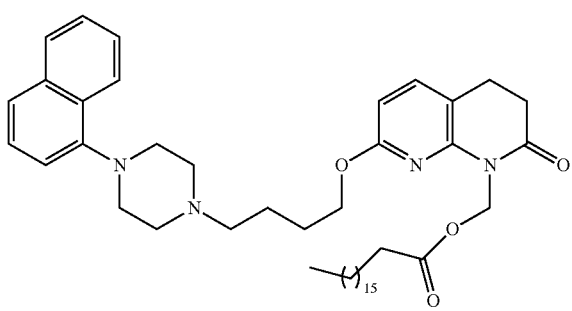 |

TABLE D-continued
| No. | Structure |
|---|---|
| 511 | 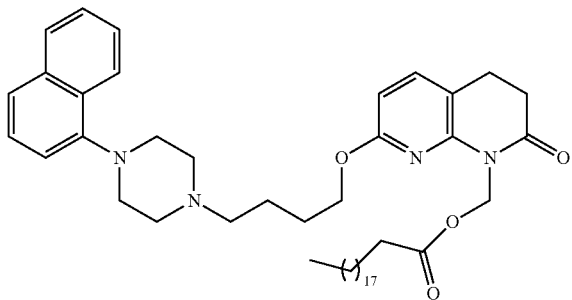 |
| 512 | 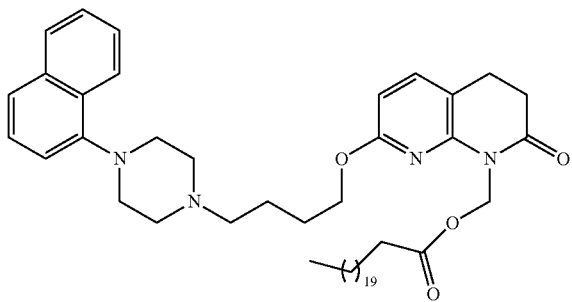 |
| 513 | 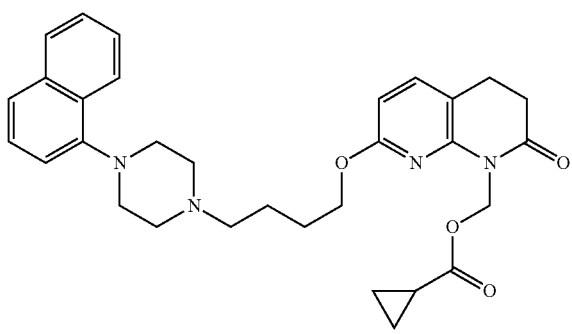 [SMILES: O=C(OCN1C(=O)CCc2ccc(OCCCCN3CCN(c4cccc5ccccc45)CC3)nc21)C1CC1] |
| 514 | 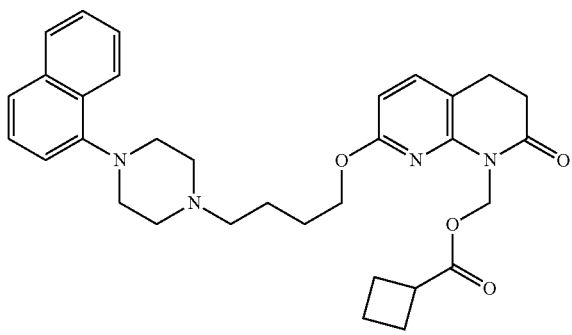 [SMILES: O=C(OCN1C(=O)CCc2ccc(OCCCCN3CCN(c4cccc5ccccc45)CC3)nc21)C1CCC1] |

TABLE D-continued
| No. | Structure |
|---|---|
| 515 | 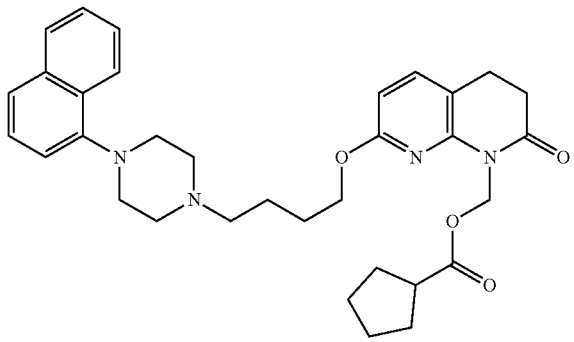 [SMILES: O=C(OCN1C(=O)CCc2ccc(OCCCCN3CCN(c4cccc5ccccc45)CC3)nc21)C1CCCC1] |
| 516 | 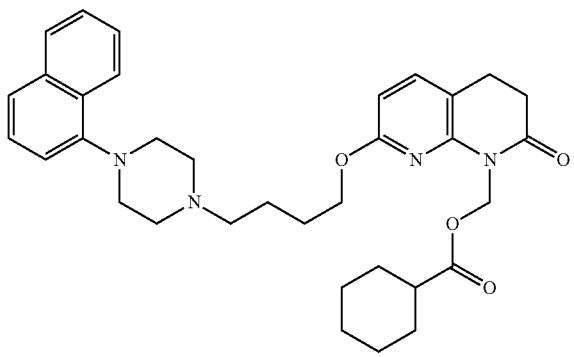 [SMILES: O=C(OCN1C(=O)CCc2ccc(OCCCCN3CCN(c4cccc5ccccc45)CC3)nc21)C1CCCCC1] |
| 533 | 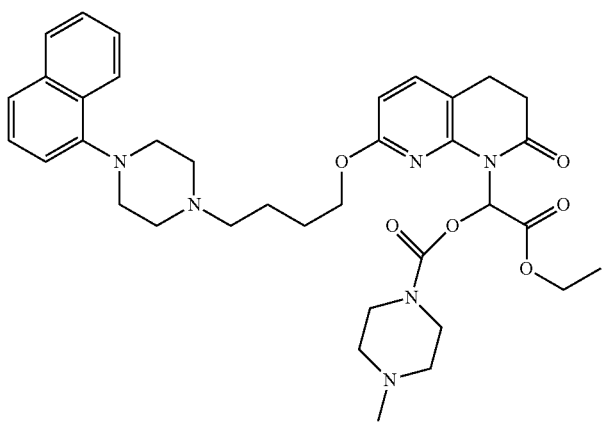 [SMILES: CCOC(=O)C(OC(=O)N1CCN(C)CC1)N1C(=O)CCc2ccc(OCCCCN3CCN(c4cccc5ccccc45)CC3)nc21] |
| 535 | 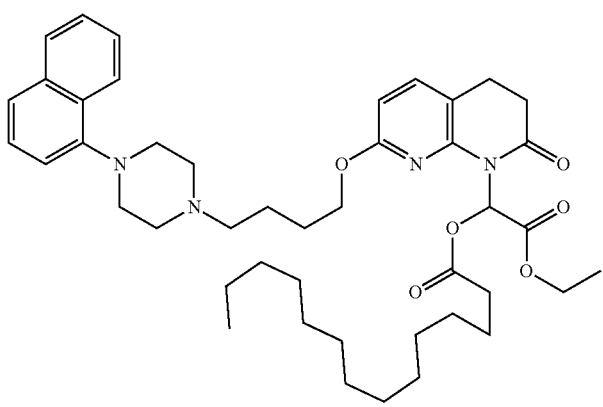 [SMILES: CCCCCCCCCCCCCC(=O)OC(C(=O)OCC)N1C(=O)CCc2ccc(OCCCCN3CCN(c4cccc5ccccc45)CC3)nc21] |

TABLE D-continued
| No. | Structure |
|---|---|
| 537 | 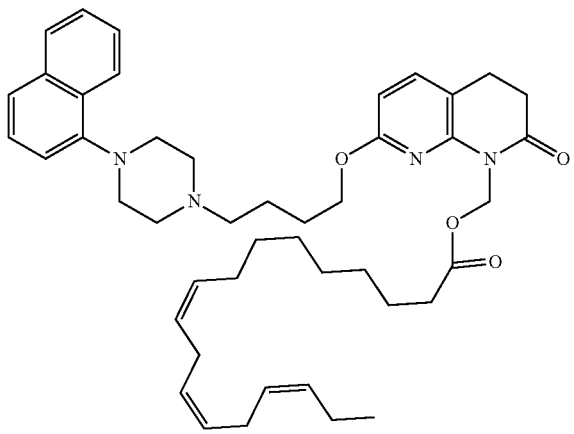 [SMILES: CC/C=C\C/C=C\C/C=C\CCCCCCCC(=O)OCN1C(=O)CCc2ccc(OCCCCN3CCN(c4cccc5ccccc45)CC3)nc21] |
| 539 | 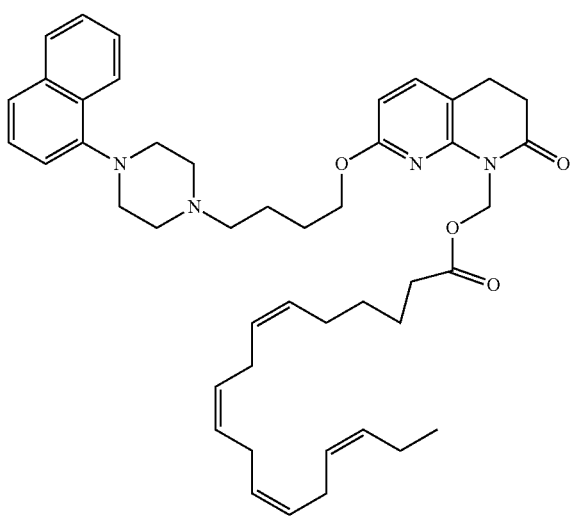 [SMILES: CC/C=C\C/C=C\C/C=C\C/C=C\CCCCC(=O)OCN1C(=O)CCc2ccc(OCCCCN3CCN(c4cccc5ccccc45)CC3)nc21] |
| 517 | 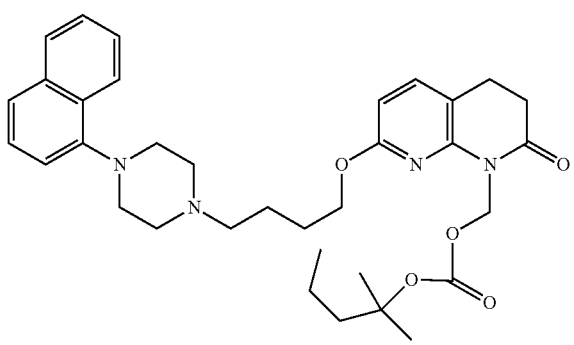 [SMILES: CCCC(C)(C)OC(=O)OCN1C(=O)CCc2ccc(OCCCCN3CCN(c4cccc5ccccc45)CC3)nc21] |
| 518 | 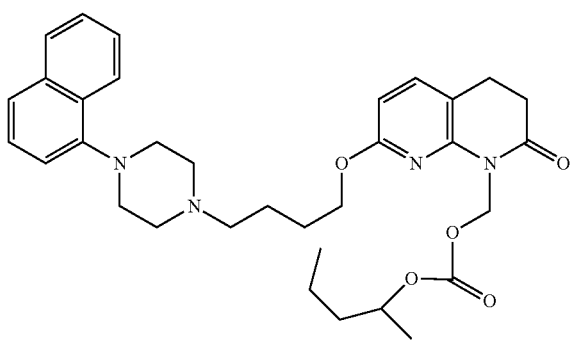 [SMILES: CCCC(C)OC(=O)OCN1C(=O)CCc2ccc(OCCCCN3CCN(c4cccc5ccccc45)CC3)nc21] |

TABLE D-continued
| No. | Structure |
|-----|-----------|
| 519 | 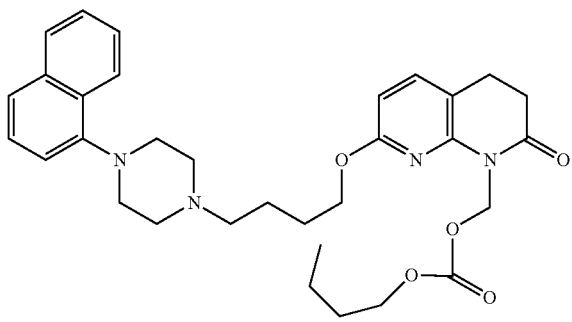 [SMILES: CCCCOC(=O)OCN1C(=O)CCc2ccc(OCCCCN3CCN(c4cccc5ccccc45)CC3)nc21] |
| 520 | 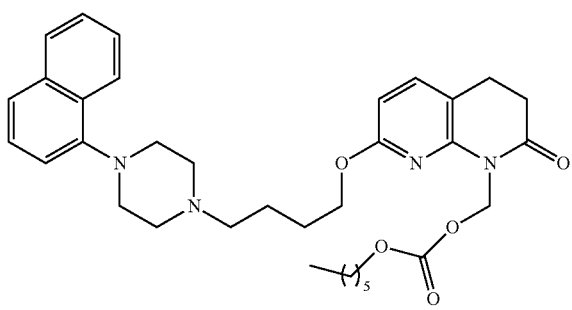 |
| 521 | 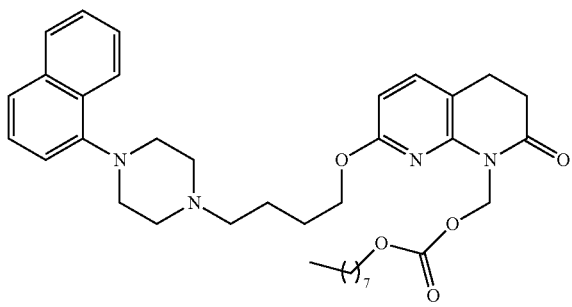 |
| 522 | 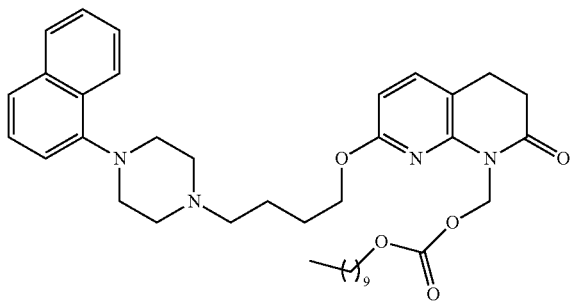 |
| 523 | 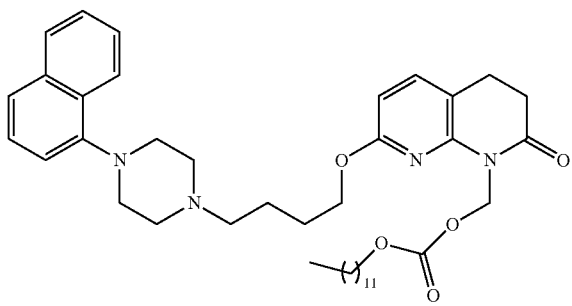 |

TABLE D-continued
| No. | Structure |
|---|---|
| 524 | 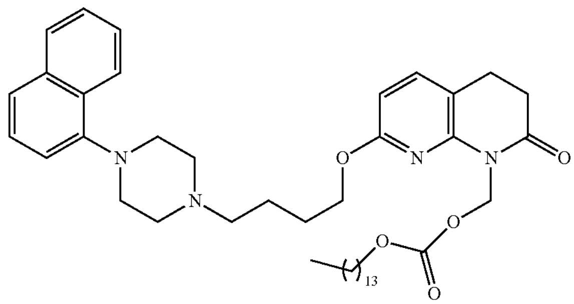 |
| 525 | 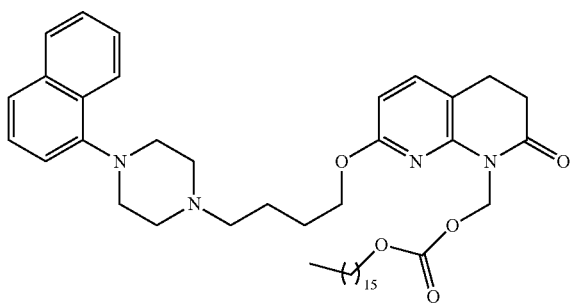 |
| 526 | 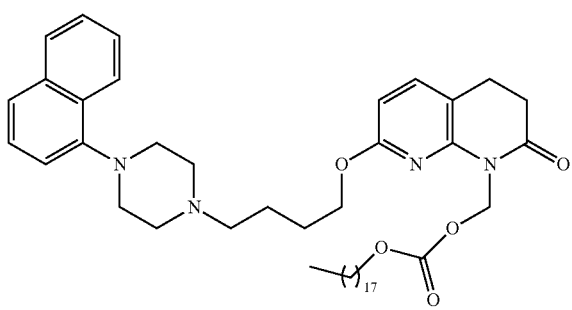 |
| 527 | 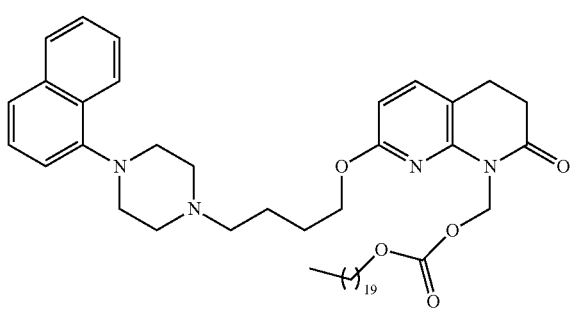 |
| 528 | 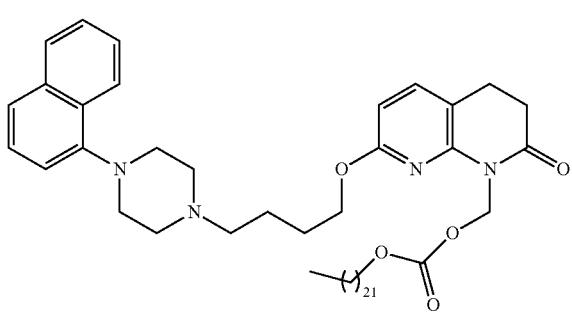 |

TABLE D-continued
| No. | Structure |
|-----|-----------|
| 529 | 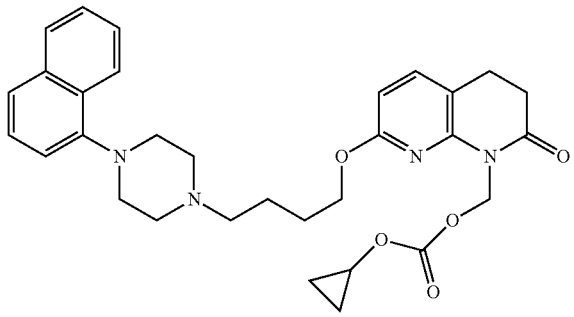 [SMILES: O=C(OCN1C(=O)CCc2ccc(OCCCCN3CCN(c4cccc5ccccc45)CC3)nc21)OC1CC1] |
| 530 | 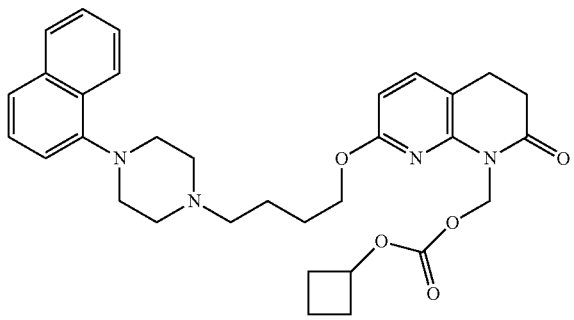 [SMILES: O=C(OCN1C(=O)CCc2ccc(OCCCCN3CCN(c4cccc5ccccc45)CC3)nc21)OC1CCC1] |
| 531 | 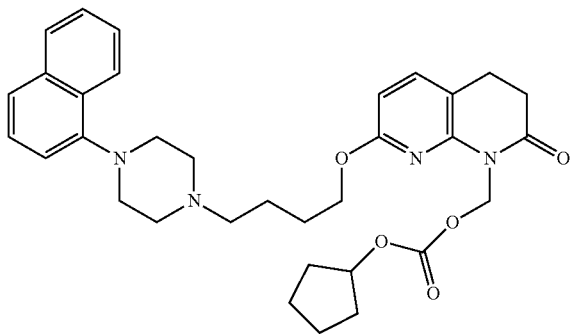 [SMILES: O=C(OCN1C(=O)CCc2ccc(OCCCCN3CCN(c4cccc5ccccc45)CC3)nc21)OC1CCCC1] |
| 532 | 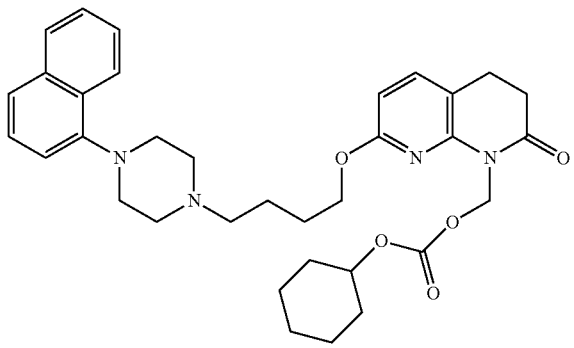 [SMILES: O=C(OCN1C(=O)CCc2ccc(OCCCCN3CCN(c4cccc5ccccc45)CC3)nc21)OC1CCCCC1] |

TABLE D-continued
| No. | Structure |
|---|---|
| 534 | 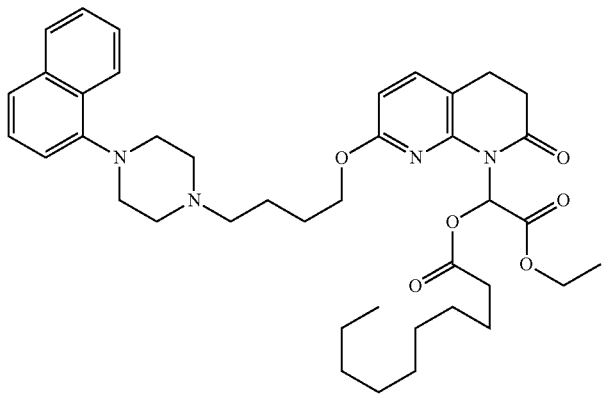 [SMILES: CCCCCCCCCC(=O)OC(C(=O)OCC)N1C(=O)CCc2ccc(OCCCCN3CCN(c4cccc5ccccc45)CC3)nc21] |
| 536 | 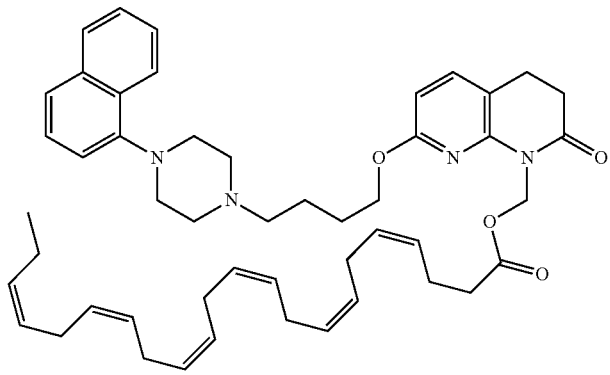 [SMILES: CC/C=C\C/C=C\C/C=C\C/C=C\C/C=C\C/C=C\CCC(=O)OCN1C(=O)CCc2ccc(OCCCCN3CCN(c4cccc5ccccc45)CC3)nc21] |

TABLE D-continued
No. Structure
538
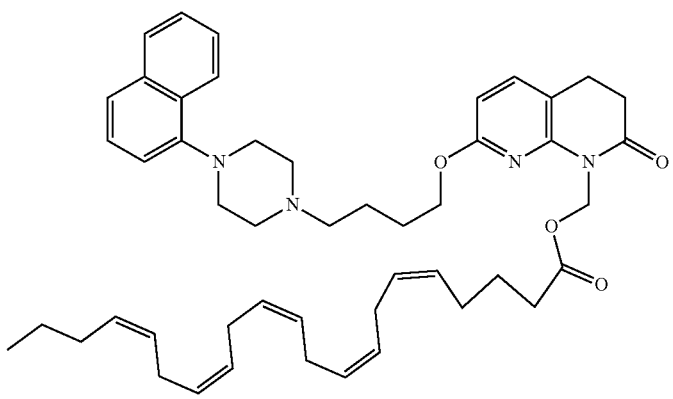 [SMILES: CCC/C=C\C/C=C\C/C=C\C/C=C\C/C=C\CCCC(=O)OCN1C(=O)CCc2ccc(OCCCCN3CCN(c4cccc5ccccc45)CC3)nc21]
540
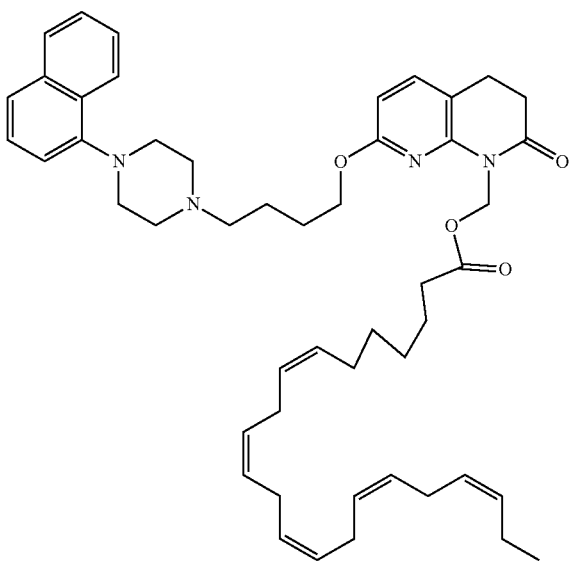 [SMILES: CC/C=C\C/C=C\C/C=C\C/C=C\C/C=C\CCCCCC(=O)OCN1C(=O)CCc2ccc(OCCCCN3CCN(c4cccc5ccccc45)CC3)nc21]
In another embodiment, the invention relates to a compound of formula LI and LII:
Formula LI
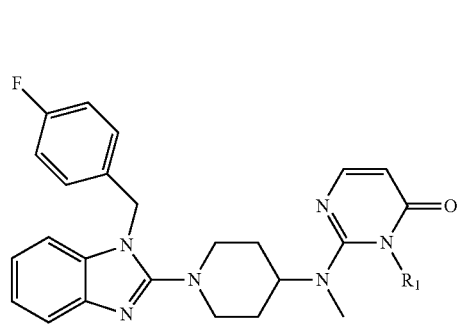
-continued
Formula LII
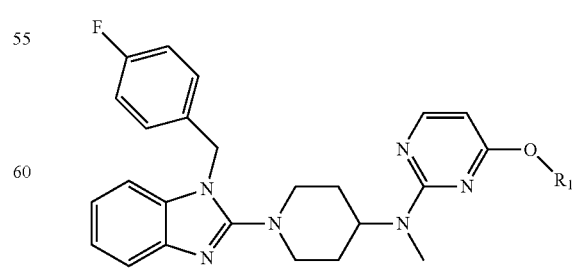
In another aspect of the invention, compounds of formula LI and LII are selected from Table E and F:

TABLE E
| No | Structure |
|---|---|
| 700 | 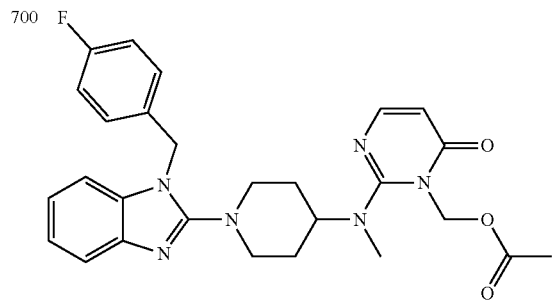 |
| 701 | 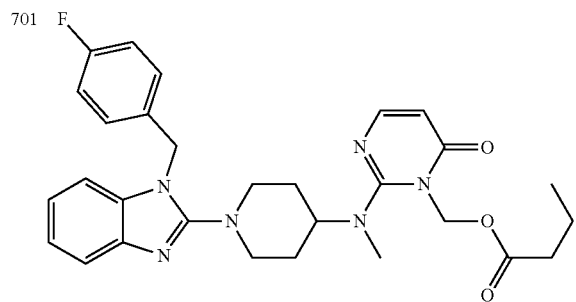 |
| 702 | 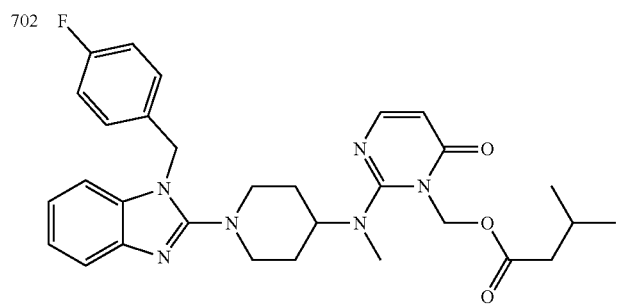 |
| 703 | 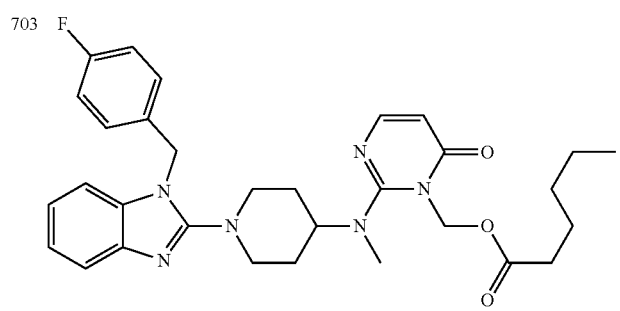 |
| 704 | 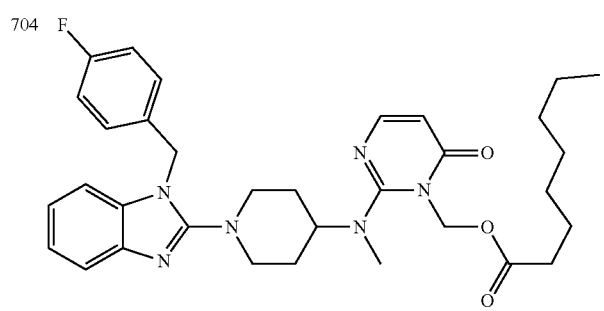 |

TABLE E-continued

| No | Structure |
|---|---|
| 705 | [structure] |
| 706 | [structure] |
| 707 | [structure] |
| 708 | [structure] |
| 709 | [structure] |

TABLE E-continued

| No | Structure |
|---|---|
| 710 | (structure) |
| 711 | (structure) |
| 712 | (structure) |
| 713 | (structure) |
| 714 | (structure) |

TABLE E-continued
| No | Structure |
|---|---|
| 715 | 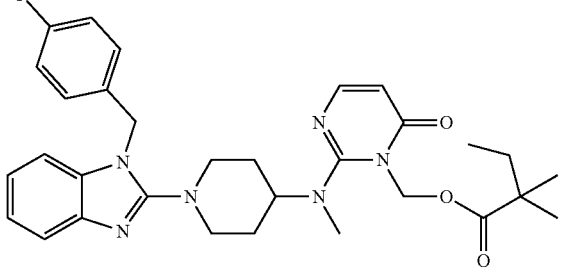 |
| 716 | 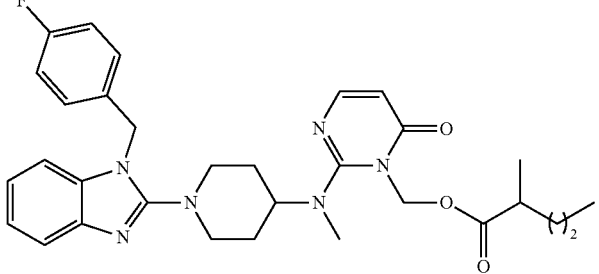 |
| 717 | 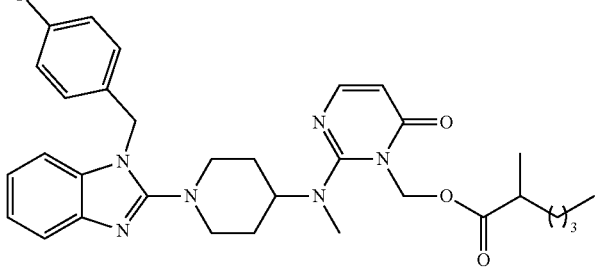 |
| 718 | 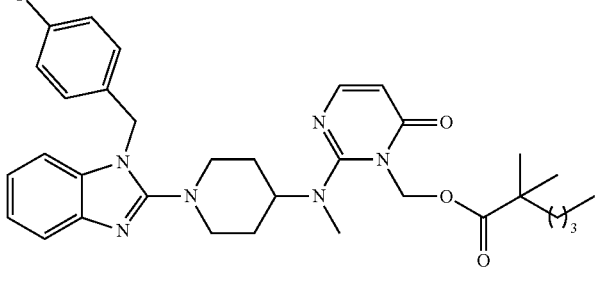 |
| 719 | 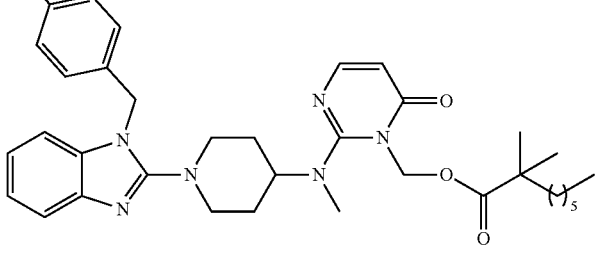 |

TABLE E-continued
| No | Structure |
|---|---|
| 720 | 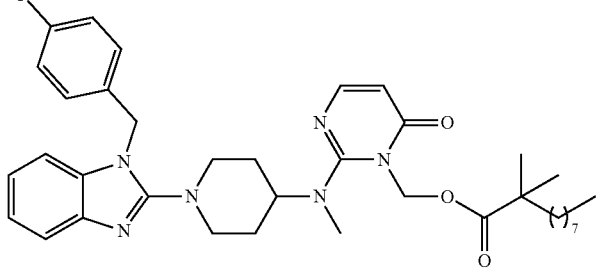 |
| 721 | 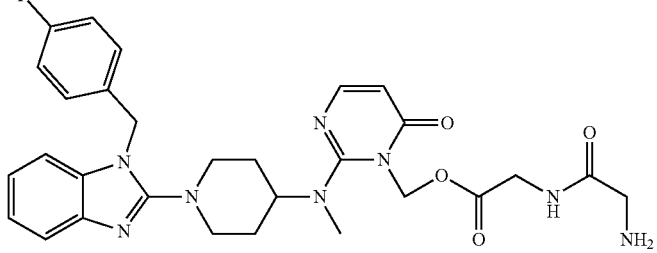 |
| 722 | 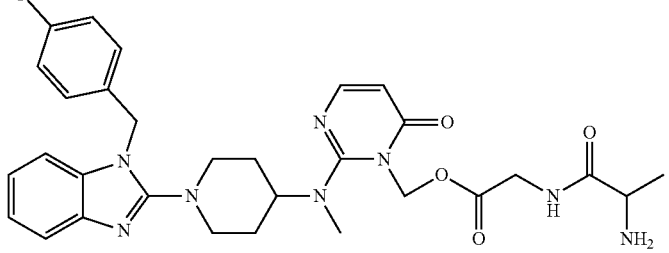 |
| 723 | 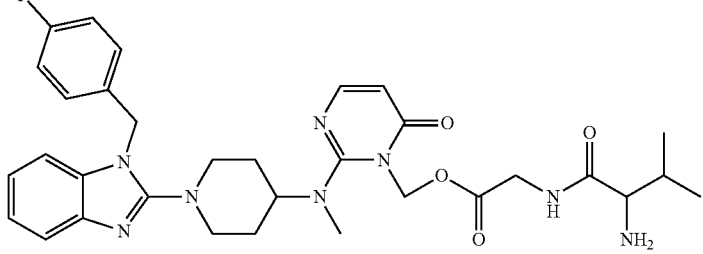 |
| 724 | 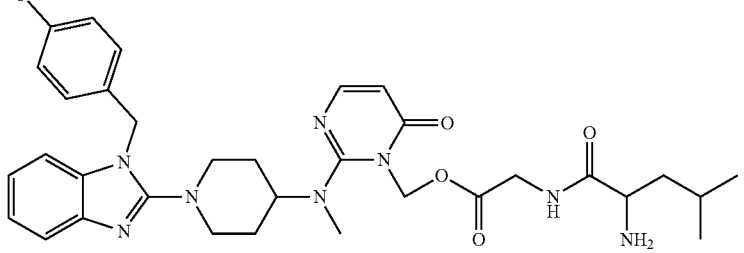 |

TABLE E-continued
| No | Structure |
|---|---|
| 725 | 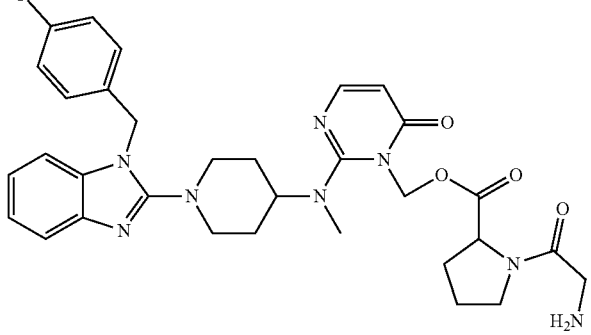 |
| 726 | 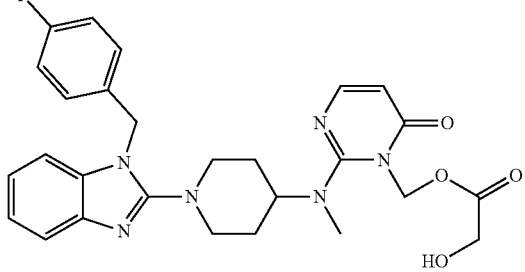 |
| 727 | 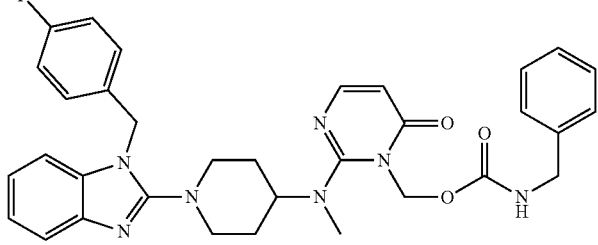 |
| 728 | 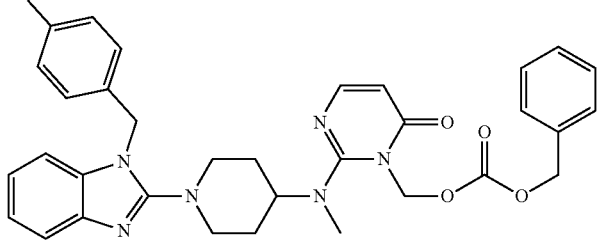 |
| 729 | 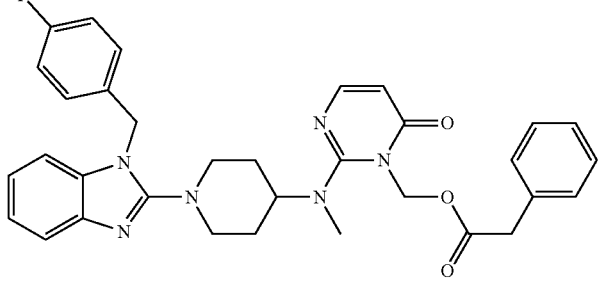 |

TABLE E-continued
| No | Structure |
|---|---|
| 730 | 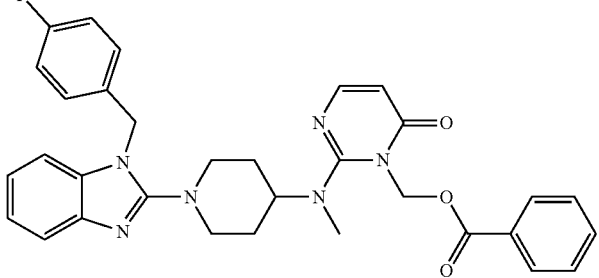 |
| 731 | 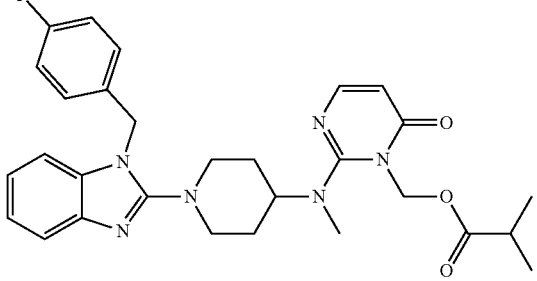 |
| 732 | 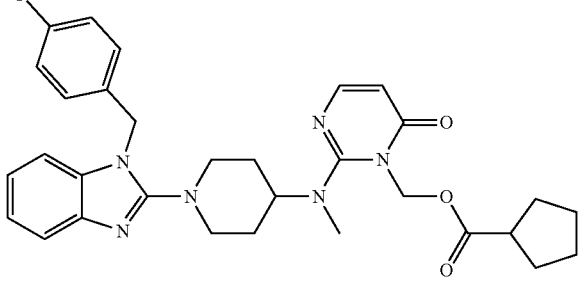 |
| 733 | 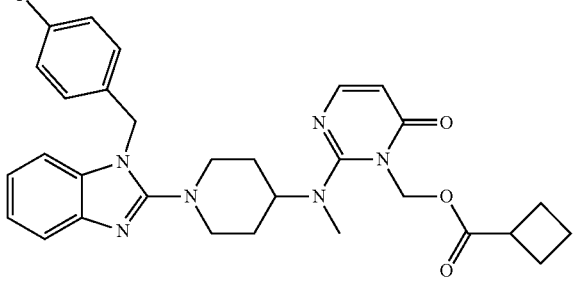 |
| 734 | 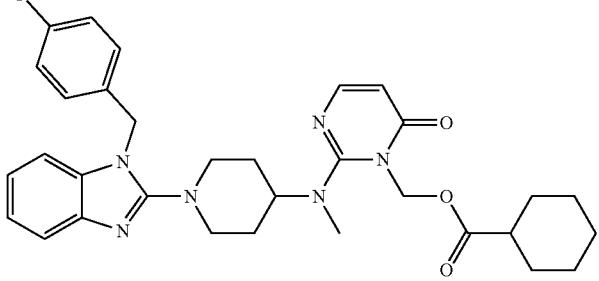 |

TABLE E-continued
| No | Structure |
|---|---|
| 735 | 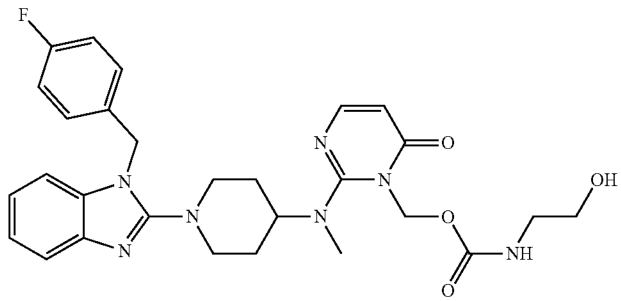 [SMILES: CN(c1nccc(=O)n1COC(=O)NCCO)C1CCN(c2nc3ccccc3n2Cc2ccc(F)cc2)CC1] |
| 736 | 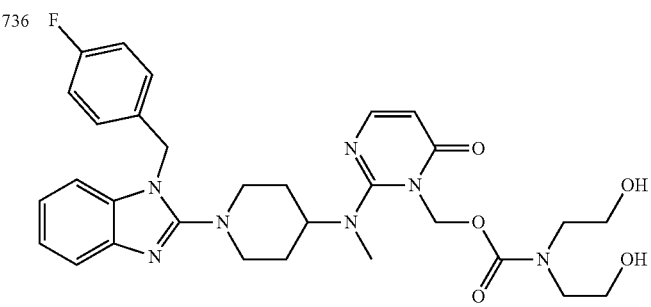 |
| 737 | 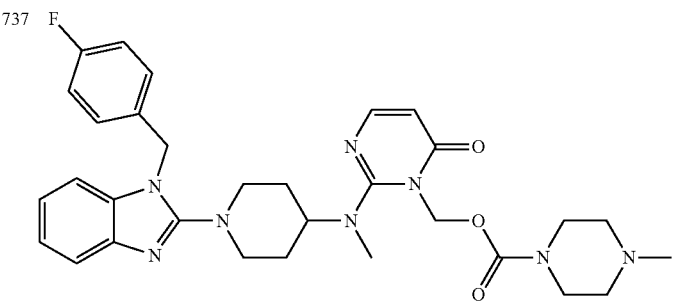 |
| 738 | 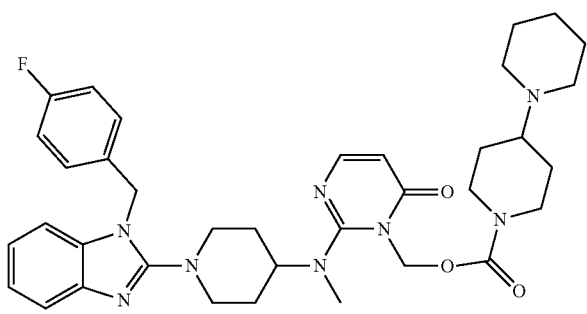 [SMILES: CN(c1nccc(=O)n1COC(=O)N1CCC(N2CCCCC2)CC1)C1CCN(c2nc3ccccc3n2Cc2ccc(F)cc2)CC1] |
| 739 | 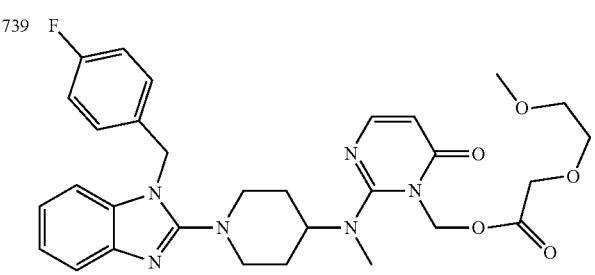 |

TABLE E-continued
| No | Structure |
|---|---|
| 740 | 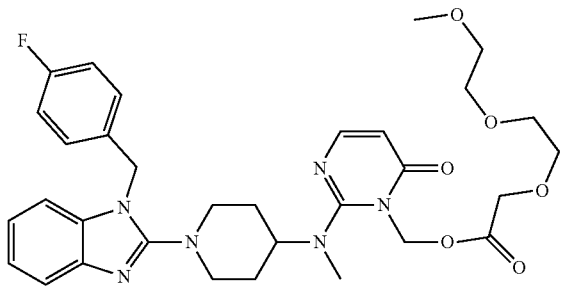 [SMILES: COCCOCCOCC(=O)OCn1c(N(C)C2CCN(c3nc4ccccc4n3Cc3ccc(F)cc3)CC2)nccc1=O] |
| 741 | 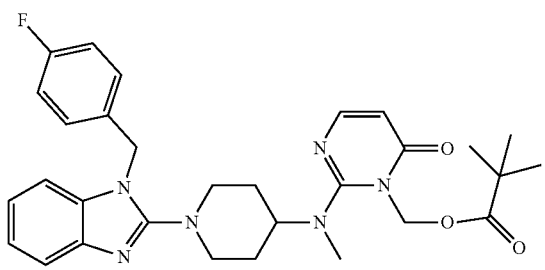 [SMILES: CN(c1nccc(=O)n1COC(=O)C(C)(C)C)C1CCN(c2nc3ccccc3n2Cc2ccc(F)cc2)CC1] |
| 742 | 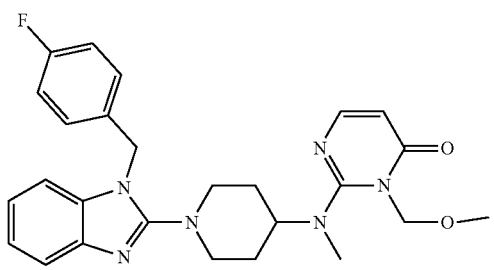 [SMILES: COCn1c(N(C)C2CCN(c3nc4ccccc4n3Cc3ccc(F)cc3)CC2)nccc1=O] |
| 743 | 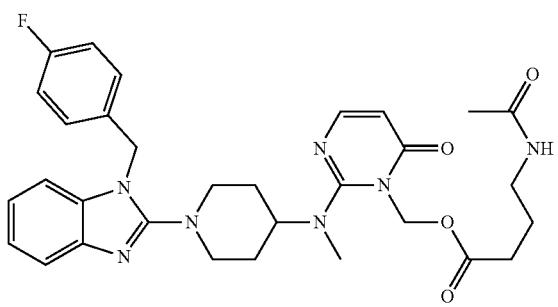 [SMILES: CC(=O)NCCCC(=O)OCn1c(N(C)C2CCN(c3nc4ccccc4n3Cc3ccc(F)cc3)CC2)nccc1=O] |
| 744 | 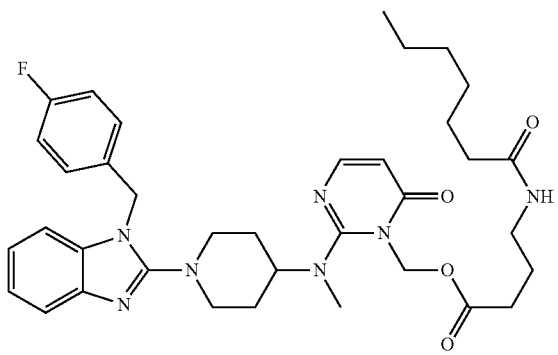 [SMILES: CCCCCCC(=O)NCCCC(=O)OCn1c(N(C)C2CCN(c3nc4ccccc4n3Cc3ccc(F)cc3)CC2)nccc1=O] |

TABLE E-continued
| No | Structure |
|---|---|
| 745 | 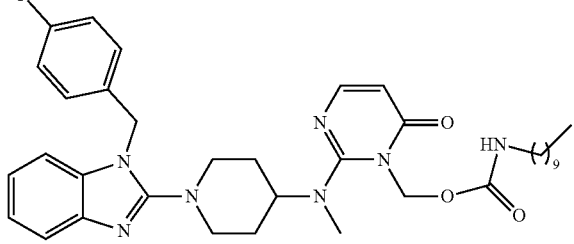 |
| 746 | 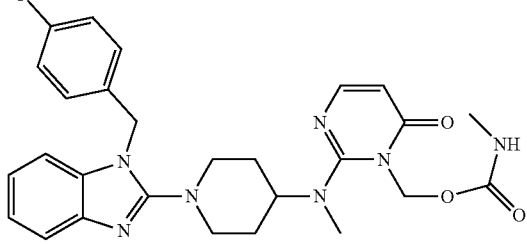 |
| 747 | 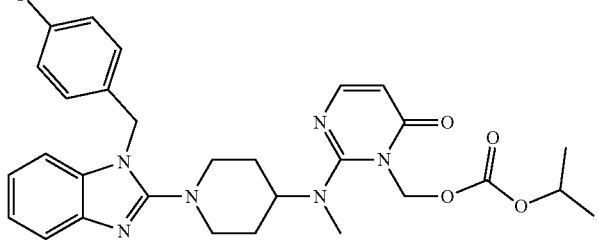 |
| 748 | 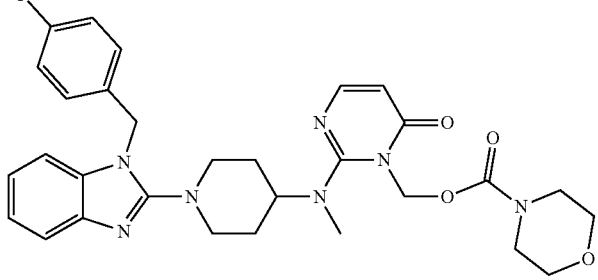 |
| 749 | 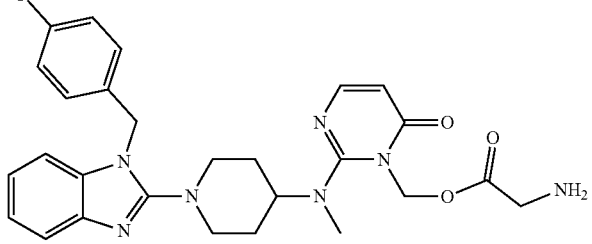 |

TABLE E-continued
| No | Structure |
|----|-----------|
| 750 | 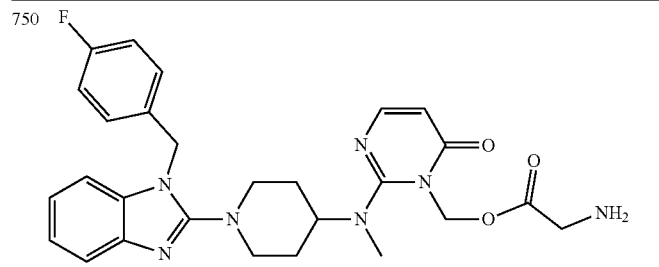 |
| 751 | 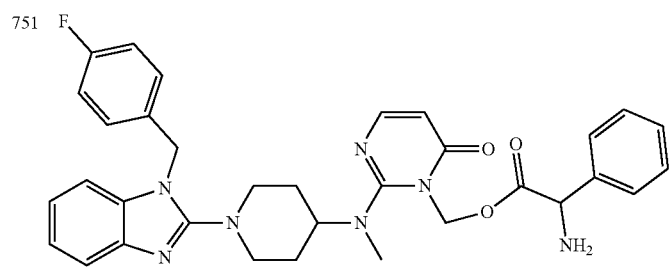 |
| 752 | 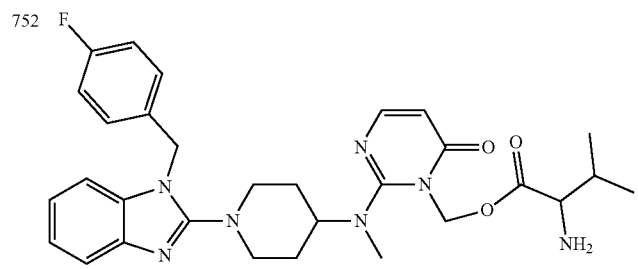 |
| 753 | 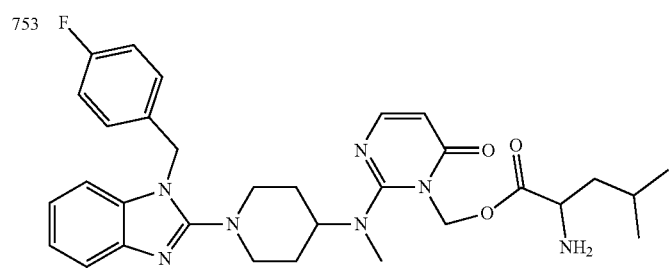 |
| 754 | 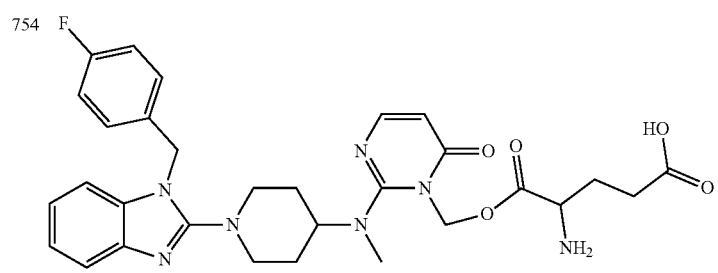 |
| 755 | 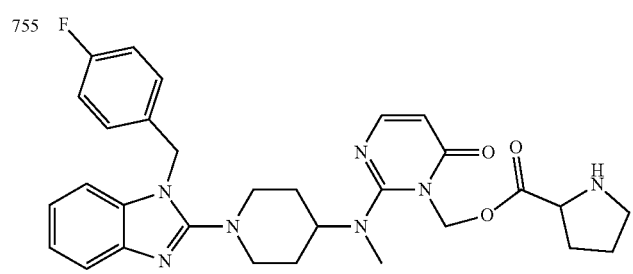 |

TABLE E-continued
| No | Structure |
|---|---|
| 756 | 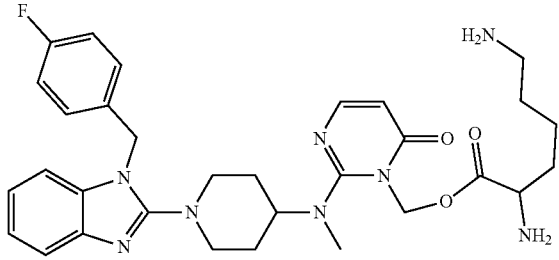 [SMILES: CN(c1nccc(=O)n1COC(=O)C(N)CCCCN)C1CCN(c2nc3ccccc3n2Cc2ccc(F)cc2)CC1] |
| 757 | 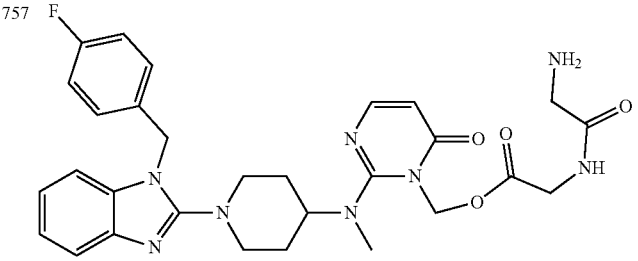 |
| 758 | 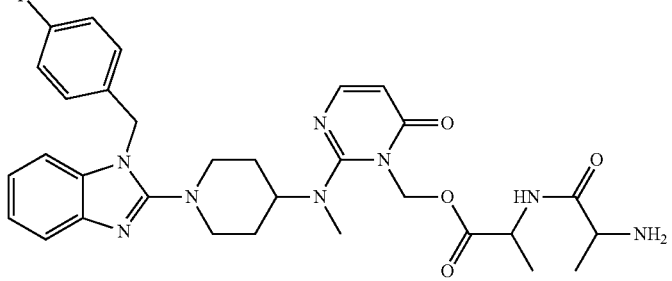 |
| 759 | 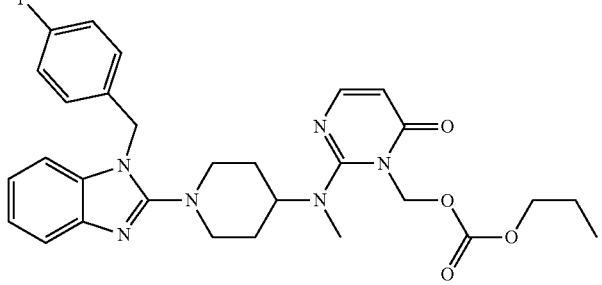 |
| 760 | 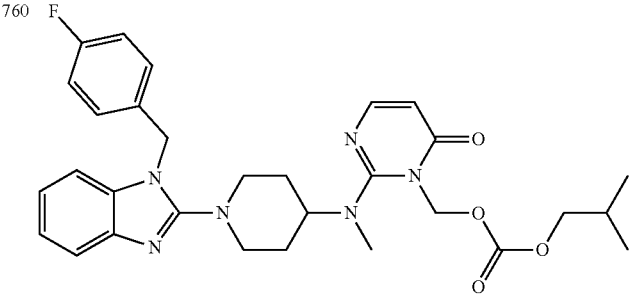 |

TABLE E-continued
| No | Structure |
|---|---|
| 761 | 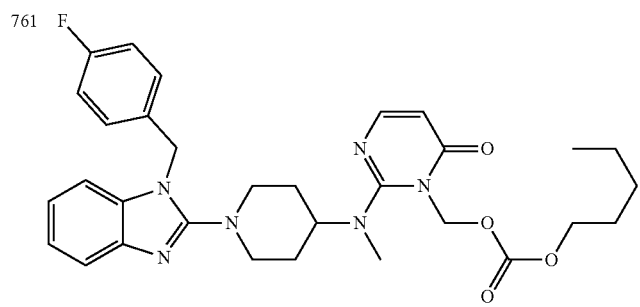 |
| 762 | 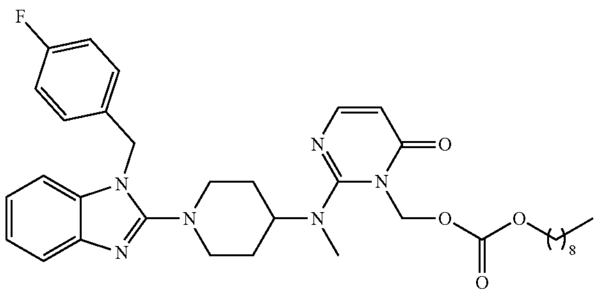 |
| 763 | 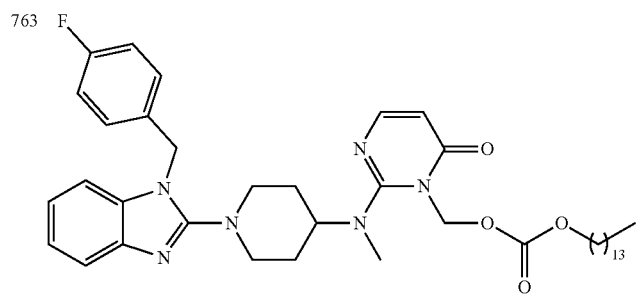 |
| 764 | 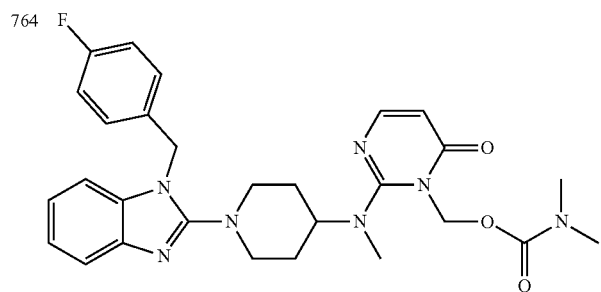 |
| 765 | 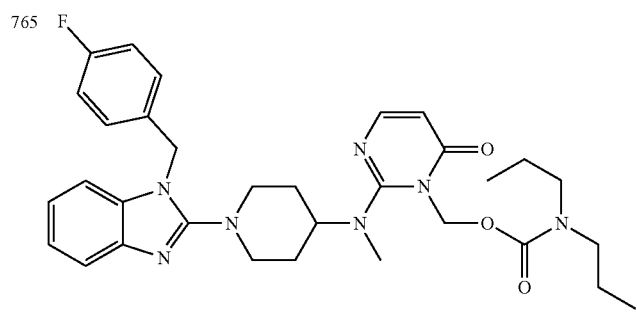 |

TABLE E-continued
| No | Structure |
|----|-----------|
| 766 | 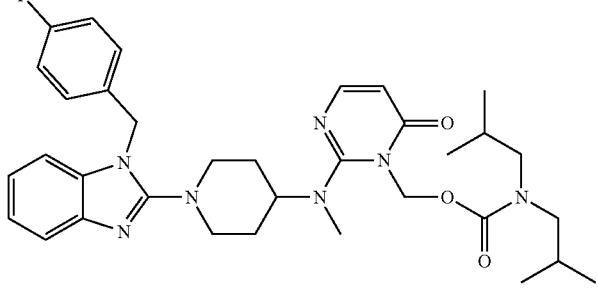 |
| 767 | 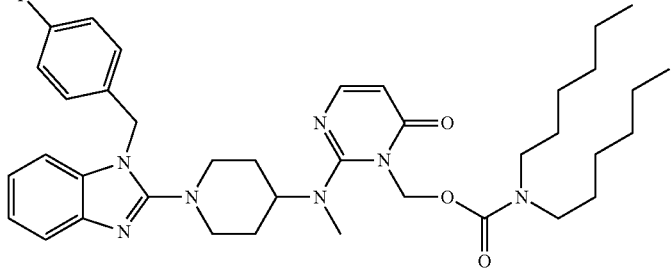 |
| 768 | 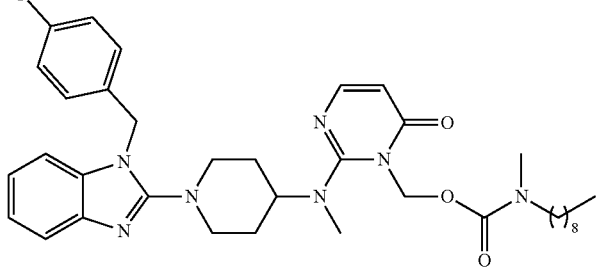 |
| 769 | 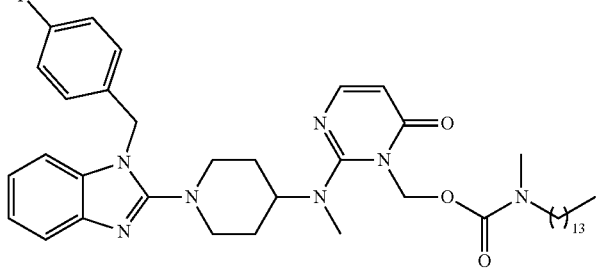 |
| 770 | 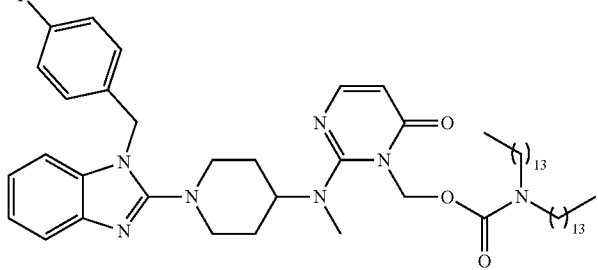 |

TABLE E-continued

| No | Structure |
|---|---|
| 771 | 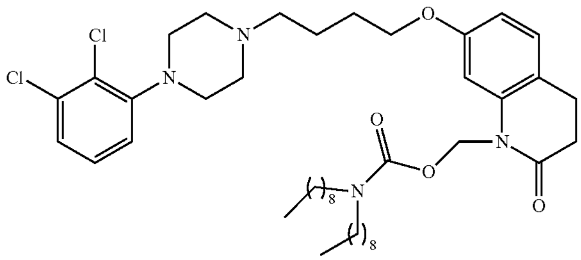 |
| 772 | 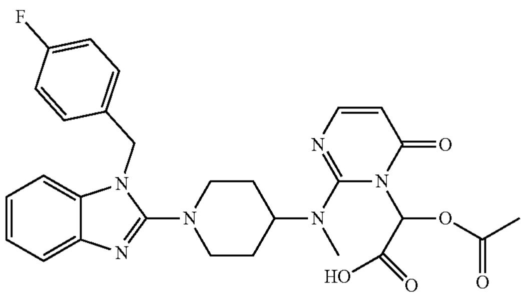 [SMILES: CC(=O)OC(C(=O)O)n1c(N(C)C2CCN(c3nc4ccccc4n3Cc3ccc(F)cc3)CC2)nccc1=O] |
| 773 | 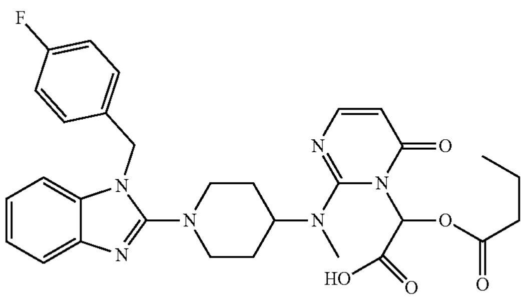 [SMILES: CCCC(=O)OC(C(=O)O)n1c(N(C)C2CCN(c3nc4ccccc4n3Cc3ccc(F)cc3)CC2)nccc1=O] |
| 774 | 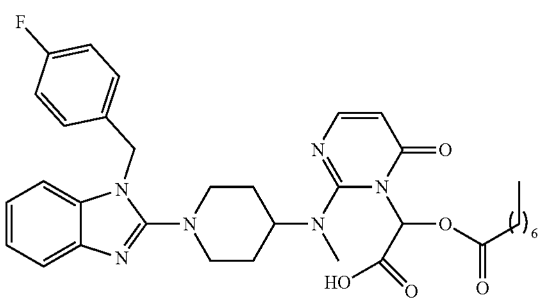 |
| 775 | 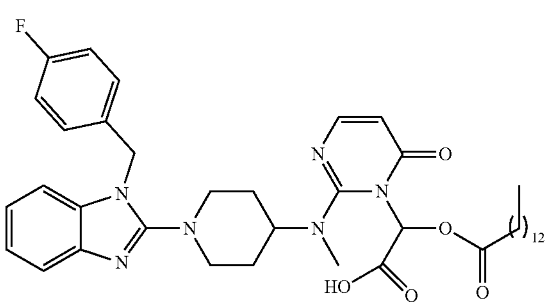 |

TABLE E-continued
| No | Structure |
|---|---|
| 776 | 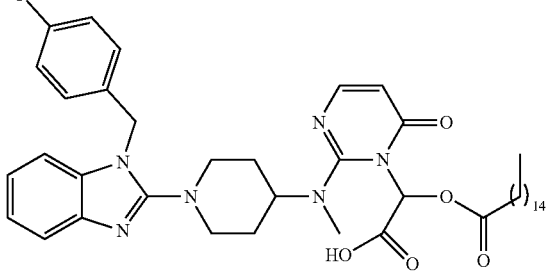 |
| 777 | 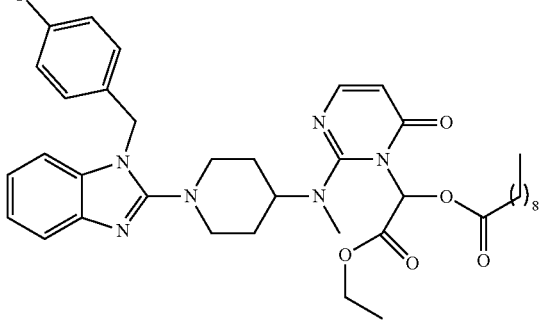 |
| 778 | 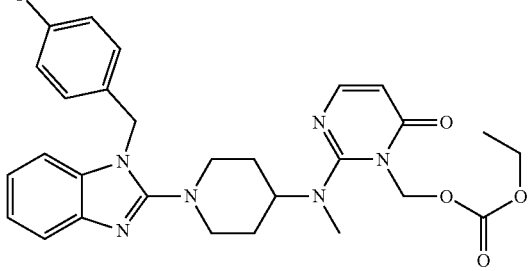 |
| 779 | 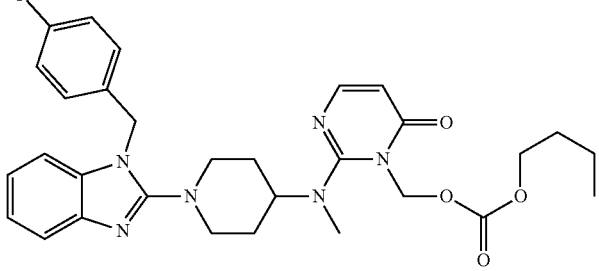 |
| 780 | 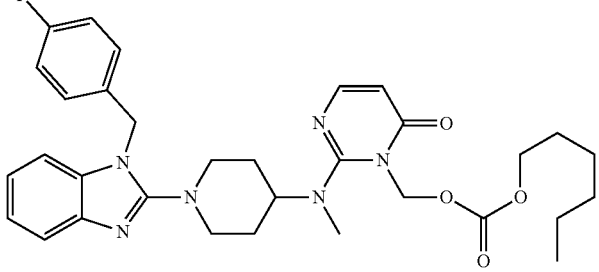 |

TABLE E-continued
| No | Structure |
|---|---|
| 781 | 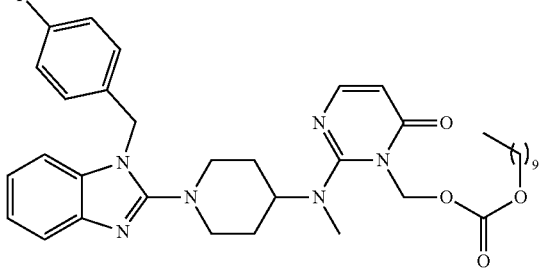 |
| 782 | 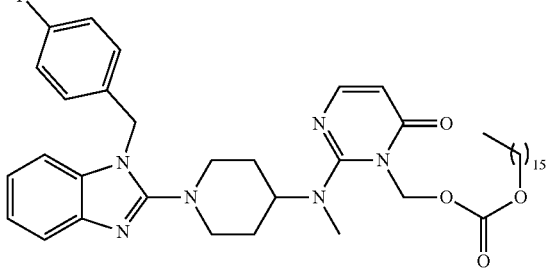 |
| 783 | 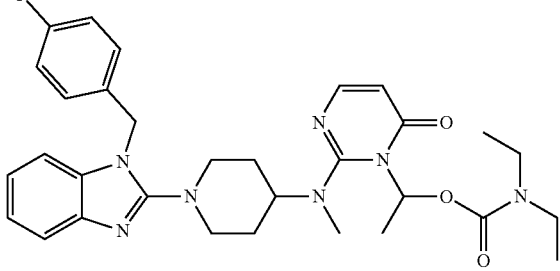 |
| 784 | 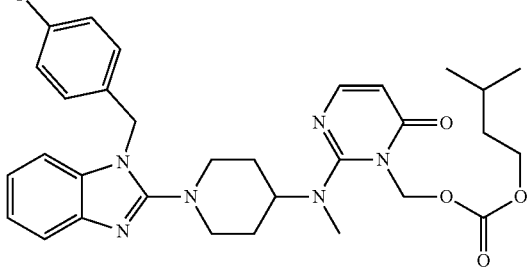 |
| 785 | 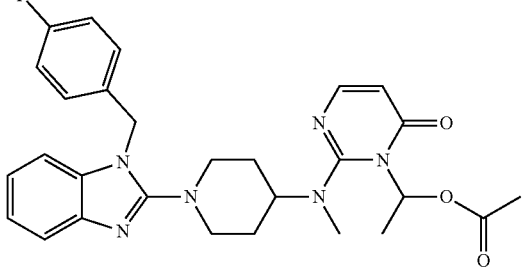 |

TABLE E-continued
| No | Structure |
|---|---|
| 786 | 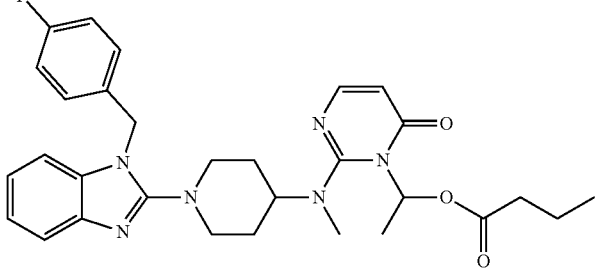 |
| 787 | 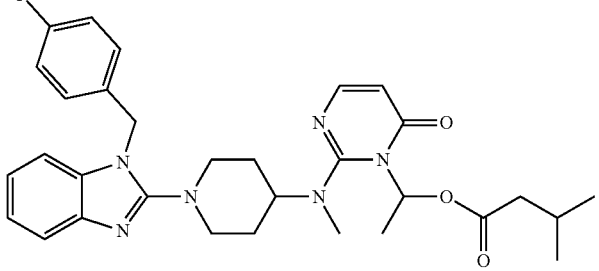 |
| 788 | 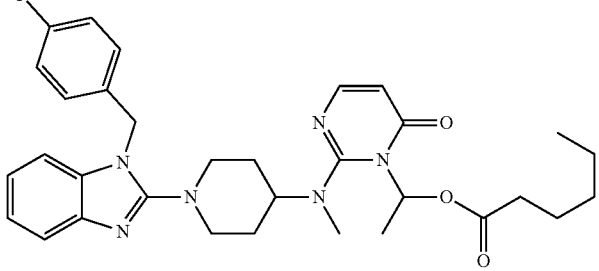 |
| 789 | 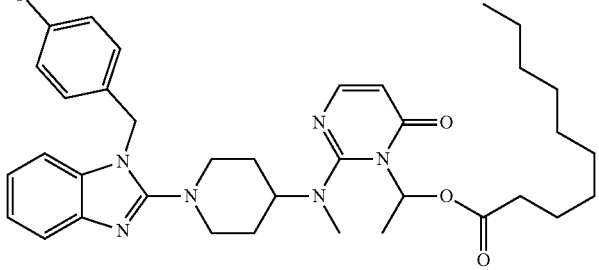 |
| 790 | 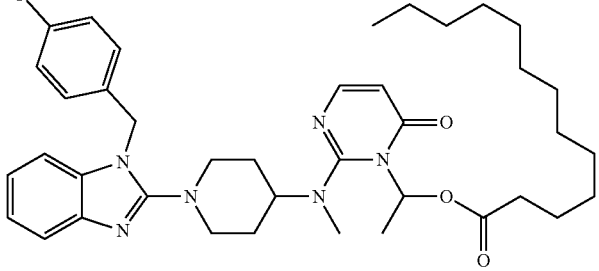 |

TABLE E-continued
| No | Structure |
|---|---|
| 791 | 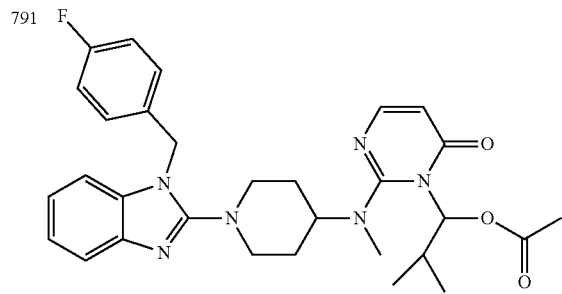 |
| 792 | 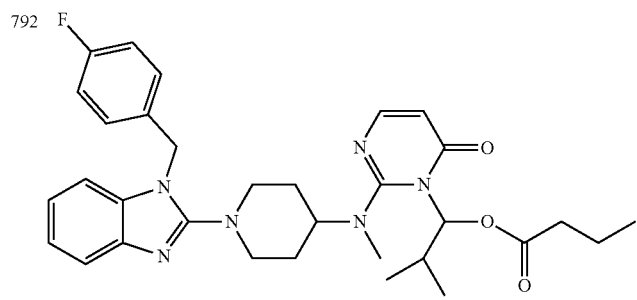 |
| 793 | 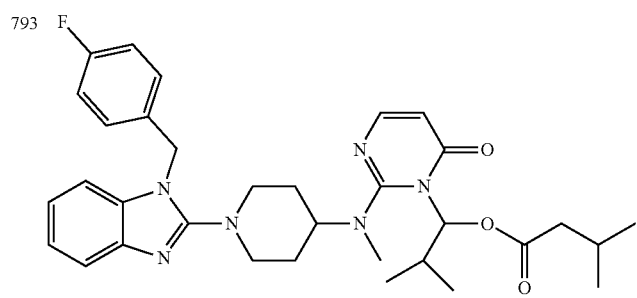 |
| 794 | 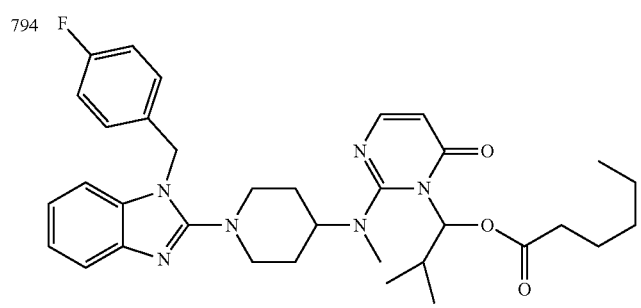 |
| 795 | 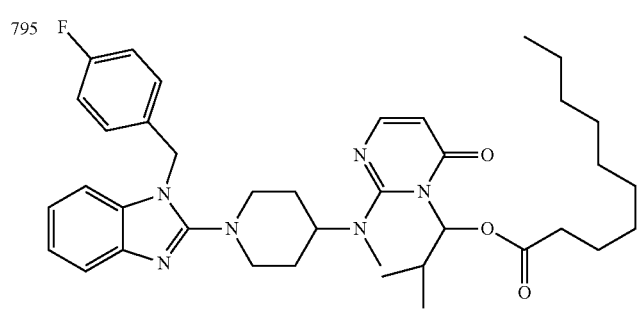 |

US 10,723,728 B2
TABLE E-continued
| No | Structure |
|---|---|
| 796 | 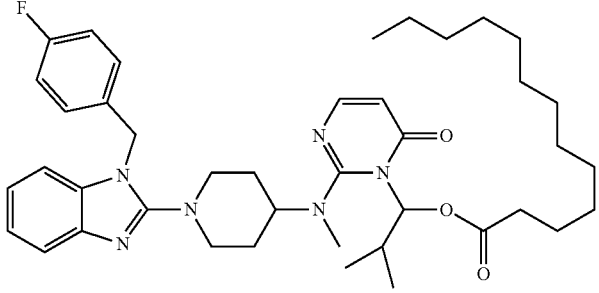 [SMILES: CCCCCCCCCCCCC(=O)OC(C(C)C)n1c(N(C)C2CCN(c3nc4ccccc4n3Cc3ccc(F)cc3)CC2)nccc1=O] |
| 797 | 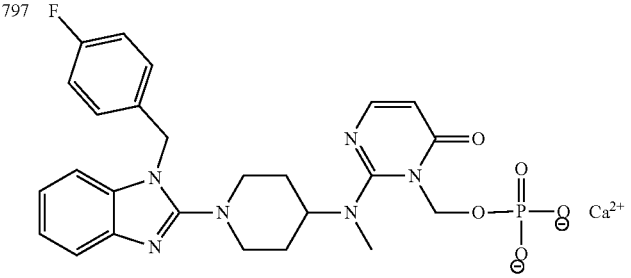 |
| 798 | 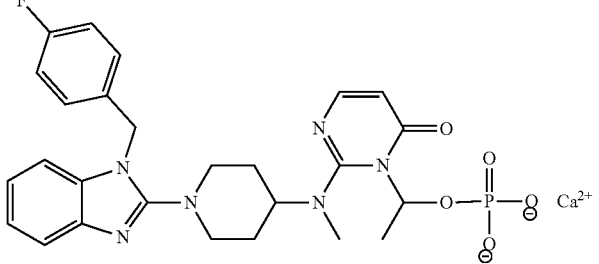 |
| 799 | 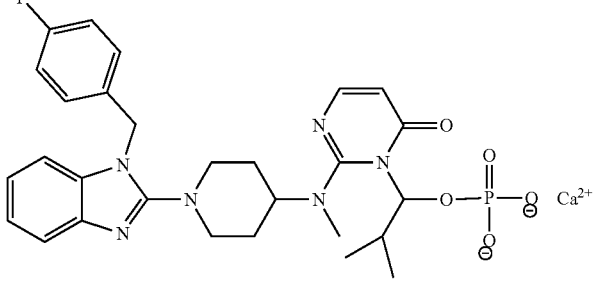 |
| 800 | 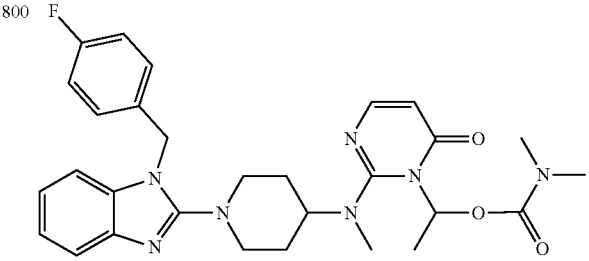 |

TABLE E-continued
| No | Structure |
|----|-----------|
| 801 | 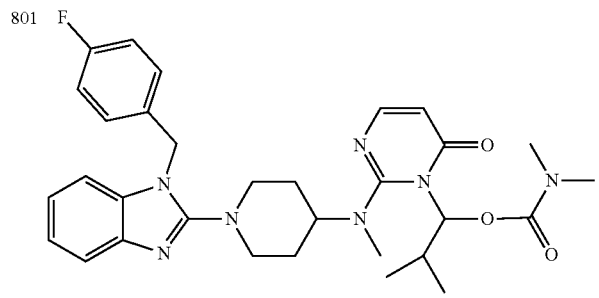 |
| 802 | 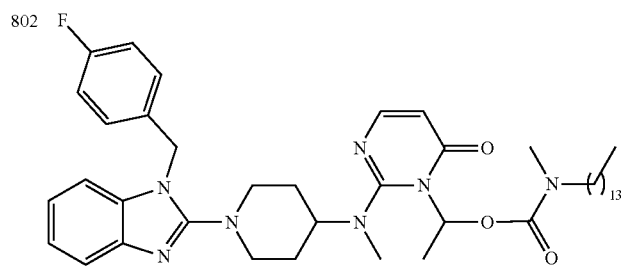 |
| 803 | 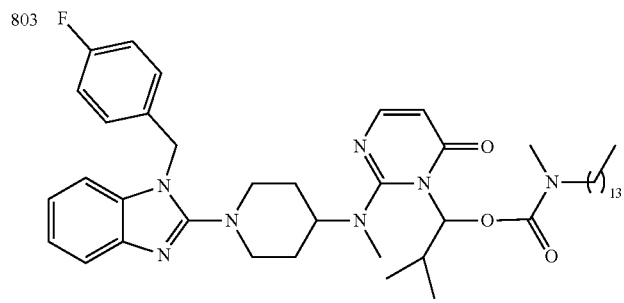 |
| 804 | 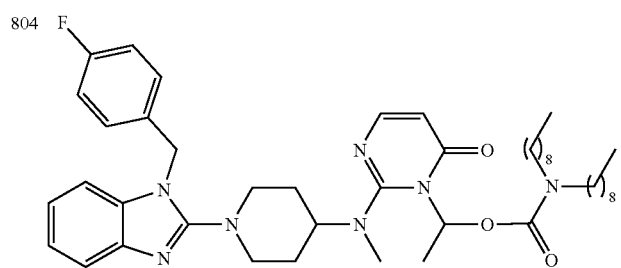 |
| 805 | 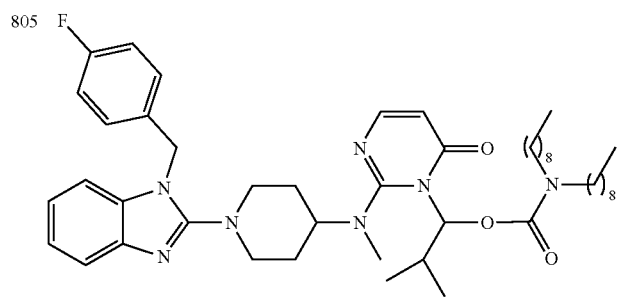 |

TABLE E-continued
| No | Structure |
|---|---|
| 806 | 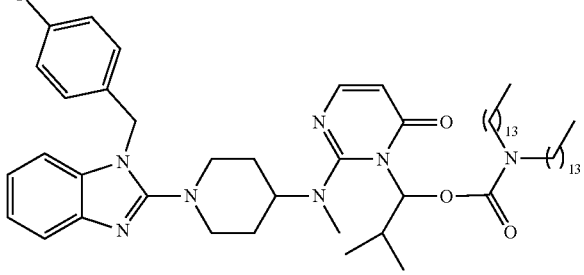 |
| 807 | 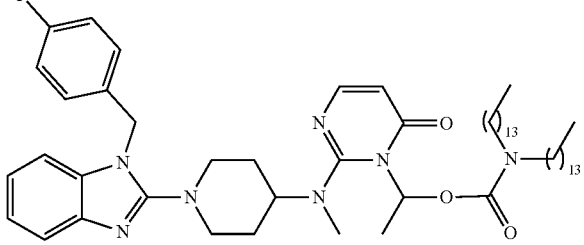 |
| 808 | 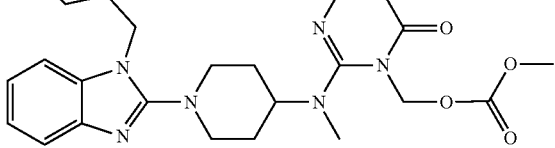 |
| 809 | 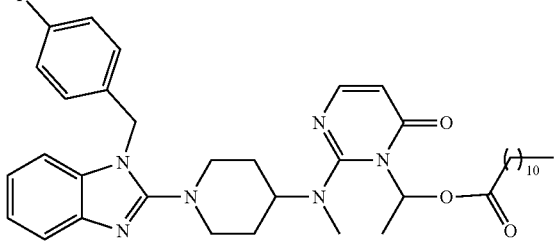 |
| 810 | 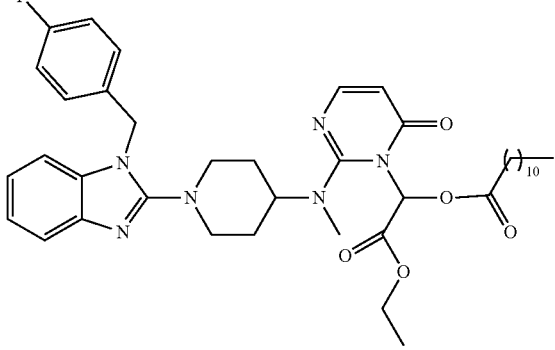 |

TABLE E-continued
| No | Structure |
|---|---|
| 811 | 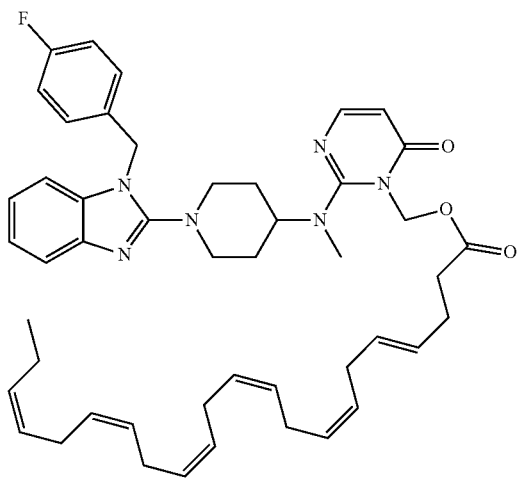 [SMILES: CC/C=C\C/C=C\C/C=C\C/C=C\C/C=C\C/C=C/CCC(=O)OCn1c(N(C)C2CCN(c3nc4ccccc4n3Cc3ccc(F)cc3)CC2)nccc1=O] |
| 812 | 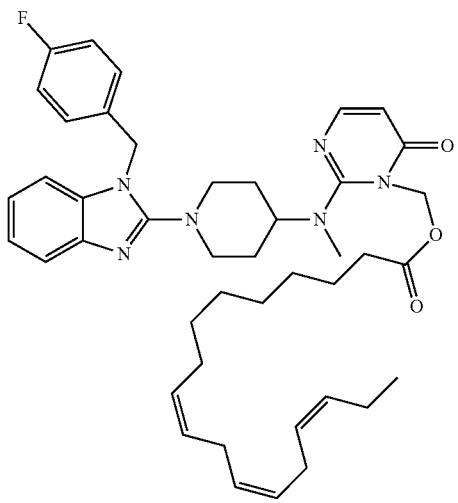 [SMILES: CC/C=C\C/C=C\C/C=C\CCCCCCCC(=O)OCn1c(N(C)C2CCN(c3nc4ccccc4n3Cc3ccc(F)cc3)CC2)nccc1=O] |
| 813 | 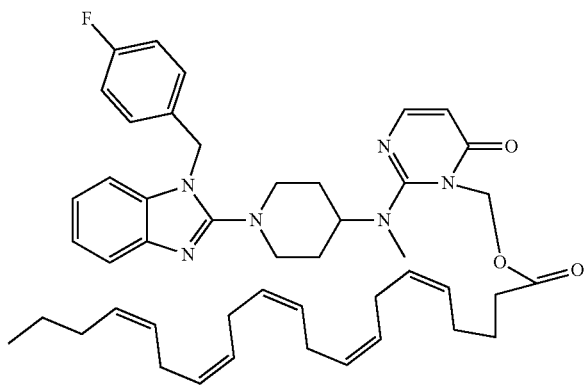 [SMILES: CCC/C=C\C/C=C\C/C=C\C/C=C\C/C=C\CCCC(=O)OCn1c(N(C)C2CCN(c3nc4ccccc4n3Cc3ccc(F)cc3)CC2)nccc1=O] |

TABLE E-continued
| No | Structure |
|----|-----------|
| 814 | 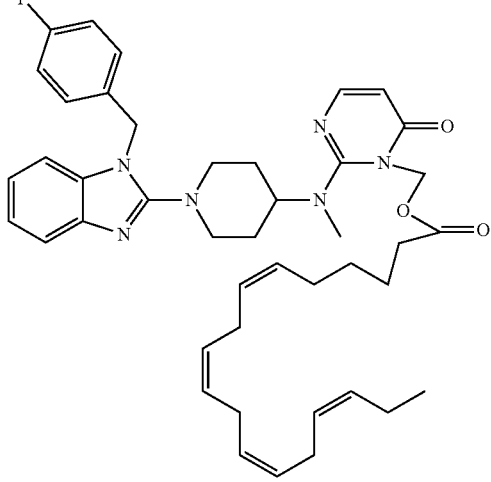 |
| 815 | 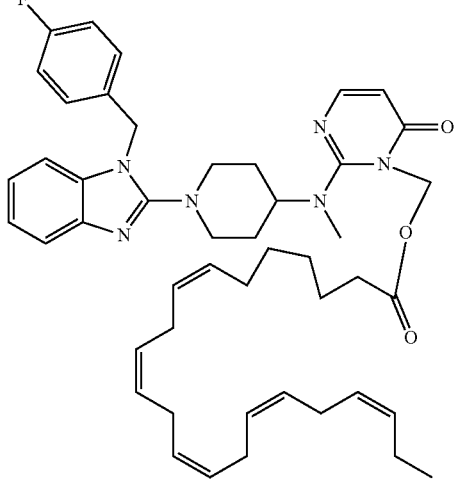 |
| 816 | 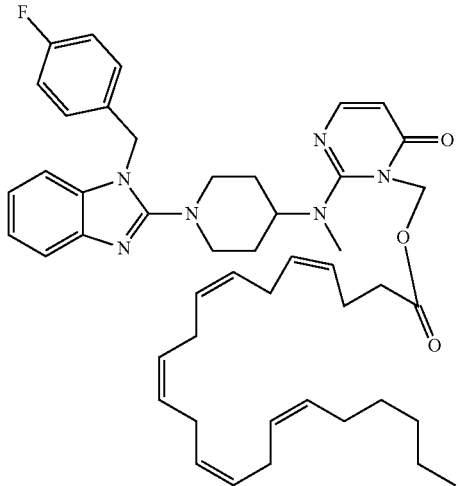 [SMILES: CCCCC/C=C\C/C=C\C/C=C\C/C=C\C/C=C\CCC(=O)OCn1c(N(C)C2CCN(c3nc4ccccc4n3Cc3ccc(F)cc3)CC2)nccc1=O] |

TABLE E-continued
| No | Structure |
|---|---|
| 817 | 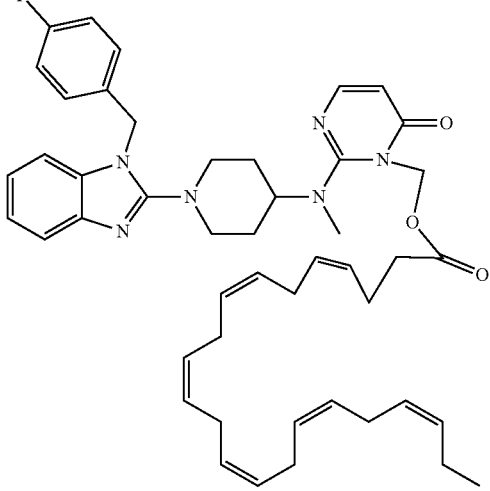 |
TABLE F
| No | Structure |
|---|---|
| 900 | 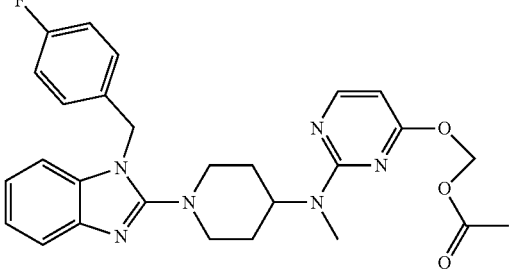 |
| 901 | 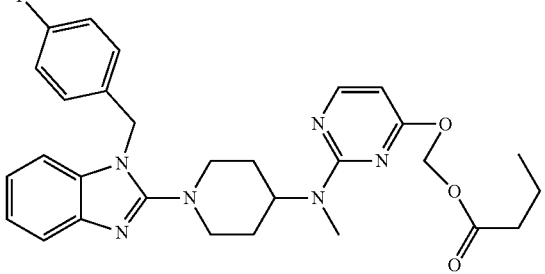 |
| 902 | 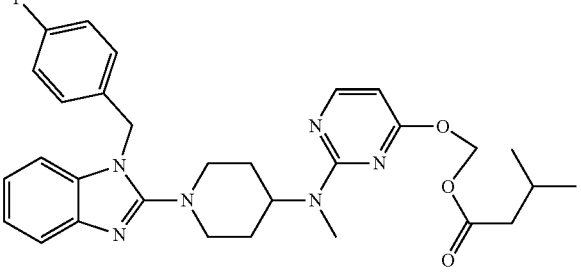 |

TABLE F-continued
| No | Structure |
|---|---|
| 903 | 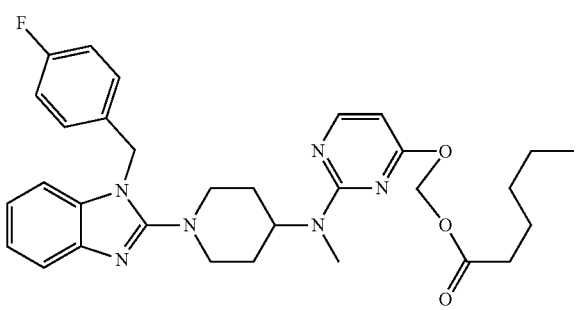 [SMILES: CCCCCC(=O)OCOc1ccnc(N(C)C2CCN(c3nc4ccccc4n3Cc3ccc(F)cc3)CC2)n1] |
| 904 | 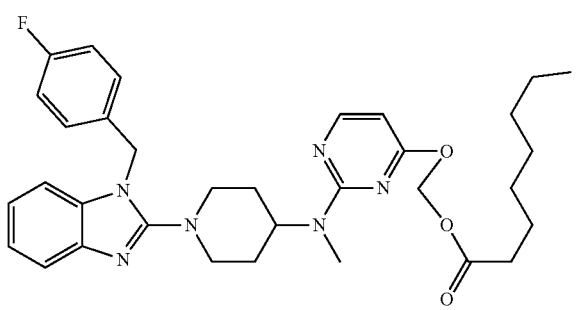 [SMILES: CCCCCCCC(=O)OCOc1ccnc(N(C)C2CCN(c3nc4ccccc4n3Cc3ccc(F)cc3)CC2)n1] |
| 905 | 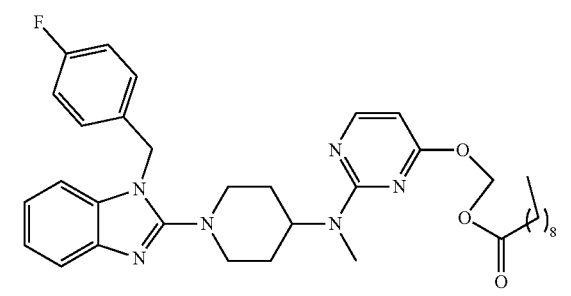 |
| 906 | 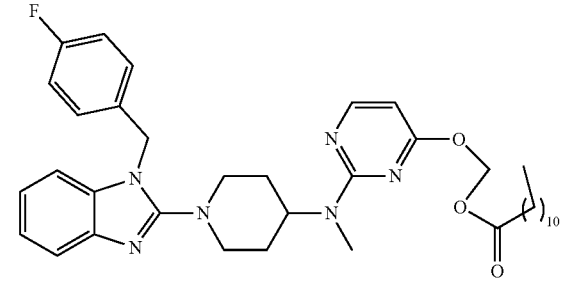 |
| 907 | 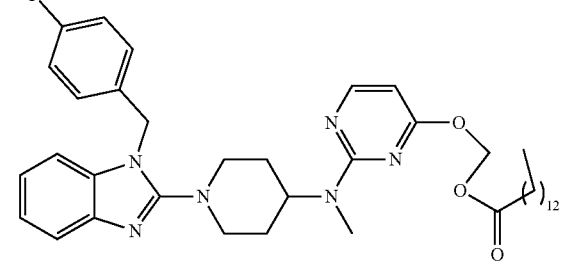 |

TABLE F-continued
| No | Structure |
|---|---|
| 908 | 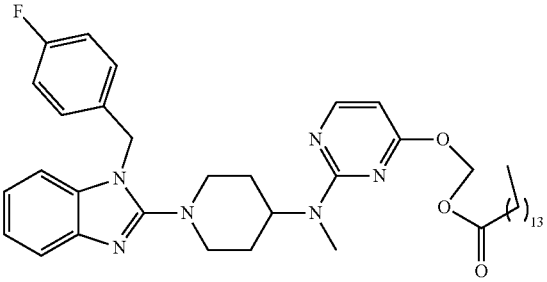 |
| 909 | 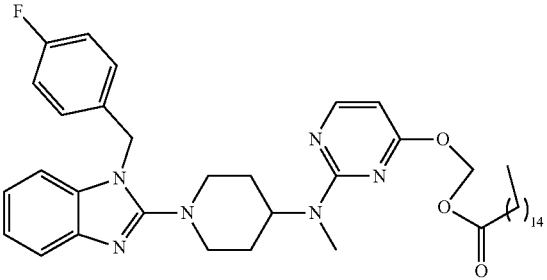 |
| 910 | 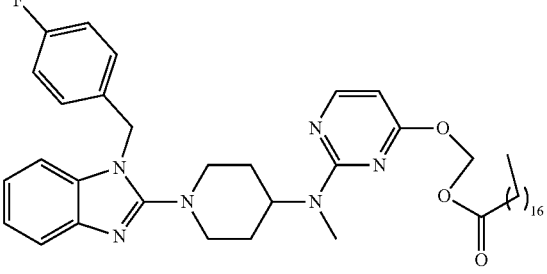 |
| 911 | 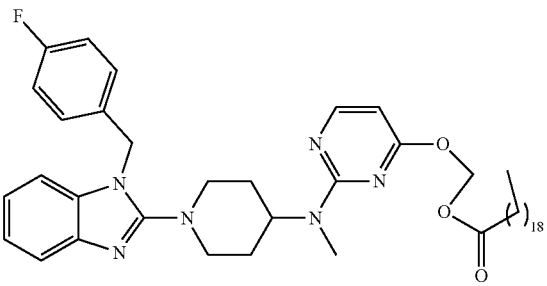 |
| 912 | 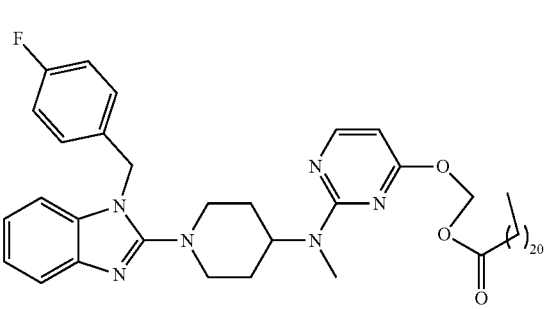 |

TABLE F-continued
| No | Structure |
|---|---|
| 913 | 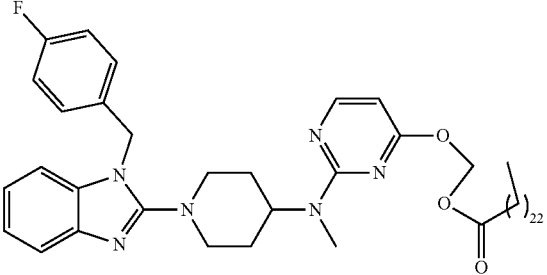 |
| 914 | 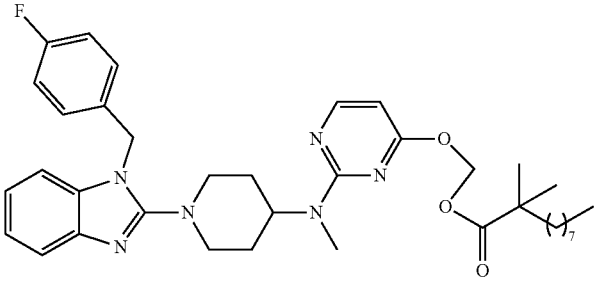 |
| 915 | 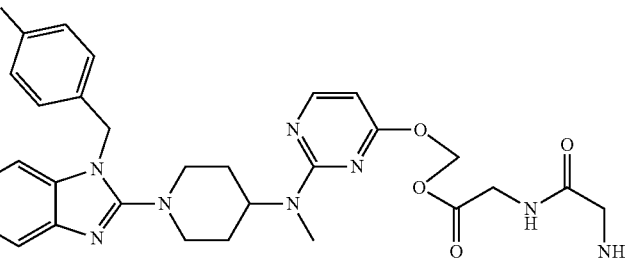 |
| 916 | 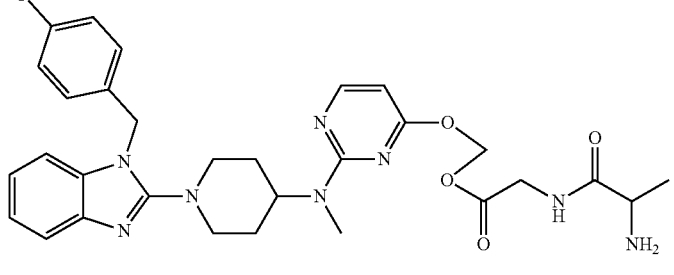 |
| 917 | 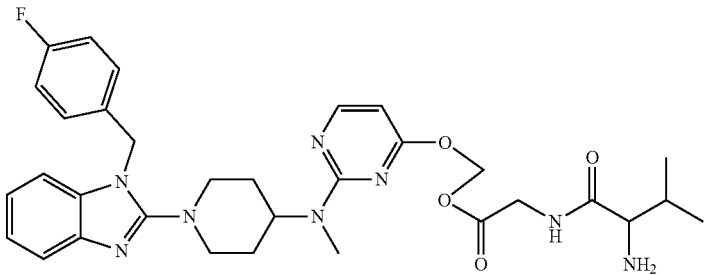 [SMILES: CC(C)C(N)C(=O)NCC(=O)OCOc1ccnc(N(C)C2CCN(c3nc4ccccc4n3Cc3ccc(F)cc3)CC2)n1] |

TABLE F-continued

| No | Structure |
|---|---|
| 918 | 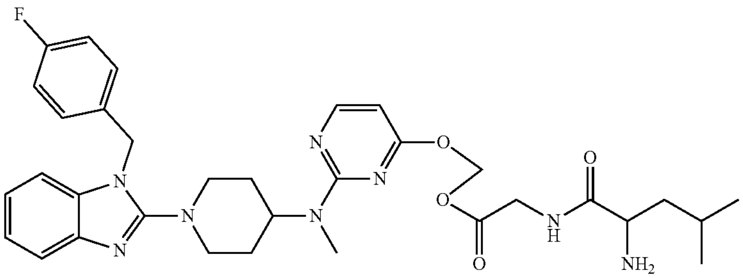 [SMILES: CC(C)CC(N)C(=O)NCC(=O)OCOc1ccnc(N(C)C2CCN(c3nc4ccccc4n3Cc3ccc(F)cc3)CC2)n1] |
| 919 | 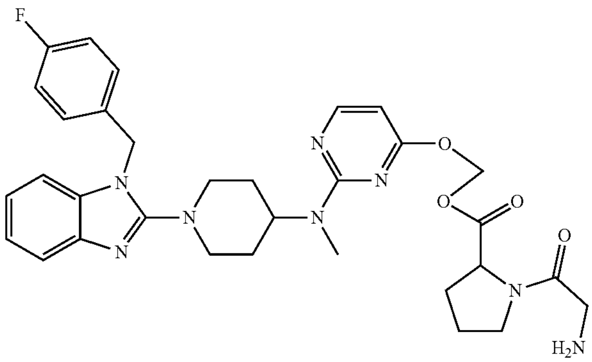 [SMILES: CN(c1nccc(OCOC(=O)C2CCCN2C(=O)CN)n1)C1CCN(c2nc3ccccc3n2Cc2ccc(F)cc2)CC1] |
| 920 | 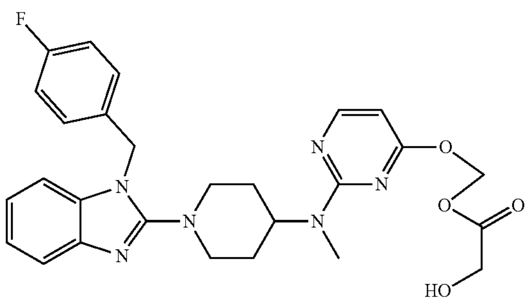 [SMILES: CN(c1nccc(OCOC(=O)CO)n1)C1CCN(c2nc3ccccc3n2Cc2ccc(F)cc2)CC1] |
| 921 | 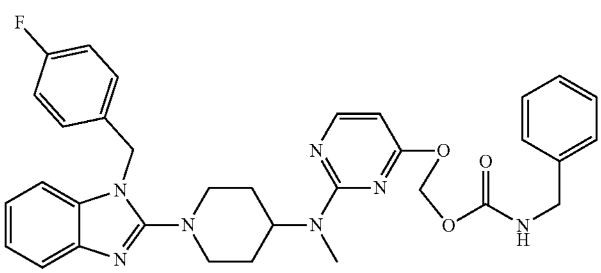 [SMILES: CN(c1nccc(OCOC(=O)NCc2ccccc2)n1)C1CCN(c2nc3ccccc3n2Cc2ccc(F)cc2)CC1] |
| 922 | 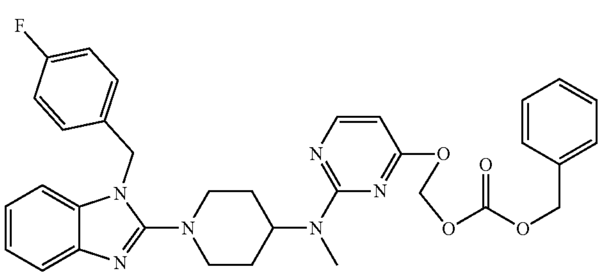 [SMILES: CN(c1nccc(OCOC(=O)OCc2ccccc2)n1)C1CCN(c2nc3ccccc3n2Cc2ccc(F)cc2)CC1] |

| No | Structure |
|---|---|
| 923 | 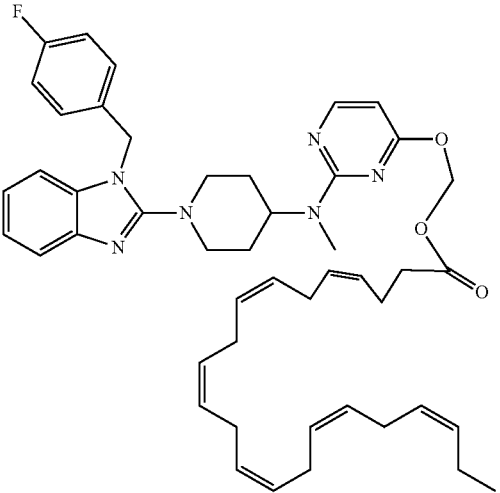 [SMILES: CC/C=C\C/C=C\C/C=C\C/C=C\C/C=C\C/C=C\CCC(=O)OCOc1ccnc(N(C)C2CCN(c3nc4ccccc4n3Cc3ccc(F)cc3)CC2)n1] |
| 924 | 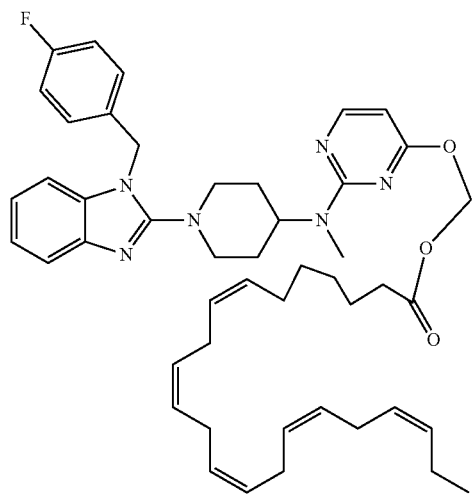 [SMILES: CC/C=C\C/C=C\C/C=C\C/C=C\C/C=C\CCCCCC(=O)OCOc1ccnc(N(C)C2CCN(c3nc4ccccc4n3Cc3ccc(F)cc3)CC2)n1] |
| 925 | 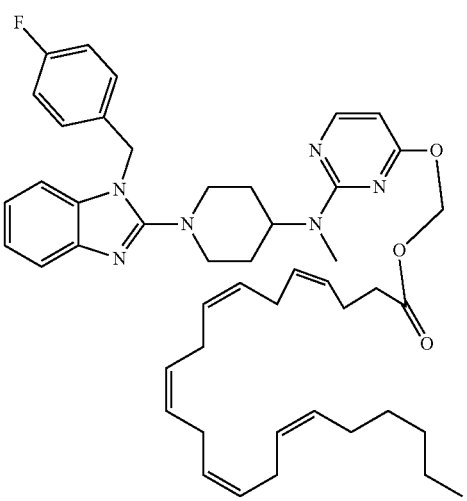 [SMILES: CCCCC/C=C\C/C=C\C/C=C\C/C=C\C/C=C\CCC(=O)OCOc1ccnc(N(C)C2CCN(c3nc4ccccc4n3Cc3ccc(F)cc3)CC2)n1] |

TABLE F-continued
| No | Structure |
|---|---|
| 926 | 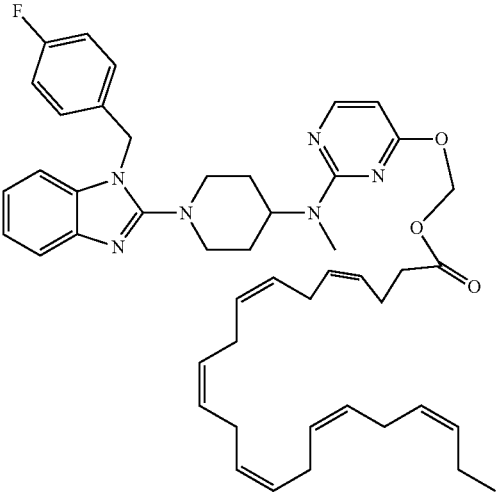 [SMILES: CC/C=C\C/C=C\C/C=C\C/C=C\C/C=C\C/C=C\CCC(=O)OCOc1ccnc(N(C)C2CCN(c3nc4ccccc4n3Cc3ccc(F)cc3)CC2)n1] |
| 927 | 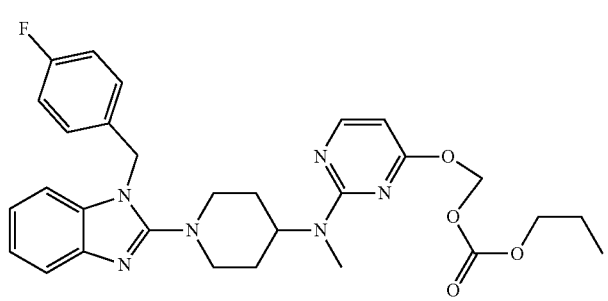 [SMILES: CCCOC(=O)OCOc1ccnc(N(C)C2CCN(c3nc4ccccc4n3Cc3ccc(F)cc3)CC2)n1] |
| 928 | 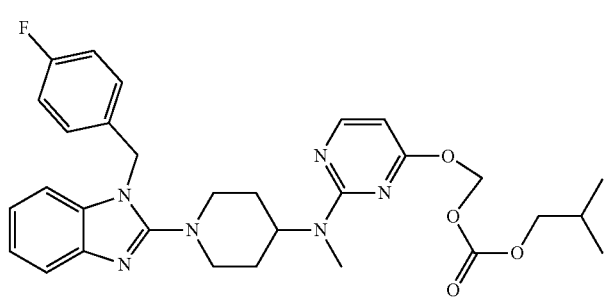 [SMILES: CC(C)COC(=O)OCOc1ccnc(N(C)C2CCN(c3nc4ccccc4n3Cc3ccc(F)cc3)CC2)n1] |
| 929 | 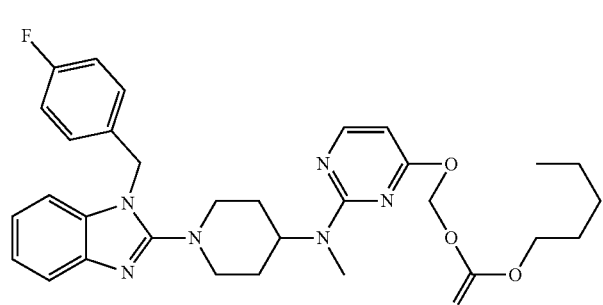 |

TABLE F-continued
| No | Structure |
|---|---|
| 930 | 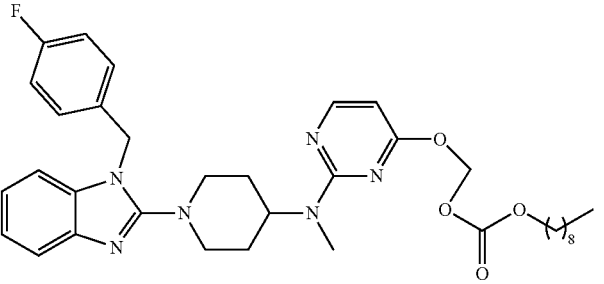 |
| 931 | 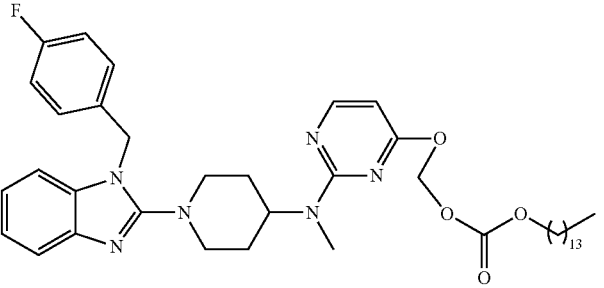 |
| 932 | 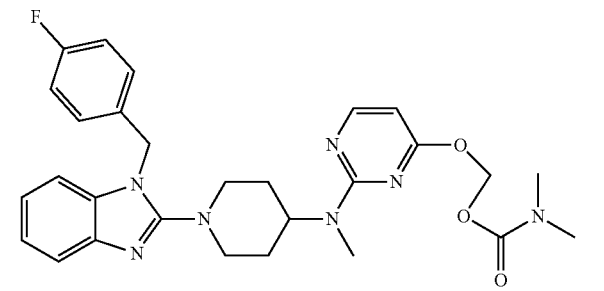 [SMILES: CN(C)C(=O)OCOc1ccnc(N(C)C2CCN(c3nc4ccccc4n3Cc3ccc(F)cc3)CC2)n1] |
| 933 | 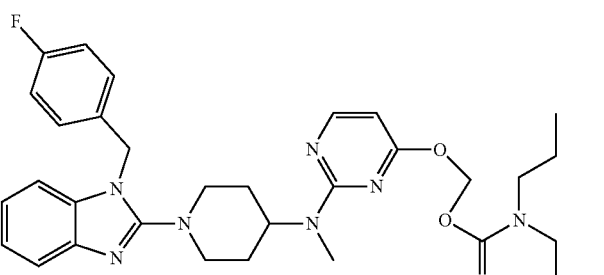 |
| 934 | 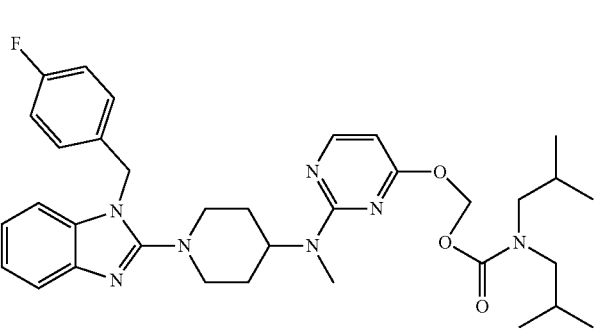 [SMILES: CC(C)CN(CC(C)C)C(=O)OCOc1ccnc(N(C)C2CCN(c3nc4ccccc4n3Cc3ccc(F)cc3)CC2)n1] |

TABLE F-continued

| No | Structure |
|---|---|
| 935 | 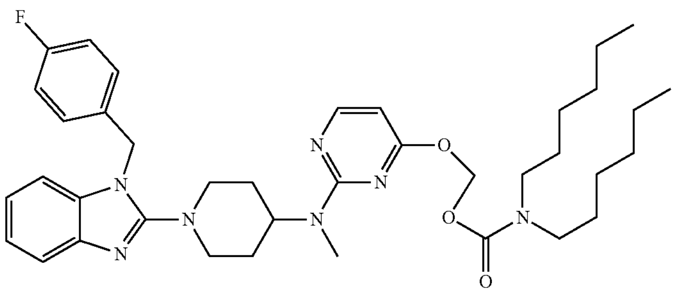 [SMILES: CCCCCCN(CCCCCC)C(=O)OCOc1ccnc(N(C)C2CCN(c3nc4ccccc4n3Cc3ccc(F)cc3)CC2)n1] |
| 936 | 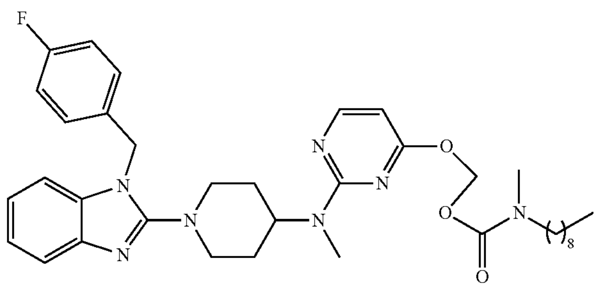 |
| 937 | 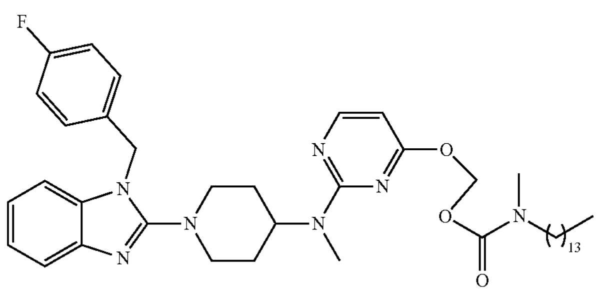 |
| 938 | 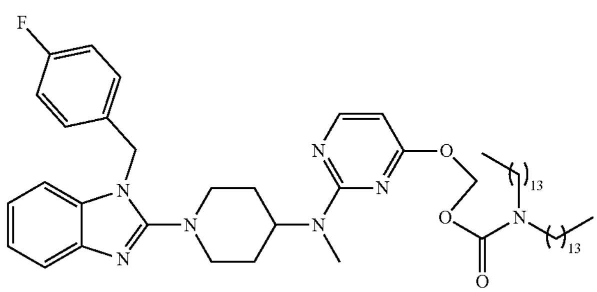 |
| 939 | 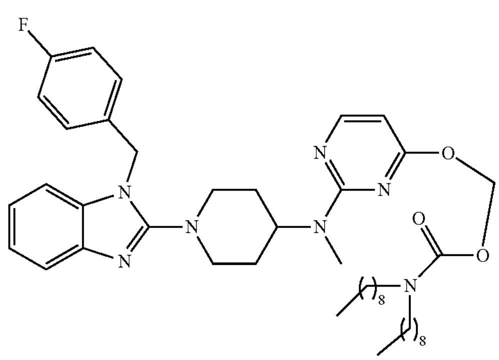 |

TABLE F-continued
| No | Structure |
|---|---|
| 940 | 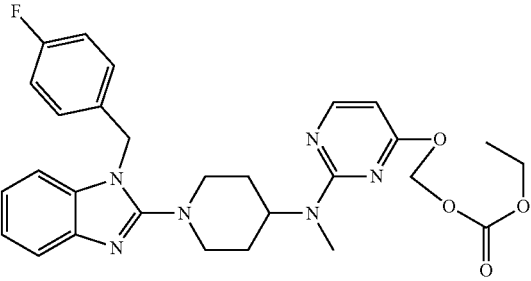 [SMILES: CCOC(=O)OCOc1ccnc(N(C)C2CCN(c3nc4ccccc4n3Cc3ccc(F)cc3)CC2)n1] |
| 941 | 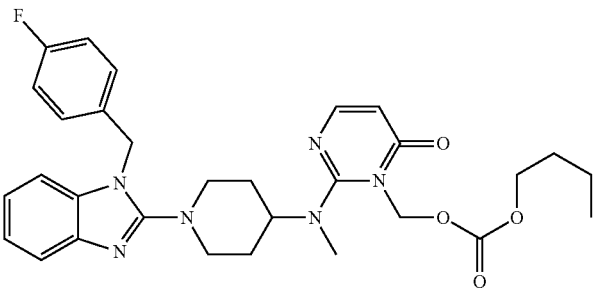 |
| 942 | 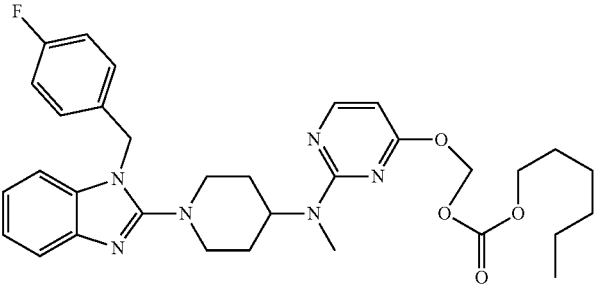 [SMILES: CCCCCCOC(=O)OCOc1ccnc(N(C)C2CCN(c3nc4ccccc4n3Cc3ccc(F)cc3)CC2)n1] |
| 943 | 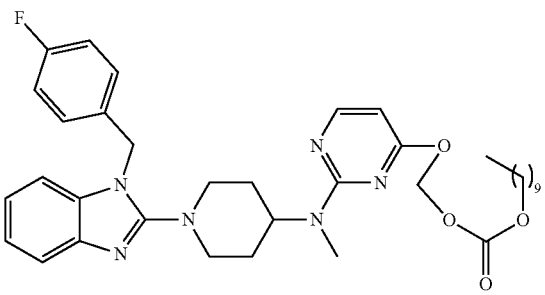 |
| 944 | 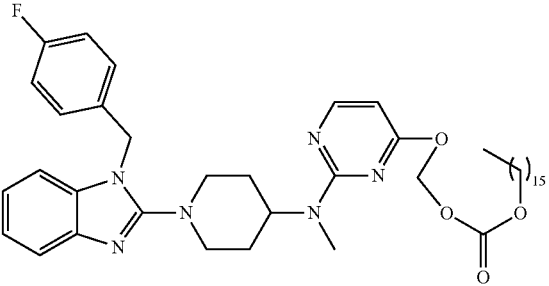 |

TABLE F-continued
| No | Structure |
|---|---|
| 945 | 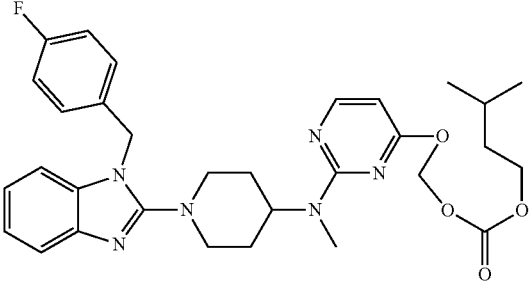 [SMILES: CC(C)CCOC(=O)OCOc1ccnc(N(C)C2CCN(c3nc4ccccc4n3Cc3ccc(F)cc3)CC2)n1] |
| 946 | 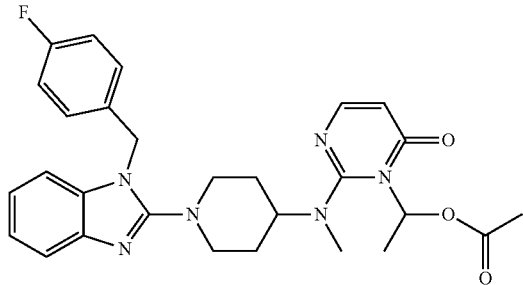 |
| 947 | 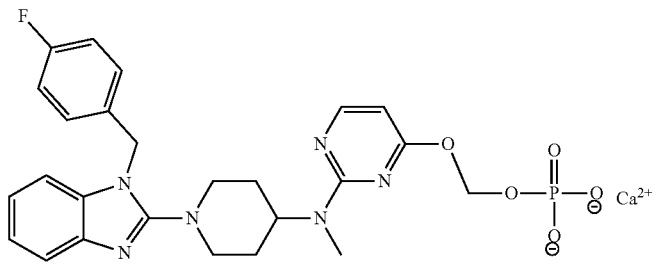 [SMILES: CN(c1nccc(OCOP(=O)([O-])[O-])n1)C1CCN(c2nc3ccccc3n2Cc2ccc(F)cc2)CC1 ; [Ca+2]] |
| 948 | 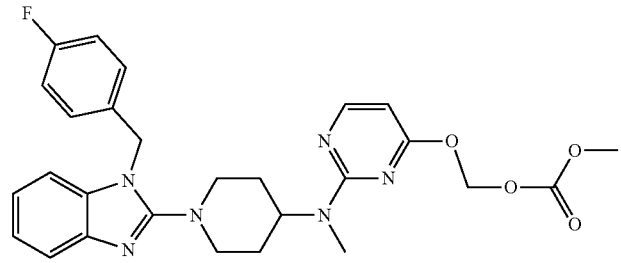 [SMILES: COC(=O)OCOc1ccnc(N(C)C2CCN(c3nc4ccccc4n3Cc3ccc(F)cc3)CC2)n1] |
| 949 | 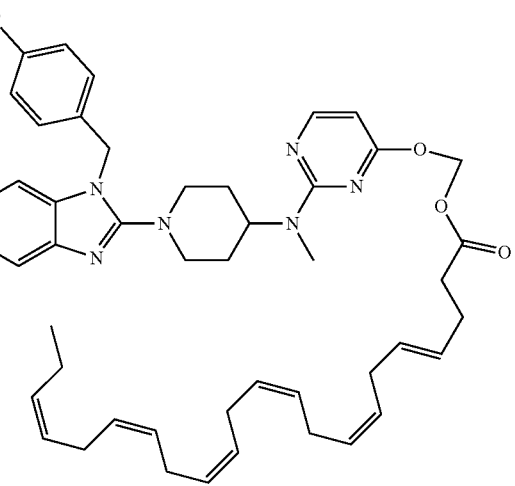 |

TABLE F-continued
| No | Structure |
|---|---|
| 950 | 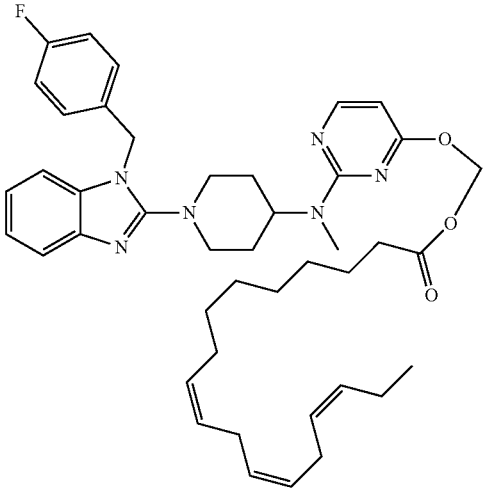 [SMILES: CC/C=C\C/C=C\C/C=C\CCCCCCCC(=O)OCOc1ccnc(N(C)C2CCN(c3nc4ccccc4n3Cc3ccc(F)cc3)CC2)n1] |
| 951 | 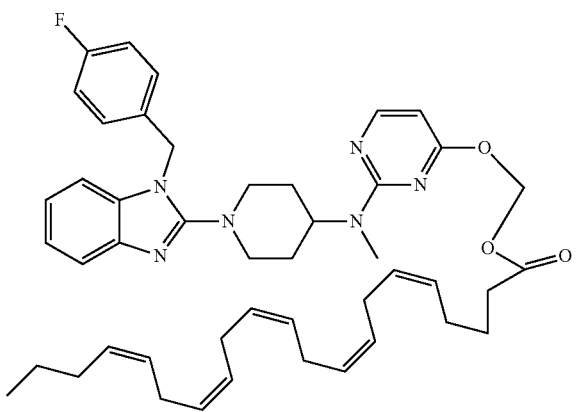 [SMILES: CCC/C=C\C/C=C\C/C=C\C/C=C\C/C=C\CCCC(=O)OCOc1ccnc(N(C)C2CCN(c3nc4ccccc4n3Cc3ccc(F)cc3)CC2)n1] |
| 952 | 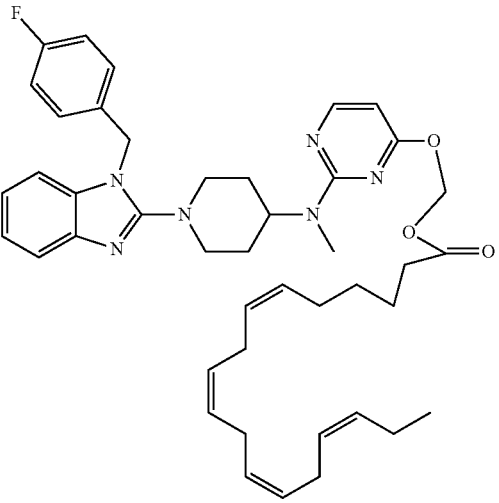 [SMILES: CC/C=C\C/C=C\C/C=C\C/C=C\CCCCC(=O)OCOc1ccnc(N(C)C2CCN(c3nc4ccccc4n3Cc3ccc(F)cc3)CC2)n1] |

TABLE F-continued

| No | Structure |
|----|-----------|
| 953 | 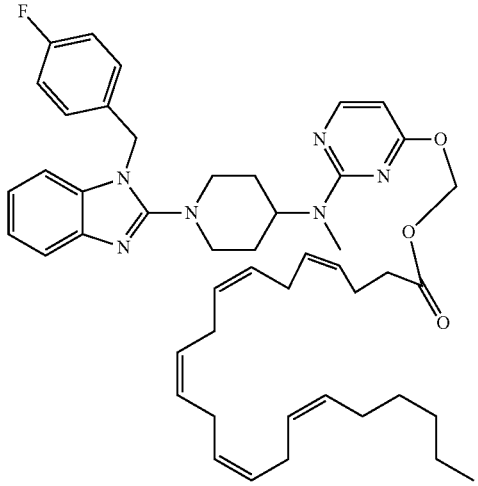 [SMILES: CCCCC/C=C\C/C=C\C/C=C\C/C=C\C/C=C\CCC(=O)OCOc1ccnc(N(C)C2CCN(c3nc4ccccc4n3Cc3ccc(F)cc3)CC2)n1] |

Compounds of formula IX, X, XI, XII and in particular compounds of tables A-D are useful for the treatment of neurological and psychiatric disorders including schizophrenia, mania, anxiety and bipolar disease. These compounds provide sustained release of parent pharmacophores by cleavage of the labile moiety, $R_1$. As such, the compounds of formula IX, X, XI, XII and in particular compounds of tables A-D are useful for the treatment of neurological disorders by providing sustained release of parent drugs.

In another embodiment, compounds of the present invention are represented by formula XIII or XIV as illustrated below, or its geometric isomers, enantiomers, diastereomers, racemates, pharmaceutically acceptable salts and solvates thereof:

Formula XIII

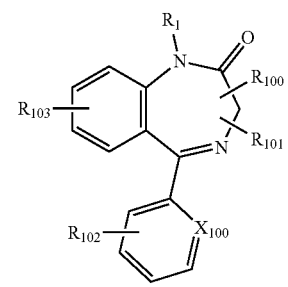

Formula XIV

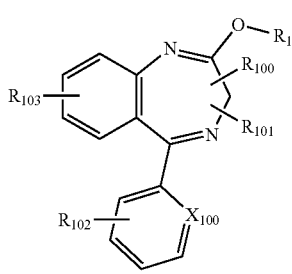

wherein $R_{100}$, $R_{101}$, $R_{102}$, and $R_{103}$ are independently selected from absent, hydrogen, halogen, —$OR_{10}$, —$SR_{10}$, —$NR_{10}R_{11}$—, optionally substituted aliphatic, optionally substituted aryl or aryl or optionally substituted heterocyclyl;

alternatively, two $R_{100}$, and $R_{101}$ together with the atoms they are attached and any intervening atoms form an optionally substituted ring; and, $X_{100}$ is —CH— or —N—.

A preferred embodiment is a compound selected from Table XIII-XIV. A more preferred embodiment is a compound from Table XIII-XIV wherein $R_1$ is selected from tables 1-4.

TABLE XIII-XIV

| | |
|---|---|
| 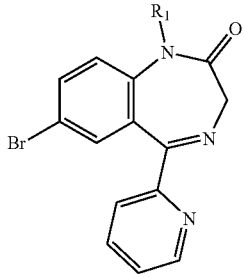 | 1 |
| 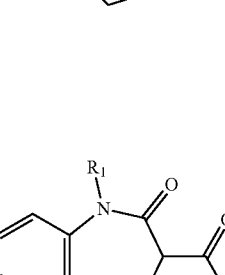 | 2 |

TABLE XIII-XIV-continued

TABLE XIII-XIV-continued

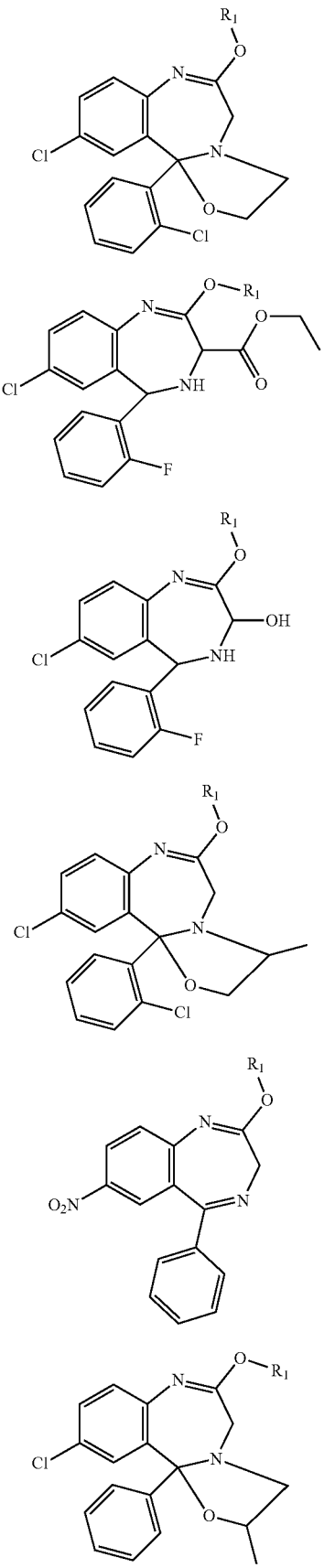

TABLE XIII-XIV-continued

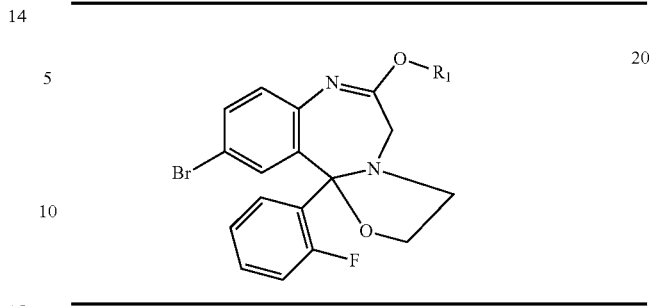

Prodrugs of Acylanilines

In another embodiment, compounds of the present invention are represented by formula XV or XVI as illustrated below, or its geometric isomers, enantiomers, diastereomers, racemates, pharmaceutically acceptable salts and solvates thereof:

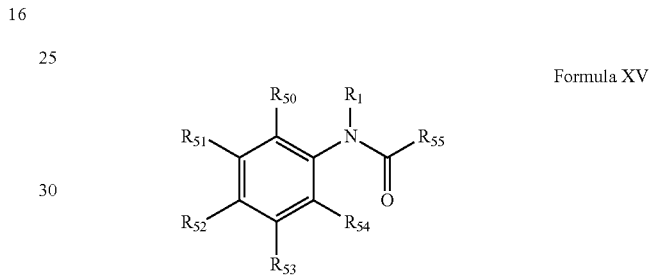

Formula XV

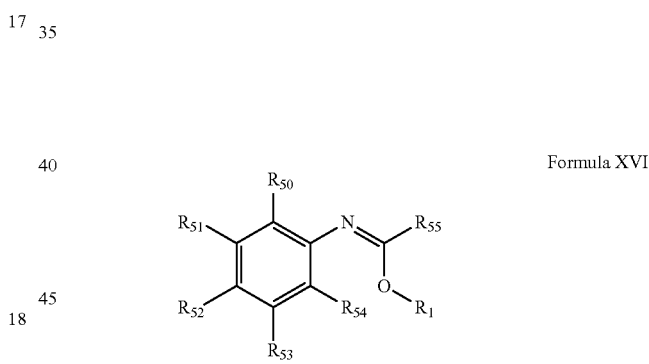

Formula XVI wherein $R_1$ is as defined above;

each $R_{50}$, $R_{51}$, $R_{52}$, $R_{53}$, $R_{54}$ and $R_{55}$ is independently selected from hydrogen, halogen, —$OR_{10}$, —$SR_{10}$, —$NR_{10}R_{11}$—, optionally substituted aliphatic, optionally substituted aryl or aryl or optionally substituted heterocyclyl;

alternatively, two or more $R_{50}$, $R_{51}$, $R_{52}$, $R_{53}$, $R_{54}$ and $R_{55}$ together with the atoms to which they are attached form an optionally substituted ring.

A preferred embodiment is a compound selected from Table XV-XVI. A more preferred embodiment is a compound from Table XV-XVI wherein $R_1$ is selected from tables 1-4.

TABLE XV-XVI
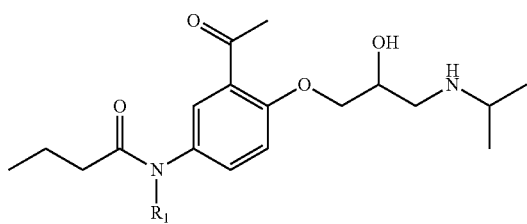
1
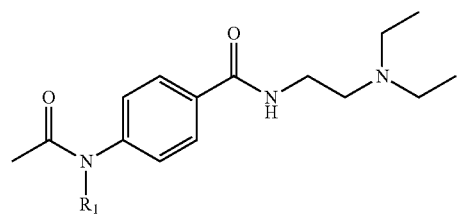
2
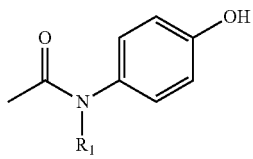
3
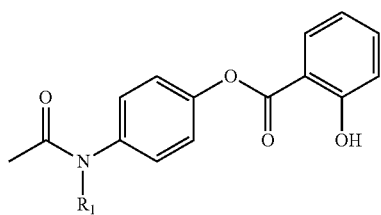
4
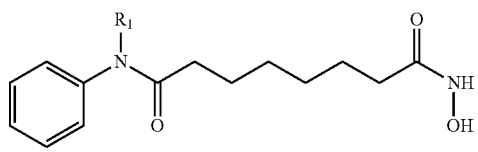
5
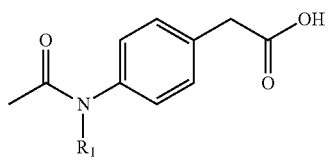
6
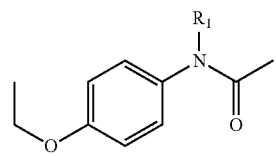
7
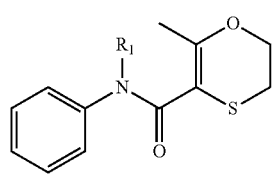
8

TABLE XV-XVI-continued
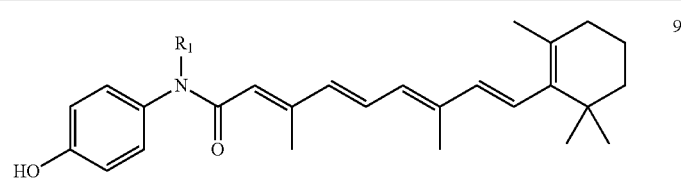
9
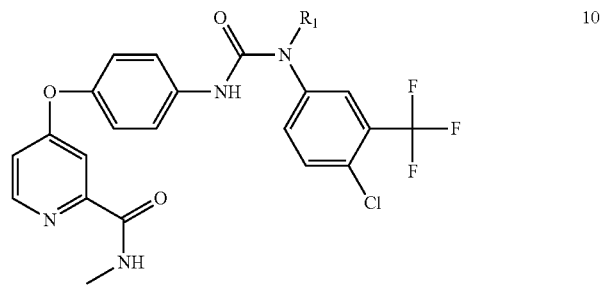
10
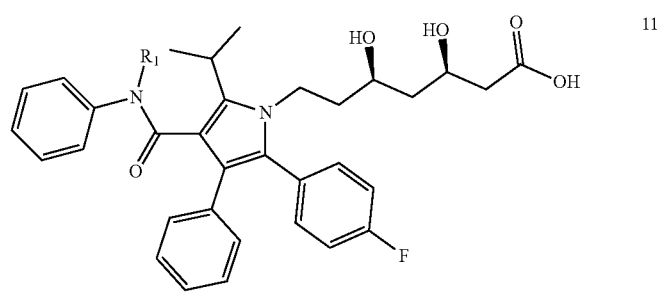
11
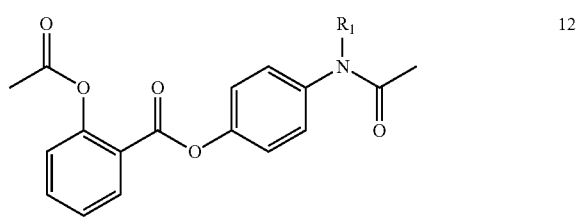
12
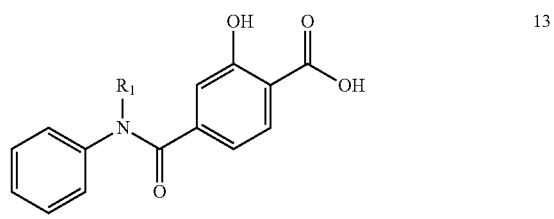
13
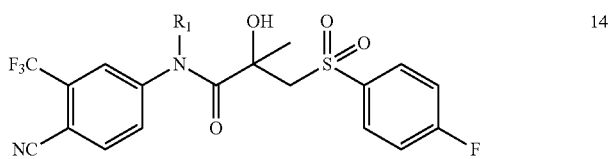
14
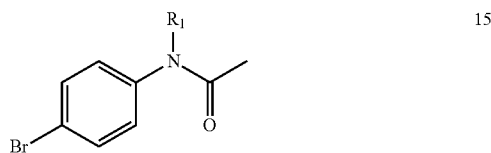
15

TABLE XV-XVI-continued

| | |
|---|---|
| (structure) | 16 |
| (structure) | 17 |
| (structure) | 18 |
| (structure) | 19 |
| (structure) | 20 |
| (structure) | 21 |
| (structure) | 22 |
| (structure) | 23 |

TABLE XV-XVI-continued
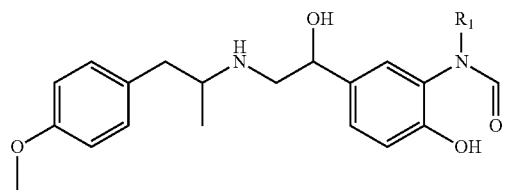
24
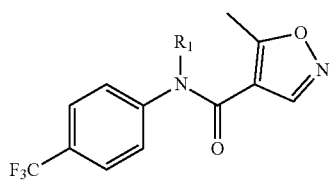
25
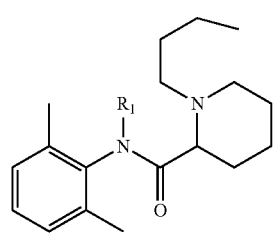
26
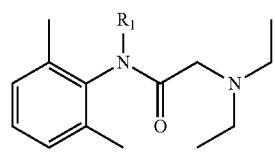
27
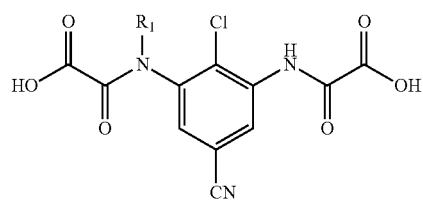
28
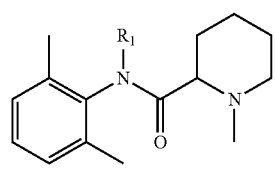
29
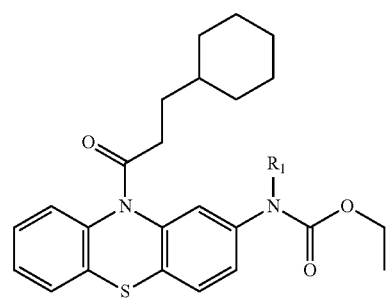
30

TABLE XV-XVI-continued
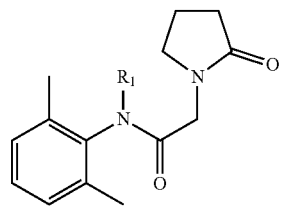
31
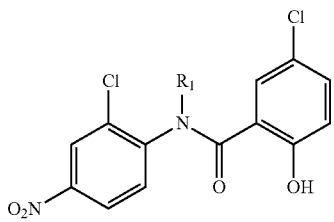
32
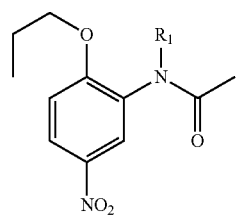
33
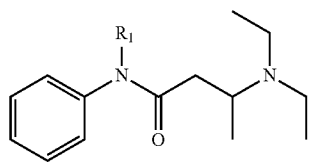
34
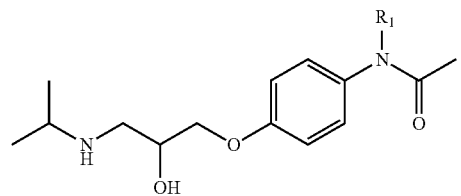
35
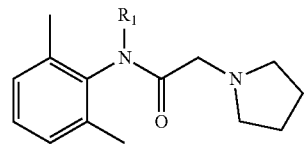
36
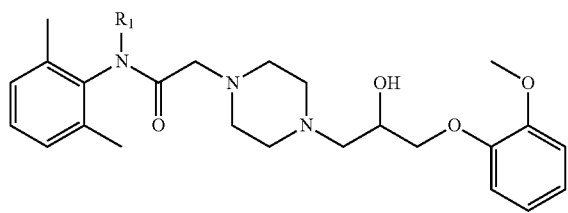
37
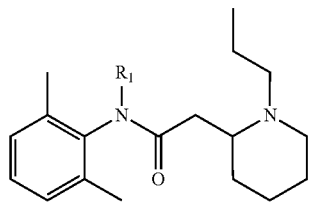
38

TABLE XV-XVI-continued
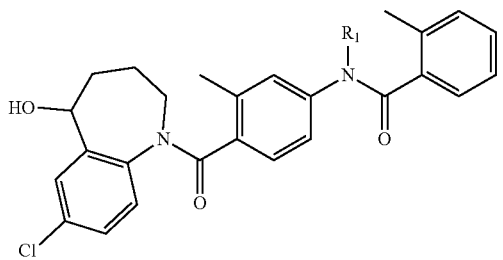 39
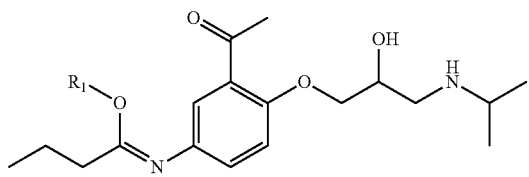 40
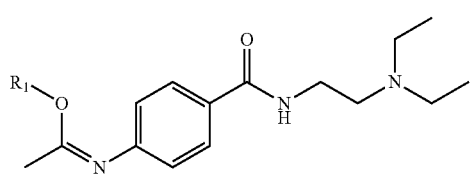 41
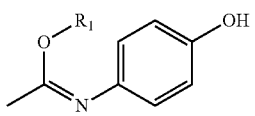 42
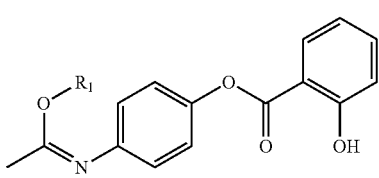 43
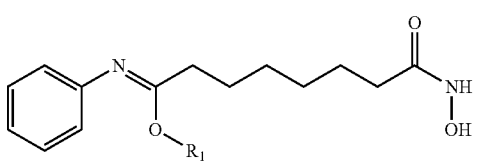 44
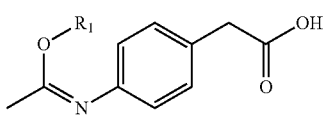 45
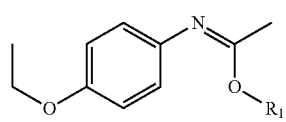 46
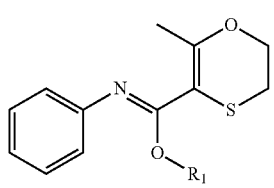 47

TABLE XV-XVI-continued
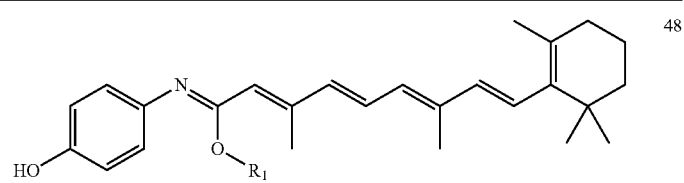
48
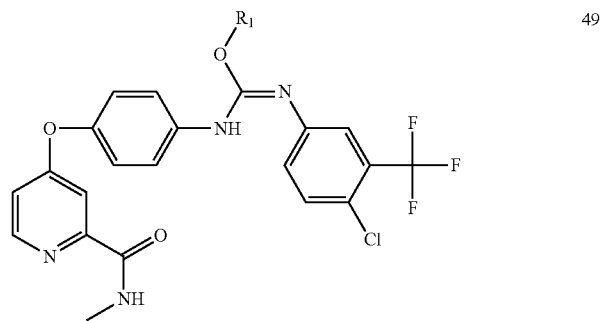
49
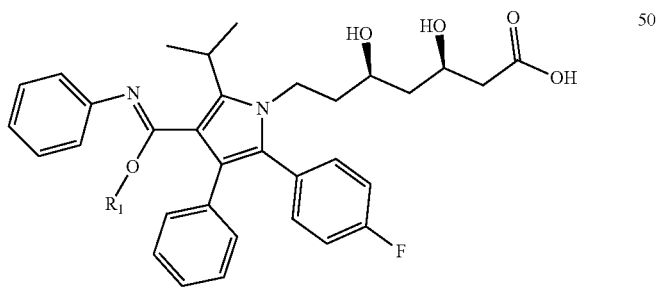
50
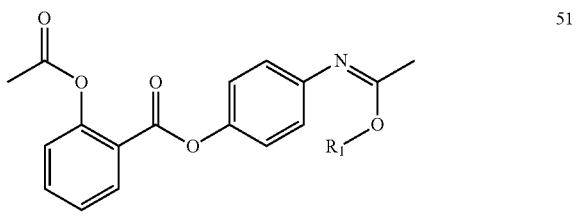
51
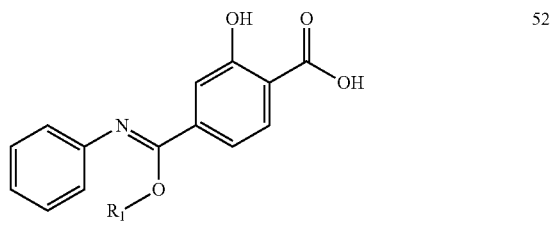
52
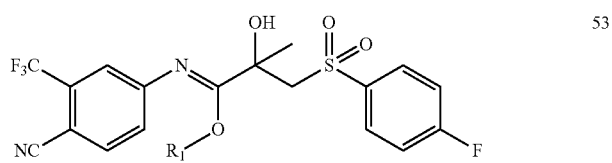
53
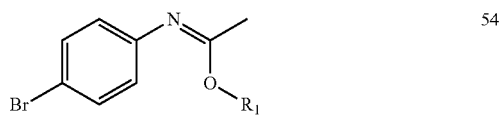
54

TABLE XV-XVI-continued
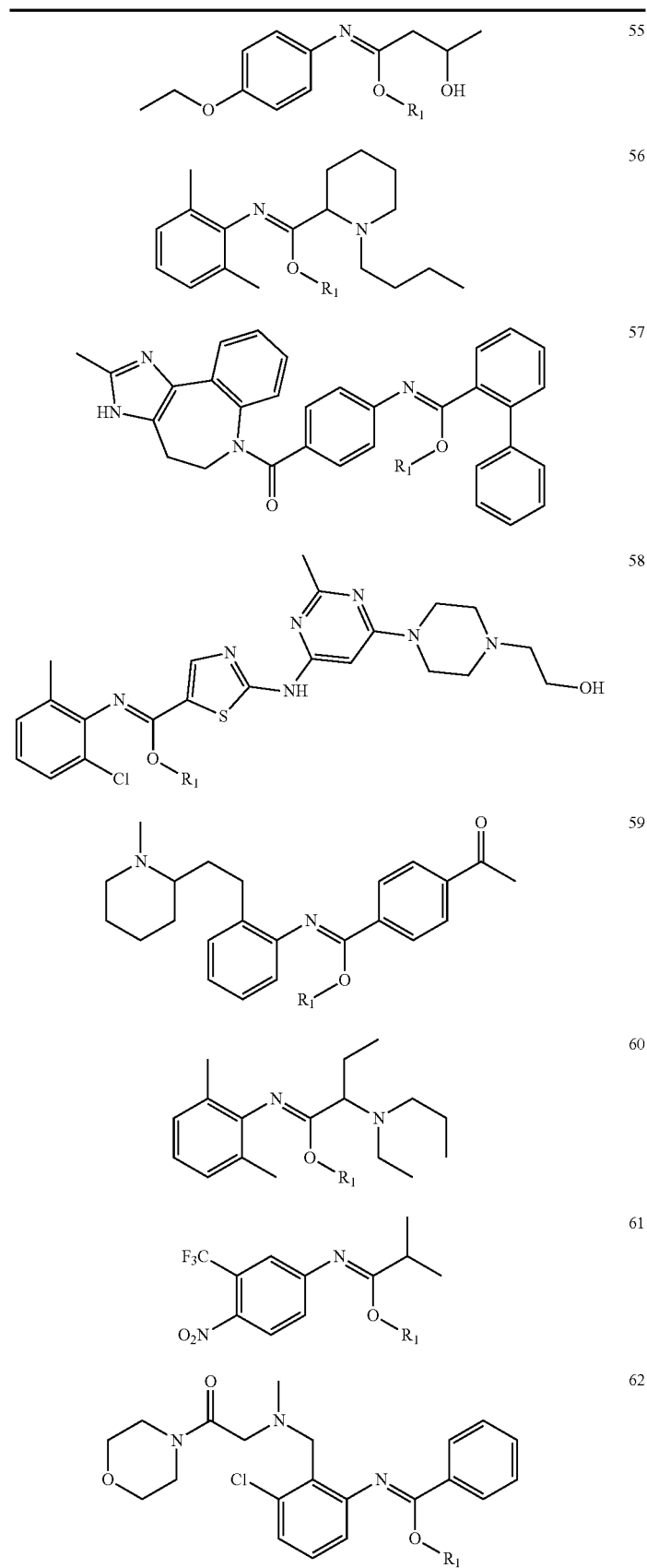

TABLE XV-XVI-continued
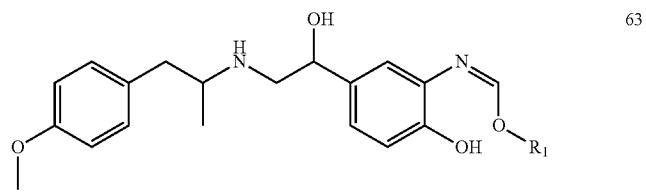
63
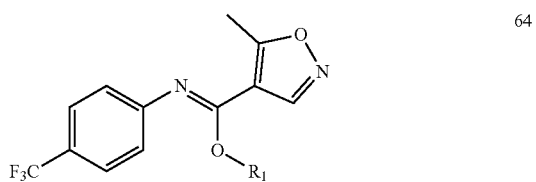
64
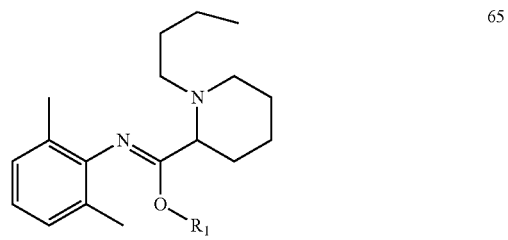
65
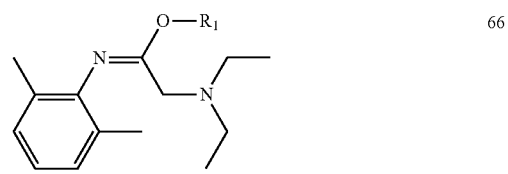
66
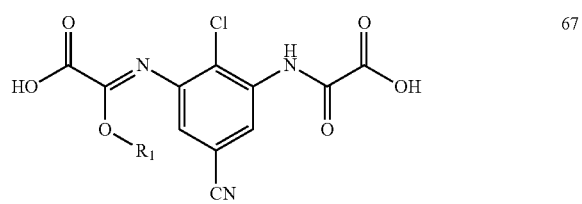
67
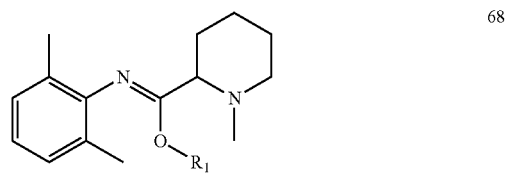
68
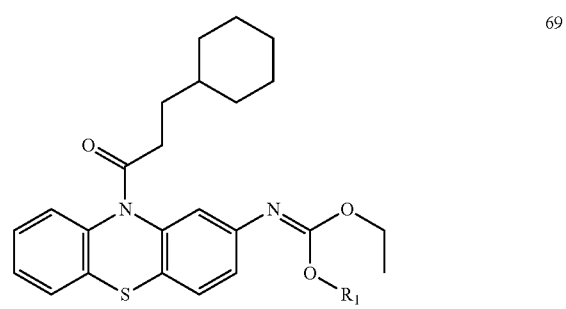
69

TABLE XV-XVI-continued
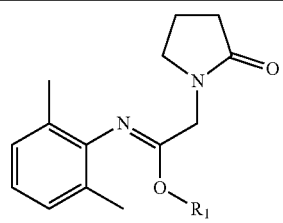
70
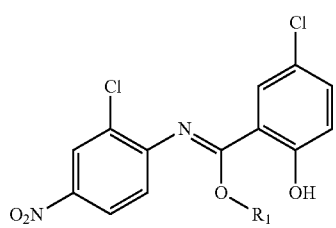
71
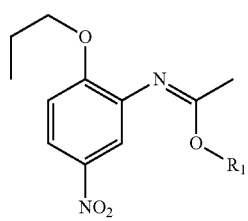
72
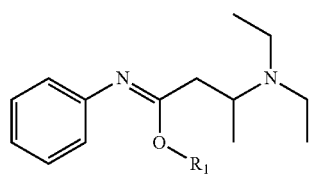
73
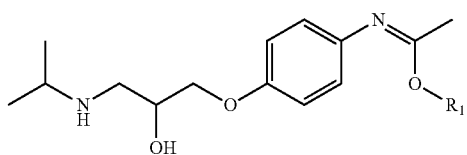
74
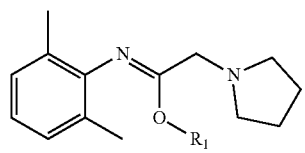
75
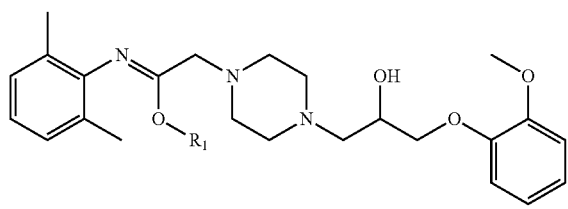
76
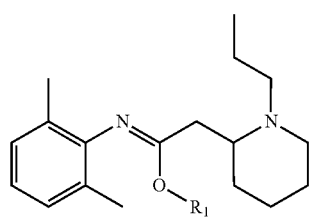
77

TABLE XV-XVI-continued

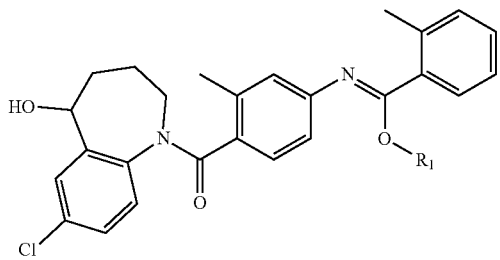

78

Thiazolidinones

In another embodiment, compounds of the present invention are represented by formula XVII, XVIII or XIX as illustrated below, and the geometric isomers, enantiomers, diastereomers, racemates, pharmaceutically acceptable salts and solvates thereof:

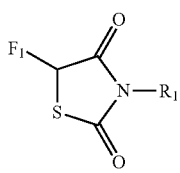

Formula XVII

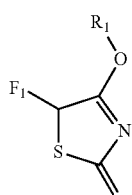

Formula XVIII

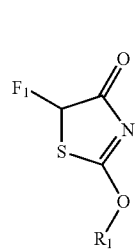

Formula XIX wherein $F_1$ and $R_1$ are as defined above.

A preferred embodiment is a compound of formula XX, XXI or XXII as illustrated below, and the geometric isomers, enantiomers, diastereomers, racemates, pharmaceutically acceptable salts and solvates thereof:

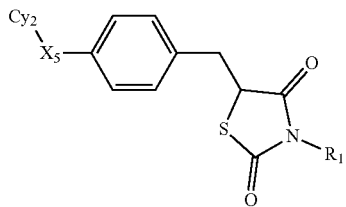

Formula XX

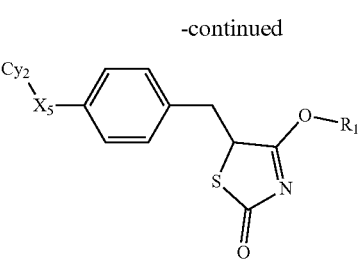

Formula XXI

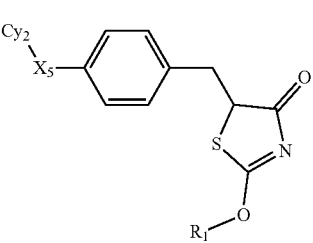

Formula XXII wherein $R_1$ is as defined above;

$Cy_2$ is an optionally substituted heterocyclic ring; and, $X_5$ is selected from absent, —S—, —O—, —S(O)—, —S(O)$_2$—, —N(R$_{10}$)—, —C(O)—, —C(OR$_{10}$)(R$_{11}$)—, —[C(R$_{10}$)(R$_{11}$)]$_v$—, —O[C(R$_{10}$)(R$_{11}$)]$_v$—, —O[C(R$_{10}$)(R$_{11}$)]$_v$O—, —S[C(R$_{10}$)(R$_{11}$)]$_v$O—, —NR$_{12}$[C(R$_{10}$)(R$_{11}$)]$_v$O—, —NR$_{12}$[C(R$_{10}$)(R$_{11}$)]$_v$S—, —S[C(R$_{10}$)(R$_{11}$)]$_v$—, —C(O)[C(R$_{10}$)(R$_{11}$)]$_v$—, and —C(R$_{10}$)=C(R$_{10}$)—; wherein v is 0, 1, 2, 3, 4, 5, 6, 7, 8, 9 or 10.

A preferred embodiment is a compound of formula XXIV as illustrated below, and the geometric isomers, enantiomers, diastereomers, racemates, pharmaceutically acceptable salts and solvates thereof:

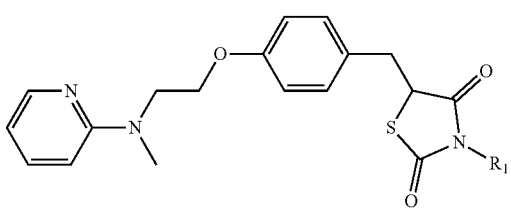

Formula XXIV

In a more preferred embodiment of formula XXIV, $R_1$ is selected from tables 1-4.

A preferred embodiment is a compound of formula XXV as illustrated below, and the geometric isomers, enantiomers, diastereomers, racemates, pharmaceutically acceptable salts and solvates thereof:

Formula XXV

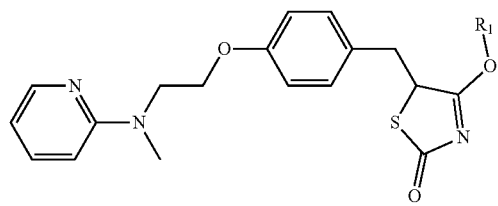

In a more preferred embodiment of formula XXV, R₁ is selected from tables 1-4.

A preferred embodiment is a compound of formula XXVI as illustrated below, and the geometric isomers, enantiomers, diastereomers, racemates, pharmaceutically acceptable salts and solvates thereof:

Formula XXVI

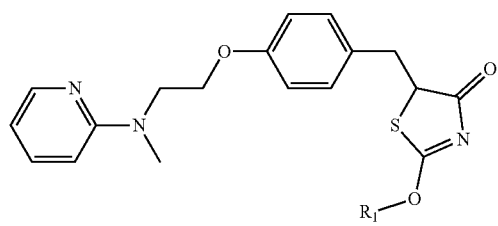

In a more preferred embodiment of formula XXVI, R₁ is selected from tables 1-4.

A preferred embodiment is a compound of formula XXVII as illustrated below, and the geometric isomers, enantiomers, diastereomers, racemates, pharmaceutically acceptable salts and solvates thereof:

Formula XXVII

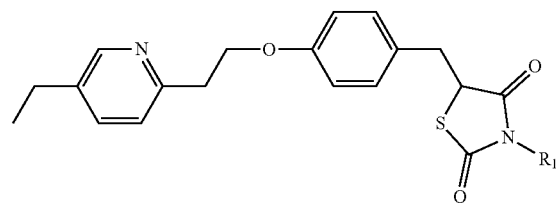

In a more preferred embodiment of formula XXVII, R₁ is selected from tables 1-4.

A preferred embodiment is a compound of formula XXVIII as illustrated below, and the geometric isomers, enantiomers, diastereomers, racemates, pharmaceutically acceptable salts and solvates thereof:

Formula XXVIII

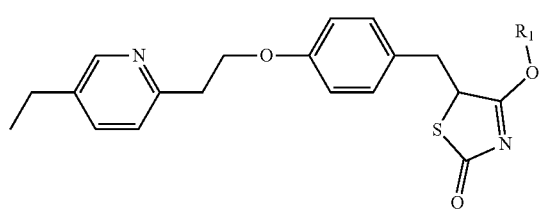

In a more preferred embodiment of formula XXVIII, R₁ is selected from tables 1-4.

A preferred embodiment is a compound of formula XXIX as illustrated below, and the geometric isomers, enantiomers, diastereomers, racemates, pharmaceutically acceptable salts and solvates thereof:

Formula XXIX

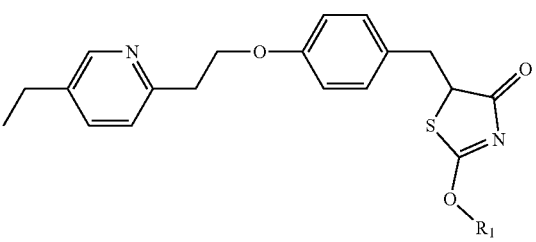

In a more preferred embodiment of formula XXIX, R₁ is selected from tables 1-4.

A preferred embodiment is a compound of formula XXX as illustrated below, and the geometric isomers, enantiomers, diastereomers, racemates, pharmaceutically acceptable salts and solvates thereof:

Formula XXX

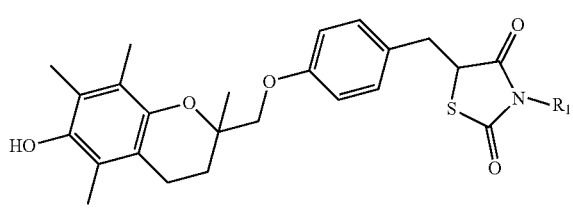

In a more preferred embodiment of formula XXX, R₁ is selected from Table 1.

A preferred embodiment is a compound of formula XXXI as illustrated below, and the geometric isomers, enantiomers, diastereomers, racemates, pharmaceutically acceptable salts and solvates thereof:

Formula XXXI

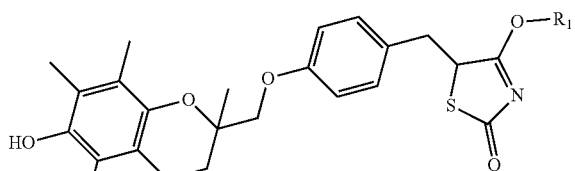

In a more preferred embodiment of formula XXXI, R₁ is selected from Table 1.

A preferred embodiment is a compound of formula XXXII as illustrated below, and the geometric isomers, enantiomers, diastereomers, racemates, pharmaceutically acceptable salts and solvates thereof:

Formula XXXII
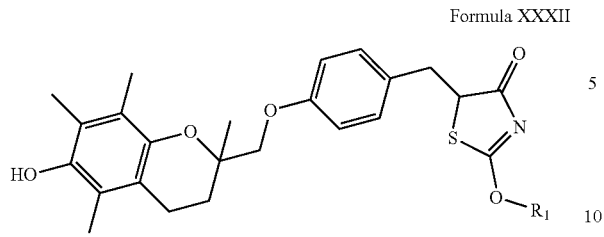
In a more preferred embodiment of formula XXXII, $R_1$ is selected from Table 1.
In a preferred embodiment a compound of formula XX-XXII is selected from table XX-XXII below, wherein $R_1$ is as described above. A more preferred embodiment is a compound of table XX-XXII wherein $R_1$ is selected from tables 1-4.
TABLE XX-XXII
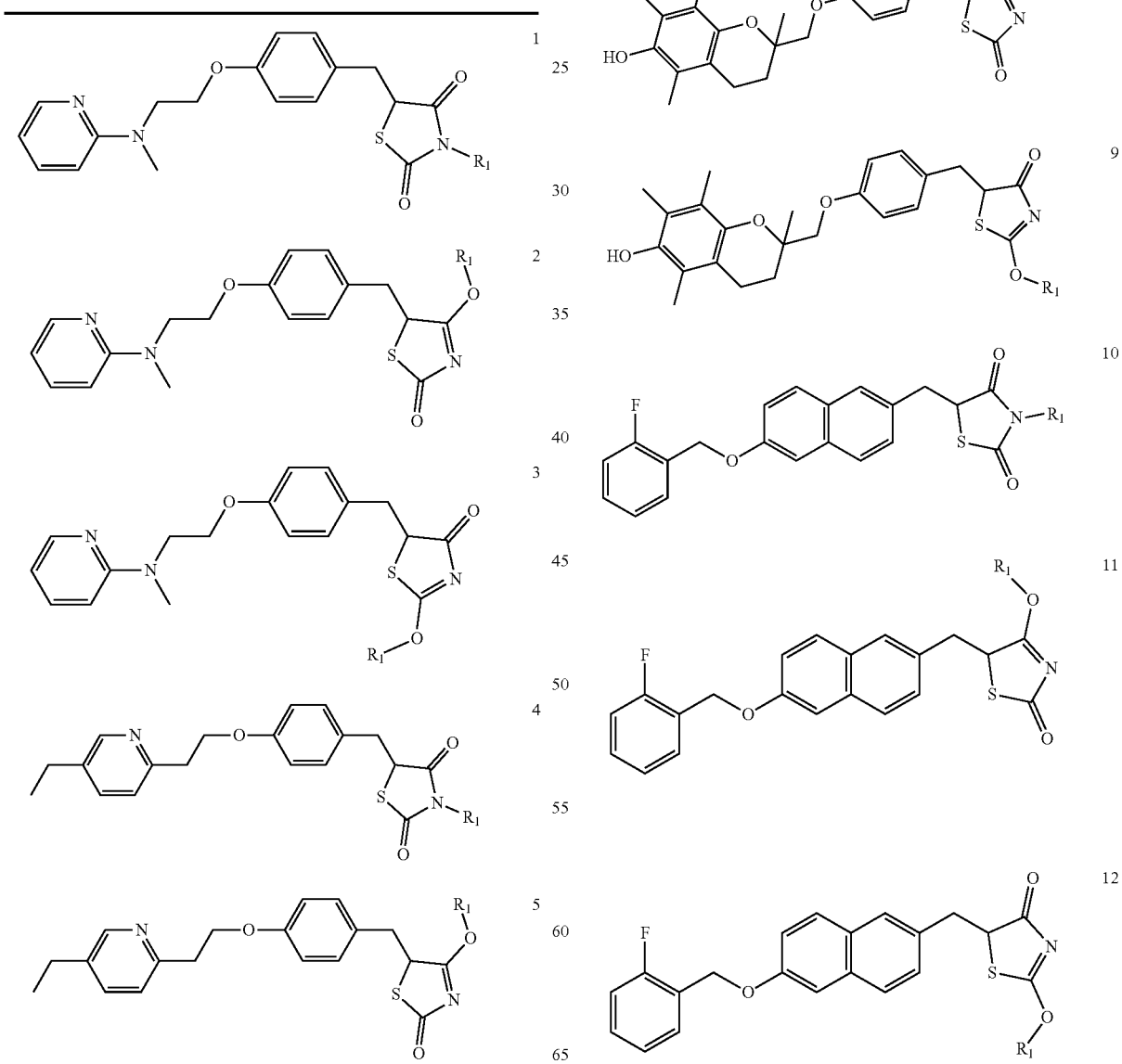

TABLE XX-XXII-continued

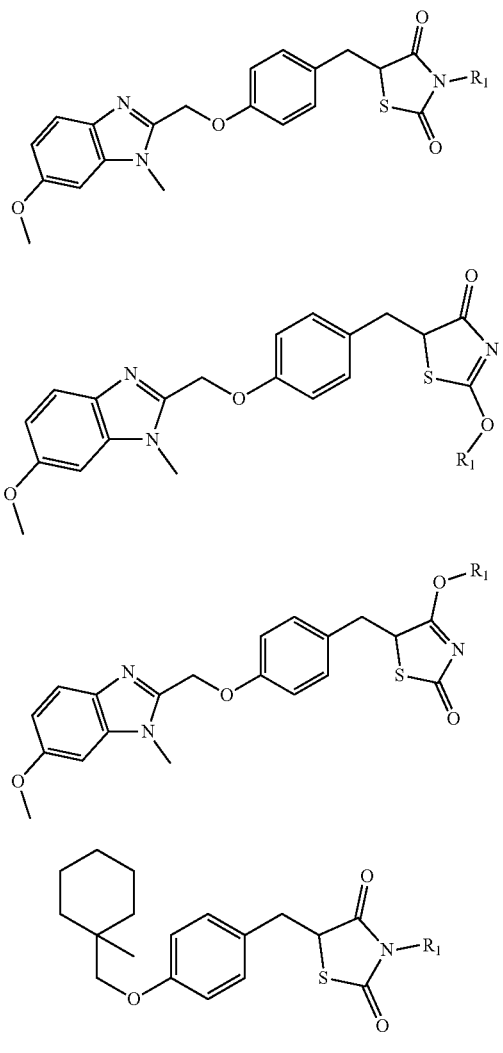

TABLE XX-XXII-continued

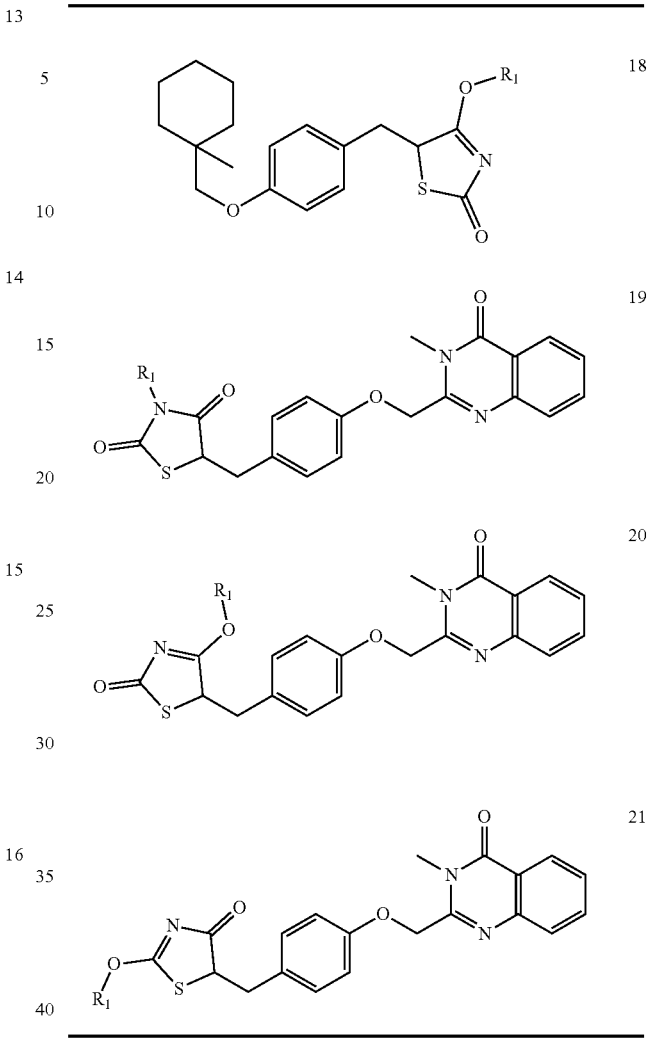

Thiazolidinedione prodrugs of formula XVII to XXXII are useful for the treatment of type 2 diabetes mellitus. Herein provided is a method of treating type 2 diabetes mellitus by the administration of a prodrug of formula XVII to XXXII, in particular a compound of table XX-XXII above wherein the prodrug provides sustained release of the parent drug. The parent drug results from the cleavage of the labile $R_1$ moiety.

In some embodiments, a compound of formula XXVII is selected from Table G:

TABLE G

| No. | Structure |
|---|---|
| 1000. | 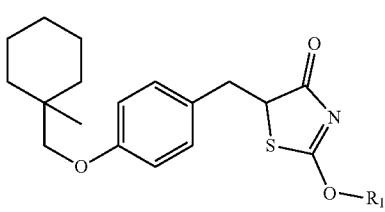 |

TABLE G-continued

| No. | Structure |
|---|---|
| 1001. | (structure) |
| 1002. | (structure) |
| 1003. | (structure) |
| 1004. | (structure) |
| 1005. | (structure) |
| 1006. | (structure) |
| 1007. | (structure) |

TABLE G-continued

| No. | Structure |
|---|---|
| 1008. | 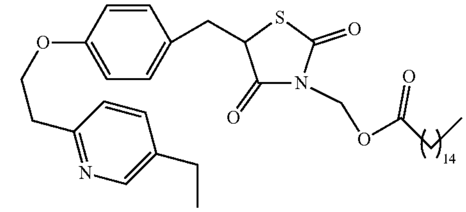 |
| 1009. | 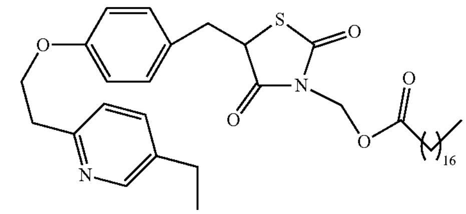 |
| 1010. | 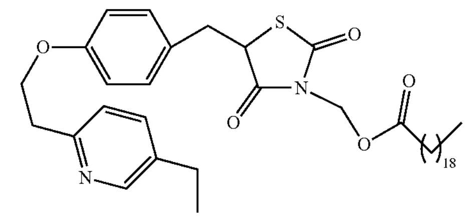 |
| 1011. | 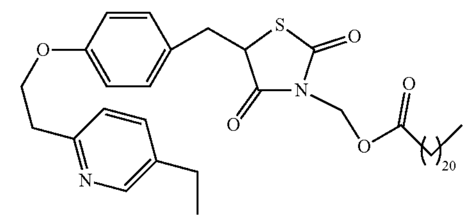 |
| 1012. | 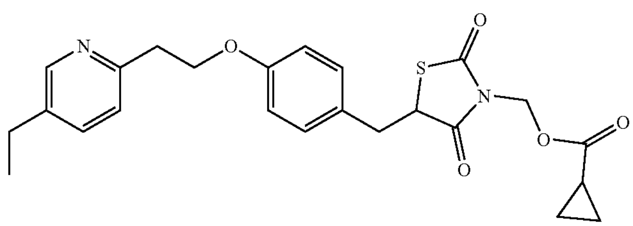 [SMILES: CCc1ccc(CCOc2ccc(CC3SC(=O)N(COC(=O)C4CC4)C3=O)cc2)nc1] |
| 1013. | 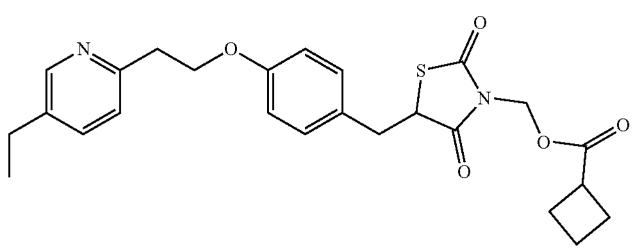 [SMILES: CCc1ccc(CCOc2ccc(CC3SC(=O)N(COC(=O)C4CCC4)C3=O)cc2)nc1] |
| 1014. | 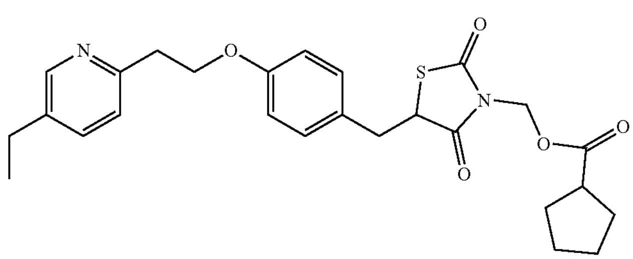 [SMILES: CCc1ccc(CCOc2ccc(CC3SC(=O)N(COC(=O)C4CCCC4)C3=O)cc2)nc1] |

TABLE G-continued
| No. | Structure |
|---|---|
| 1015. | 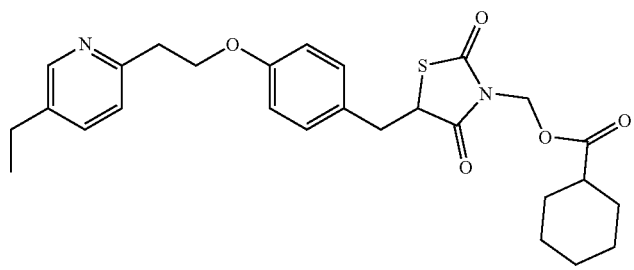 [SMILES: CCc1ccc(CCOc2ccc(CC3SC(=O)N(COC(=O)C4CCCCC4)C3=O)cc2)nc1] |
| 1016. | 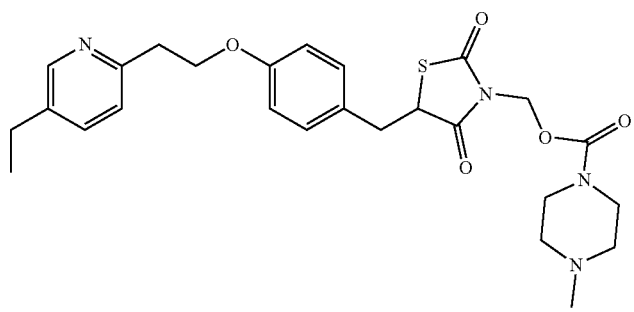 [SMILES: CCc1ccc(CCOc2ccc(CC3SC(=O)N(COC(=O)N4CCN(C)CC4)C3=O)cc2)nc1] |
| 1017. | 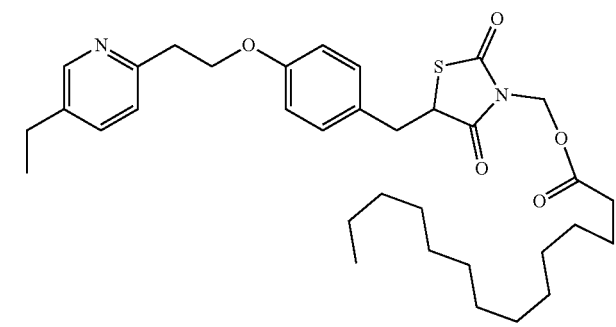 [SMILES: CCCCCCCCCCCCCC(=O)OCN1C(=O)SC(Cc2ccc(OCCc3ccc(CC)cn3)cc2)C1=O] |
| 1018. | 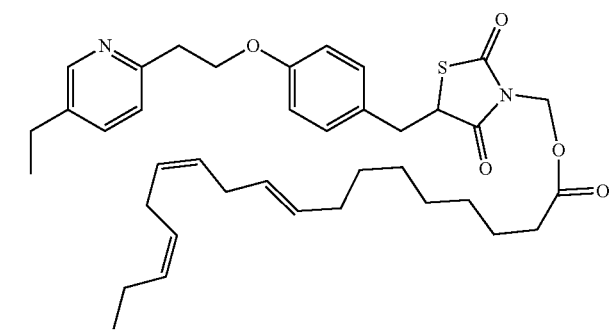 [SMILES: CC/C=C\C/C=C\C/C=C/CCCCCCCC(=O)OCN1C(=O)SC(Cc2ccc(OCCc3ccc(CC)cn3)cc2)C1=O] |
| 1019. | 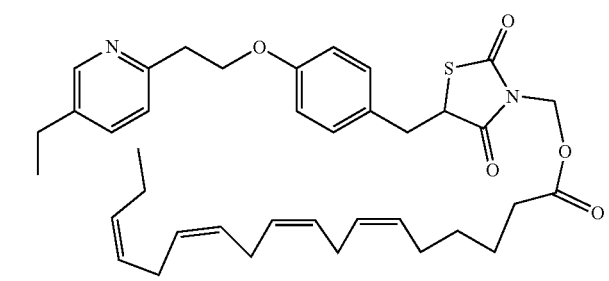 [SMILES: CC/C=C\C/C=C\C/C=C\C/C=C\CCCCC(=O)OCN1C(=O)SC(Cc2ccc(OCCc3ccc(CC)cn3)cc2)C1=O] |

TABLE G-continued

| No. | Structure |
| --- | --- |
| 1020. | 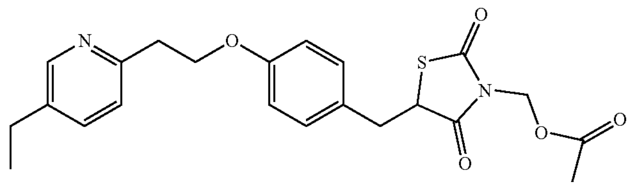 [SMILES: CCc1ccc(CCOc2ccc(CC3SC(=O)N(COC(C)=O)C3=O)cc2)nc1] |
| 1021. | 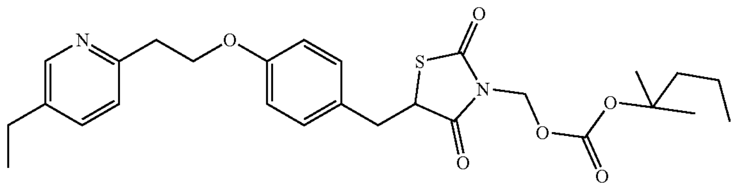 [SMILES: CCCC(C)(C)OC(=O)OCN1C(=O)SC(Cc2ccc(OCCc3ccc(CC)cn3)cc2)C1=O] |
| 1022. | 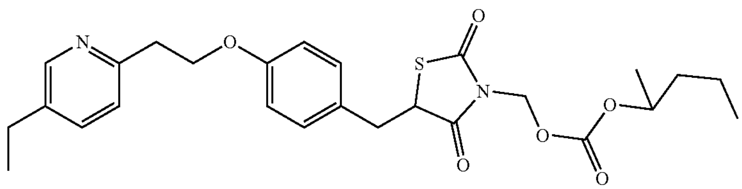 [SMILES: CCCC(C)OC(=O)OCN1C(=O)SC(Cc2ccc(OCCc3ccc(CC)cn3)cc2)C1=O] |
| 1023. | 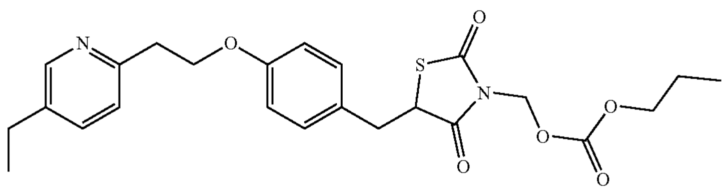 [SMILES: CCCOC(=O)OCN1C(=O)SC(Cc2ccc(OCCc3ccc(CC)cn3)cc2)C1=O] |
| 1024. | 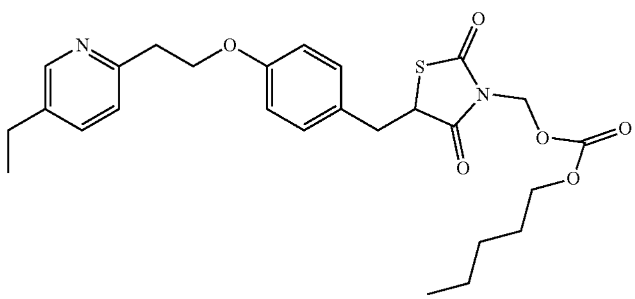 [SMILES: CCCCCOC(=O)OCN1C(=O)SC(Cc2ccc(OCCc3ccc(CC)cn3)cc2)C1=O] |
| 1025. | 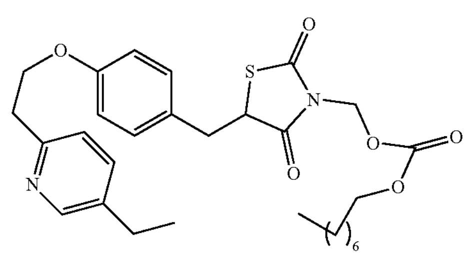 |
| 1026. | 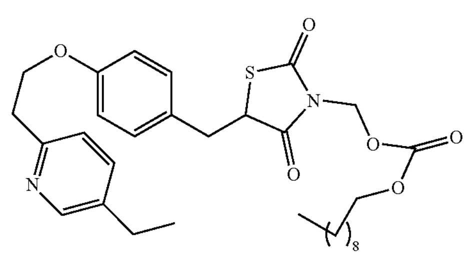 |

TABLE G-continued
| No. | Structure |
|---|---|
| 1027. | 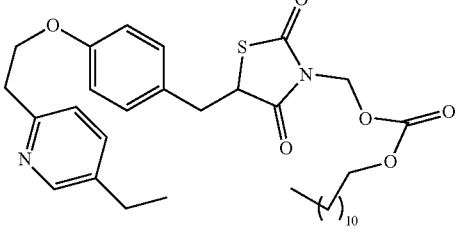 |
| 1028. | 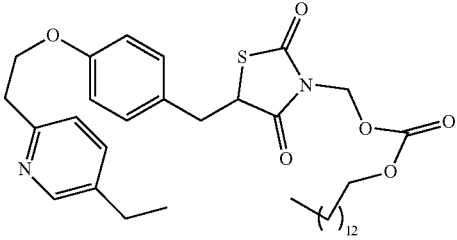 |
| 1029. | 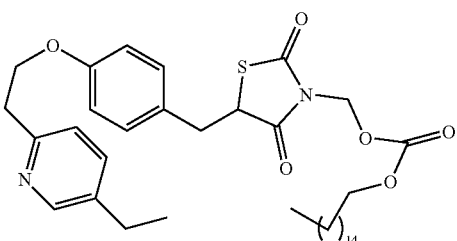 |
| 1030. | 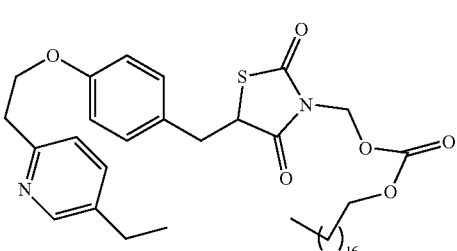 |
| 1031. | 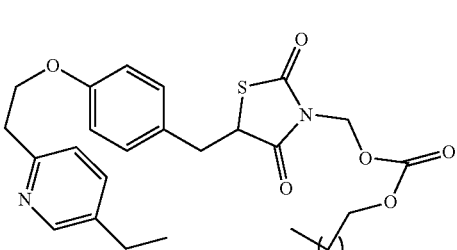 |
| 1032. | 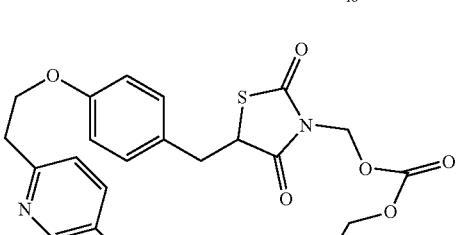 |

TABLE G-continued
| No. | Structure |
|---|---|
| 1033. | 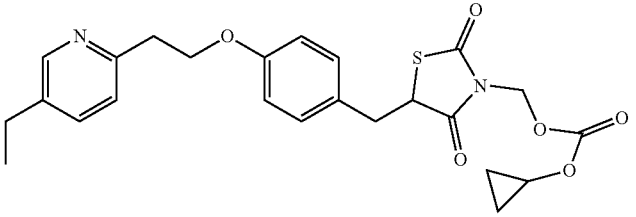 [SMILES: CCc1ccc(CCOc2ccc(CC3SC(=O)N(COC(=O)OC4CC4)C3=O)cc2)nc1] |
| 1034. | 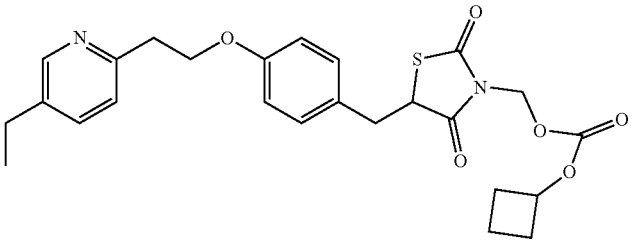 [SMILES: CCc1ccc(CCOc2ccc(CC3SC(=O)N(COC(=O)OC4CCC4)C3=O)cc2)nc1] |
| 1035. | 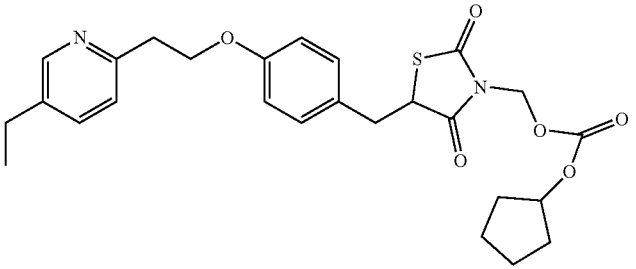 [SMILES: CCc1ccc(CCOc2ccc(CC3SC(=O)N(COC(=O)OC4CCCC4)C3=O)cc2)nc1] |
| 1036. | 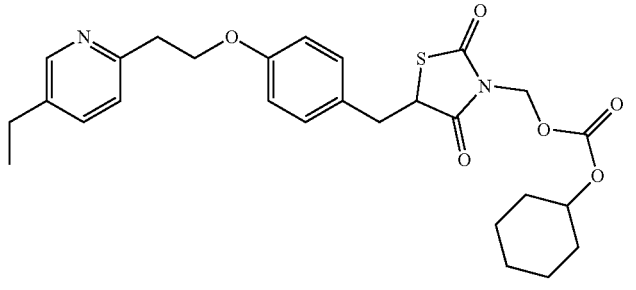 [SMILES: CCc1ccc(CCOc2ccc(CC3SC(=O)N(COC(=O)OC4CCCCC4)C3=O)cc2)nc1] |
| 1037. | 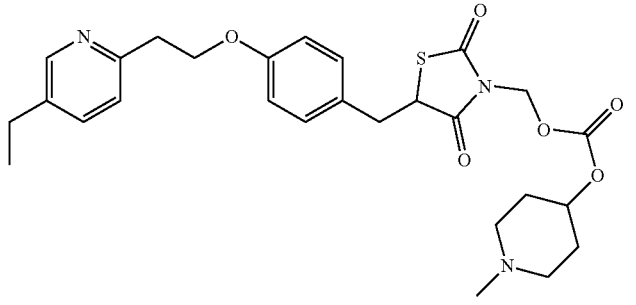 [SMILES: CCc1ccc(CCOc2ccc(CC3SC(=O)N(COC(=O)OC4CCN(C)CC4)C3=O)cc2)nc1] |

TABLE G-continued
| No. | Structure |
|---|---|
| 1038. | 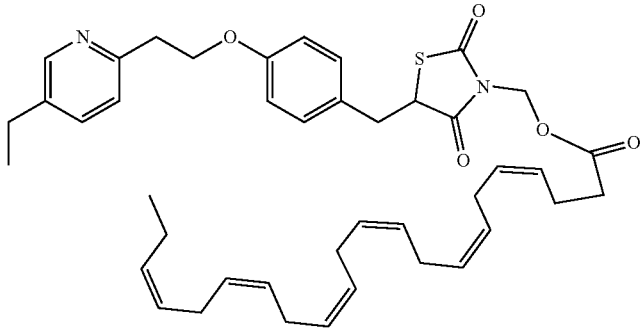 [SMILES: CC/C=C\C/C=C\C/C=C\C/C=C\C/C=C\C/C=C\CCC(=O)OCN1C(=O)SC(Cc2ccc(OCCc3ccc(CC)cn3)cc2)C1=O] |
| 1039. | 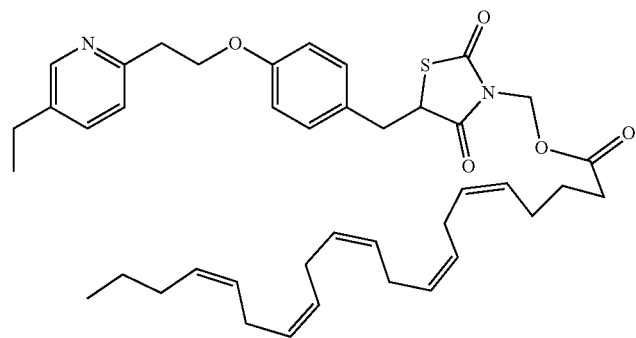 [SMILES: CCC/C=C\C/C=C\C/C=C\C/C=C\C/C=C\CCCC(=O)OCN1C(=O)SC(Cc2ccc(OCCc3ccc(CC)cn3)cc2)C1=O] |
| 1040. | 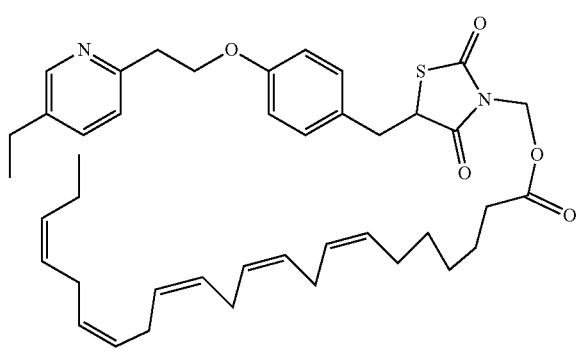 [SMILES: CC/C=C\C/C=C\C/C=C\C/C=C\C/C=C\CCCCCC(=O)OCN1C(=O)SC(Cc2ccc(OCCc3ccc(CC)cn3)cc2)C1=O] |
| 1041. | 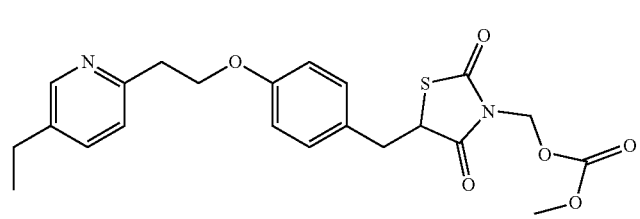 [SMILES: CCc1ccc(CCOc2ccc(CC3SC(=O)N(COC(=O)OC)C3=O)cc2)nc1] |

TABLE H
| No | Structure |
|---|---|
| 1100. | 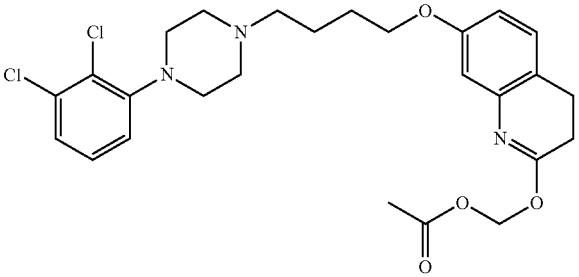 [SMILES: CC(=O)OCOC1=Nc2cc(OCCCCN3CCN(c4cccc(Cl)c4Cl)CC3)ccc2CC1] |
| 1101. | 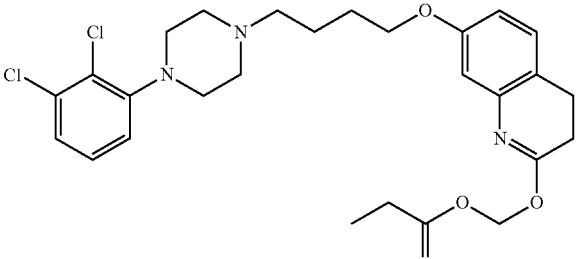 |
| 1102. | 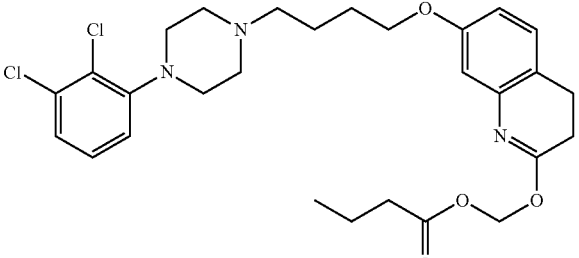 |
| 1103. | 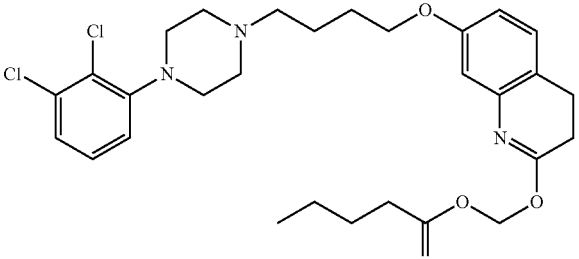 |
| 1104. | 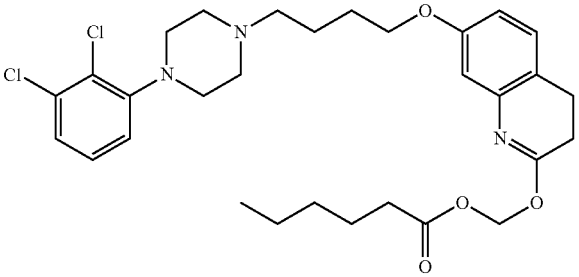 [SMILES: CCCCCC(=O)OCOC1=Nc2cc(OCCCCN3CCN(c4cccc(Cl)c4Cl)CC3)ccc2CC1] |

TABLE H-continued
| No | Structure |
|---|---|
| 1105. | 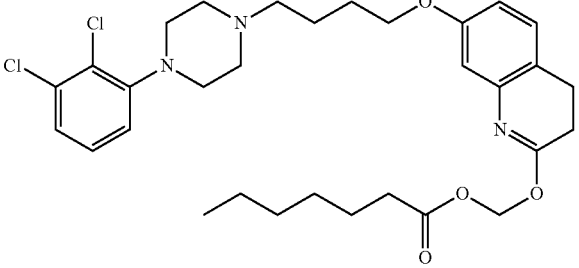 |
| 1106. | 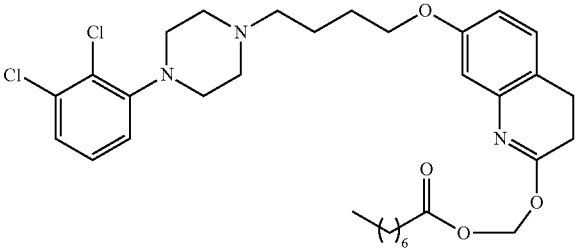 |
| 1107. | 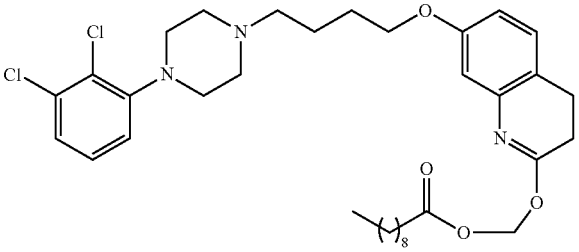 |
| 1108. | 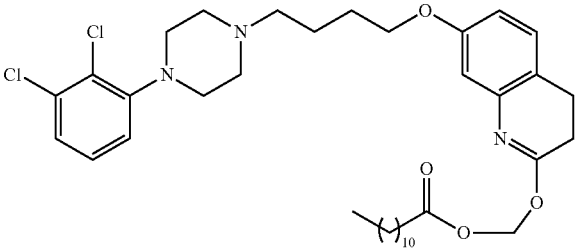 |
| 1109. | 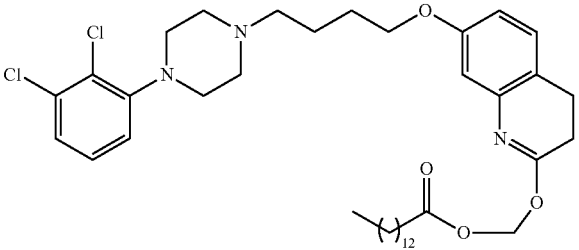 |
| 1110. | 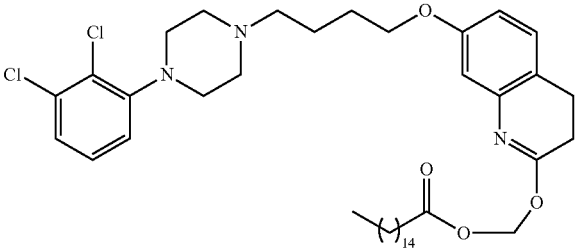 |

TABLE H-continued
| No | Structure |
|---|---|
| 1111. | 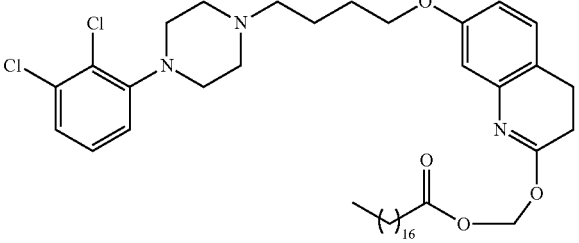 |
| 1112. | 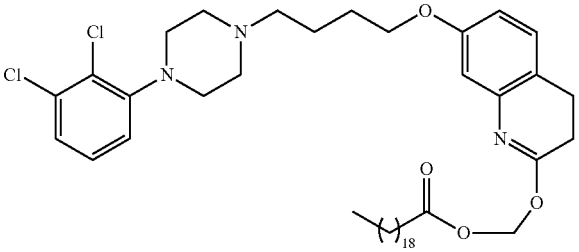 |
| 1113. | 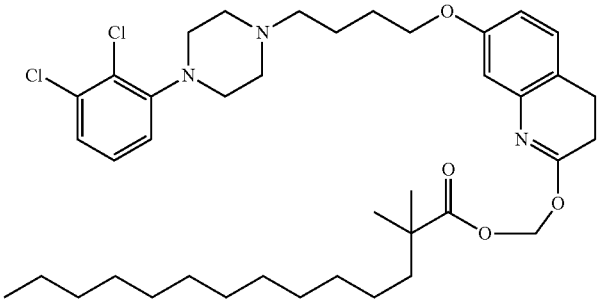 |
| 1114. | 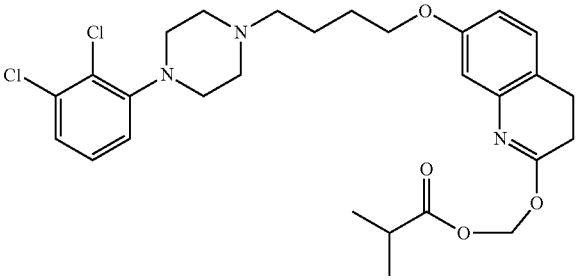 [SMILES: CC(C)C(=O)OCOC1=Nc2cc(OCCCCN3CCN(c4cccc(Cl)c4Cl)CC3)ccc2CC1] |
| 1115. | 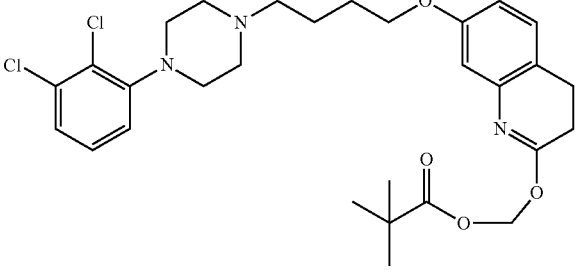 |

TABLE H-continued

| No | Structure |
|---|---|
| 1116. | 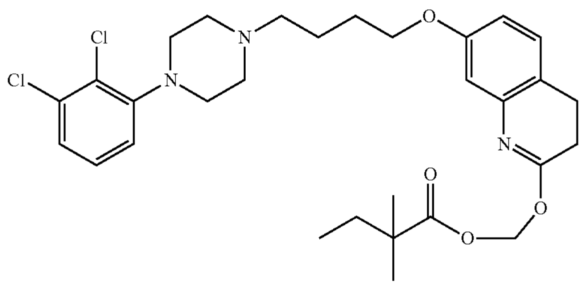 [SMILES: CCC(C)(C)C(=O)OCOC1=Nc2cc(OCCCCN3CCN(c4cccc(Cl)c4Cl)CC3)ccc2CC1] |
| 1117. | 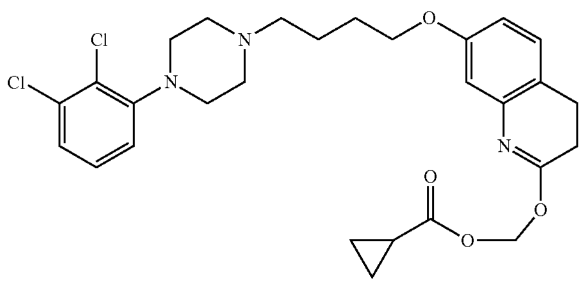 [SMILES: O=C(OCOC1=Nc2cc(OCCCCN3CCN(c4cccc(Cl)c4Cl)CC3)ccc2CC1)C1CC1] |
| 1118. | 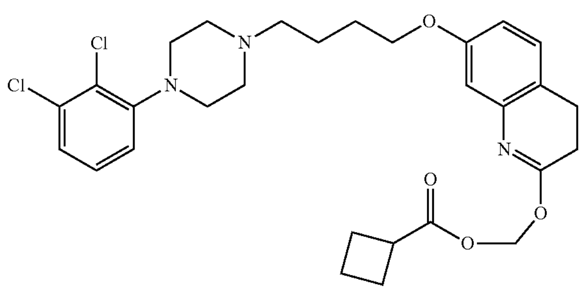 [SMILES: O=C(OCOC1=Nc2cc(OCCCCN3CCN(c4cccc(Cl)c4Cl)CC3)ccc2CC1)C1CCC1] |
| 1119. | 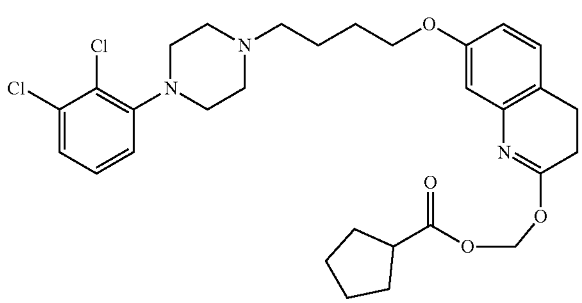 [SMILES: O=C(OCOC1=Nc2cc(OCCCCN3CCN(c4cccc(Cl)c4Cl)CC3)ccc2CC1)C1CCCC1] |
| 1120. | 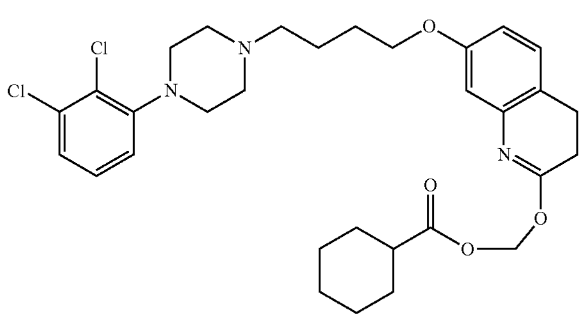 [SMILES: O=C(OCOC1=Nc2cc(OCCCCN3CCN(c4cccc(Cl)c4Cl)CC3)ccc2CC1)C1CCCCC1] |

TABLE H-continued
| No | Structure |
|---|---|
| 1121. | 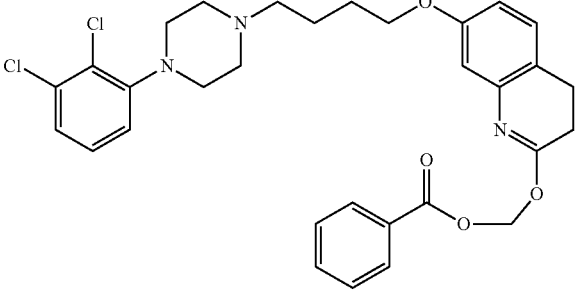 |
| 1122. | 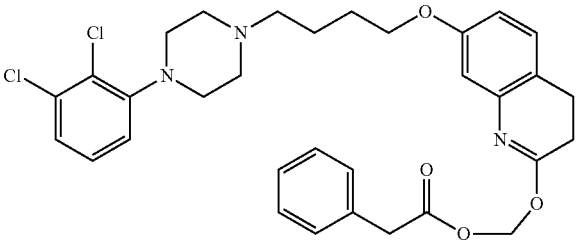 [SMILES: O=C(Cc1ccccc1)OCOC1=Nc2cc(OCCCCN3CCN(c4cccc(Cl)c4Cl)CC3)ccc2CC1] |
| 1123. | 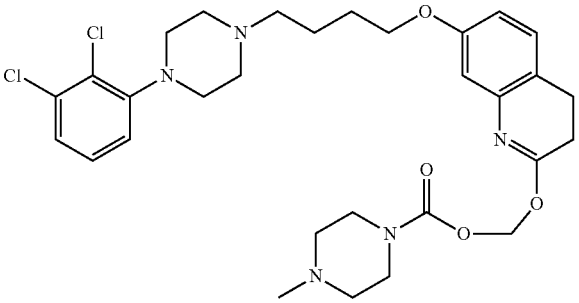 [SMILES: CN1CCN(C(=O)OCOC2=Nc3cc(OCCCCN4CCN(c5cccc(Cl)c5Cl)CC4)ccc3CC2)CC1] |
| 1124. | 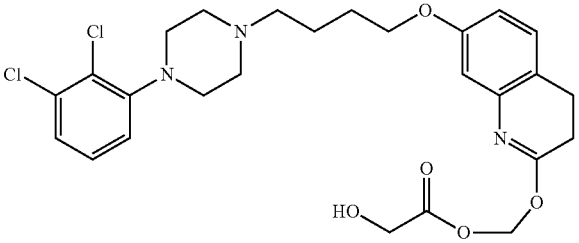 [SMILES: O=C(CO)OCOC1=Nc2cc(OCCCCN3CCN(c4cccc(Cl)c4Cl)CC3)ccc2CC1] |
| 1125. | 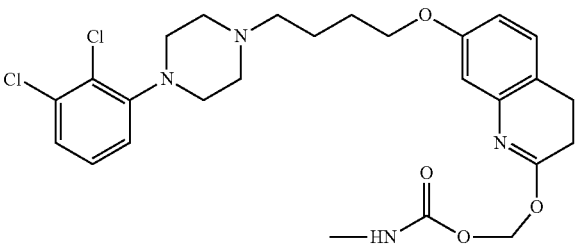 [SMILES: CNC(=O)OCOC1=Nc2cc(OCCCCN3CCN(c4cccc(Cl)c4Cl)CC3)ccc2CC1] |

TABLE H-continued
| No | Structure |
|---|---|
| 1126. | 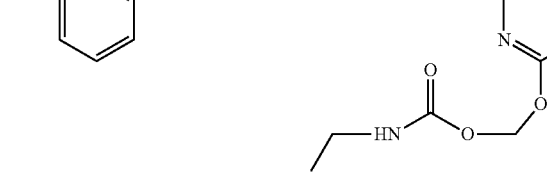 |
| 1127. | 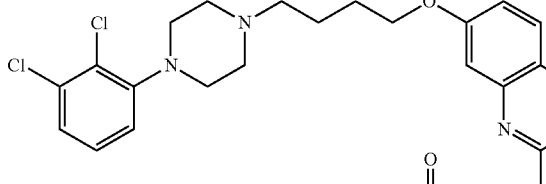 |
| 1128. | 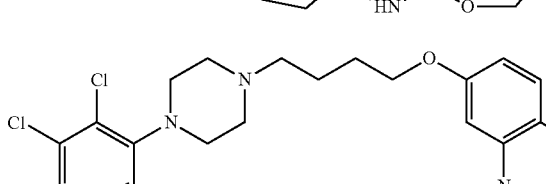 |
| 1129. | 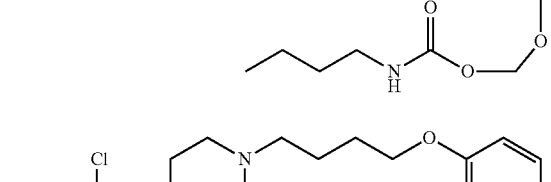 |
| 1130. | 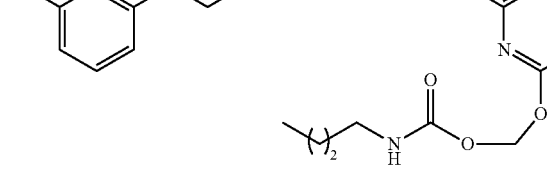 |

327
328
TABLE H-continued
| No | Structure |
|---|---|
| 1131. | 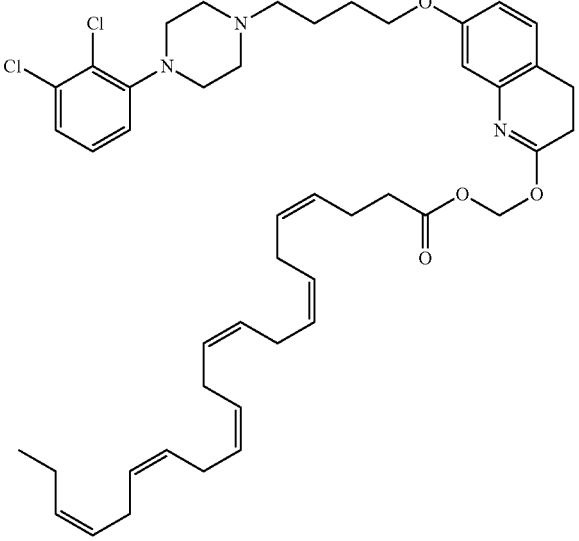 |
| 1132. | 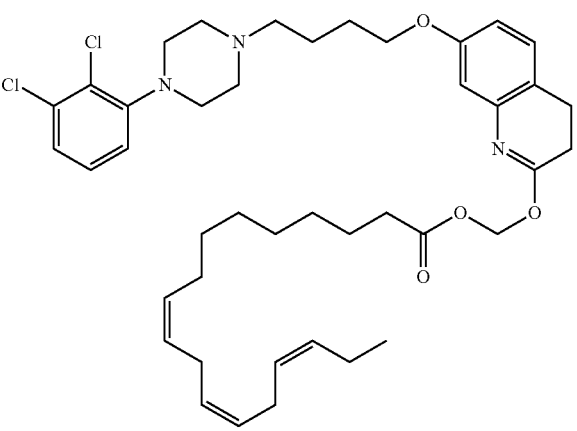 [SMILES: CC/C=C\C/C=C\C/C=C\CCCCCCCC(=O)OCOC1=Nc2cc(OCCCCN3CCN(c4cccc(Cl)c4Cl)CC3)ccc2CC1] |
| 1133. | 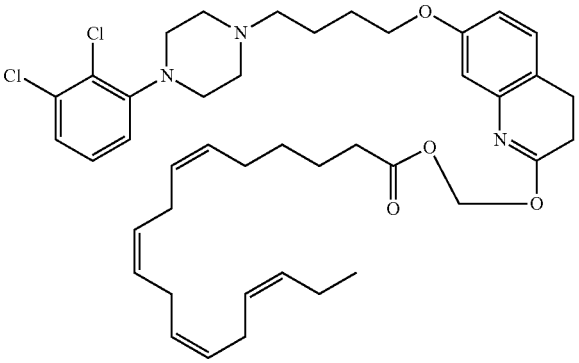 [SMILES: CC/C=C\C/C=C\C/C=C\C/C=C\CCCCC(=O)OCOC1=Nc2cc(OCCCCN3CCN(c4cccc(Cl)c4Cl)CC3)ccc2CC1] |
| 1134. | 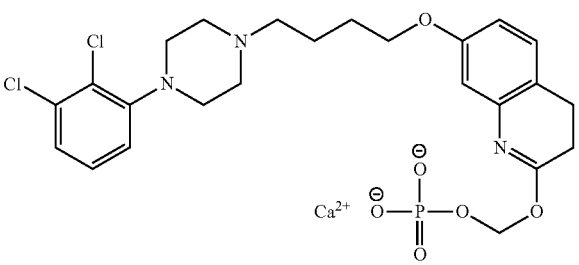 [SMILES: O=P([O-])([O-])OCOC1=Nc2cc(OCCCCN3CCN(c4cccc(Cl)c4Cl)CC3)ccc2CC1 ; [Ca+2]] |

TABLE H-continued
| No | Structure |
|---|---|
| 1135. | 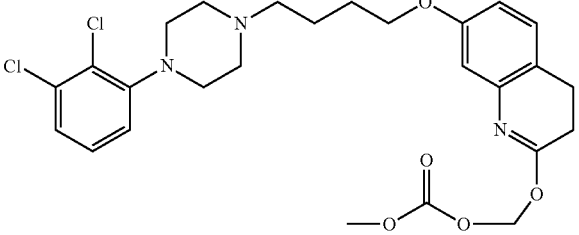 |
| 1136. | 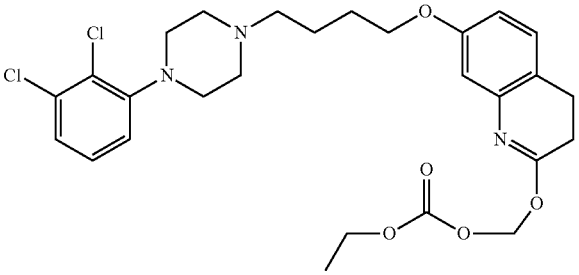 [SMILES: CCOC(=O)OCOC1=Nc2cc(OCCCCN3CCN(c4cccc(Cl)c4Cl)CC3)ccc2CC1] |
| 1137. | 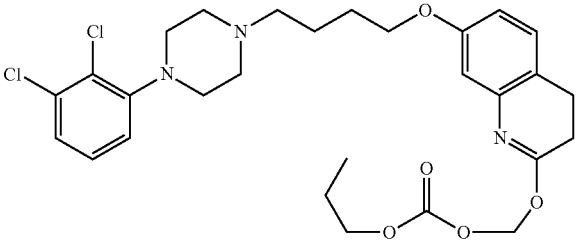 [SMILES: CCCOC(=O)OCOC1=Nc2cc(OCCCCN3CCN(c4cccc(Cl)c4Cl)CC3)ccc2CC1] |
| 1138. | 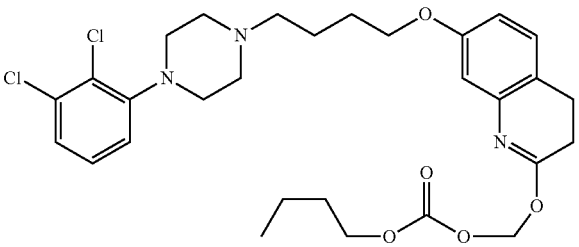 [SMILES: CCCCOC(=O)OCOC1=Nc2cc(OCCCCN3CCN(c4cccc(Cl)c4Cl)CC3)ccc2CC1] |
| 1139. | 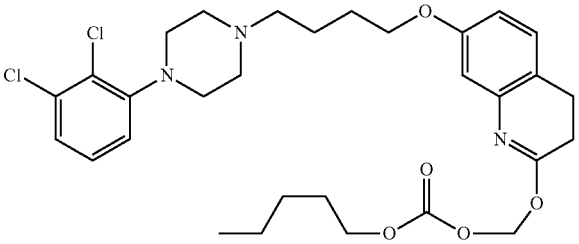 [SMILES: CCCCCOC(=O)OCOC1=Nc2cc(OCCCCN3CCN(c4cccc(Cl)c4Cl)CC3)ccc2CC1] |
| 1140. | 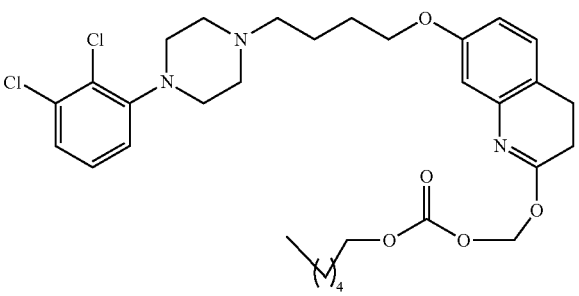 |

TABLE H-continued
| No | Structure |
|---|---|
| 1141. | 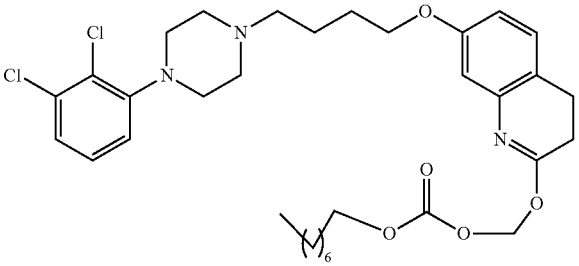 |
| 1142. | 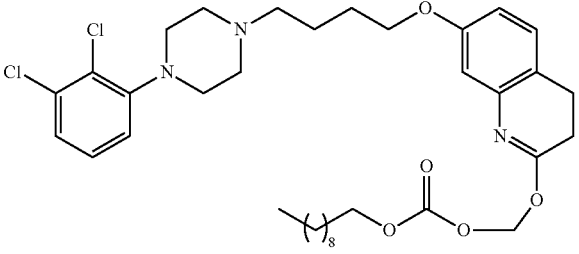 |
| 1143. | 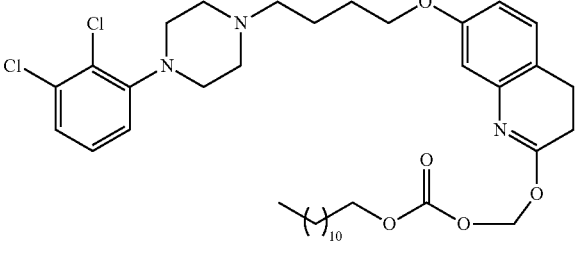 |
| 1144. | 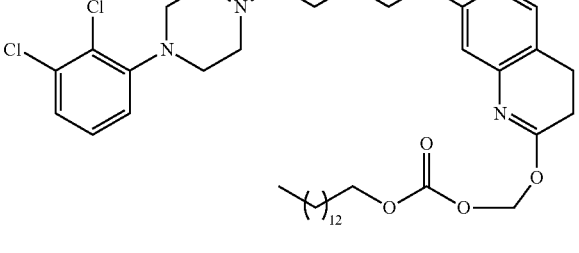 |
| 1145. | 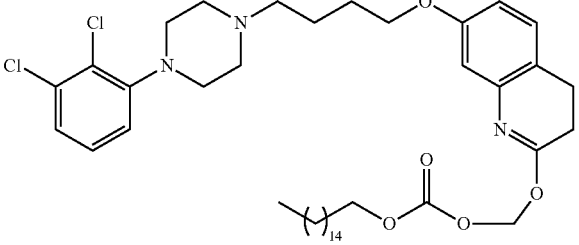 |

TABLE H-continued
| No | Structure |
|---|---|
| 1146. | 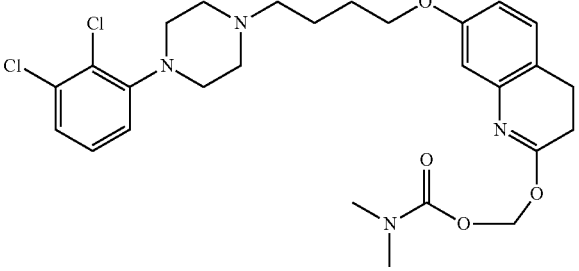 |
| 1147. | 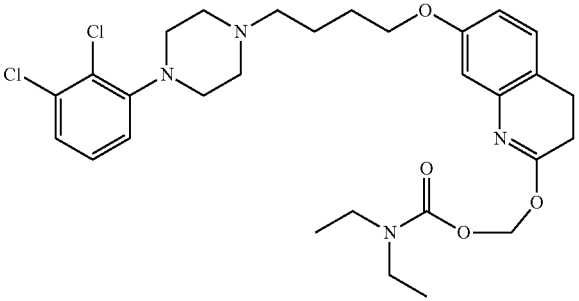 [SMILES: CCN(CC)C(=O)OCOC1=Nc2cc(OCCCCN3CCN(c4cccc(Cl)c4Cl)CC3)ccc2CC1] |
| 1148. | 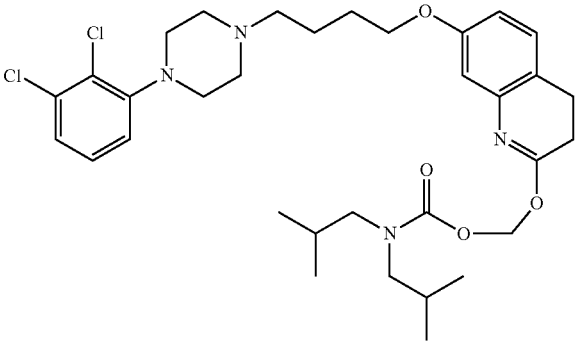 [SMILES: CC(C)CN(CC(C)C)C(=O)OCOC1=Nc2cc(OCCCCN3CCN(c4cccc(Cl)c4Cl)CC3)ccc2CC1] |
| 1149. | 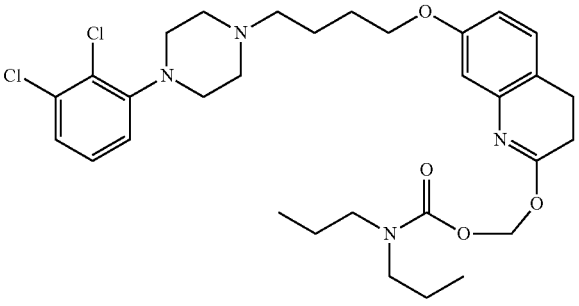 [SMILES: CCCN(CCC)C(=O)OCOC1=Nc2cc(OCCCCN3CCN(c4cccc(Cl)c4Cl)CC3)ccc2CC1] |
| 1150. | 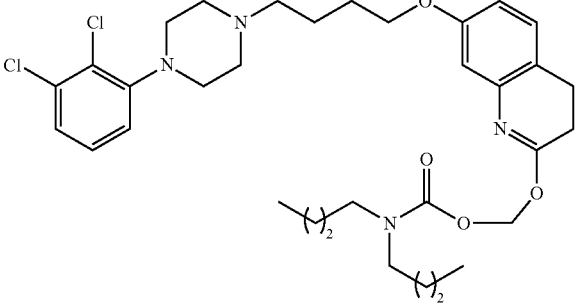 |

TABLE H-continued
| No | Structure |
|---|---|
| 1151. | 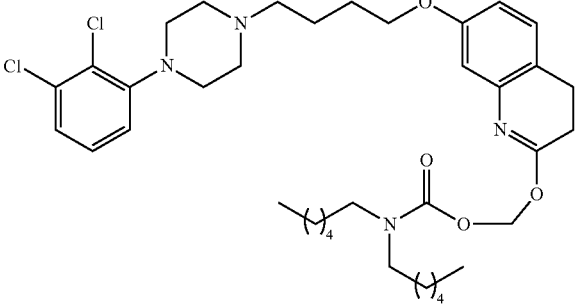 |
| 1152. | 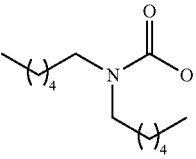 |
| 1153. | 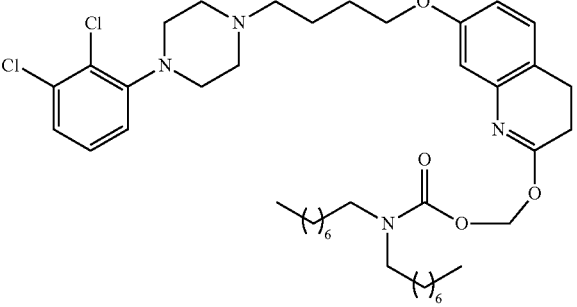 |
| 1154. | 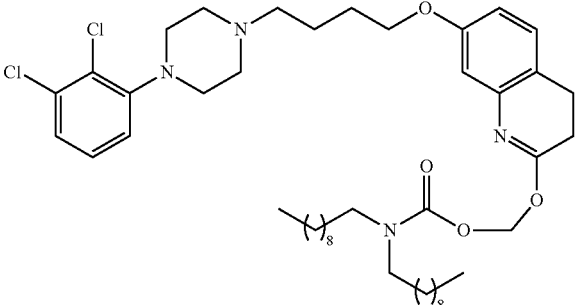 |

TABLE H-continued
| No | Structure |
|---|---|
| 1155. | 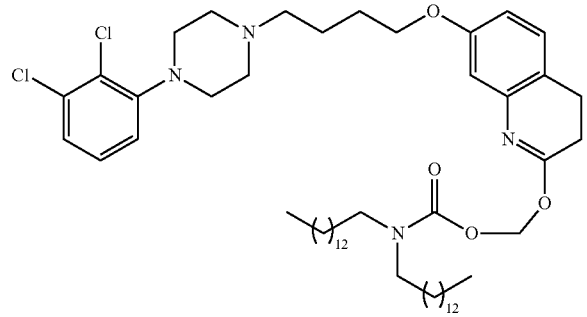 |
| 1156. | 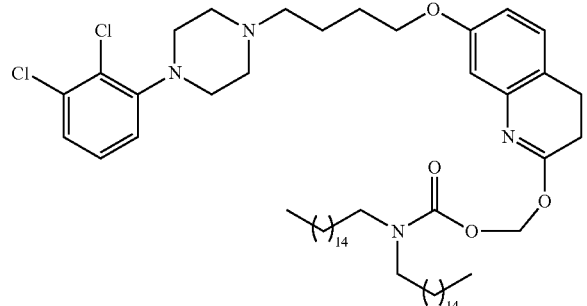 |
| 1157. | 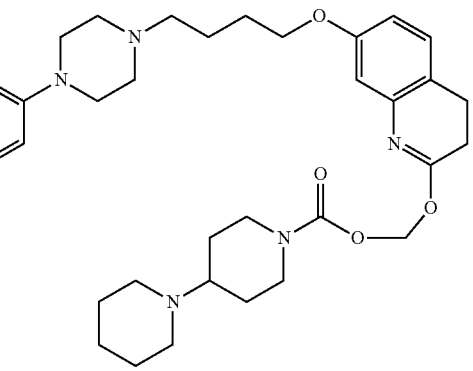 |
| 1158. | 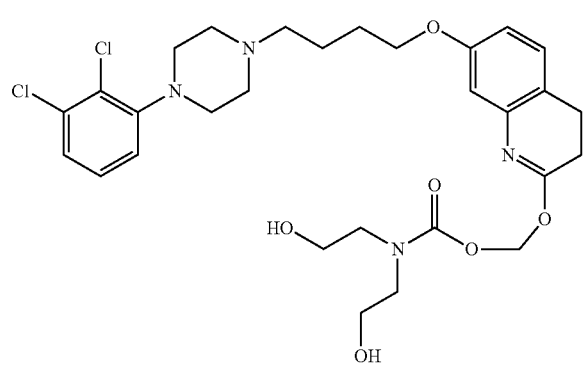 [SMILES: O=C(OCOC1=Nc2cc(OCCCCN3CCN(c4cccc(Cl)c4Cl)CC3)ccc2CC1)N(CCO)CCO] |

TABLE H-continued
| No | Structure |
|---|---|
| 1159. | 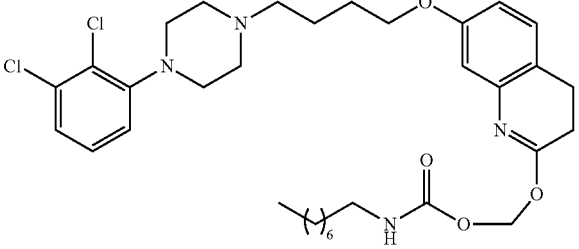 |
| 1160. | 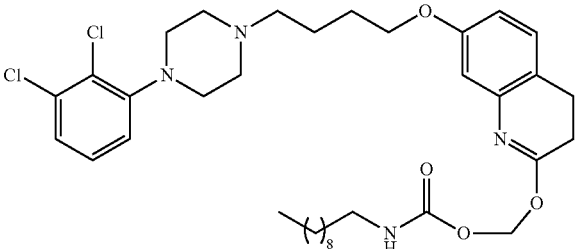 |
| 1161. | 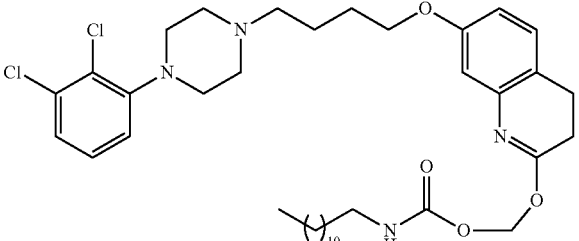 |
| 1162. | 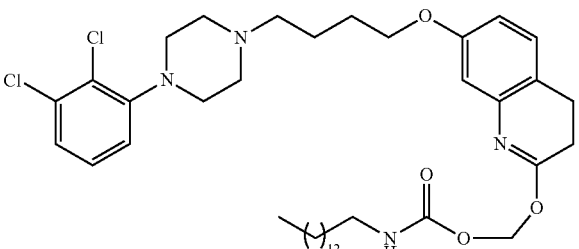 |
| 1163. | 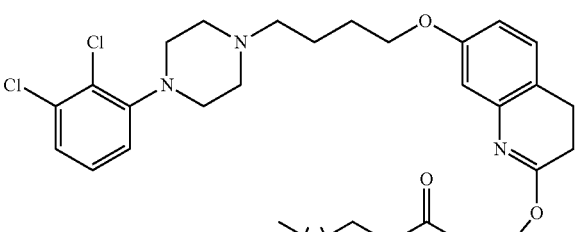 |

TABLE H-continued

| No | Structure |
|---|---|
| 1164. | 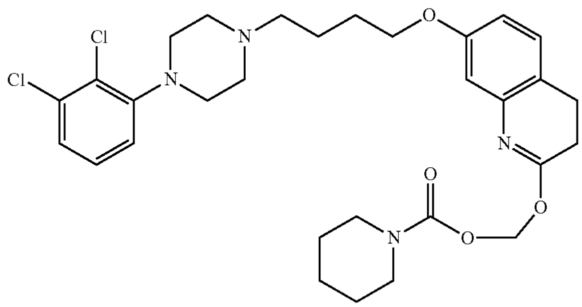 |
| 1165. | 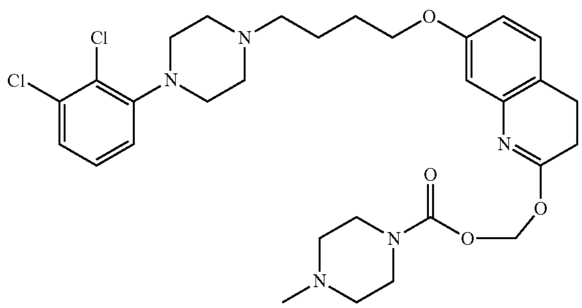 [SMILES: CN1CCN(C(=O)OCOC2=Nc3cc(OCCCCN4CCN(c5cccc(Cl)c5Cl)CC4)ccc3CC2)CC1] |
| 1166. | 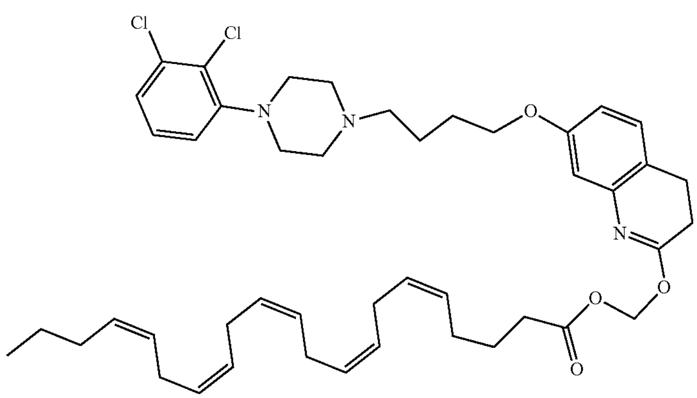 [SMILES: CCC/C=C\C/C=C\C/C=C\C/C=C\C/C=C\CCCC(=O)OCOC1=Nc2cc(OCCCCN3CCN(c4cccc(Cl)c4Cl)CC3)ccc2CC1] |
| 1167. | 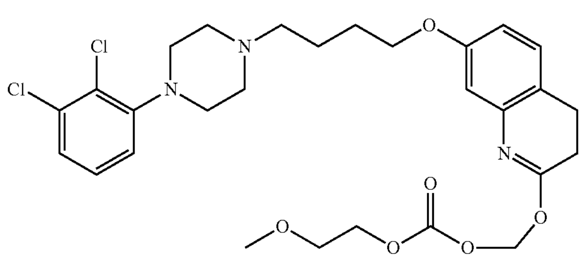 [SMILES: COCCOC(=O)OCOC1=Nc2cc(OCCCCN3CCN(c4cccc(Cl)c4Cl)CC3)ccc2CC1] |

TABLE I
| No | Structure |
|---|---|
| 1200. | 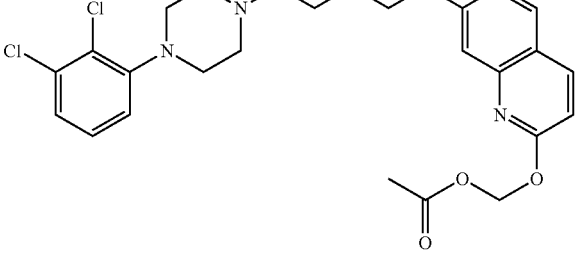 |
| 1201. | 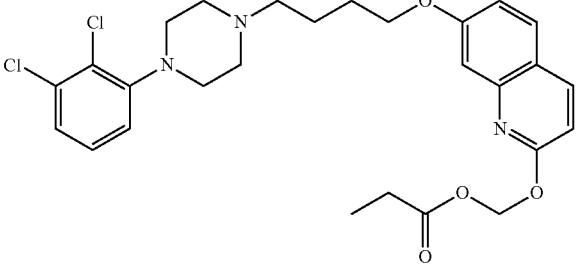 |
| 1202. | 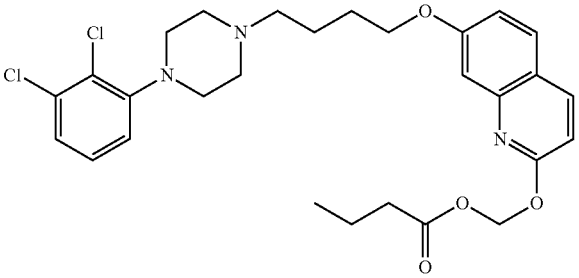 [SMILES: CCCC(=O)OCOc1ccc2ccc(OCCCCN3CCN(c4cccc(Cl)c4Cl)CC3)cc2n1] |
| 1203. | 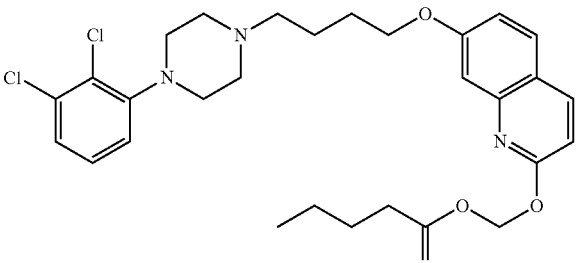 |
| 1204. | 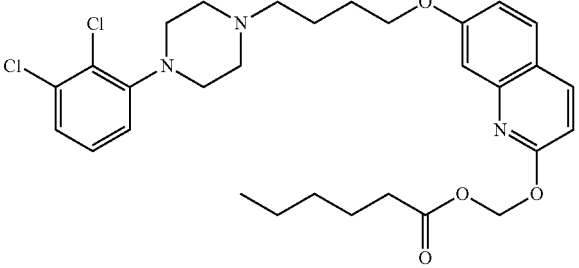 |

TABLE I-continued
| No | Structure |
|---|---|
| 1205. | 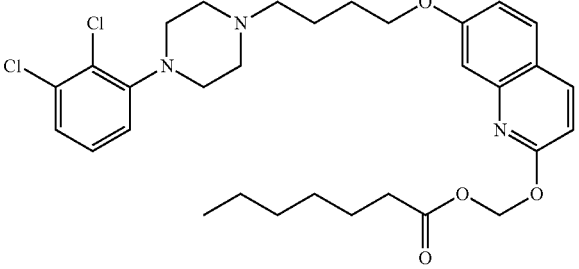 |
| 1206. | 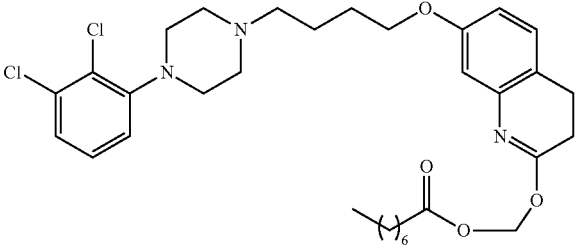 |
| 1207. | 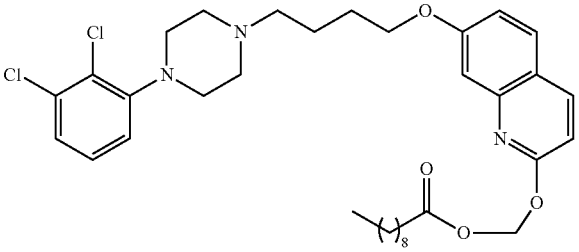 |
| 1208. | 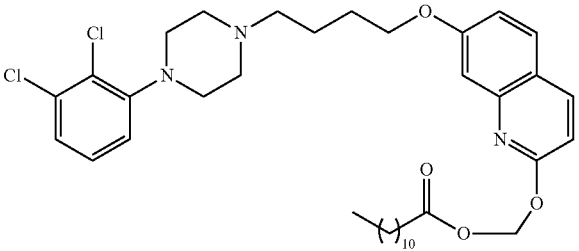 |
| 1209. | 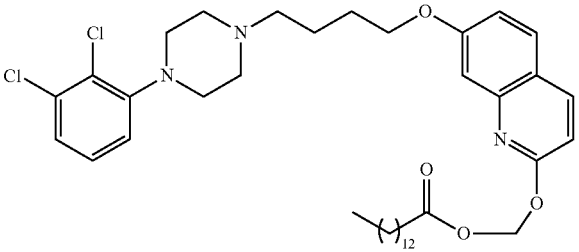 |
| 1210. | 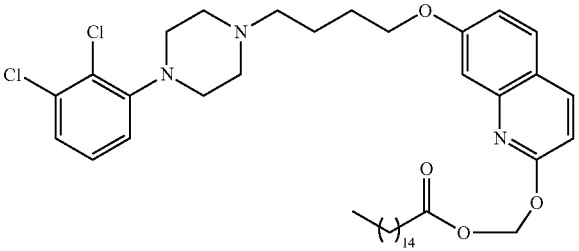 |

TABLE I-continued

| No | Structure |
|---|---|
| 1211. | 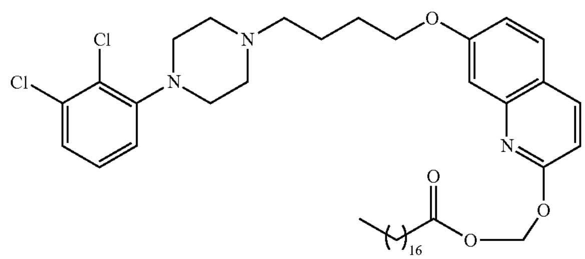 |
| 1212. | 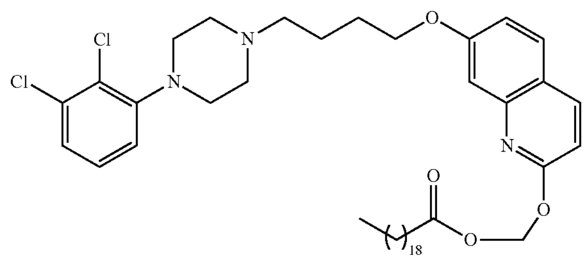 |
| 1213. | 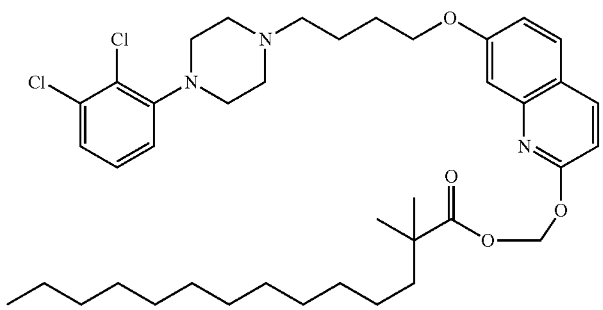 [SMILES: CCCCCCCCCCCCC(C)(C)C(=O)OCOc1ccc2ccc(OCCCCN3CCN(c4cccc(Cl)c4Cl)CC3)cc2n1] |
| 1214. | 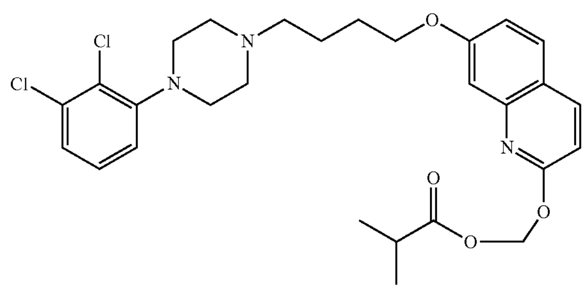 [SMILES: CC(C)C(=O)OCOc1ccc2ccc(OCCCCN3CCN(c4cccc(Cl)c4Cl)CC3)cc2n1] |
| 1215. | 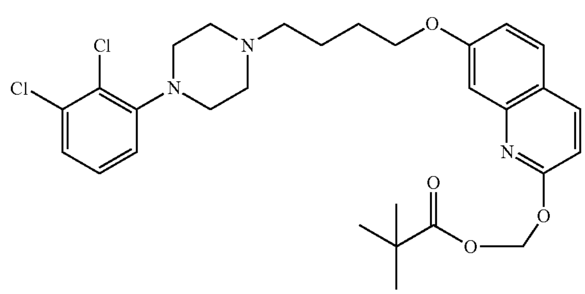 [SMILES: CC(C)(C)C(=O)OCOc1ccc2ccc(OCCCCN3CCN(c4cccc(Cl)c4Cl)CC3)cc2n1] |

TABLE I-continued
| No | Structure |
|---|---|
| 1216. | 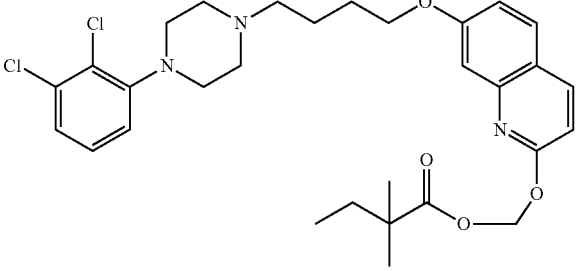 |
| 1217. | 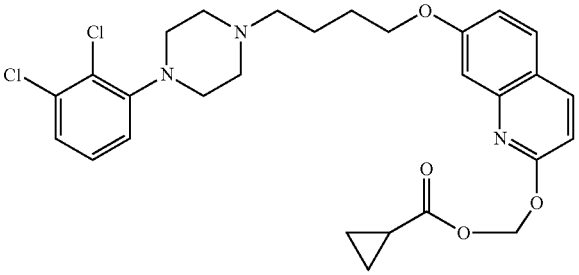 [SMILES: O=C(OCOc1ccc2ccc(OCCCCN3CCN(c4cccc(Cl)c4Cl)CC3)cc2n1)C1CC1] |
| 1218. | 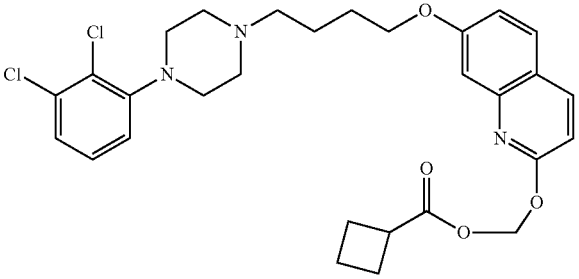 [SMILES: O=C(OCOc1ccc2ccc(OCCCCN3CCN(c4cccc(Cl)c4Cl)CC3)cc2n1)C1CCC1] |
| 1219. | 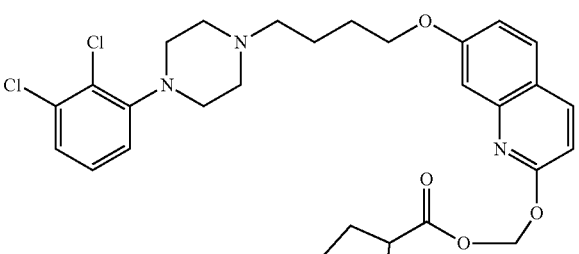 |
| 1220. | 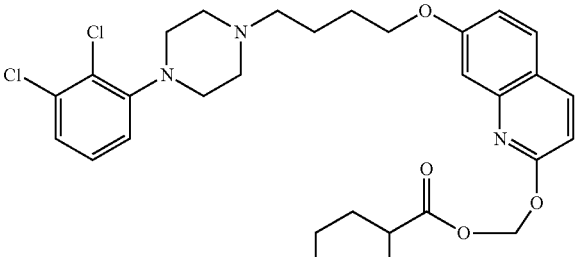 |

TABLE I-continued
| No | Structure |
|---|---|
| 1221. | 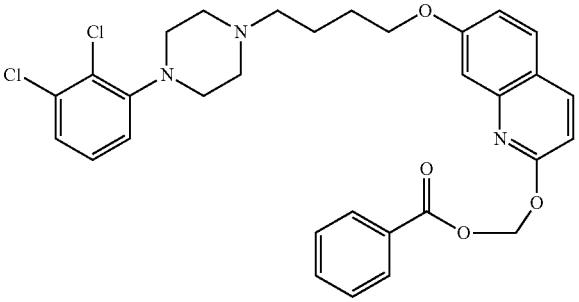 [SMILES: O=C(OCOc1ccc2ccc(OCCCCN3CCN(c4cccc(Cl)c4Cl)CC3)cc2n1)c1ccccc1] |
| 1222. | 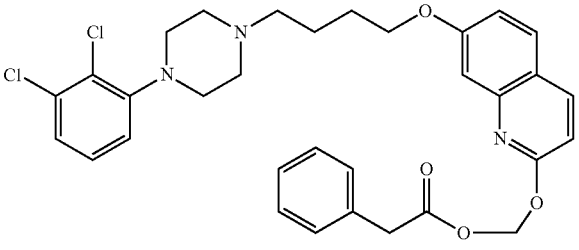 [SMILES: O=C(Cc1ccccc1)OCOc1ccc2ccc(OCCCCN3CCN(c4cccc(Cl)c4Cl)CC3)cc2n1] |
| 1223. | 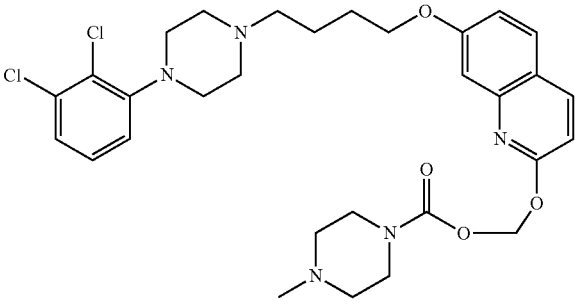 [SMILES: CN1CCN(C(=O)OCOc2ccc3ccc(OCCCCN4CCN(c5cccc(Cl)c5Cl)CC4)cc3n2)CC1] |
| 1224. | 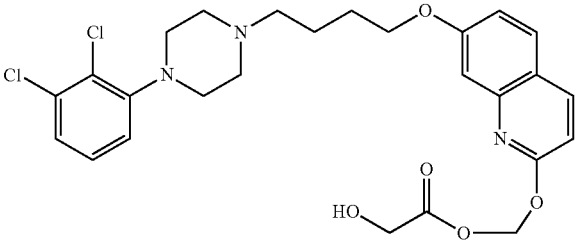 [SMILES: O=C(CO)OCOc1ccc2ccc(OCCCCN3CCN(c4cccc(Cl)c4Cl)CC3)cc2n1] |
| 1225. | 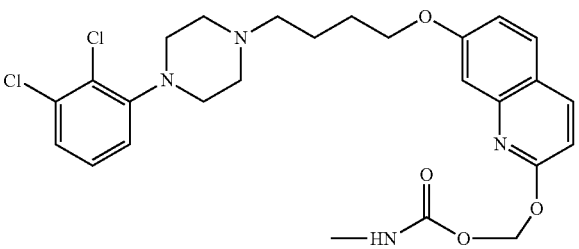 [SMILES: CNC(=O)OCOc1ccc2ccc(OCCCCN3CCN(c4cccc(Cl)c4Cl)CC3)cc2n1] |

TABLE I-continued
| No | Structure |
|---|---|
| 1226. | 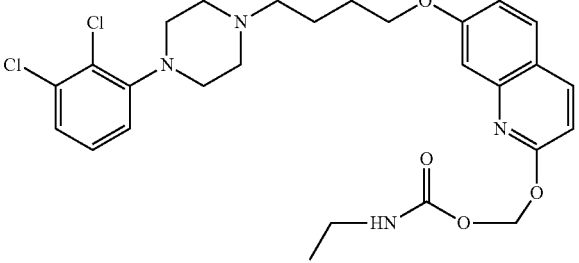 |
| 1227. | 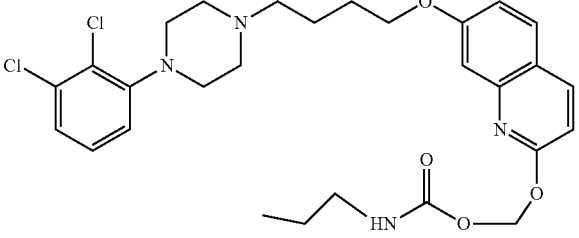 |
| 1228. | 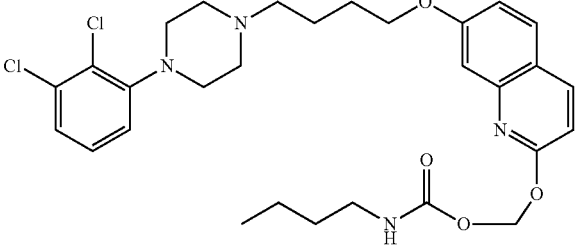 |
| 1229. | 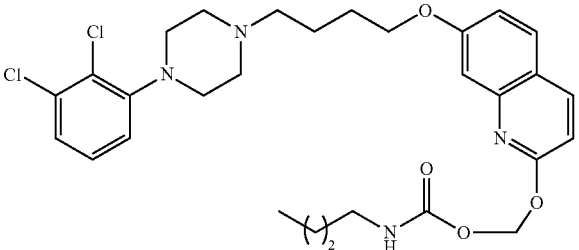 |
| 1230. | 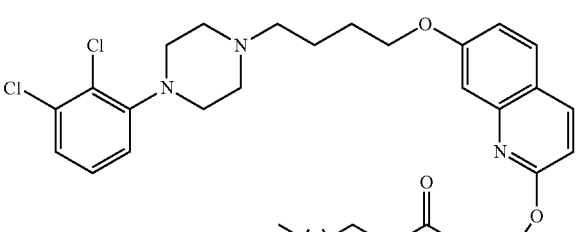 |

TABLE I-continued

| No | Structure |
|---|---|
| 1231. | 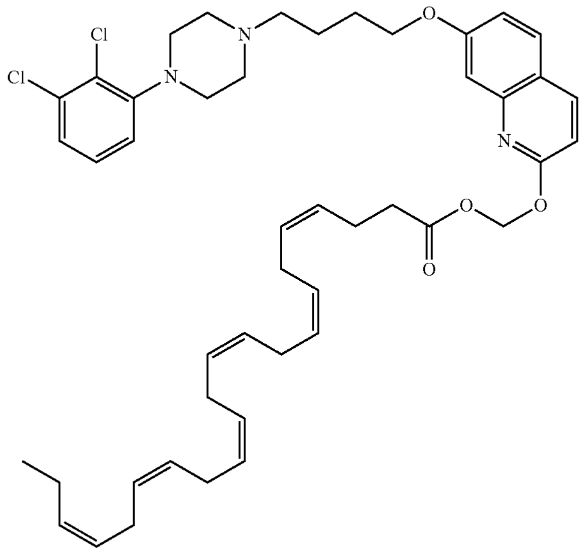 [SMILES: CC/C=C\C/C=C\C/C=C\C/C=C\C/C=C\C/C=C\CCC(=O)OCOc1ccc2ccc(OCCCCN3CCN(c4cccc(Cl)c4Cl)CC3)cc2n1] |
| 1232. | 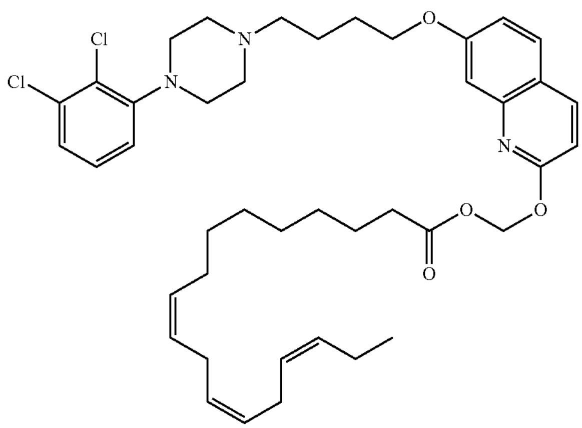 [SMILES: CC/C=C\C/C=C\C/C=C\CCCCCCCC(=O)OCOc1ccc2ccc(OCCCCN3CCN(c4cccc(Cl)c4Cl)CC3)cc2n1] |
| 1233. | 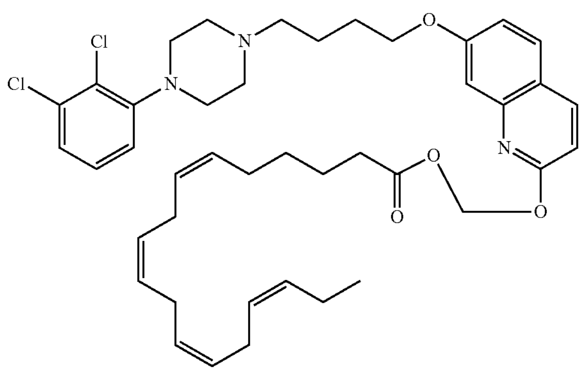 [SMILES: CC/C=C\C/C=C\C/C=C\C/C=C\CCCCC(=O)OCOc1ccc2ccc(OCCCCN3CCN(c4cccc(Cl)c4Cl)CC3)cc2n1] |
| 1234. | 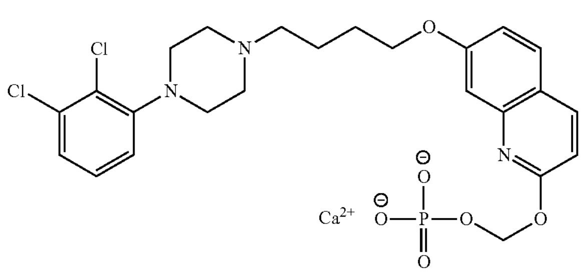 |

TABLE I-continued
| No | Structure |
|---|---|
| 1235. | 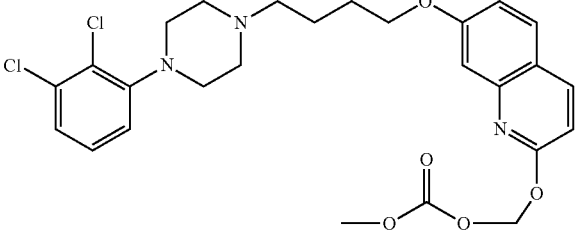 |
| 1236. | 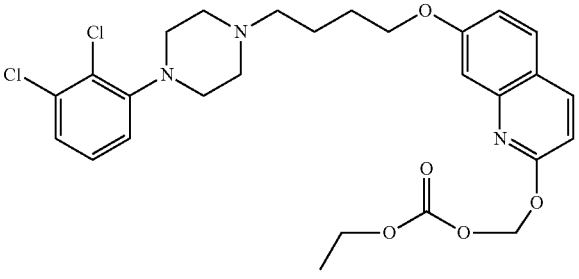 [SMILES: CCOC(=O)OCOc1ccc2ccc(OCCCCN3CCN(c4cccc(Cl)c4Cl)CC3)cc2n1] |
| 1237. | 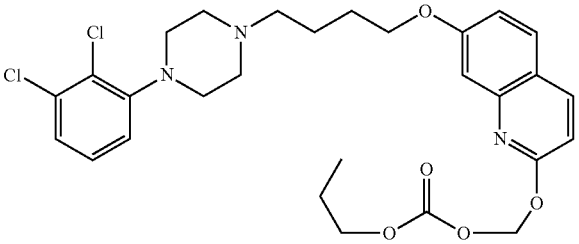 [SMILES: CCCOC(=O)OCOc1ccc2ccc(OCCCCN3CCN(c4cccc(Cl)c4Cl)CC3)cc2n1] |
| 1238. | 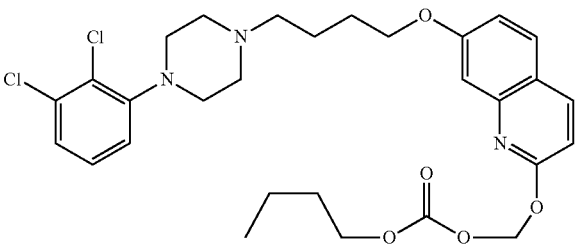 [SMILES: CCCCOC(=O)OCOc1ccc2ccc(OCCCCN3CCN(c4cccc(Cl)c4Cl)CC3)cc2n1] |
| 1239. | 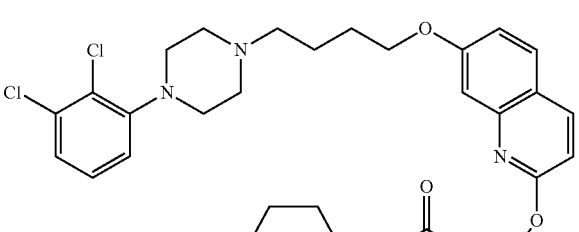 |
| 1240. | 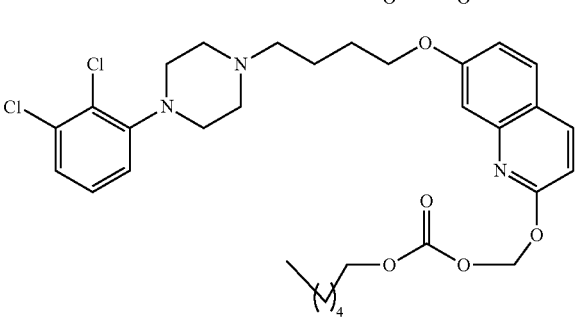 |

TABLE I-continued
| No | Structure |
|---|---|
| 1241. | 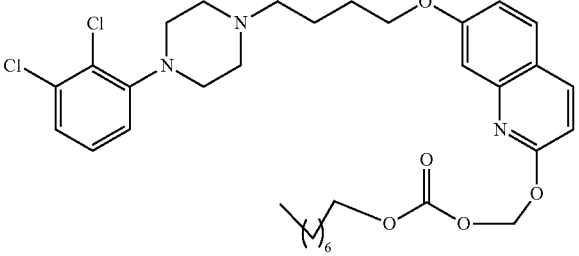 |
| 1242. | 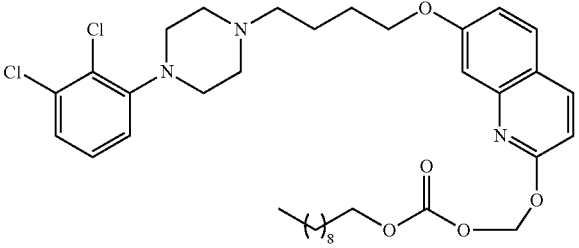 |
| 1243. | 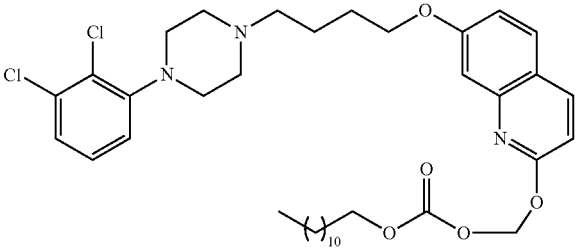 |
| 1244. | 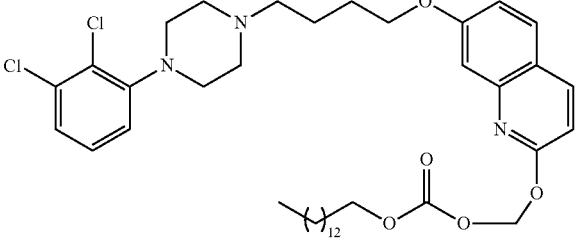 |
| 1245. | 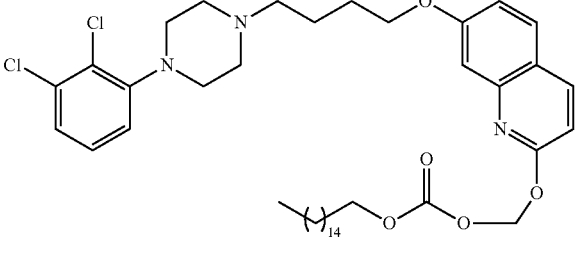 |
| 1246. | 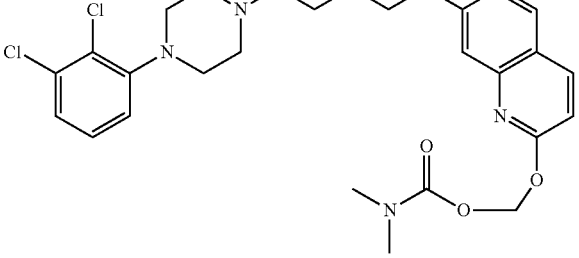 |

TABLE I-continued
| No | Structure |
|---|---|
| 1247. | 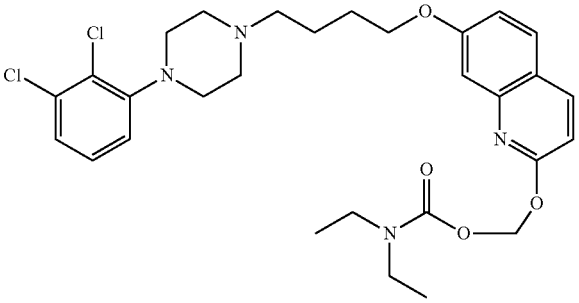 [SMILES: CCN(CC)C(=O)OCOc1ccc2ccc(OCCCCN3CCN(c4cccc(Cl)c4Cl)CC3)cc2n1] |
| 1248. | 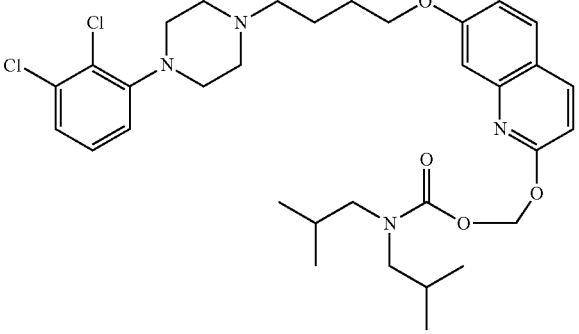 |
| 1249. | 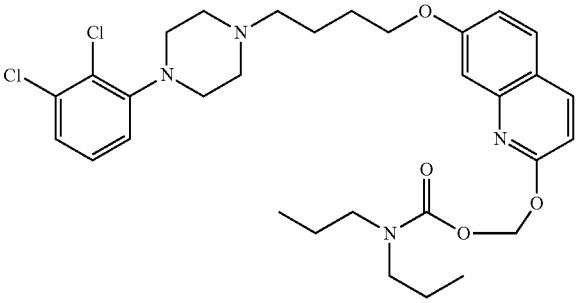 [SMILES: CCCN(CCC)C(=O)OCOc1ccc2ccc(OCCCCN3CCN(c4cccc(Cl)c4Cl)CC3)cc2n1] |
| 1250. | 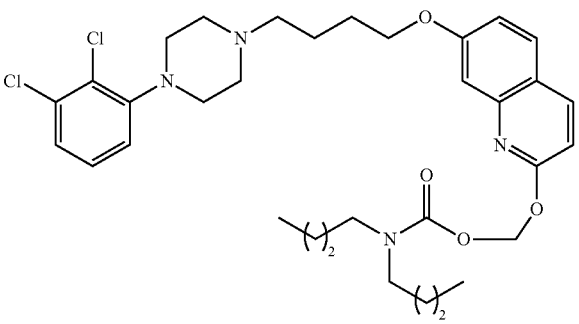 |

TABLE I-continued
| No | Structure |
|---|---|
| 1251. | 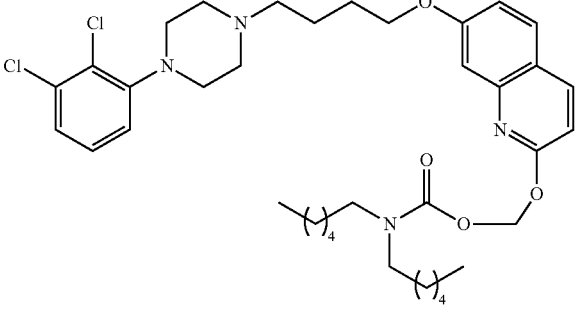 |
| 1252. | 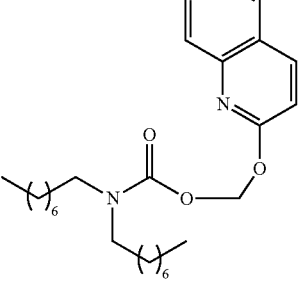 |
| 1253. | 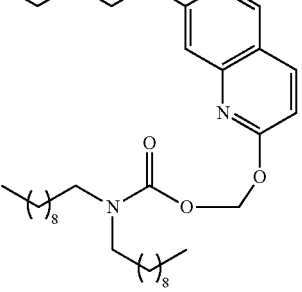 |
| 1254. | 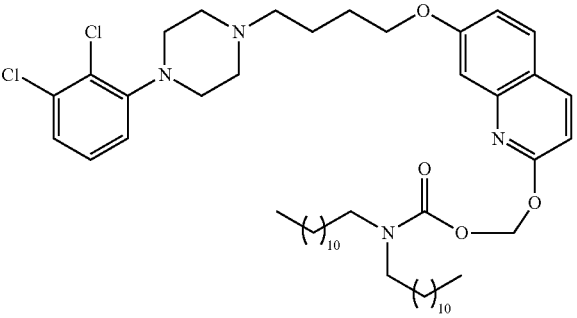 |

TABLE I-continued
| No | Structure |
|---|---|
| 1255. | 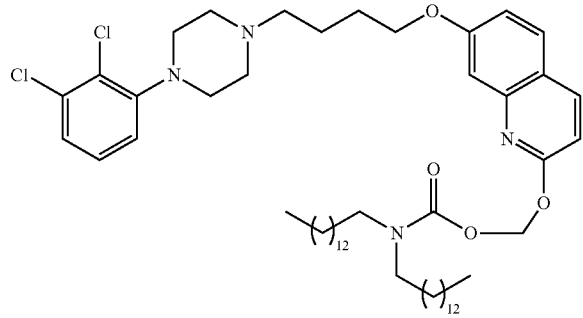 |
| 1256. | 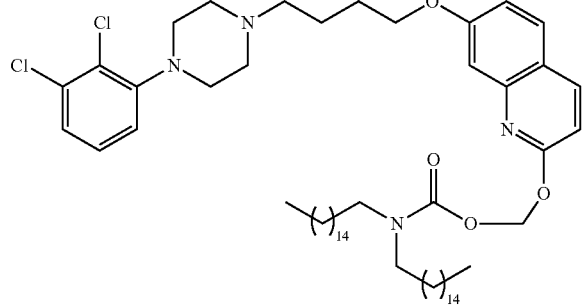 |
| 1257. | 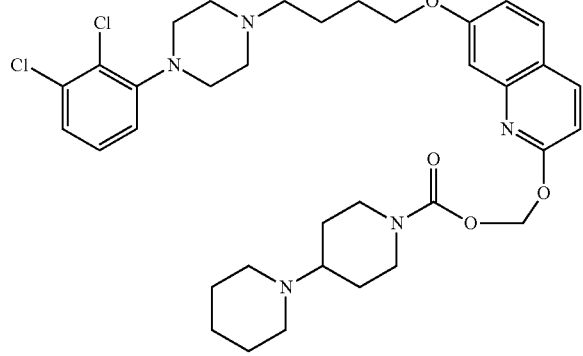 |
| 1258. | 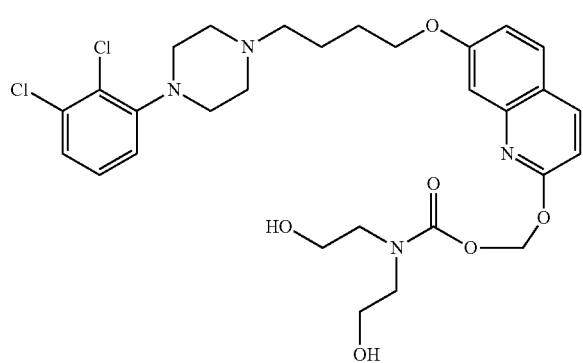 [SMILES: O=C(OCOc1ccc2ccc(OCCCCN3CCN(c4cccc(Cl)c4Cl)CC3)cc2n1)N(CCO)CCO] |

TABLE I-continued

| No | Structure |
|---|---|
| 1259. | 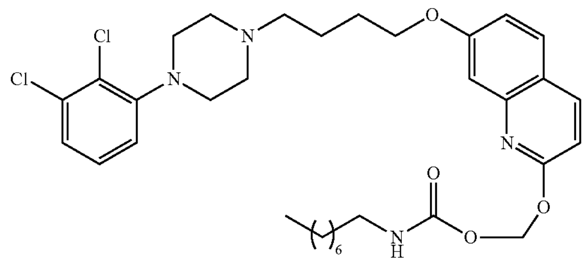 |
| 1260. | 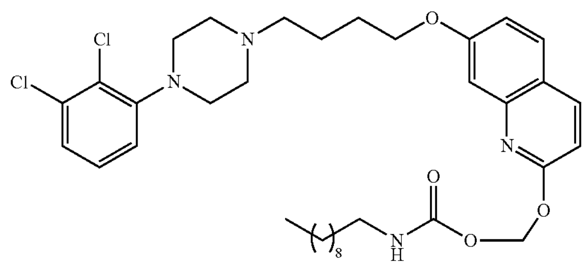 |
| 1261. | 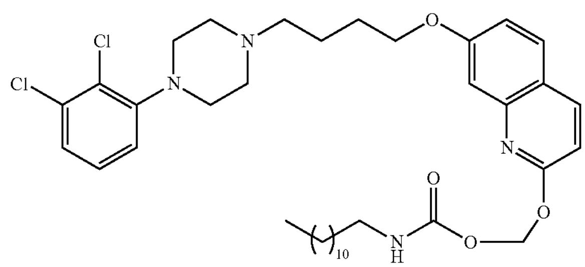 |
| 1262. | 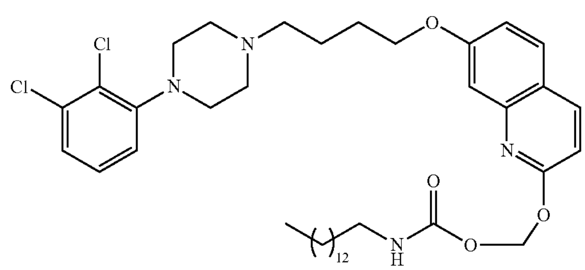 |
| 1263. | 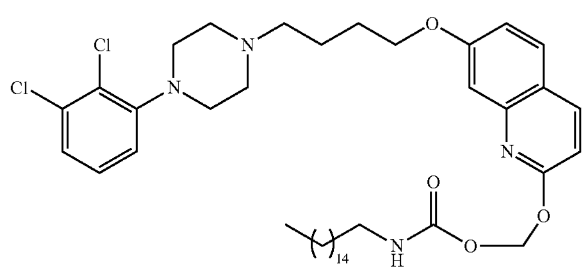 |

TABLE I-continued
| No | Structure |
|---|---|
| 1264. | 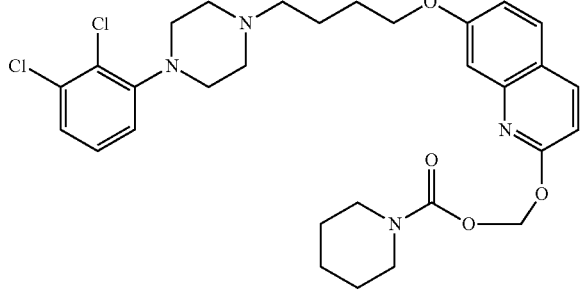 |
| 1265. | 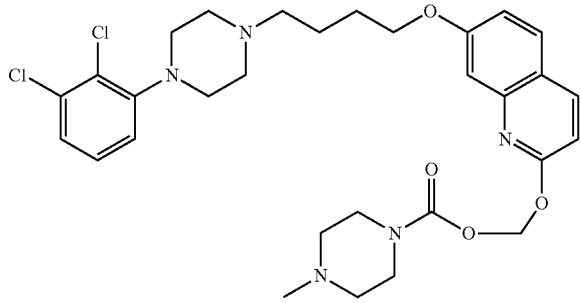 |
| 1266. | 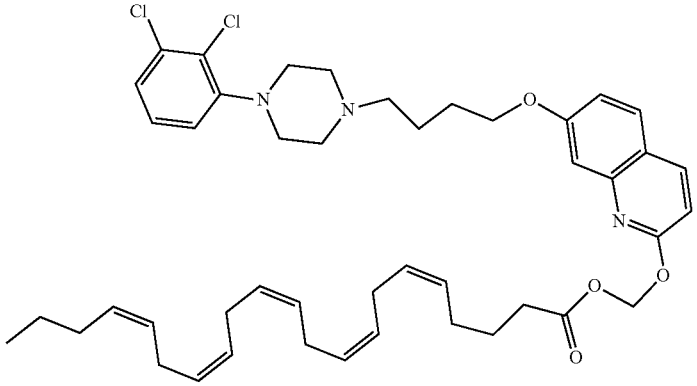 [SMILES: CCC/C=C\C/C=C\C/C=C\C/C=C\C/C=C\CCCC(=O)OCOc1ccc2ccc(OCCCCN3CCN(c4cccc(Cl)c4Cl)CC3)cc2n1] |
| 1267. | 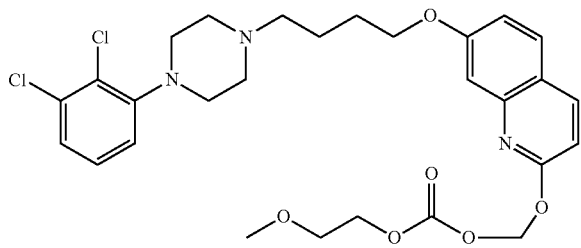 [SMILES: COCCOC(=O)OCOc1ccc2ccc(OCCCCN3CCN(c4cccc(Cl)c4Cl)CC3)cc2n1] |

Barbiturates

In another embodiment, compounds of the present invention are represented by formula XXXIII-XXXVII as illustrated below, and the geometric isomers, enantiomers, diastereomers, racemates, pharmaceutically acceptable salts and solvates thereof:

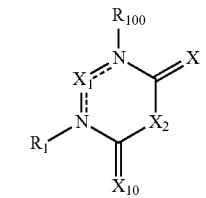

Formula XXXIII

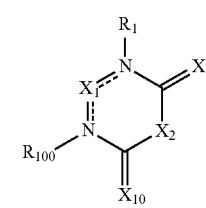

Formula XXXIV

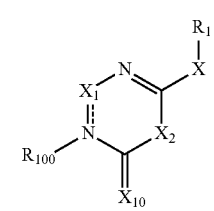

Formula XXXV

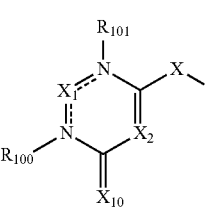

Formula XXXVI

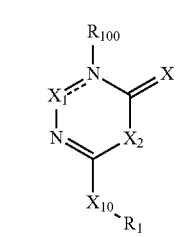

Formula XXXVII wherein, X, $X_1$, $X_2$, $R_{100}$, $R_{101}$, and $R_1$ are as defined above; $X_{10}$ is —S or —O.

In a preferred embodiment a compound from Table XXXIII-XXXVII is provided. A more preferred embodiment is a compound of table XXXIII-XXXVII wherein $R_1$ is selected from tables 1-4.

TABLE XXXIII-XXXIV

| | |
|---|---|
| 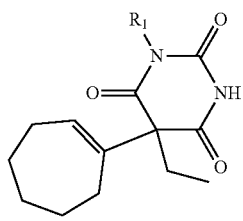 | 1 |
| 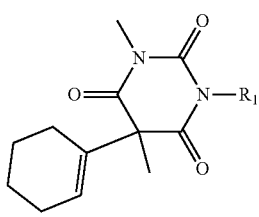 | 2 |
| 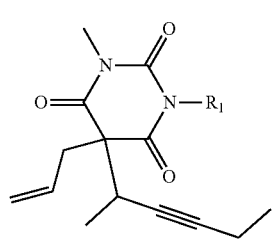 | 3 |
| 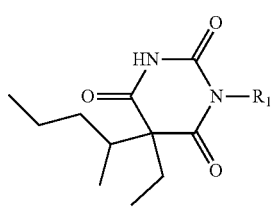 | 4 |
|  | 5 |
| 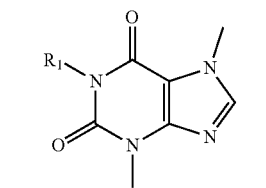 | 6 |
| 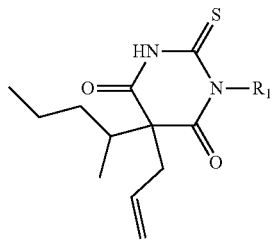 | 7 |

TABLE XXXIII-XXXIV-continued

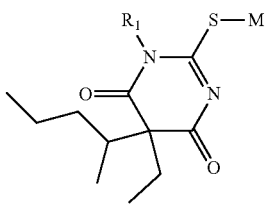
8

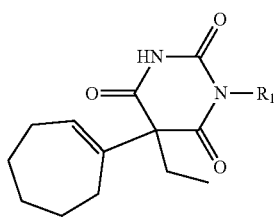
9

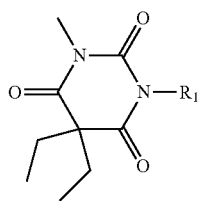
10

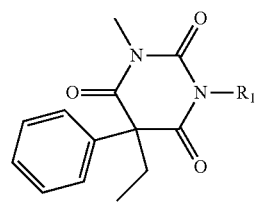
11

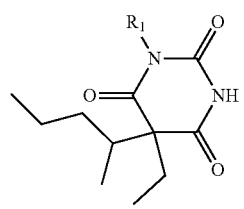
12

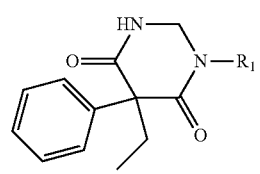
13

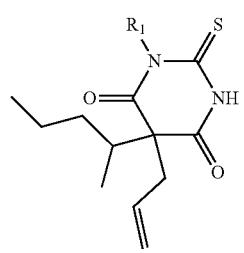
14

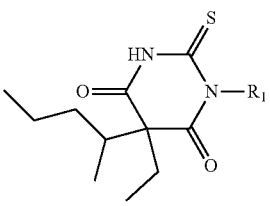
15

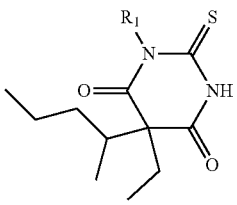
16

Pyridone Pyrimidone and Pyrimidone Prodrugs

In another embodiment, compounds of the present invention are represented by formula XXXVIII or XXXIX as illustrated below, and the geometric isomers, enantiomers, diastereomers, racemates, pharmaceutically acceptable salts and solvates thereof:

Formula XXXVIII

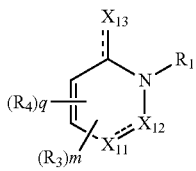

Formula XXXIX

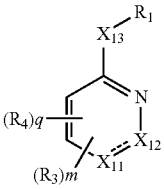

wherein X, $R_1$, $R_3$, $R_4$, m and q are as defined above;
$X_{11}$ is —N— or —C($R_{10}$)—;
$X_{12}$ is —C(O)—, —C(S)—, —C($R_{10}$)($R_{11}$)— or —C($R_{10}$)(O$R_{11}$)—; and,
$X_{13}$ is —O, —S, —N($R_{10}$)($R_{11}$), —O$R_{10}$.

A preferred embodiment is a compound selected from table XXXVIII-XXXIX. A more preferred embodiment is a compound from table XXXVIII-XXXVIX wherein $R_1$ is selected from tables 1-4.

TABLE XXXVIII

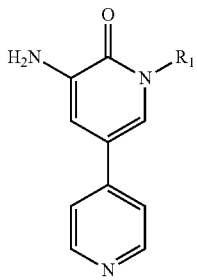
1

TABLE XXXVIII-continued
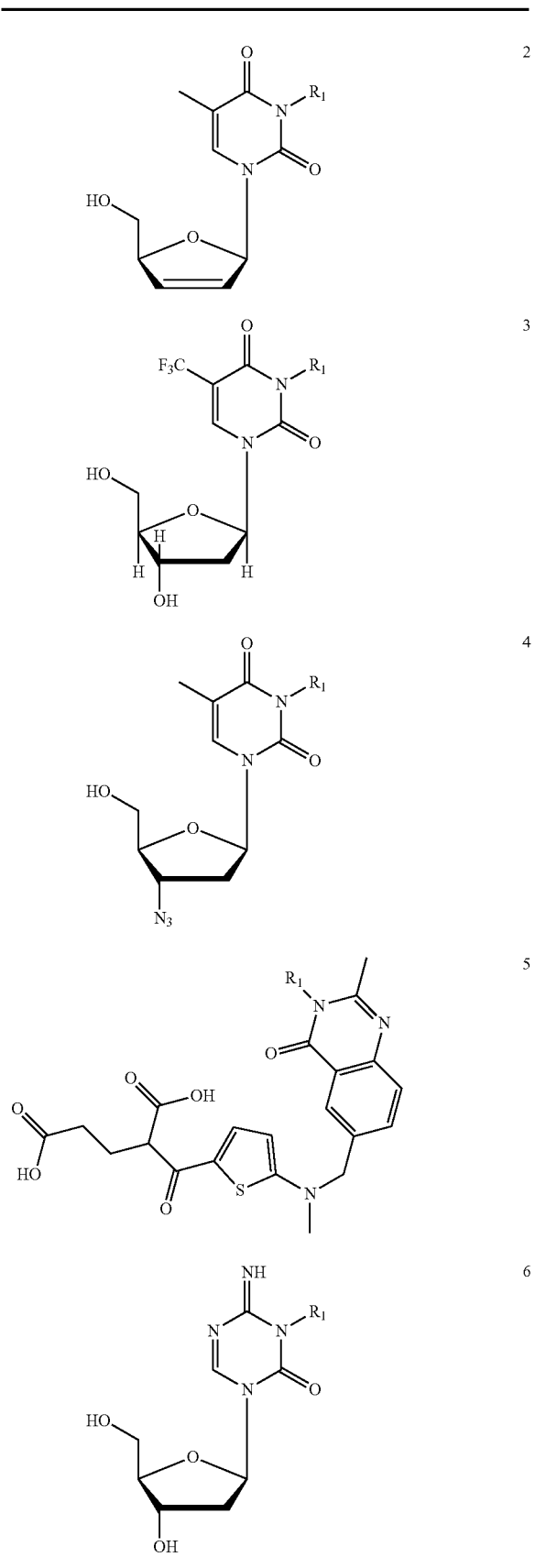
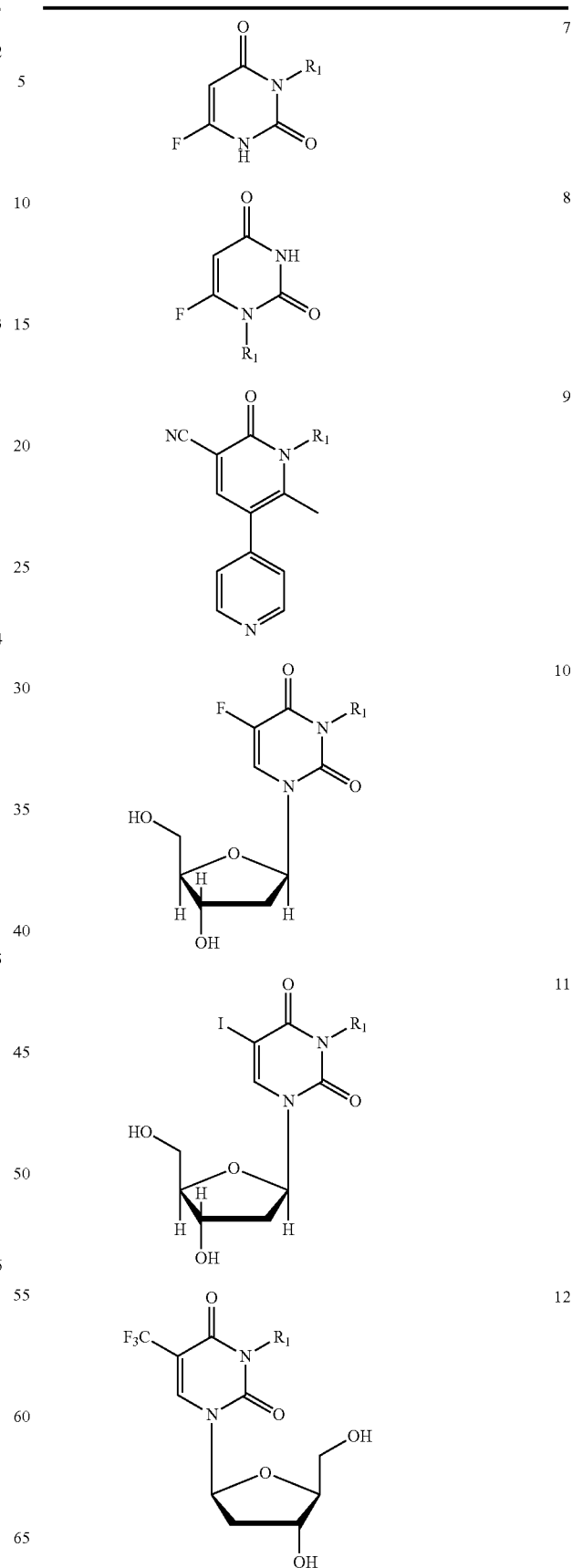

TABLE XXXVIII-continued

| | |
|---|---|
| 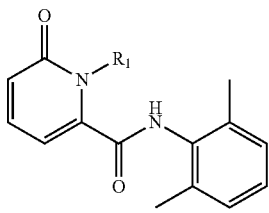 | 13 |
| 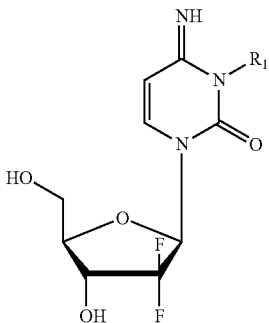 | 14 |
| 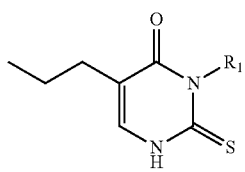 | 15 |
| 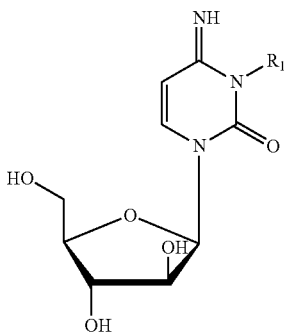 | 16 |

Prodrugs of Benzamide Pharmacophores

In another embodiment, compounds of the present invention are represented by formula XL or XLI as illustrated below, and the geometric isomers, enantiomers, diastereomers, racemates, pharmaceutically acceptable salts and solvates thereof:

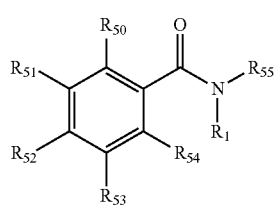

Formula XL

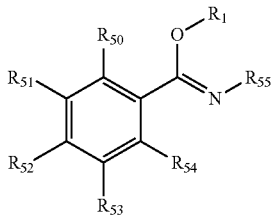

Formula XLI wherein $R_1$, $R_{50}$, $R_{51}$, $R_{52}$, $R_{53}$, $R_{54}$ and $R_{55}$ are as defined above.

TABLE XL-XLI

| | |
|---|---|
| 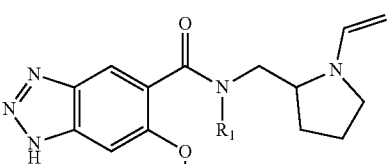 | 1 |
| 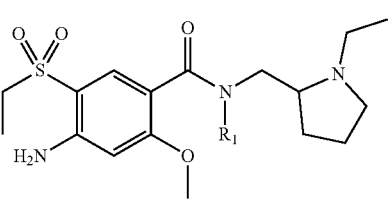 | 2 |
| 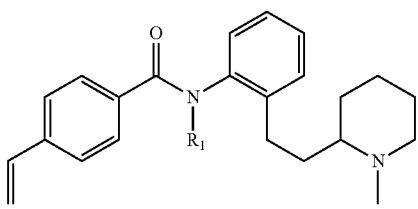 | 3 |
| 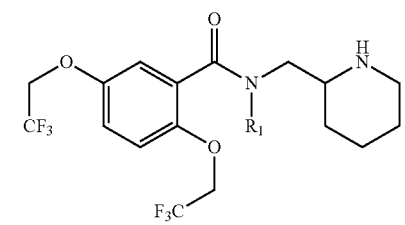 | 4 |
| 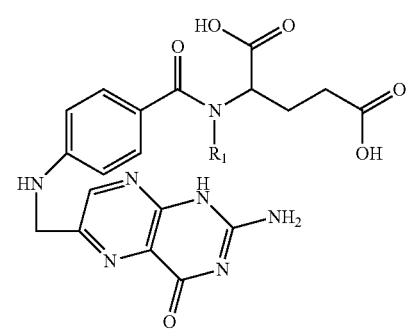 | 5 |

TABLE XL-XLI-continued
6
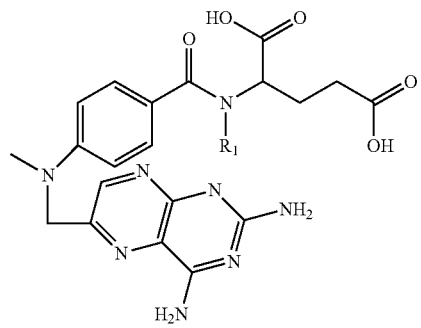
7
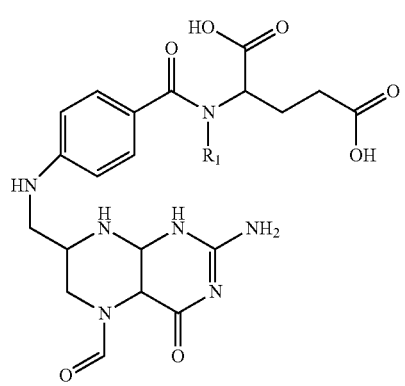
8
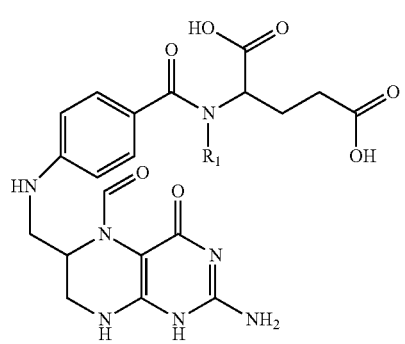
9
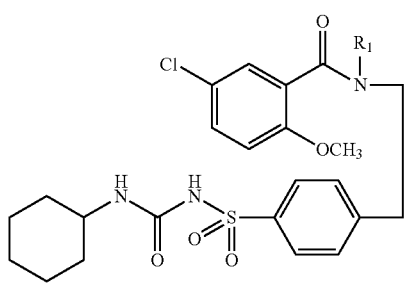
10
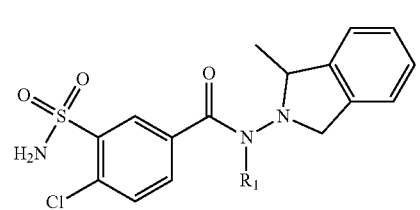
TABLE XL-XLI-continued
11
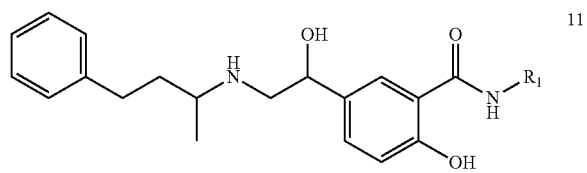
12
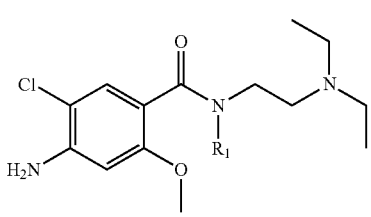
13
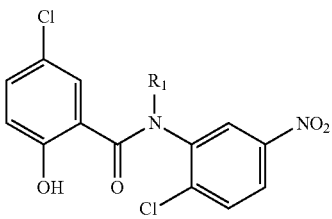
14
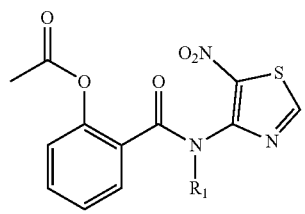
15
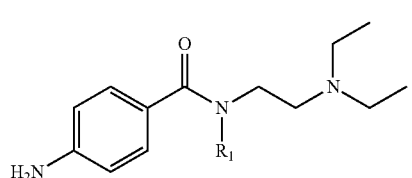
16
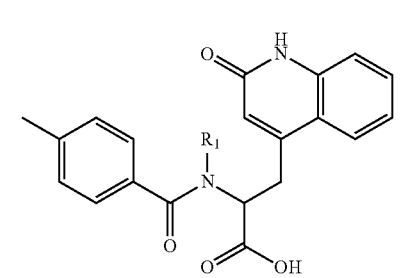
17
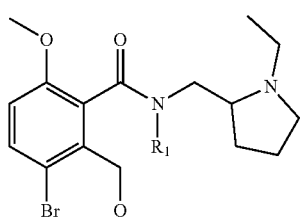

TABLE XL-XLI-continued
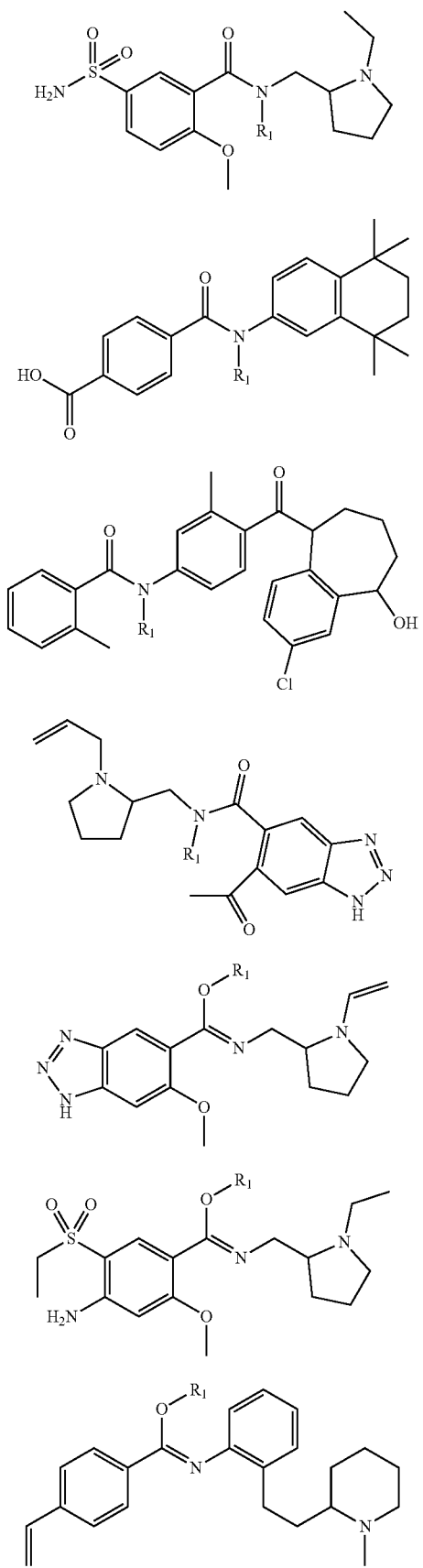
TABLE XL-XLI-continued
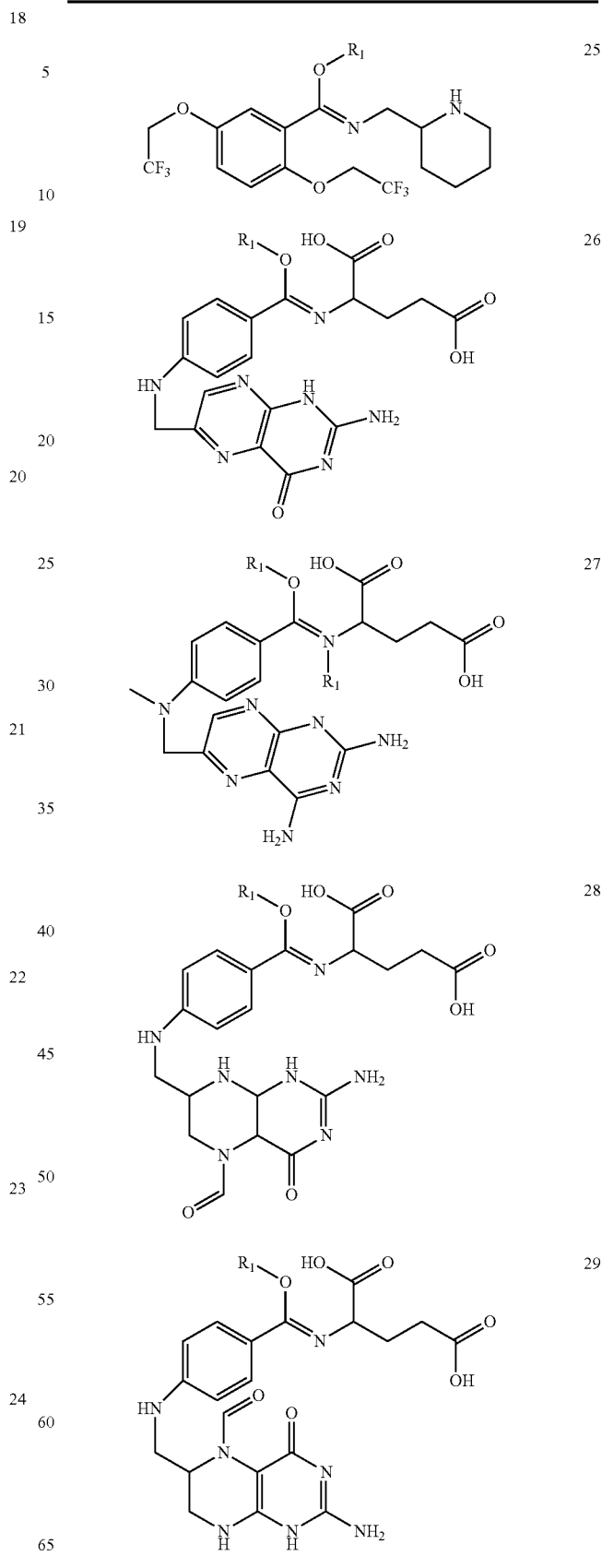

TABLE XL-XLI-continued
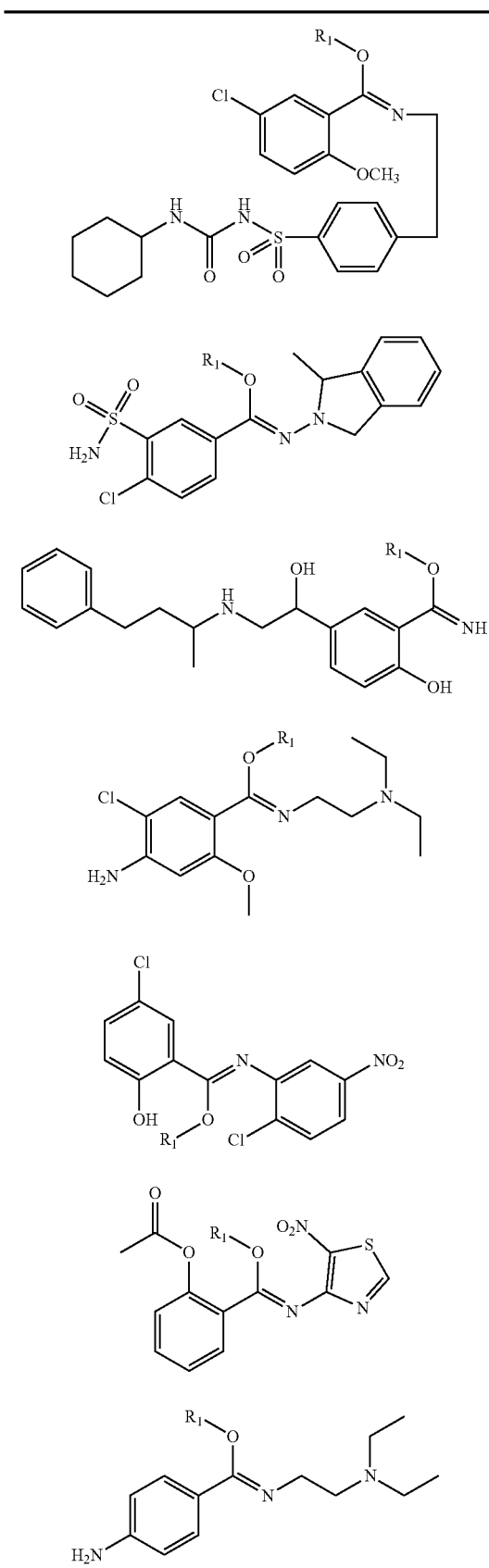
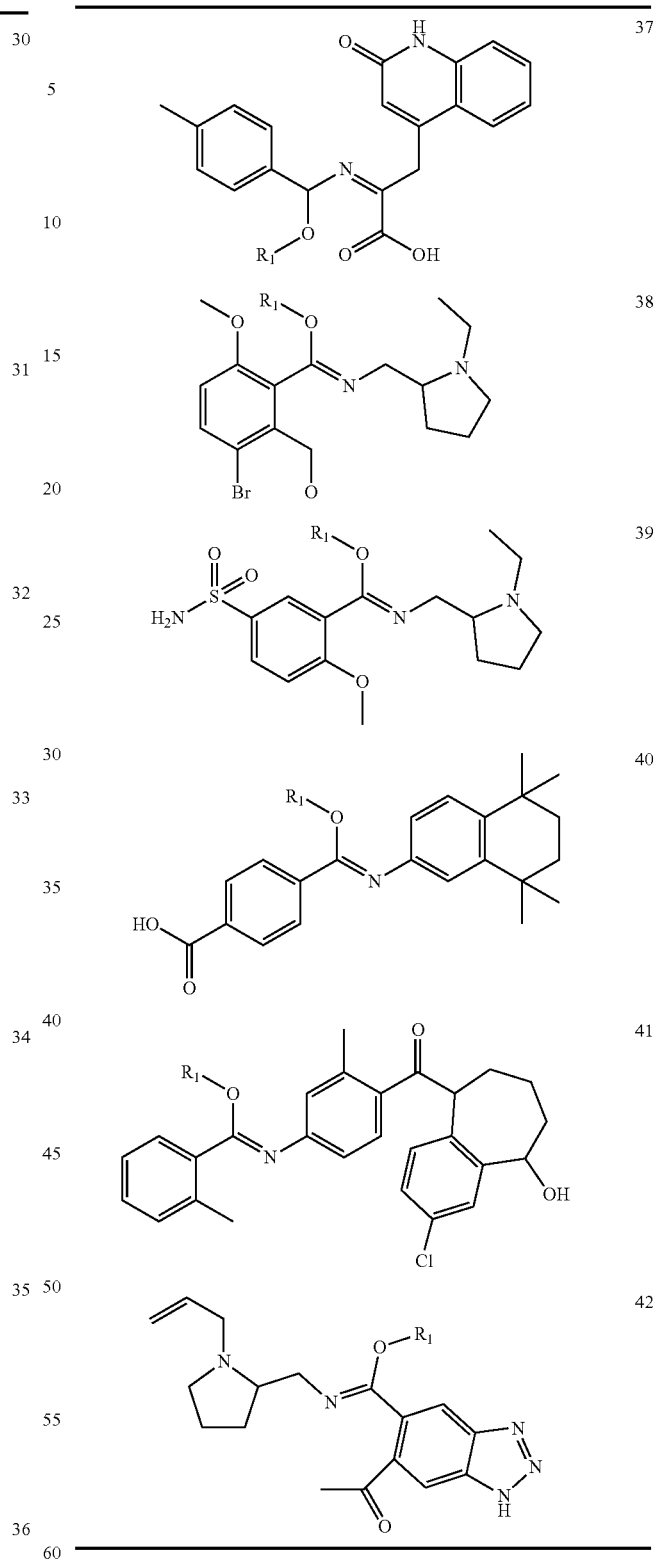
Prodrugs of Imide Pharmacophores
In another embodiment, compounds of the present invention are represented by formula XLII, XLIII or XLIV as illustrated below, and the geometric isomers, enantiomers, diastereomers, racemates, pharmaceutically acceptable salts and solvates thereof:

Formula XLII

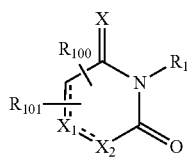

Formula XLIII

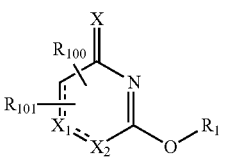

Formula XLIV

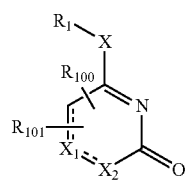

wherein $R_1$ $R_{100}$, $R_{101}$, X, $X_1$ and $X_2$ are as defined above; alternatively $R_{100}$ and $R_{101}$ together with the atoms to which they are attached form an optionally substituted 3, 4, 5, 6, or 7 membered ring.

A preferred embodiment is a compound selected from table XLII-XLIV. A more preferred embodiment is a compound from table XLII-XLIV wherein $R_1$ is selected from tables 1-4.

TABLE XLII-XLIV

XLII-

| | |
|---|---|
| 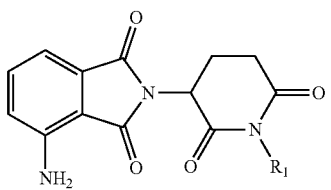 | 1 |
| 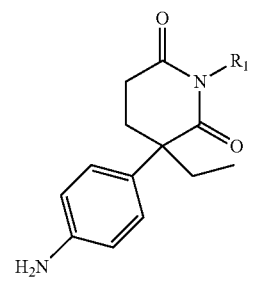 | 2 |
| 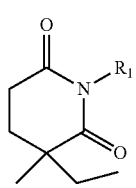 | 3 |

TABLE XLII-XLIV-continued

| | |
|---|---|
| 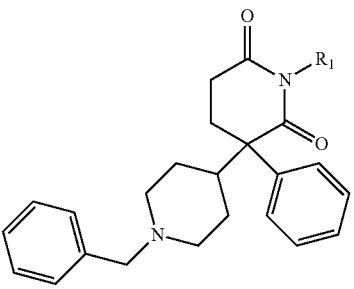 | 4 |
| 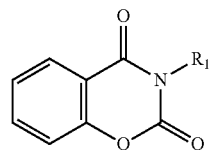 | 5 |
| 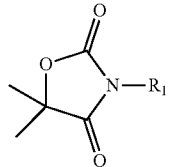 | 6 |
| 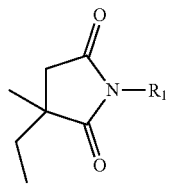 | 7 |
| 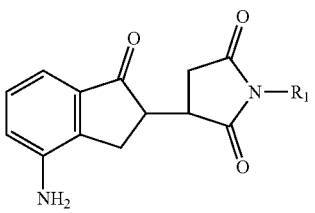 | 8 |
| 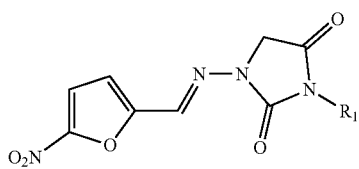 | 9 |
| 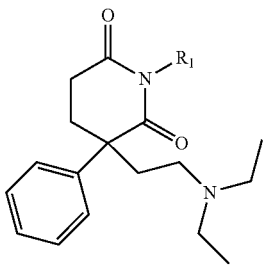 | 10 |
| 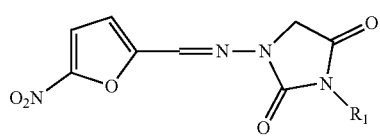 | 11 |

TABLE XLII-XLIV-continued
| | |
|---|---|
| 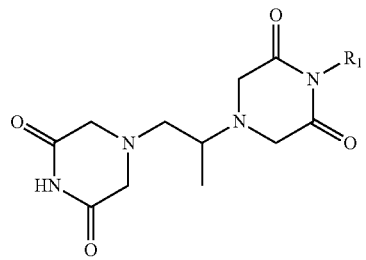 | 12 |
| 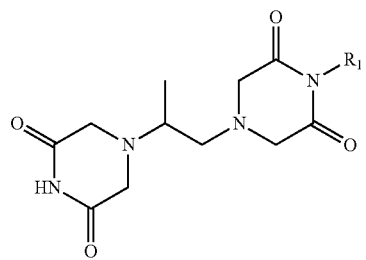 | 13 |
| 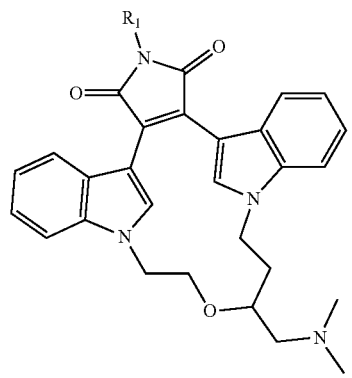 | 14 |
| 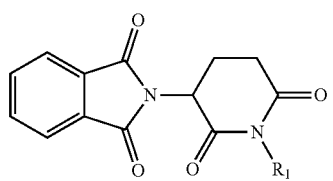 | 15 |
| 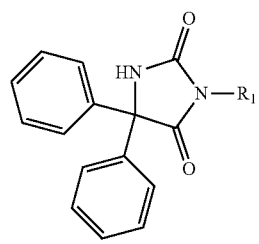 | 16 |
XLIII-
| | |
|---|---|
| 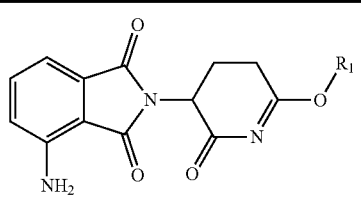 | 1 |
TABLE XLII-XLIV-continued
| | |
|---|---|
| 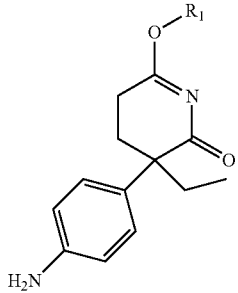 | 2 |
| 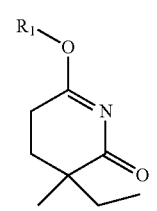 | 3 |
| 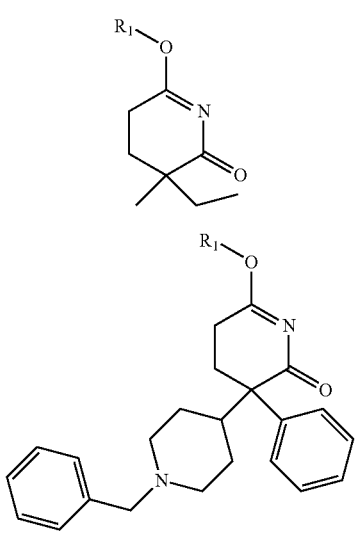 | 4 |
| 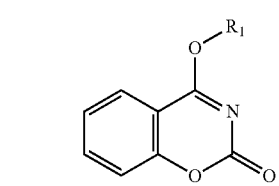 | 5 |
| 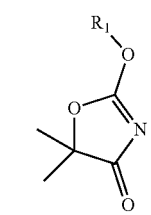 | 6 |
| 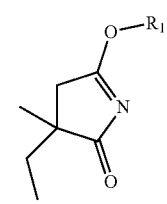 | 7 |
| 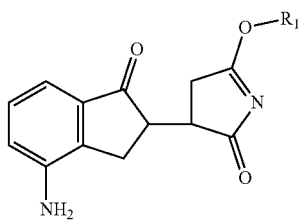 | 8 |

TABLE XLII-XLIV-continued
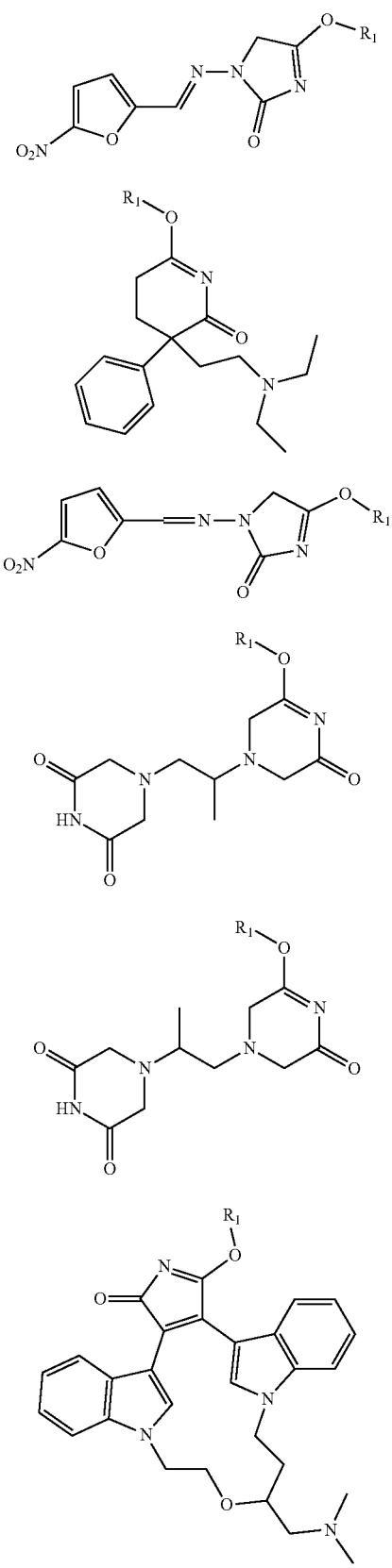
TABLE XLII-XLIV-continued
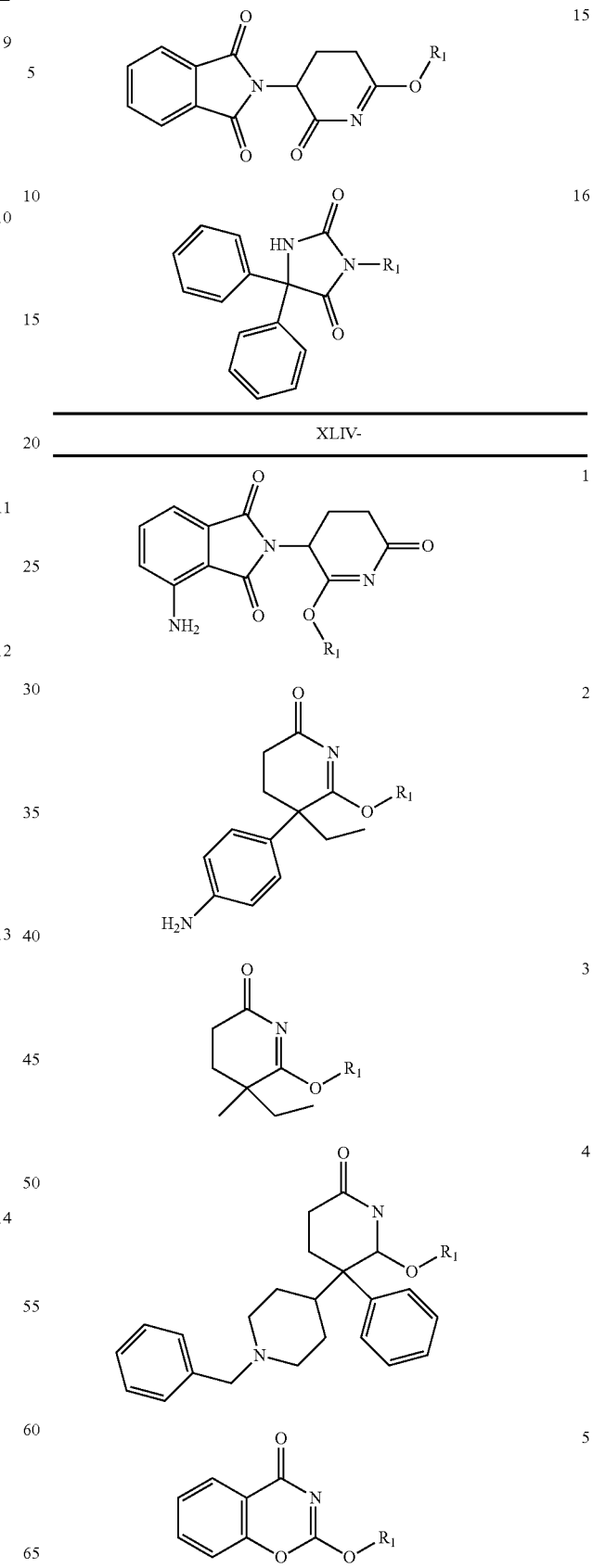
XLIV- TABLE XLII-XLIV-continued
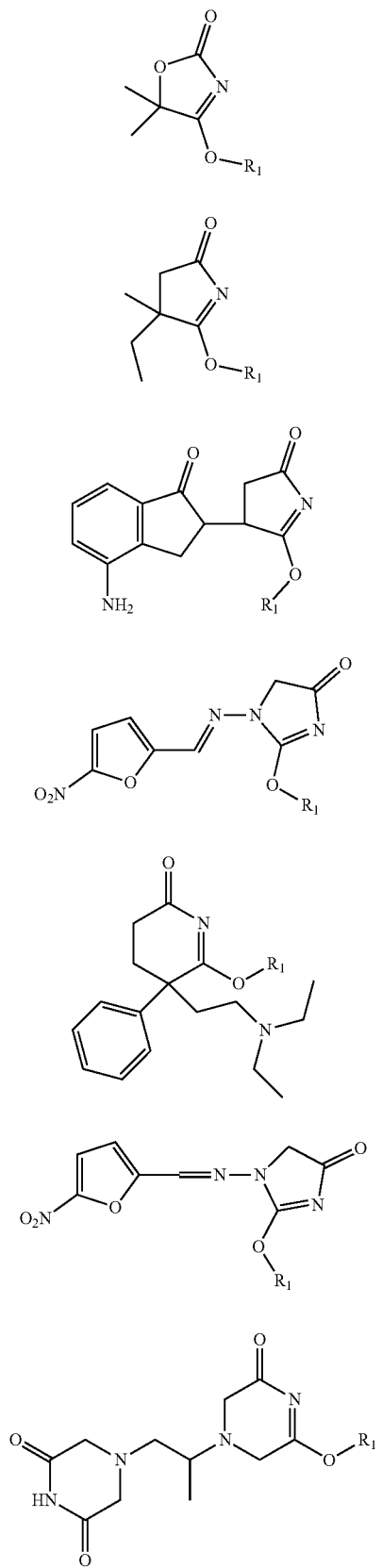
TABLE XLII-XLIV-continued
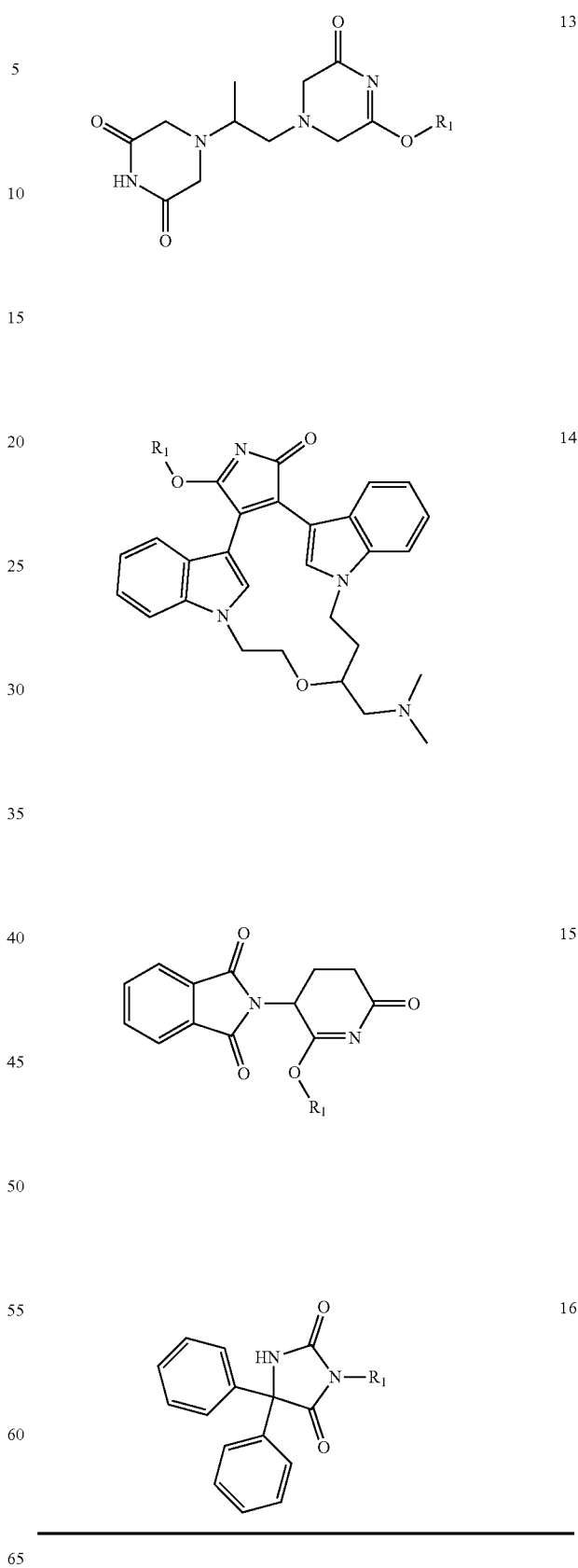
In another embodiment, compounds of the present invention having the formula IV-VII is selected from table IV-V.

TABLE IV-VII
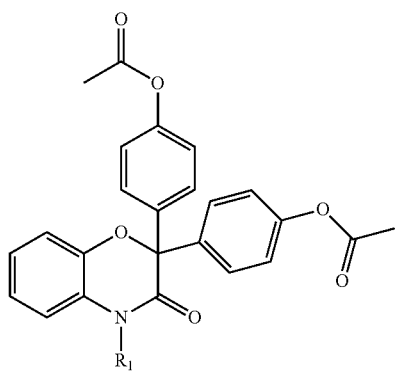
1
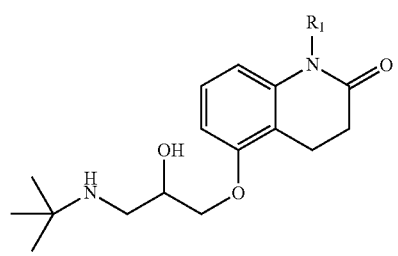
2
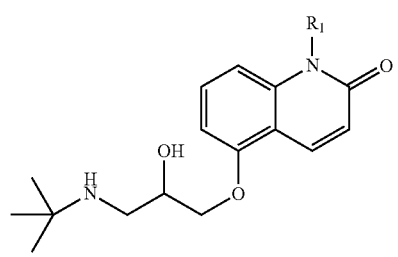
3
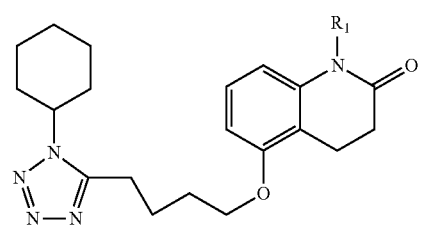
4
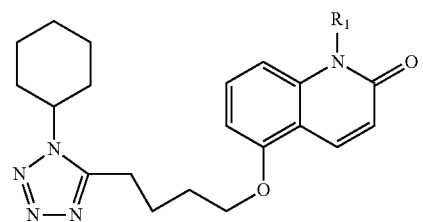
5
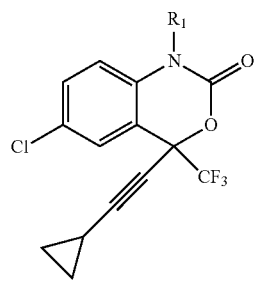
6

TABLE IV-VII-continued
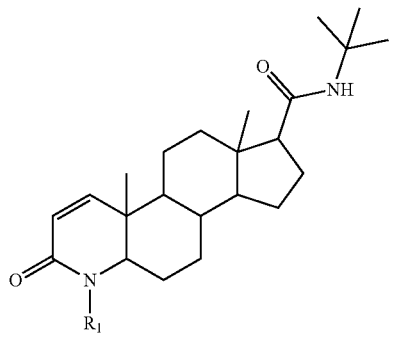
7
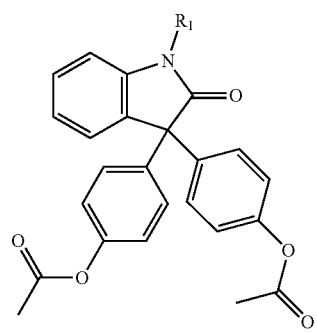
8
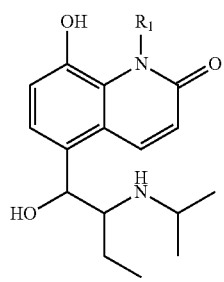
9
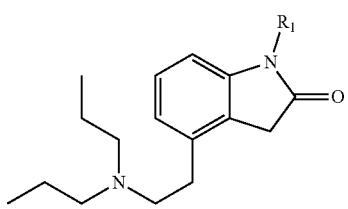
10
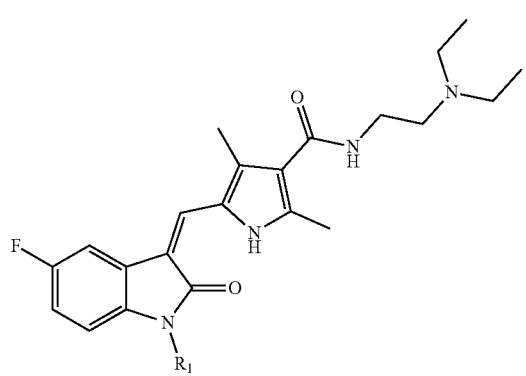
11

TABLE IV-VII-continued
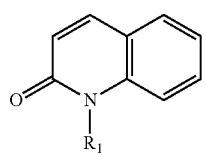
12
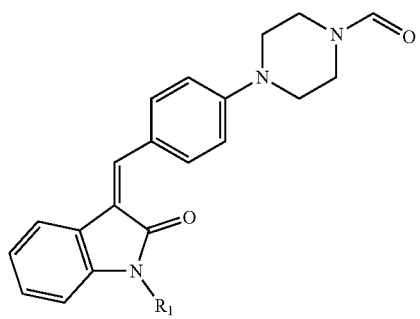
13
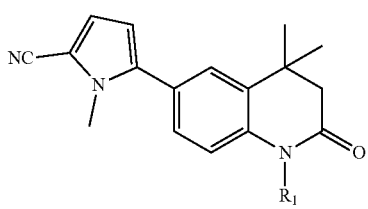
14
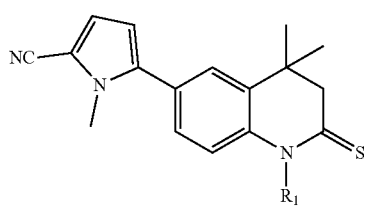
15
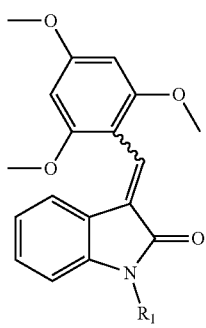
16
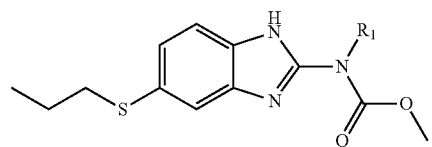
17
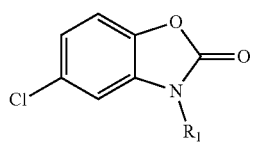
18

TABLE IV-VII-continued
| | |
|---|---|
| 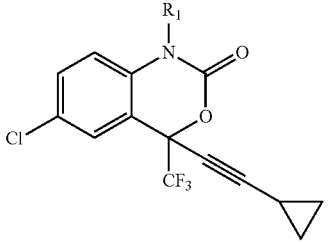 | 19 |
| 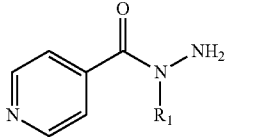 | 20 |
| 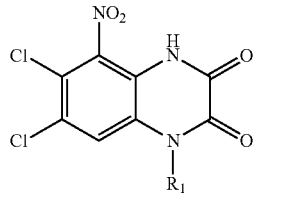 | 21 |
| 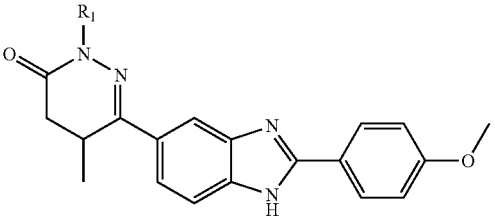 | 22 |
| 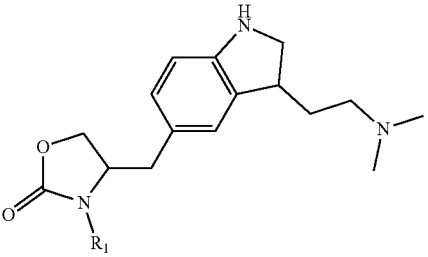 | 23 |
| 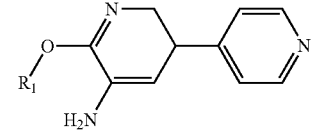 | 24 |
| 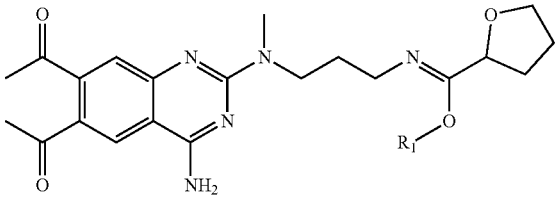 | 25 |

TABLE IV-VII-continued
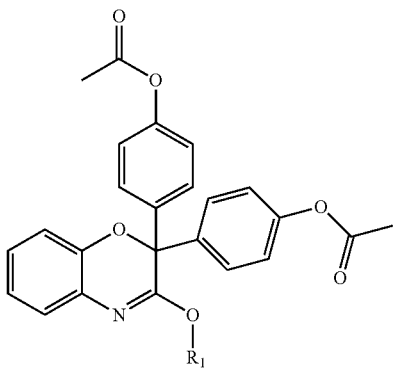
26
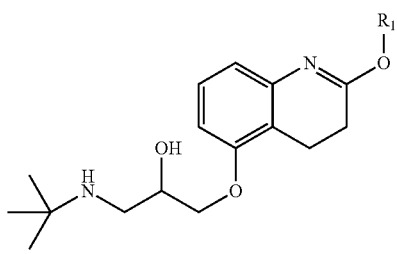
27
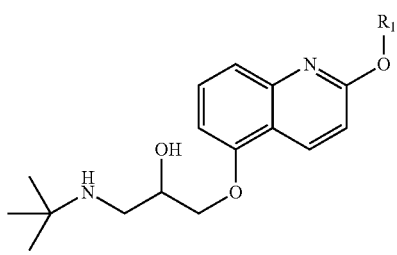
28
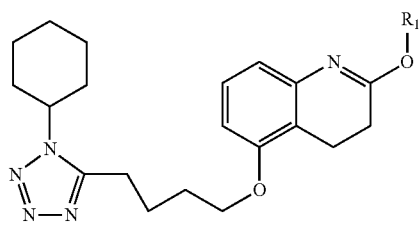
29
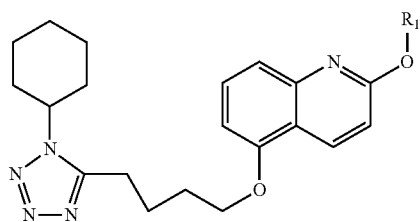
30
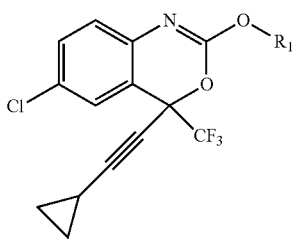
31

TABLE IV-VII-continued
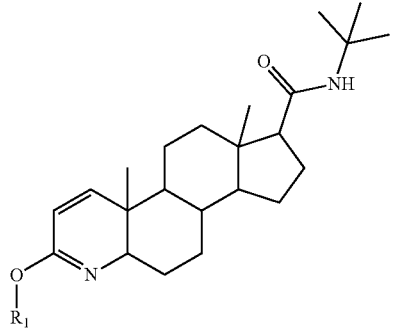
32
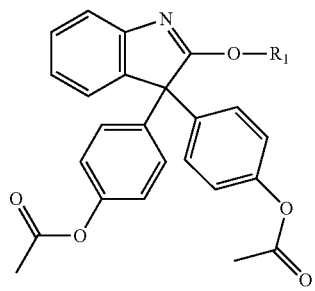
33
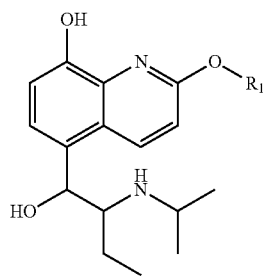
34
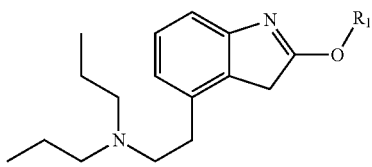
35
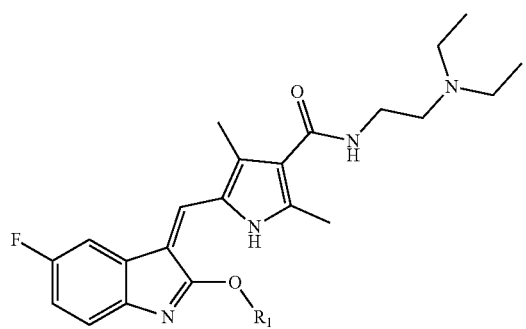
36
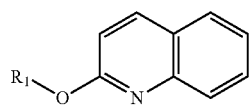
37

TABLE IV-VII-continued
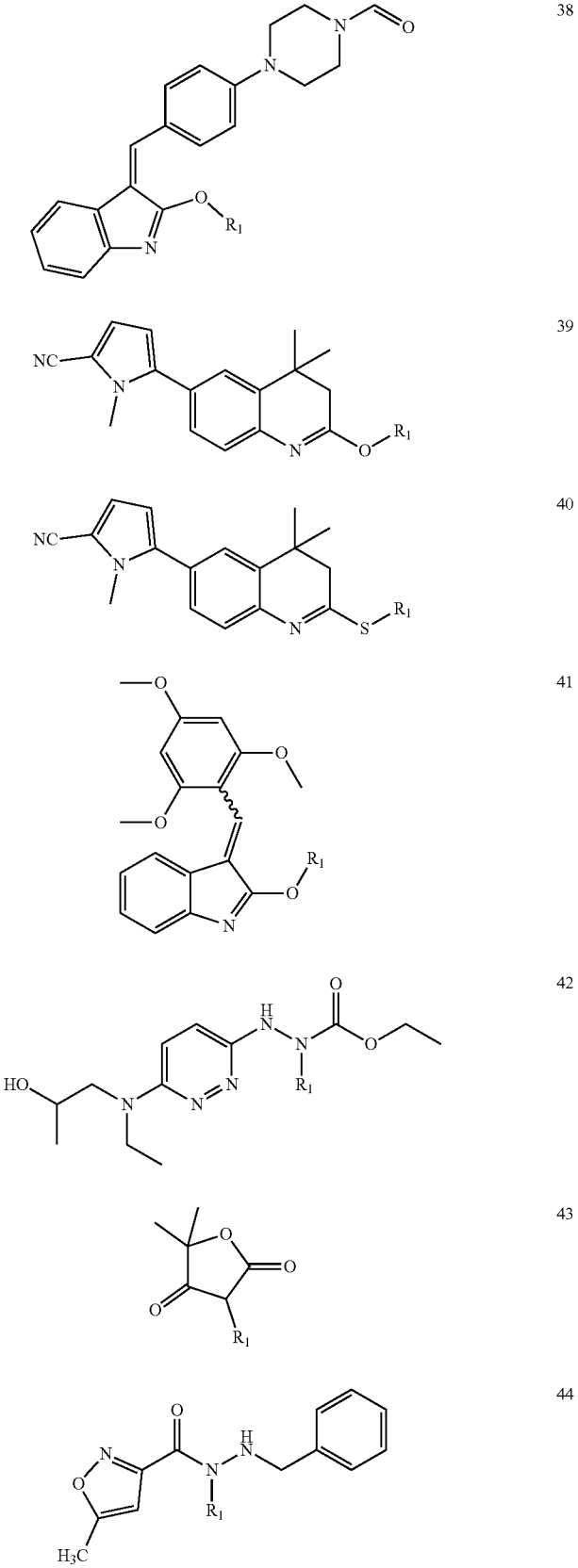
| | |
|---|---|
| | 38 |
| | 39 |
| | 40 |
| | 41 |
| | 42 |
| | 43 |
| | 44 |

TABLE IV-VII-continued
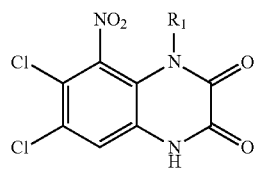
45
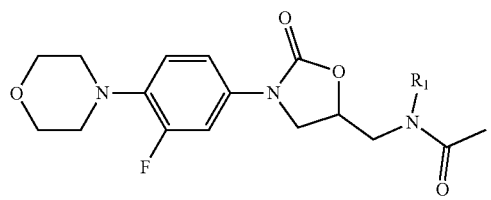
46
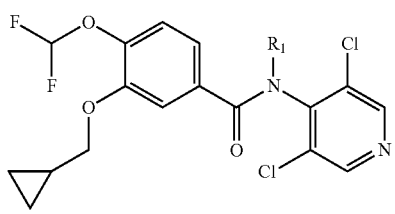
47
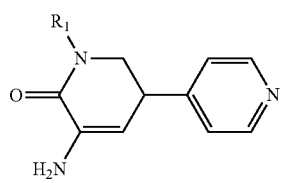
48
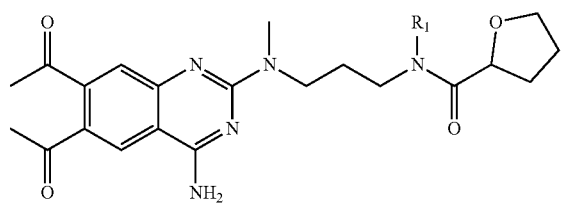
49
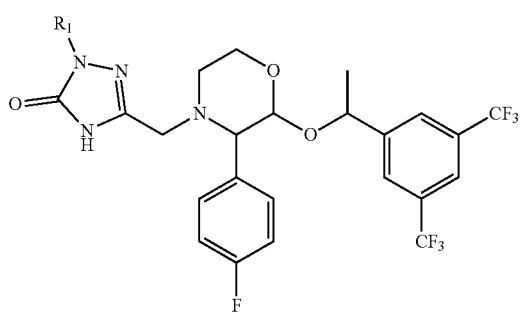
50
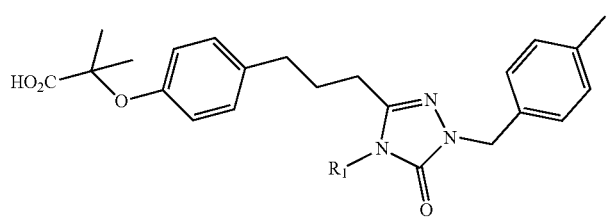
51

TABLE IV-VII-continued

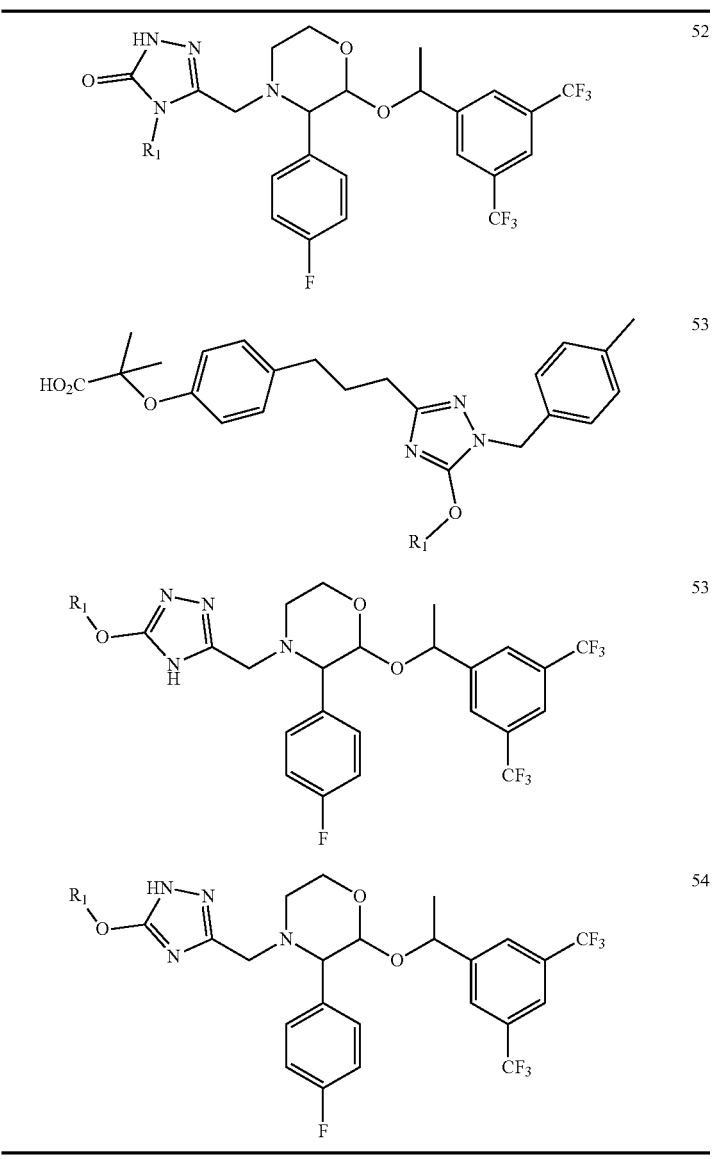

Prodrugs of Sulfonamide Pharmacophores

In another embodiment, compounds of the present invention are represented by formula II as illustrated below, or its geometric isomers, enantiomers, diastereomers, racemates, pharmaceutically acceptable salts and solvates thereof:

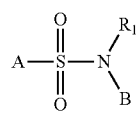

Formula III

A preferred embodiment is a compound selected from table III. A more preferred embodiment is a compound from table III wherein $R_1$ is selected from tables 1-4.

TABLE III

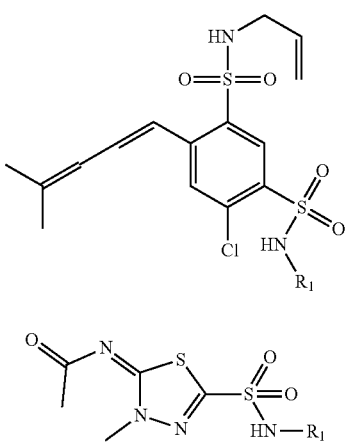

TABLE III-continued
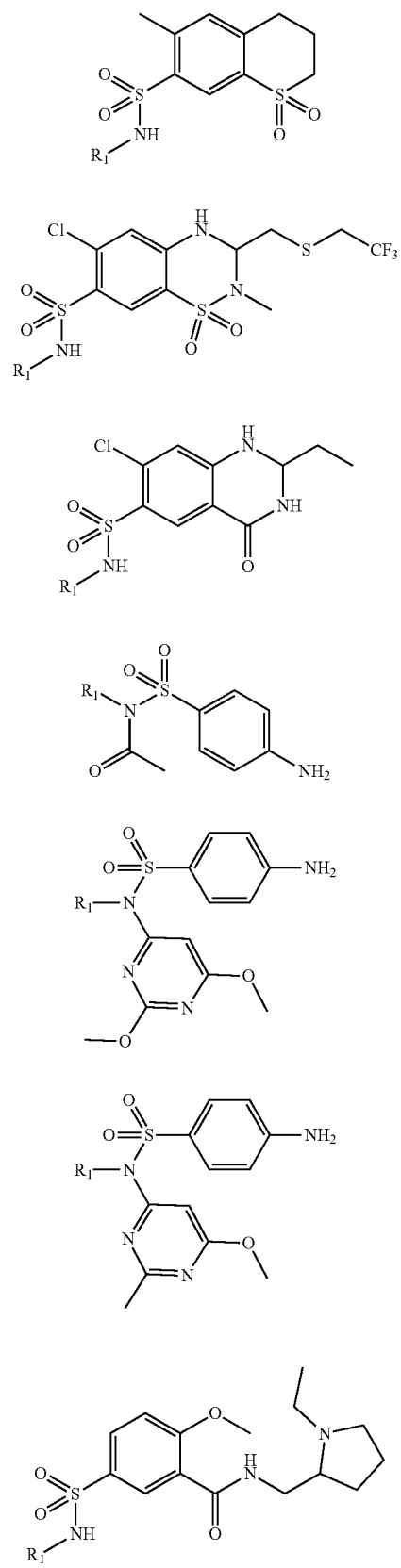
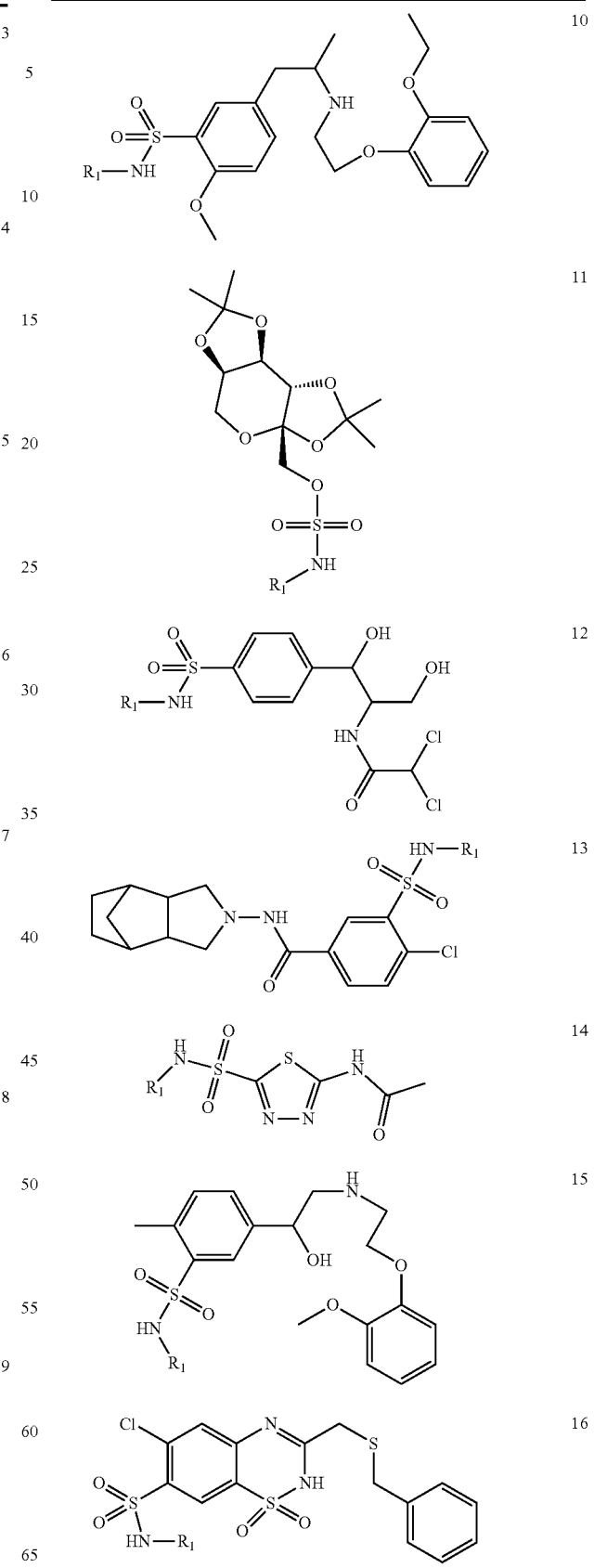

TABLE III-continued
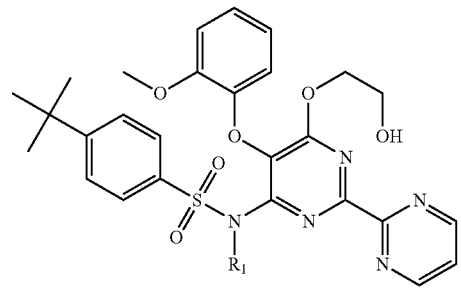
17
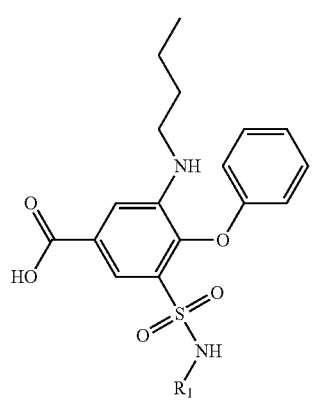
18
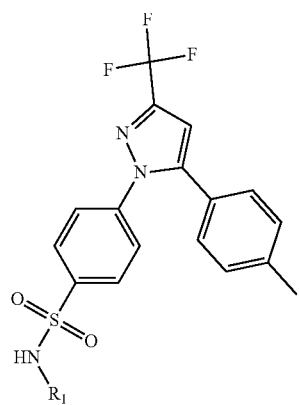
19
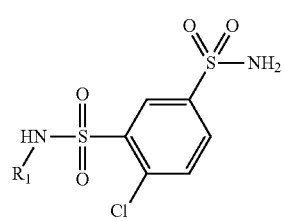
20
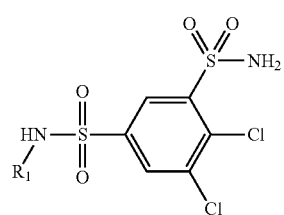
21
TABLE III-continued
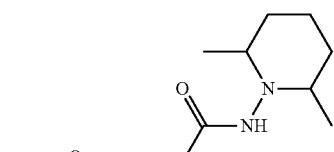
22
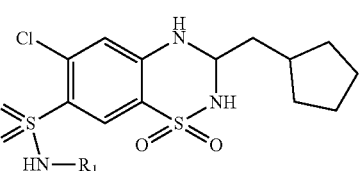
23
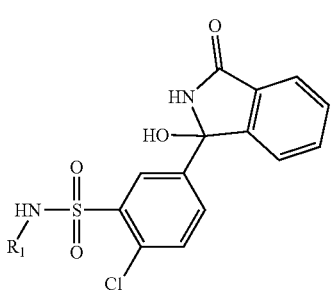
24
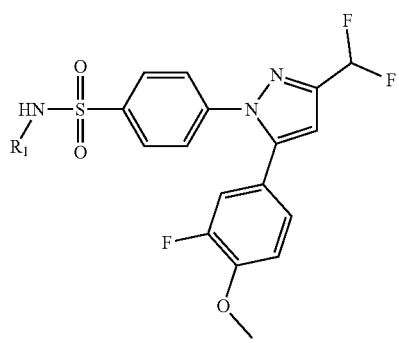
25
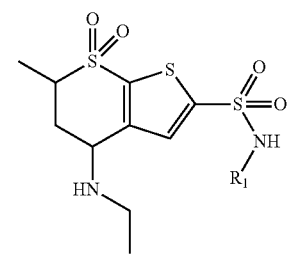
26
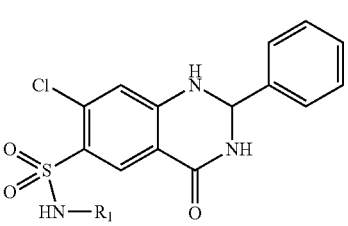
27

TABLE III-continued
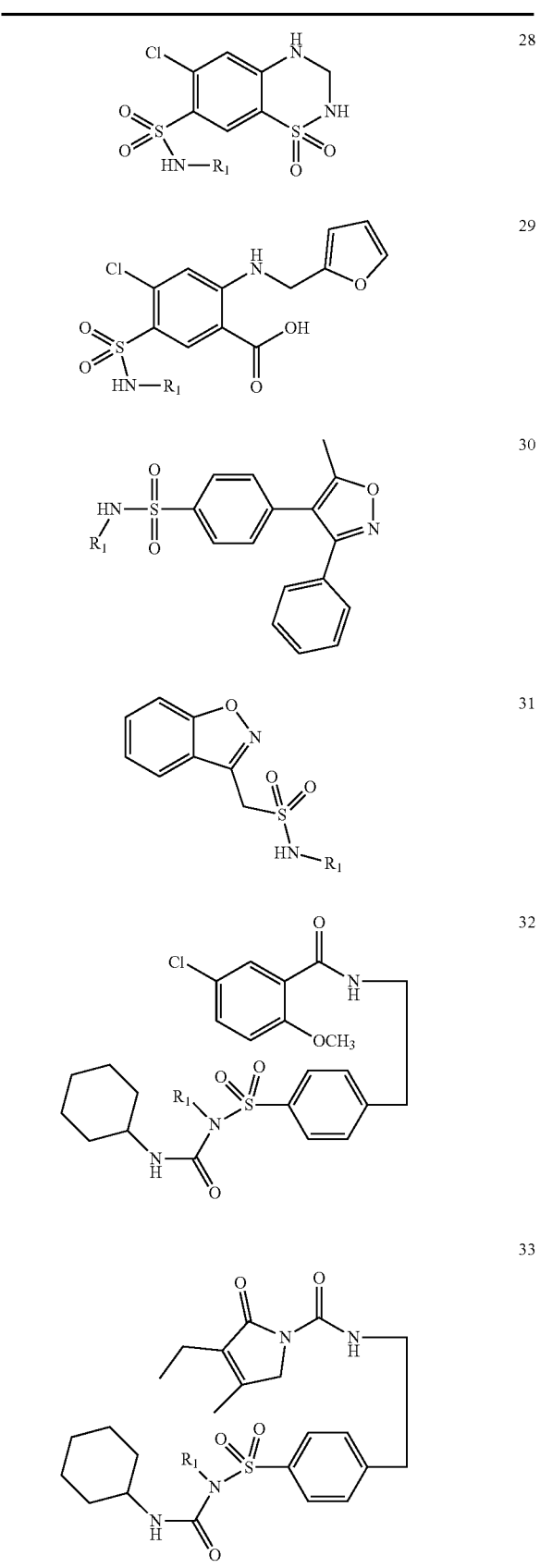
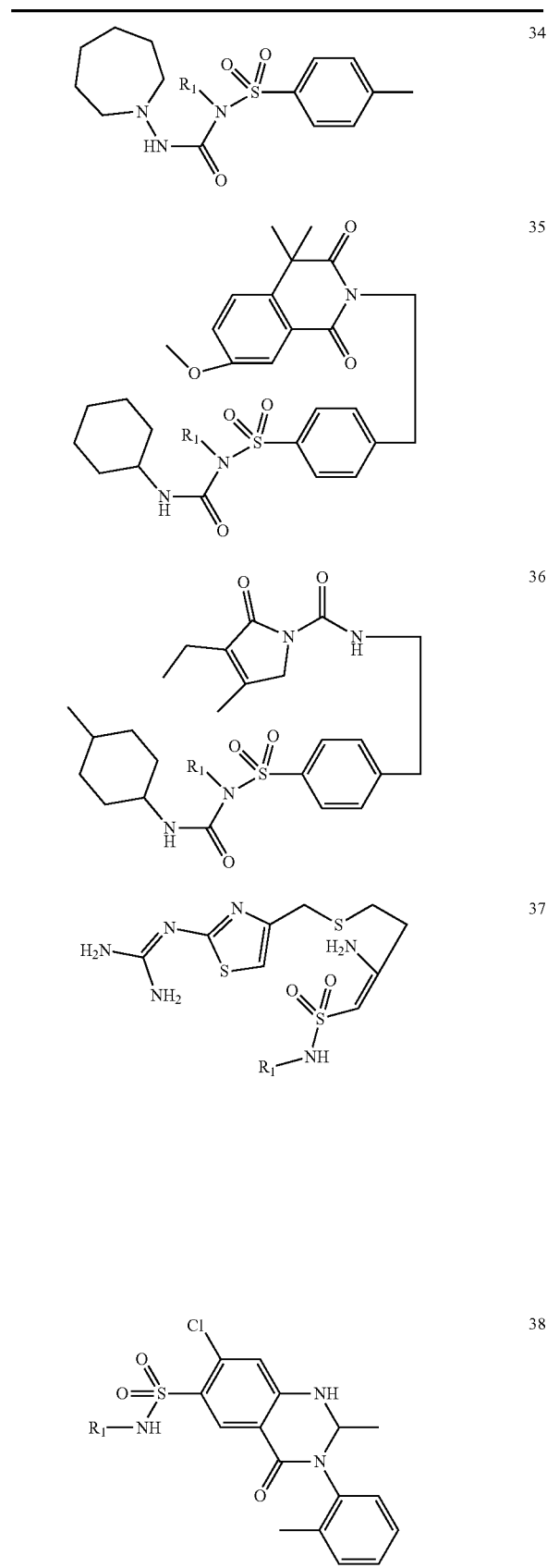

TABLE III-continued
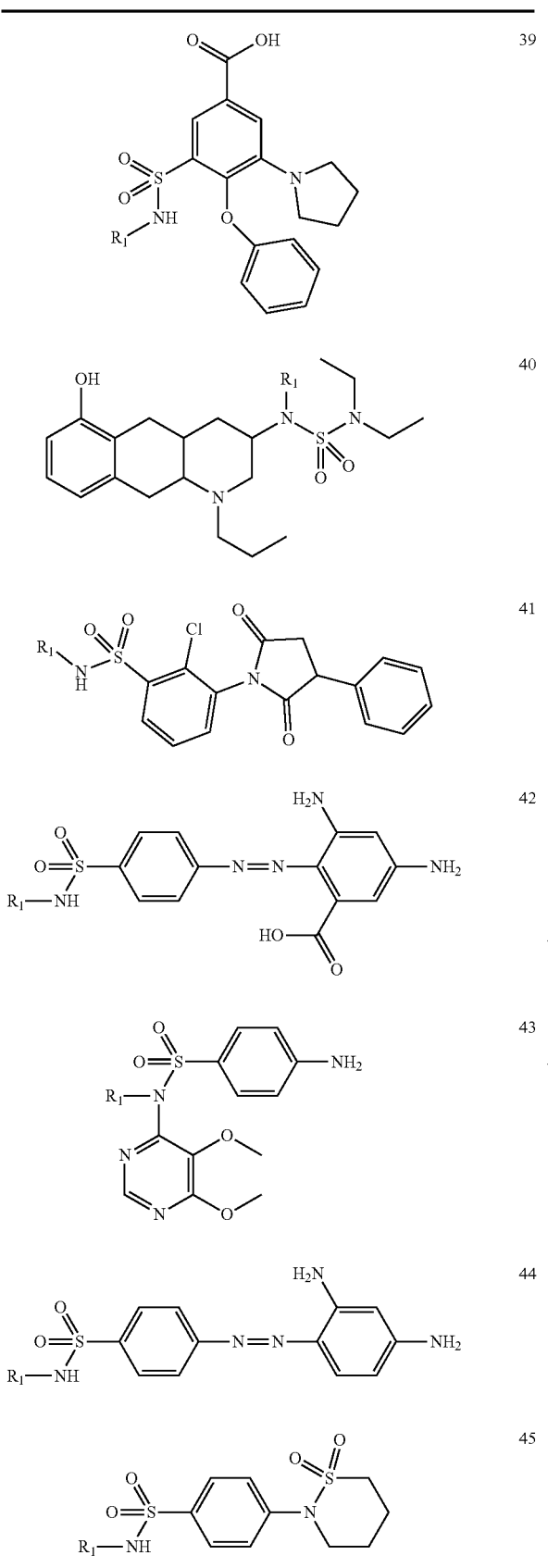
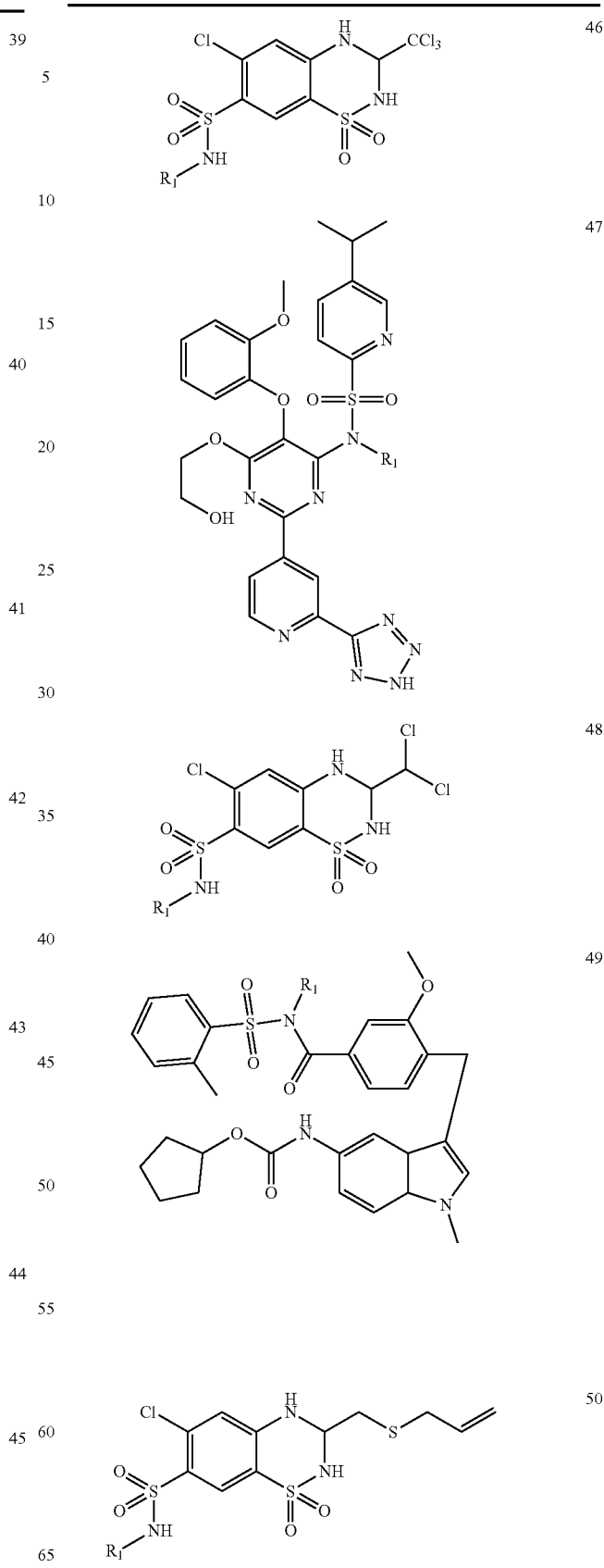

TABLE III-continued
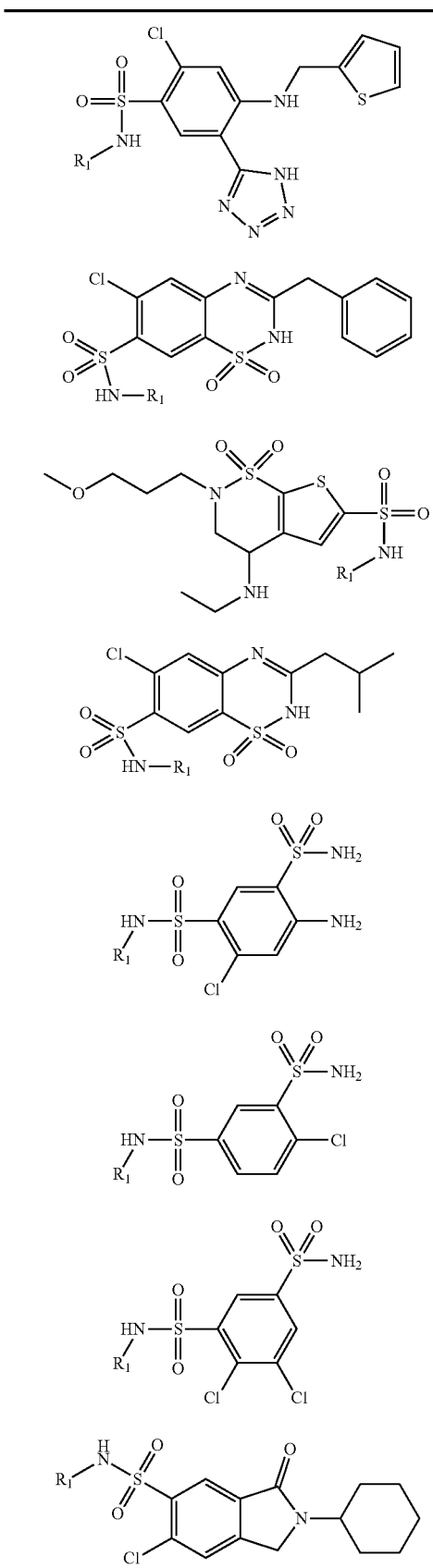
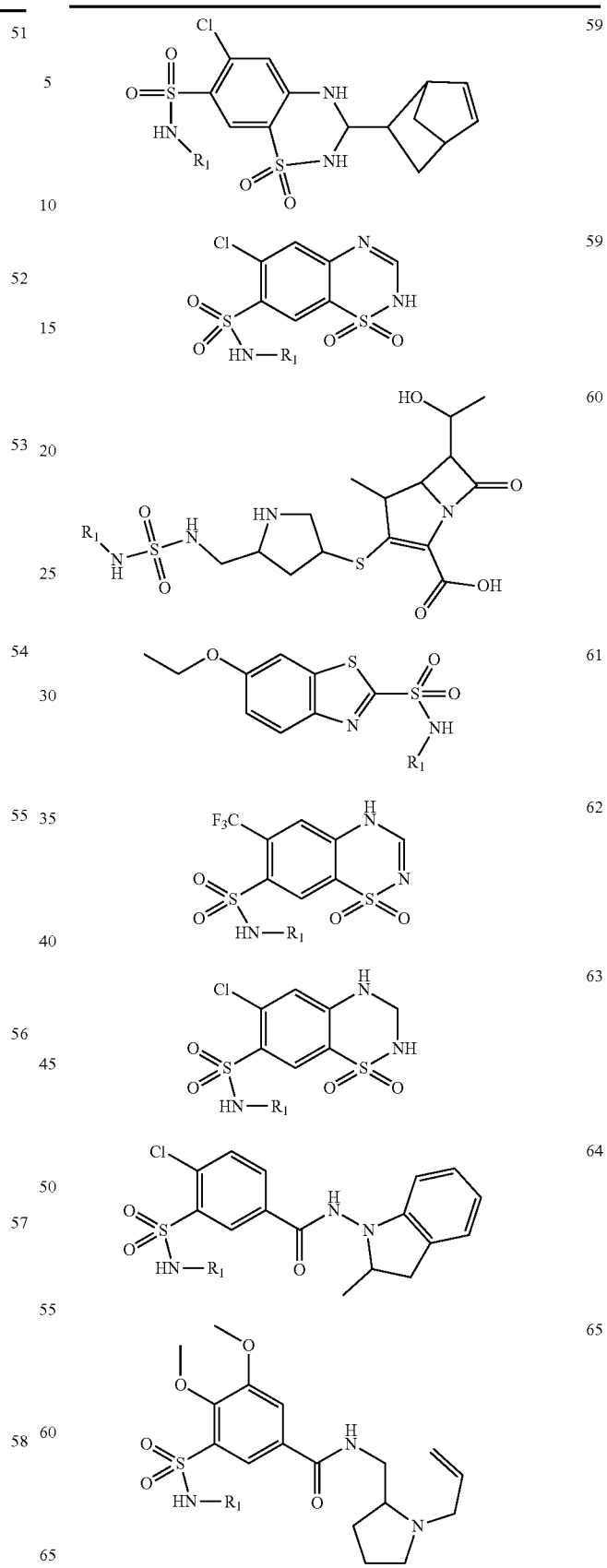

TABLE III-continued

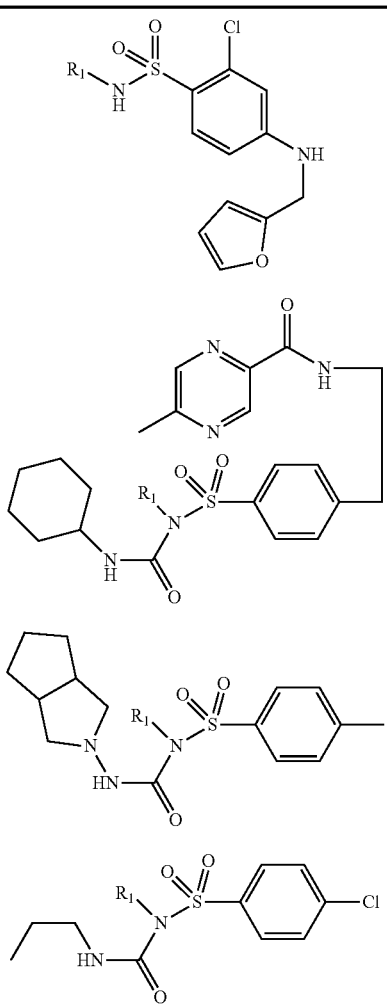

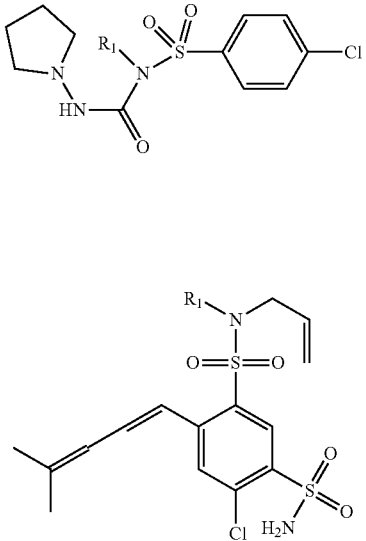

Chlorothiazide and hydrochlorothiazide compounds of formula III and in particular table III are useful for the treatment of hypertension, congestive heart failure, osteoporosis, symptomatic edema peripheral edema, kidney stones, diabetes, nephrogenic diabetes insipidus, hypercalcaemia, Dent's disease and Meniere's disease. Compounds of formula III and table III provide sustained release of parent drugs by cleavage of the labile $R_1$ moiety. Compounds of formula III, for example III-63 to III-71 are useful as prodrugs for the treatment of diabetes.

In another aspect of the invention a general method to convert compounds of Formula XLV with secondary amides to substituted tertiary amides is provided (Scheme 1).

Scheme 1

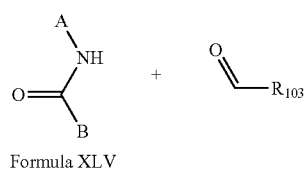

Formula XLV

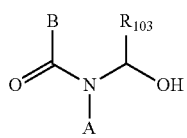

Formula XLVI

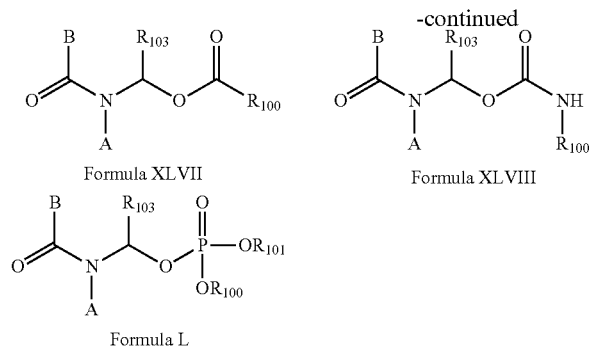
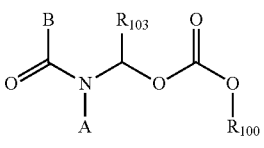

Formula XLVII     Formula XLVIII     Formula XLIX

Formula L

In addition to the reaction of aldehyde or ketone to compounds of formula XLV, other process for converting secondary lactam groups can be used. For example, alkylation followed by addition of sodium in inert solvents, or addition of potassium hydroxide or sodium hydroxide followed by alkyl halide addition can be used. Microwave based synthetic procedures can also be used to convert secondary lactams to substituted tertiary lactam compounds of the instant application. (For a general review see March J. *Advanced Organic Chemistry*, Wiley, 1992; Inoue et al., *Bull. Chem. Soc. Jpn.*, 58, 2721-2722, 1985; Mijin et al., *J. Serb. Chem. Soc.*, 73(10) 945-950, 2008; Bogdal et al. *Molecules*, 1999, 4, 333-337; U.S. Pat. No. 5,041,659).

The invention further relates the sustained delivery of a compound of formula XLV by the administration of a compound of formula I-III. Upon administration of a compound of formula I-III, the labile $R_1$ moiety may be cleaved off enzymatically, chemically or through first phase metabolism giving a compound of formula XLV. Without being bound to any theory, it is postulated that for some of the compounds of formula I-III, the release of a compound of formula XLV upon cleavage of the $R_1$ moiety results in a therapeutically active agent. For example, such active ingredient can be aripiprazole, ziprasidone or bifeprunox. In one embodiment, the sustained release comprises a therapeutically effective amount of a compound of formula XLV in the blood stream of the patient for a period of at least about 8, preferably at least about 12, more preferably at least about 24 and even more preferably at least about 36 hours after administration of a compound of formula I-III. In one embodiment, the compound of formula XLV is present in the blood stream of the patient for a period selected from: at least 48 hours, at least 4 days, at least one week, and at least one month. In one embodiment, a compound of formula I-III is administered by injection.

Compounds of formula IX, X, XI, XII, XIII, XIV, XXXIII, XXXIV, XXXV, XXXVI, and XXXVII are useful for the treatment of neurological and psychological disorders. Neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, eating disorders and conduct disorder.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2- carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

The term "labile" as used herein refers to the capacity of the prodrug of the invention to undergo enzymatic and/or chemical cleavage in vivo thereby forming the parent parent drug. As used herein the term "prodrug" means a compounds as disclosed herein which is a labile derivative compound of a heteroaromatic NH-containing parent drug which when administered to a patient in vivo becomes cleaved by chemical and/or enzymatic hydrolysis thereby forming the parent drug such that a sufficient amount of the compound intended to be delivered to the patient is available for its intended therapeutic use in a sustained release manner.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha- ($\alpha$), beta- ($\beta$) and gamma- ($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. Omegaven® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Additional sustained release in accordance with the invention may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

In one preferred embodiment, the formulation provides a sustained release delivery system that is capable of minimizing the exposure of the prodrug to water. This can be accomplished by formulating the prodrug with a sustained release delivery system that is a polymeric matrix capable of minimizing the diffusion of water into the matrix. Suitable polymers comprising the matrix include polylactide (PLA) polymers and the lactide/glycolide (PLGA) co-polymers.

Alternatively, the sustained release delivery system may comprise poly-anionic molecules or resins that are suitable for injection or oral delivery. Suitable polyanionic molecules include cyclodextrins and polysulfonates formulated to form a poorly soluble mass that minimizes exposure of the prodrug to water and from which the prodrug slowly leaves.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a)

fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a prodrug compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect).

In accordance with the invention, the therapeutically effective amount of a prodrug of the invention is typically based on the target therapeutic amount of the parent drug. Information regarding dosing and frequency of dosing is readily available for many parent drugs from which the prodrugs of the invention are derived and the target therapeutic amount can be calculated for each prodrug of the invention. In accordance with the invention, the same dose of a prodrug of the invention provides a longer duration of therapeutic effect as compared to the parent drug. Thus if a single dose of the parent drug provides 12 hours of therapeutic effectiveness, a prodrug of that same parent drug in accordance with the invention that provides therapeutic effectiveness for greater than 12 hours will be considered to achieve a "sustained release".

The precise dose of a prodrug of the invention depends upon several factors including the nature and dose of the parent drug and the chemical characteristics of the prodrug moiety linked to the parent drug. Ultimately, the effective dose and dose frequency of a prodrug of the invention will be decided by the attending physician within the scope of sound medical judgment. The specific therapeutically effective dose level and dose frequency for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. General methodology for the preparation of lactam compounds can be found in the following publications: U.S. Pat. Nos. 7,160,888; 5,462,934; 4,914,094; 4,234,584; 4,514,401; 5,462,934; 4,468,402; WO 2006/090273 A2; WO 2008/150848 A1; WO 2006/112464 A1; WO 2008/132600 A1.

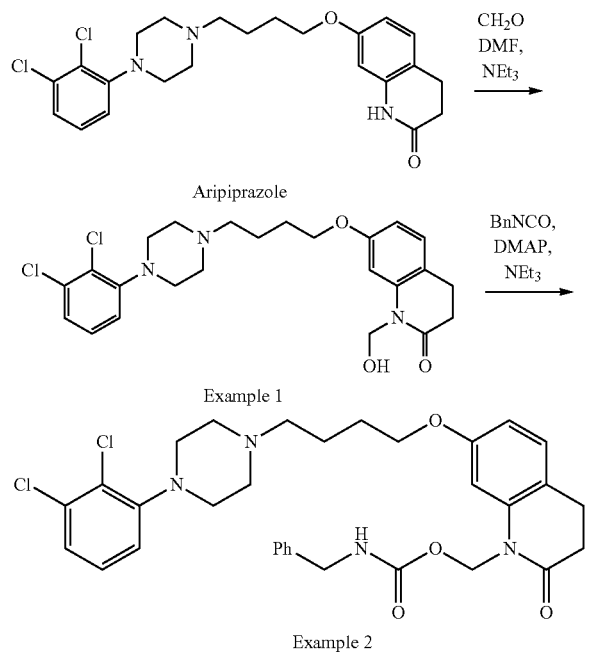

Preparation of 7-(4-(4-(2,3-dichlorophenyl)piperazin-1-yl)butoxy)-1-(hydroxymethyl)-3,4-dihydroquinolin-2(1H)-one (Example 1: Compound A1)

A mixture of Aripiprazole (20 g, 45 mmol), triethylamine (1 mL, 7.1 mmol), formaldehyde (37% aqueous solution, 70 mL) and dimethylformamide (200 mL) was heated to 80° C. for 20 h. The reaction mixture was cooled, diluted with ethyl acetate (400 mL) and washed with water/brine (1:1, 3×500 mL). The organic phase was dried over MgSO$_4$, filtered and evaporated to dryness under vacuum to give hemi-aminal A1 as a white solid (18.6 g, containing 25% Aripiprazole, 65% yield based on A1).

$^1$H NMR (CDCl$_3$, 300 MHz) complex mixture of signals due to contamination with Aripiprazole, main signal δ 5.34 (s, 2H, OHC$\underline{H}_2$N); m/z (M$^+$H) 478 and 480.

(7-(4-(4-(2,3-dichlorophenyl)piperazin-1-yl)butoxy)-2-oxo-3,4-dihydroquinolin-1(2H)-yl)methyl benzylcarbamate (Example 2: Compound 28)

To a solution of hemi-aminal, A1, from Example 1 (4 g, 8.4 mmol), 4-dimethylaminopyridine (0.15 g, 1.3 mmol) and triethylamine (1.1 mL, 7.5 mmol) in dichloromethane (30 mL) was added benzylisocyanate (1.03 mL, 8.3 mmol) and the reaction mixture stirred for 24 hours. The reaction mixture was then heated at 35° C. for 20 hours, cooled and washed with water/brine (1:1, 50 mL). The organic phase was dried over MgSO$_4$, filtered and evaporated under vacuum. The residue was further purified by chromatography on silica eluting with ethyl acetate/dichloromethane/methanol (1:1:0.1) to give the desired product as an off white foam (530 mg, 14% yield). $^1$H NMR (CDCl$_3$, 300 MHz) δ 1.58-1.88 (m, 4H), 2.48 (t, 2H), 2.60-2.72 (m, 6H), 2.85 (m, 2H), 3.00-3.12 (m, 4H), 3.96 (t, 2H), 4.40 (d, 2H), 5.13 (NH), 5.96 (s, 2H), 6.58 (dd, 1H), 6.79 (d, 1H), 6.92-6.98 (m, 1H), 7.04 (d, 1H), 7.12-7.16 (m, 1H), 7.23-7.35 (m, 6H); m/z (M$^+$H) 611.12 and 613.10.

The following compounds were prepared in an analogous fashion to Example 2.

(7-(4-(4-(2,3-dichlorophenyl)piperazin-1-yl)butoxy)-2-oxo-3,4-dihydroquinolin-1(2H)-yl)methyl ethyl carbonate (Example 3: Compound 79)

The desired product was isolated as a yellow oil (830 mg, 24% yield). $^1$H NMR (d$_6$-DMSO, 300 MHz) δ 1.78 (t, 3H), 1.52-1.61 (m, 2H), 1.63-1.76 (m, 2H), 2.31-2.40 (m, 2H), 2.40-2.60 (m, 6H), 2.73-2.80 (m, 2H), 2.91-2.99 (m, 4H), 3.96 (t, 3H), 4.11 (q, 2H), 5.87 (s, 2H), 6.60-6.70 (m, 2H), 7.07-7.12 (m, 2H), 7.24-7.30 (m, 2H); m/z (M$^+$H) 550.48 and 552.40.

butyl (7-(4-(4-(2,3-dichlorophenyl)piperazin-1-yl)butoxy)-2-oxo-3,4-dihydroquinolin-1(2H)-yl)methyl carbonate (Example 4: Compound 80)

The desired product was isolated as a yellow oil (750 mg, 21% yield). $^1$H NMR (CDCl$_3$, 300 MHz) δ 0.92 (t, 3H), 1.33-1.45 (m, 2H), 1.59-1.80 (m, 4H), 1.80-1.92 (m, 2H), 2.49 (t, 2H), 2.58-2.75 (m, 6H), 2.85 (t, 2H), 3.00-3.13 (m, 4H), 3.98 (t, 2H), 4.18 (t, 2H), 5.92 (s, 2H), 6.58 (dd, 1H), 6.67 (d, 1H), 6.92-6.99 (m, 1H), 7.03 (dd, 1H), 7.10-7.20 (m, 2H); m/z (M$^+$H) 578.10 and 580.08.

(7-(4-(4-(2,3-dichlorophenyl)piperazin-1-yl)butoxy)-2-oxo-3,4-dihydroquinolin-1(2H)-yl)methyl hexyl carbonate (Example 5: Compound 81)

The desired product was isolated as a yellow oil (1.77 g, 62% yield). $^1$H NMR (d$_6$-DMSO, 300 MHz) δ 0.80 (t, 3H), 1.15-1.30 (m, 6H), 1.50-1.60 (m, 4H), 1.65-1.73 (m, 2H), 2.35 (t, 2H), 2.41-2.60 (m, 6H), 2.78 (t, 2H), 2.88-3.00 (m, 4H), 3.95 (t, 2H), 4.06 (t, 2H), 5.86 (s, 2H), 6.60-6.70 (m, 2H), 7.05-7.15 (m, 2H), 7.22-7.28 (m 2H); m/z (M$^+$H) 606.15 and 608.15.

decyl (7-(4-(4-(2,3-dichlorophenyl)piperazin-1-yl)butoxy)-2-oxo-3,4-dihydroquinolin-1(2H)-yl)methyl carbonate (Example 6: Compound 82)

The desired product was isolated as a yellow oil (1.42 g, 46% yield). $^1$H NMR (d$_6$-DMSO, 300 MHz) δ 0.79 (m, 3H), 1.13-1.30 (m, 14H), 1.48-1.60 (m, 4H), 1.65-1.75 (m, 2H), 2.33 (t, 2H), 2.41-2.60 (m, 6H), 2.72-2.80 (m, 2H), 2.89-2.98 (m, 4H), 3.95 (t, 2H), 4.05 (t, 2H), 5.86 (s, 2H), 6.60-6.70 (m, 2H), 7.05-7.13 (m, 2H), 7.22-7.28 (m, 2H); m/z (M$^+$H) 662.56 and 664.54.

(7-(4-(4-(2,3-dichlorophenyl)piperazin-1-yl)butoxy)-2-oxo-3,4-dihydroquinolin-1(2H)-yl)methyl hexadecyl carbonate (Example 7: Compound 83)

The desired product was isolated as a yellow oil (1.55 g, 44% yield). $^1$H NMR (d$_6$-DMSO, 300 MHz) δ 0.80 (t, 3H), 1.10-1.29 (m, 26H), 1.49-1.60 (m, 4H), 1.65-1.75 (m, 2H), 2.33 (t, 2H), 2.43-2.55 (m, 6H), 2.78 (t, 2H), 2.90-2.95 (m, 4H), 3.95 (t, 2H), 4.05 (t, 2H), 5.84 (s, 2H), 6.60-6.68 (m, 2H), 7.05-7.12 (m, 2H), 7.24-7.29 (m, 2H); m/z (M-C$_{10}$H$_{20}$)$^+$ 606.52 and 608.54.

(7-(4-(4-(2,3-dichlorophenyl)piperazin-1-yl)butoxy)-2-oxo-3,4-dihydroquinolin-1(2H)-yl)methyl morpholine-4-carboxylate (Example 8: Compound 49)

The desired product was isolated as a yellow oil (1.52 g, 55% yield). $^1$H NMR (d$_6$-DMSO, 300 MHz) δ 1.50-1.75 (m, 4H), 2.35 (t, 2H), 2.42-2.61 (m, 6H), 2.70-2.82 (m, 2H), 2.88-3.00 (m, 4H), 3.26-3.40 (m, 4H), 3.40-3.60 (m, 4H), 3.94 (t, 2H), 5.81 (s, 2H), 6.61 (dd, 1H), 6.68 (d, 1H), 7.05-7.13 (m, 2H), 7.20-7.30 (m, 2H); m/z (M$^+$H) 591.11 and 593.15.

(7-(4-(4-(2,3-dichlorophenyl)piperazin-1-yl)butoxy)-2-oxo-3,4-dihydroquinolin-1(2H)-yl)methyl diethylcarbamate (Example 9: Compound 84)

The desired product was isolated as a yellow oil (0.83 g, 31% yield). $^1$H NMR (CDCl$_3$, 300 MHz) δ 1.00-1.20 (m, 6H), 1.65-1.88 (m, 4H), 2.45-2.52 (m, 2H), 2.58-2.83 (m, 6H), 2.82-2.90 (m, 2H), 3.00-3.12 (m, 4H), 3.18-3.38 (m, 4H), 3.97 (t, 2H), 5.91 (s, 2H), 6.58 (dd, 1H), 6.77 (d, 1H), 6.94-6.98 (m, 1H), 7.06 (d, 1H), 7.15-7.20 (m, 2H); m/z (M$^+$H) 577.48 and 579.46.

(7-(4-(4-(2,3-dichlorophenyl)piperazin-1-yl)butoxy)-2-oxo-3,4-dihydroquinolin-1(2H)-yl)methyl isopentyl carbonate (Example 10: Compound 85)

To a solution of phosgene (20% in toluene, 54 mL, 110 mmol) in tetrahydrofuran (100 mL) was added a solution of 3-methyl-1-butanol (1.7 mL, 15.7 mmol) in tetrahydrofuran (50 mL) over 1 hour. After 4 hours the volatiles were removed under vacuum and the residue added to a solution of the hemi-aminal A1 (3 g, 4.7 mmol), 4-dimethylaminopyridine (0.3 g, 1.9 mmol), pyridine (10 mL) and triethylamine (1.3 mL, 9.4 mmol) in dichloromethane (30 mL). After being stirred for 72 hours, the reaction mixture was diluted with ethyl acetate (100 mL) and washed with 5% aqueous NaHCO$_3$/brine (1:1, 100 mL). The organic phase was dried over MgSO$_4$, filtered and evaporated under vacuum. The residue was further purified by chromatography on silica eluting with ethyl acetate/dichloromethanel-methanol (1:1:0.1) to give the desired product as a yellow oil (1.54 g, 55% yield). $^1$H NMR (CDCl$_3$, 300 MHz) δ 1.90-1.95 (m, 6H), 1.50-1.60 (m, 4H), 1.65-1.79 (m, 2H), 1.79-1.89 (m, 2H), 2.50 (t, 2H), 2.60-2.72 (m, 6H), 2.82-2.90 (m, 2H), 3.02-3.11 (m, 4H), 3.98 (t, 2H), 4.21 (t, 2H), 5.92 (s, 2H), 6.56 (dd, 1H), 6.67 (d, 1H), 6.95-7.00 (m, 1H), 7.05 (d, 1H), 7.13-7.19 (m, 2H); m/z (M$^+$H) 592.48 and 594.46.

(7-(4-(4-(2,3-dichlorophenyl)piperazin-1-yl)butoxy)-2-oxo-3,4-dihydroquinolin-1(2H)-yl)methyl acetate (Example 11: Compound 1)

A solution of Compound-A1 from Example-1, (50.63 g, 0.105 mol) in anhydrous tetrahydrofuran (THF, 80 mL) was treated with acetic anhydride (15.3 mL, 0.16 mol) and heated for 2.0 hours at 60° C. (oil-bath). To the above solution, triethylamine (2.0 mL, 0.014 mol) was added and stirred for 16 hours at 60° C. The solvent was removed using a rotator evaporator. To the resulting crude mixture, ethyl acetate (150 mL) and heptane (50 mL) was added. The solution was washed with NaHCO$_3$ (5% aqueous solution, 250 mL). After separation of the two layers, pH of the aqueous layer was adjusted to above 7. The aqueous layer was further extracted using the organic mixture. The organic layer was separated and washed with 5% NaHCO$_3$ solution, followed by deionized water, and brine. The solution was dried using anhydrous MgSO$_4$, filtered and evaporated under vacuum. The resulting product was purified using silica gel column chromatography using ethanol:ethyl acetate (5:95) as the eluent. Fractions containing the desired product were combined and d-tartaric acid (12.5 g dissolved in 60:5 ethanol:water) was added, resulting in the precipitation of the desired product (48.78 g, 89% yield). $^1$H NMR (CDCl3, 300 MHz) δ 1.73 (m, 2H), 1.84 (m, 2H), 2.12 (s, 3H), 2.50 (t, 2H), 2.68 (m, 6H), 2.87 (dd, 2H), 3.08 (m, 4H), 3.98 (t, 2H), 5.91 (s, 2H), 6.59 (m, 2H), 6.96 (dd, 1H), 7.08 (dd, 1H), 7.15 (m, 2H).

The following compounds were prepared in an analogous fashion to Example 11.

(7-(4-(4-(2,3-dichlorophenyl)piperazin-1-yl)butoxy)-2-oxo-3,4-dihydroquinolin-1(2H)-yl)methyl dodecanoate (Example 12: Compound 7)

The desired product was isolated as a crystalline solid (0.3 g, 21% yield). The molecular weight was confirmed by mass spectrometer analysis. FIG. 2-6 shows the PXRD, IR, Raman, TGA spectrum of the desired product. $^1$H NMR (CDCl3, 300 MHz) δ 0.87 (t, 3H), 1.24 (m, 16H), 1.62 (m, 2H), 1.83 (m, 2H), 1.86 (m, 2H), 2.36 (t, 2H), 2.49 (t, 2H), 2.68 (m, 6H), 2.86 (dd, 2H), 3.08 (m, 4H), 3.97 (t, 2H), 5.91 (s, 2H), 6.59 (m, 2H), 6.96 (dd, 1H), 7.07 (dd, 1H), 7.14 (m, 2H). See Figures x-y for further characterization (PXRD, IR, Raman, TGA and DSC spectra) of Compound 7.

(7-(4-(4-(2,3-dichlorophenyl)piperazin-1-yl)butoxy)-2-oxo-3,4-dihydroquinolin-1(2H)-yl)methyl palmitate (Example 13: Compound 10)

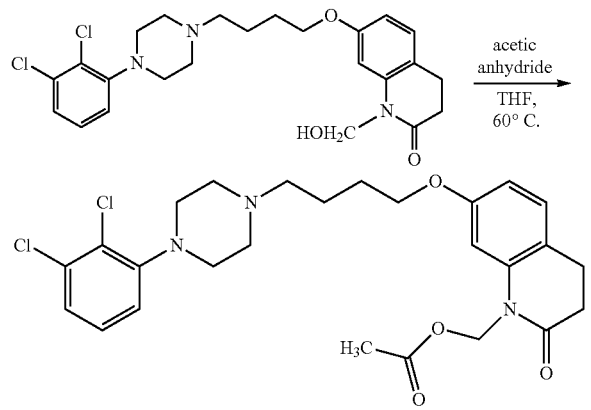

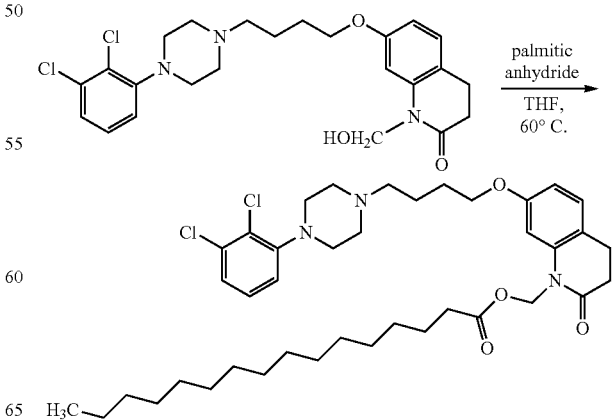

The desired product was isolated as a crystalline solid (4.2 g, 70% yield). The molecular weight (716.6) was confirmed by mass spectrometer analysis. ¹H NMR (CDCl3, 300 MHz) δ 0.88 (t, 3H), 1.25 (m, 24H), 1.64 (m, 2H), 1.72 (m, 2H), 1.84 (m, 2H), 2.36 (t, 2H), 2.49 (t, 2H), 2.68 (m, 6H), 2.86 (dd, 2H), 3.08 (m, 4H), 3.97 (t, 2H), 5.92 (br s, 2H), 6.59 (dd, 1H), 6.60 (s, 1H), 6.96 (dd, 1H), 7.07 (d, 1H), 7.14 (m, 2H).

(7-(4-(4-(2,3-dichlorophenyl)piperazin-1-yl)butoxy)-2-oxo-3,4-dihydroquinolin-1(2H)-yl)methyl decanoate (Example 14: Compound 6)

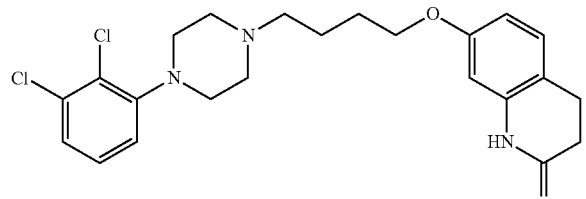

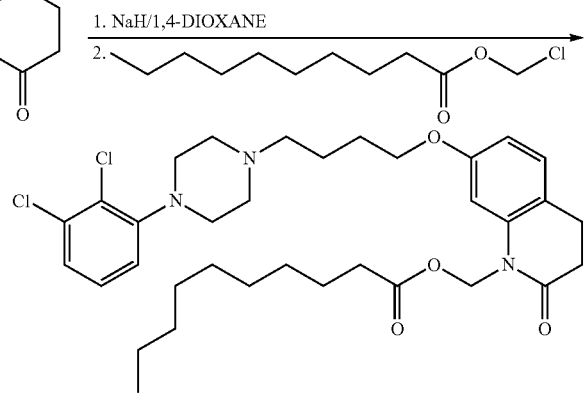

The chloromethyl ester above is dried over 4 Å molecular sieves. A solution of aripiprazole (45 grams, 0.1 mol) in 1,4-dioxane (800 mL) was sonicated to dissolve the aripiprazole completely, and then treated with NaH (38 g, 0.95 mol, 60% dispersion) in one portion. After stirring this reaction mixture for 15 minutes at room temperature, the reaction mixture was treated dropwise with chloromethyl ester (0.3 mol.) and a catalytic amount of sodium iodide (0.05 mol). The resultant cloudy mixture was heated to 90° C. for 2 hours, cooled to ambient temperature and poured into water. The product was extracted with ethyl acetate, and the combined ethyl acetate layers washed with brine, dried over sodium sulfate, filtered and concentrated under reduced pressure. Column chromatography over silica gel provided the desired product (12.5 gram, 70% yield). ¹H NMR (CDCl3, 300 MHz) δ 0.87 (t, 3H), 1.20 (m, 12H), 1.63 (m, 2H), 1.70 (m, 2H), 1.83 (m, 2H), 2.35 (t, 2H), 2.50 (t, 2H), 2.68 (m, 6H), 2.86 (t, 2H), 3.08 (m, 4H), 3.97 (t, 2H), 5.92 (s, 2H), 6.58 (dd, 1H), 6.61 (d, 1H), 6.94 (dd, 1H), 7.06 (d, 1H), 7.14-7.17 (m, 2H); m/z (M⁺H) 632.88.

The following compounds (Examples 15-29) were prepared in an analogous fashion to Example 2:

(7-(4-(4-(2,3-dichlorophenyl)piperazin-1-yl)butoxy)-2-oxo-3,4-dihydroquinolin-1(2H)-yl)methyl benzoate (Example 15, Compound 31)

The desired product was isolated as a yellow oil.
¹H NMR (CDCl₃, 300 MHz) δ 1.60-1.85 (m, 4H), 2.45 (t, 2H), 2.55-2.70 (m, 4H), 2.70-2.78 (m, 2H), 2.85-2.92 (m, 2H), 3.00-3.10 (m, 4H), 3.94 (t, 2H), 6.16 (s, 2H), 6.60 (d, 1H), 6.72 (dd, 1H), 6.90-6.95 (m, 1H), 7.05-7.18 (m, 2H), 7.35-7.42 (m, 2H), 7.52-7.60 (m, 1H), 8.00-8.08 (m, 2H). m/z (M⁺H) 582.3.

(7-(4-(4-(2,3-dichlorophenyl)piperazin-1-yl)butoxy)-2-oxo-3,4-dihydroquinolin-1(2H)-yl)methyl butyrate (Example 16, Compound 2)

The desired product was isolated by chromatography on silica eluting with ethyl acetate/dichloromethane/methanol (1:1:0.1) to give a yellow oil (2.0 g, 87% yield). ¹H NMR (CDCl₃, 300 MHz) δ 0.94 (t, 3H), 1.60-1.90 (m, 6H), 2.34 (t, 2H), 2.51 (t, 2H), 2.61-2.73 (m, 6H), 2.82-2.90 (m, 2H), 3.02-3.12 (m, 4H), 3.96 (t, 2H), 5.91 (s, 1H), 6.55-6.61 (m, 2H), 6.93-6.98 (m, 1H), 7.05 (d, 1H), 7.11-7.18 (m, 2H). m/z (M⁺H) 548.2 and 550.2.

(7-(4-(4-(2,3-dichlorophenyl)piperazin-1-yl)butoxy)-2-oxo-3,4-dihydroquinolin-1(2H)-yl)methyl hexanoate (Example 17, Compound 4)

The desired product was isolated as a yellow solid (3.69 g, 87% yield). ¹H NMR (CDCl₃, 300 MHz) δ 0.78 (t, 3H), 1.11-1.28 (m, 4H), 1.40-1.78 (m, 6H), 2.20-2.40 (m, 4H), 2.40-2.60 (m, 6H), 2.73-2.81 (m, 2H), 2.85-3.00 (m, 4H), 3.88-4.00 (m, 2H), 5.75-5.83 (m, 2H), 6.55-6.62 (m, 2H), 7.03-7.12 (m, 2H), 7.20-7.26 (m, 2H). m/z (M⁺H) 576.4 and 578.4.

(7-(4-(4-(2,3-dichlorophenyl)butoxy)-2-oxo-3,4-dihydroquinolin-1(2H)-yl)methyl tetradecanoate (Example 18, Compound 8)

The desired product was isolated as a pale yellow solid (5.3 g, 74% yield). ¹H NMR (CDCl₃, 300 MHz) δ 0.87 (t, 3H), 1.07-1.37 (m, 22H), 1.55-1.70 (m, 2H), 1.70-1.90 (m, 4H), 2.34 (t, 2H), 2.53 (t, 2H), 2.65-2.78 (m, 6H), 2.82-2.90 (m, 2H), 3.02-3.12 (m, 4H), 3.96 (t, 2H), 5.91 (s, 2H), 6.55-6.62 (m, 2H), 6.92-6.98 (m, 1H), 7.05 (d, 1H), 7.11-7.18 (m, 2H). m/z (M⁺H) 688.4 and 690.4.

(7-(4-(4-(2,3-dichlorophenyl)piperazin-1-yl)butoxy)-2-oxo-3,4-dihydroquinolin-1(2H)-yl)methyl octanoate (Example 19, Compound 5)

The desired product was isolated as a yellow oil (2.2 g, 87% yield). ¹H NMR (CDCl₃, 300 MHz) δ 0.82 (t, 3H), 1.15-1.35 (m, 10H, 1.55-1.87 (m, 6H), 2.34 (t, 2H), 2.53 (t, 2H), 2.65-2.73 (m, 4H), 2.85 (dd, 2H), 3.01-3.11 (m, 4H), 3.95 (t, 2H), 5.85-5.92 (m, 2H), 2.53-2.60 (m, 2H), 6.91-6.97 (m, 1H), 7.05 (d, 1H), 7.10-7.16 (m, 2H). m/z (M⁺H) 604.3 and 606.3.

(7-(4-(4-(2,3-dichlorophenyl)piperazin-1-yl)butoxy)-2-oxo-3,4-dihydroquinolin-1(2H)-yl)methyl isopropyl carbonate (Example 20, Compound 48)

The desired product was isolated as an orange oil (2.4 g, 68% yield). ¹H NMR (CDCl₃, 300 MHz) δ 1.31 (d, 6H), 1.62-1.77 (m, 2H), 1.77-1.89 (m, 2H), 2.48 (t, 2H), 2.60-2.71 (m, 6H), 2.81-2.90 (m, 2H), 3.01-3.11 (m, 4H), 3.98 (t, 2H), 4.89-4.97 (m, 1H), 5.92 (s, 2H), 6.57 (d, 1H), 6.68 (d, 1H), 6.91-7.00 (m, 1H), 7.05 (dd, 1H), 7.11-7.18 (m, 2H). m/z (M⁺H) 564.3 and 566.3.

(7-(4-(4-(2,3-dichlorophenyl)piperazin-1-yl)butoxy)-2-oxo-3,4-dihydroquinolin-1(2H)-yl)methyl methylcarbamate (Example 21, Compound 47)

The desired product was isolated as a yellow solid (1.3 g, 52% yield). ¹H NMR (CDCl₃, 300 MHz) δ 1.68-1.88 (m, 4H), 2.49 (dd, 2H), 2.60-2.73 (m, 6H), 2.80-2.90 (m, 5H), 3.02-3.12 (m, 4H), 3.95-4.02 (m, 2H), 5.90 (s, 2H), 6.57 (d, 1H), 6.77 (d, 1H), 6.93-6.70 (m, 1H), 7.05 (d, 1H), 7.10-7.19 (m, 2H). m/z (M⁺H) 535.5 and 537.5.

(7-(4-(4-(2,3-dichlorophenyl)piperazin-1-yl)butoxy)-2-oxo-3,4-dihydroquinolin-1(2H)-yl)methyl decylcarbamate (Example 22, Compound 46)

The desired product was isolated as a yellow solid (0.50 g, 14% yield). ¹H NMR (CDCl₃, 300 MHz) δ 0.86 (t, 3H), 1.18-1.35 (m, 16H), 1.42-1.53 (m, 2H), 1.67-1.79 (m, 2H), 1.79-1.87 (m, 2H), 2.48 (t, 2H), 2.58-2.72 (m, 4H), 2.80-2.90 (m, 2H), 3.01-3.12 (m, 4H), 3.15-3.22 (m, 2H), 3.98 (t, 2H), 4.78 (NH), 5.90 (s, 2H), 6.58 (d, 1H), 6.78 (d, 1H), 6.93-7.00 (m, 1H), 7.04 (d, 1H), 7.10-7.16 (m, 2H). m/z (M⁺H) 661.6 and 663.6.

(7-(4-(4-(2,3-dichlorophenyl)piperazin-1-yl)butoxy)-2-oxo-3,4-dihydroquinolin-1(2H)-yl)methyl isobutyrate (Example 23, Compound 32)

¹H NMR (CDCl₃, 300 MHz) δ 1.18 (d, 6H), 1.68-1.88 (m, 4H), 2.45-2.73 (m, 9H), 2.87 (dd, 2H), 3.03-3.12 (m, 2H), 3.95 (t, 2H), 5.91 (s, 2H), 6.55-6.60 (m, 2H), 6.93-6.97 (m, 1H), 7.04-7.09 (m, 1H), 7.12-7.19 (m, 2H). m/z (M⁺H) 548.15.

(7-(4-(4-(2,3-dichlorophenyl)piperazin-1-yl)butoxy)-2-oxo-3,4-dihydroquinolin-1(2H)-yl)methyl cyclopentanecarboxylate (Example 24, Compound 33)

¹H NMR (CDCl₃, 300 MHz) δ 1.47-1.93 (m, 13H), 2.50-2.60 (m, 2H), 2.60-2.90 (m, 8H), 3.02-3.15 (m, 4H), 3.95 (t, 2H), 5.89 (s, 2H), 6.50-6.60 (m, 2H), 6.90-6.95 (m, 1H), 7.02-7.07 (m, 1H), 7.10-7.19 (m, 2H). m/z (M⁺H) 574.15.

(7-(4-(4-(2,3-dichlorophenyl)piperazin-1-yl)butoxy)-2-oxo-3,4-dihydroquinolin-1(2H)-yl)methyl cyclobutanecarboxylate (Example 25, Compound 34)

¹H NMR (CDCl₃, 300 MHz) δ 1.82-1.91 (m, 3H), 1.22-1.30 (m, 2H), 1.75-2.05 (m, 6H), 2.05-2.40 (m, 6H), 2.68-2.73 (m, 2H), 2.84-2.90 (m, 2H), 3.06-3.22 (m, 4H), 3.96 (t, 2H), 5.91 (s, 2H), 6.55-6.59 (m, 2H), 6.97 (dd, 1H), 7.07 (d, 1H), 7.12-7.18 (m, 2H). m/z (M⁺H) 560.19.

(7-(4-(4-(2,3-dichlorophenyl)piperazin-1-yl)butoxy)-2-oxo-3,4-dihydroquinolin-1(2H)-yl)methyl cyclohexanecarboxylate (Example 26, Compound 35)

¹H NMR (CDCl₃, 300 MHz) δ 1.15-1.35 (m, 3H), 1.35-1.55 (m, 2H), 1.55-1.95 (m, 10H), 2.21-2.40 (m, 1H), 2.52-2.60 (m, 1H), 2.62-3.00 (m, 8H), 3.02-3.12 (m, 4H), 3.95 (t, 2H), 5.89 (s, 2H), 6.50-6.60 (m, 2H), 6.93-6.97 (m, 1H), 7.02-7.06 (m, 1H), 7.10-7.15 (m, 2H). m/z (M⁺H) 588.24.

(7-(4-(4-(2,3-dichlorophenyl)piperazin-1-yl)butoxy)-2-oxo-3,4-dihydroquinolin-1(2H)-yl)methyl 2-(2-methoxyethoxy)acetate (Example 27, Compound 40)

¹H NMR (CDCl₃, 300 MHz) δ 1.56-1.90 (m, 6H), 2.43-2.55 (m, 2H), 2.55-2.80 (m, 4H), 2.81-2.90 (m, 2H), 3.37 (s, 3H), 3.55-3.61 (m, 2H), 3.72-3.79 (m, 2H), 4.20 (s, 2H), 5.97 (s, 2H), 6.55-6.59 (m, 2H), 6.91-6.98 (m, 1H), 7.09 (d, 1H), 7.11-7.15 (m, 2H). m/z (M⁺H) 594.17.

(7-(4-(4-(2,3-dichlorophenyl)piperazin-1-yl)butoxy)-2-oxo-3,4-dihydroquinolin-(2H)-yl)methyl 2-(2-(2-methoxyethoxy)ethoxy)acetate (Example 28, Compound 41)

¹H NMR (CDCl₃, 300 MHz) δ 1.65-1.93 (m, 6H), 2.49-2.60 (m, 2H), 2.61-2.77 (m, 4H), 2.81-2.90 (m, 2H), 3.02-3.20 (m, 4H), 3.36 (s, 3H), 3.51-3.57 (m, 2H), 3.60-3.70 (m, 4H), 3.72-3.78 (m, 2H), 3.92-3.99 (m, 2H), 4.20 (s, 2H), 5.97 (s, 2H), 6.55-6.59 (m, 2H), 6.95-6.99 (m, 1H), 7.05-7.09 (m, 1H), 7.11-7.18 (m, 2H). m/z (M⁺H) 638.30.

(7-(4-(4-(2,3-dichlorophenyl)piperazin-1-yl)butoxy)-2-oxo-3,4-dihydroquinolin-1(2H)-yl)methyl pivalate (Example 29, Compound 42)

¹H NMR (CDCl₃, 300 MHz) δ 1.21 (s, 9H), 1.65-1.88 (m, 4H), 2.45-2.55 (m, 2H), 2.60-2.73 (m, 6H), 2.82-2.91 (m, 2H), 3.02-3.13 (m, 4H), 3.95 (t, 2H), 5.89 (s, 2H), 6.54-6.60 (m, 2H), 6.92-6.99 (m, 1H), 7.06 (d, 1H), 7.13-7.17 (m, 2H); m/z (M⁺H) 562.39.

(7-(4-((2,3-dichlorophenyl)piperazin-1-yl)butoxy)-2-oxo-3,4-dihydroquinolin-1(2H)-yl)methyl 2-hydroxyethylcarbamate (Example 30, Compound 36)

2-(((7-(4-(4-(2,3-dichlorophenyl)piperazin-1-yl)butoxy)-2-oxo-3,4-dihydroquinolin-1(2H)-yl)methoxy)carbonylamino)ethyl methacrylate (2.0 g) was synthesized in a similar manner to Example 2. This was reacted with 16% NH₃/MeOH at room temperature for 18 hours and then concentrated at 40° C. The residue was purified by silica chromatography eluting with 1:1:0.1 to 1:1:0.2 DCM/EtOAc/MeOH. The resulting yellow oil was re-crystallised from EtOAc/heptane to give the title compound as a white solid (1.2 g, 67%).

¹H NMR (CDCl₃, 300 MHz) δ 1.60-1.88 (m, 4H), 2.40-2.50 (m, 2H), 2.50-2.75 (m, 6H), 2.75-2.89 (m, 2H), 2.95-3.15 (m, 4H), 3.20-3.40 (m, 2H), 2.58-3.78 (m, 2H), 3.89-4.05 (m, 2H), 5.30-5.45 (m, NH), 5.91 (s, 2H), 6.55 (dd, 1H), 6.73 (d, 1H), 6.91-6.96 (m, 1H), 6.98-7.03 (m, 1H), 7.04-7.18 (m, 2H). m/z (M$^+$H) 565.16.

(7-(4-(4-(2,3-dichlorophenyl)piperazin-1-yl)butoxy)-2-oxo-3,4-dihydroquinolin-1(2H)-yl)methyl bis(2-hydroxyethyl)carbamate (Example 31, Compound 37)

To a solution of hemiaminal A1 (2 g, 0.0042 mol) in dichloromethane (30 mL) at room temperature was added pyridine (0.68 mL), followed by p-nitrophenylchloroformate (1.27 g, 0.0063 mol). After 90 minutes diethanolamine (3.5 g, 0.0334 mol) and triethylamine (1.2 mL, 0.084 mol) were added. After 3 h the reaction was diluted with dichloromethane and washed with sat. NaHCO$_3$, dried over MgSO$_4$ and evaporated. The residue was purified on silica eluting with 1:1:0.1 to 1:1:0.2 DCM/EtOAc/MeOH to give the title compound as a colourless gum (0.83 g, 33%).
$^1$H NMR (CDCl$_3$, 300 MHz) δ 1.70-1.82 (m, 4H), 2.42-2.52 (m, 2H), 2.59-2.79 (m, 6H), 2.80-2.90 (m, 2H), 3.00-3.12 (m, 4H), 3.40-3.48 (m, 2H), 3.50-3.58 (m, 2H), 3.61-3.70 (m, 2H), 3.85-3.90 (m, 2H), 3.99-4.06 (m, 2H), 5.90 (m, 2H), 6.57 (d, 1H), 6.70 (dd, 1H), 6.92-6.98 (m, 1H), 7.07 (d, 1H), 7.10-7.20 (m, 2H). m/z (M$^+$H) 609.21.

(7-(4-(4-(2,3-dichlorophenyl)piperazin-1-yl)butoxy)-2-oxo-3,4-dihydroquinolin-1(2H)-yl)methyl 4-methylpiperazine-1-carboxylate (Example 32, Compound 38)

Compound 141 was synthesized in a similar manner to Example 28.
$^1$H NMR (CDCl$_3$, 300 MHz) δ 1.68-1.88 (m, 4H), 2.25-2.42 (m, 7H), 2.45-2.55 (m, 2H), 2.61-2.76 (m, 6H), 2.85 (dd, 2H), 3.02-3.16 (m, 4H), 3.40-3.60 (m, 4H), 3.97 (t, 2H), 5.92 (s, 2H), 6.59 (d, 1H), 6.74 (d, 1H), 6.92-6.98 (m, 1H), 7.02-7.07 (m, 1H), 7.10-7.16 (m, 2H). m/z (M$^+$H) 604.24.

(7-(4-(4-(2,3-dichlorophenyl)piperazin-1-yl)butoxy)-2-oxo-3,4-dihydroquinolin-1(2H)-yl)methyl 1,4'-bipiperidine-1'-carboxylate (Example 33, Compound 39)

Compound 142 was synthesized in a similar manner to Example 28.
$^1$H NMR (CDCl$_3$, 300 MHz) δ 1.26-2.06 (m, 14H), 2.31-2.91 (m, 17H), 2.95-3.18 (m, 4H), 3.97 (t, 2H), 4.0-4.37 (m, 2H), 5.91 (s, 2H), 6.58 (dd, 1H), 6.74 (d, 1H), 6.90-6.99 (m, 1H), 7.05 (d, 1H), 7.11-7.18 (m, 2H); m/z (M$^+$H) 672.25.

7-(4-(4-(2,3-dichlorophenyl)piperazin-1-yl)butoxy)-1-(methoxymethyl)-3,4-dihydroquinolin-2(1H)-one (Example 34, Compound 100)

To a mixture of hemiaminal A1 (2.0 g, 4.2 mmol) in dichloromethane (20 mL) was added thionyl chloride (1.5 mL, 12.6 mmol) and stirred for 2 h at room temperature. To the reaction mixture was added methanol (10 mL) and stirred a further 2 h. The reaction poured into NaHCO$_3$ (aq) and extracted with dichloromethane. The organic phase dried over MgSO$_4$, evaporated and the residue purified on silica eluting with 1:1:0.1 dichloromethane/ethyl acetate/methanol to give the title compound as a cream solid (1.3 g, 63%).
$^1$H NMR (CDCl$_3$, 300 MHz) δ 1.65-1.83 (m, 4H), 2.47 (t, 2H), 2.58-2.70 (m, 6H), 2.82 (dd, 2H), 2.99-3.01 (m, 4H), 3.38 (s, 3H), 3.96 (t, 2H), 5.27 (s, 2H), 6.55 (dd, 1H), 6.88 (dd, 1H), 6.91-6.96 (m, 1H), 7.03 (d, 1H), 7.08-7.15 (m, 2H). m/z (M$^+$H) 492.05.

1-(7-(4-(4-(2,3-dichlorophenyl)piperazin-1-yl)butoxy)-2-oxo-3,4-dihydroquinolin-1(2H)-yl)-2-ethoxy-2-oxoethyl decanoate (Example 35, Compound 111)

A mixture of Aripiprazole (2.0 g, 4.5 mmol), ethyl glyoxylate (50% soln. in toluene, 2.7 mL), K$_2$CO$_3$ (0.49 g, 3.6 mmol), tetrabutylammonium bromide (0.57 g, 1.8 mmol) and dichloromethane (20 mL) was heated at reflux for 4 h. The reaction mixture was cooled and quickly washed with water, dried over MgSO$_4$ and filtered. The resulting solution was treated with pyridine (1.8 mL, 22.2 mmol) and then decanoylchloride (4.6 mL, 22.2 mmol). After being stirred for 3 h, methanol (1 mL) was added and stirred a further 10 min. The reaction mixture was washed with sat.NaHCO$_3$ (aq), dried over MgSO$_4$ and evaporated. The residue was purified on silica eluting with 1:1:0.1 dichloromethane/ethyl acetate/methanol to give the title compound as a yellow oil (1.2 g, 38%).
$^1$H NMR (CDCl$_3$, 300 MHz) δ 0.86 (t, 3H), 1.11 (t, 3H), 1.05-1.40 (m, 12H), 1.59-1.75 (m, 2H), 1.75-1.98 (m, 4H), 2.40-2.54 (m, 2H), 2.60-3.07 (m, 10H), 3.15-3.32 (m, 4H), 3.89-3.99 (m, 2H), 4.09-4.21 (m, 2H), 6.57 (dd, 1H), 6.67 (d, 1H), 6.95-7.00 (m, 1H), 7.08 (dd, 1H), 7.12-7.20 (m, 2H), 7.27-7.32 (m, 1H). m/z (M$^+$H) 704.38.

(7-(4-(4-(2,3-dichlorophenyl)piperazin-1-yl)butoxy)-2-oxo-3,4-dihydroquinolin-1(2H)-yl)methyl 4-acetamidobutanoate (Example 36, Compound 44)

To a suspension of hemiaminal A1 (2.6 g, 5.5 mmol) in dichloromethane (30 mL) was added triethylamine (2.3 mL, 16.4 mmol), followed by addition of methanesulfonyl chloride (0.47 g, 6.0 mmol) over 3 min. The reaction mixture was stirred for 25 min and then N-acetyl-4-aminobutyric acid (1.6 g, 10.1 mmol) added. The reaction mixture was then heated at reflux for 18 h, cooled and washed with sat. NaHCO$_3$ (aq). The organic phase was dried over MgSO$_4$, filtered and evaporated. The residue was further purified on silica eluting with 1:1:0.1 to 1:1:0.2 dichloromethane/ethyl acetate/methanol to give the title compound as an off white solid (1.1 g, 34%).
$^1$H NMR (CDCl$_3$, 300 MHz) δ 1.70-1.80 (m, 2H), 1.80-1.90 (m, 4H), 1.97 (s, 3H), 2.41 (t, 2H), 2.50-2.57 (m, 2H), 2.60-2.75 (m, 6H), 2.83-2.88 (m, 2H), 3.03-3.12 (m, 4H), 3.24-3.32 (m, 2H), 3.95-4.00 (m, 2H), 5.85-5.92 (m, 3H), 6.58 (d, 2H), 6.92-6.96 (m, 1H), 7.05 (d, 1H), 7.12-7.16 (m, 2H) m/z (M$^+$H) 605.08.

(7-(4-(4-(2,3-dichlorophenyl)piperazin-1-yl)butoxy)-2-oxo-3,4-dihydroquinolin-1(2H)-yl)methyl 4-octanamidobutanoate (Example 37, Compound 45)

Compound 149 (1.4 g) was synthesized in a similar manner to Compound 148.
$^1$H NMR (d$_6$-DMSO, 300 MHz) δ 0.79 (t, 3H), 1.10-1.28 (m, 8H), 1.38-1.48 (m, 2H), 1.50-1.77 (m, 6H), 1.93-2.00 (m, 2H), 2.25-2.40 (m, 4H), 2.40-2.60 (m, 6H), 2.72-2.81 (m, 2H), 2.87-3.02 (m, 6H), 3.90-4.00 (m, 2H), 5.82 (s, 2H), 6.58-6.63 (m, 2H), 7.04-7.02 (m, 2H), 7.20-7.30 (m, 2H). m/z (M$^+$H) 689.47.

(5-(2-(4-(benzo[d]isothiazol-3-yl)piperazin-1-yl) ethyl)-6-chloro-2-oxoindolin-1-yl)methyl hexanoate (Example 38, Compound 322)

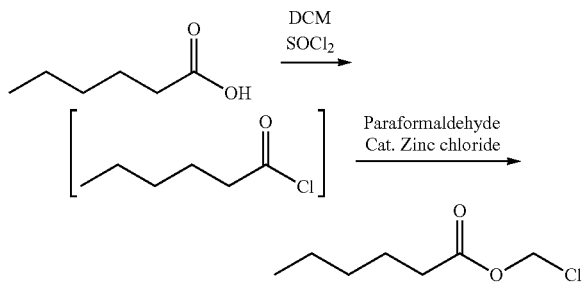

Step 1:

Thionyl chloride (12.31 g, 103 mmol) followed by catalytic amount of N,N-dimethyl formamide (DMF, 0.1 mL) was added to a solution of Hexanoic acid (10 g, 86 mmol) in dichloromethane (DCM, 100 mL) at 25-30° C. The reaction solution was stirred at same temperature for 2 hours under nitrogen atmosphere, upon completion of the starting material by TLC analysis. The volatiles were evaporated under reduced pressure below 40° C., which provided a viscous liquid material, hexanoyl chloride (about 10.5 g).

Step 2:

To the above hexanoyl chloride, para formaldehyde (3.8 g, 128 mmol) and anhydrous $ZnCl_2$ (0.232 g, 17 mmol) were added at 25-30° C. under inert atmosphere and then heated to 90° C. The thick mass was stirred at 90-95° C. for 5 hours, which after cooling provided crude product, chloromethyl hexanoate which was purified by silica gel column chromatography.

$^1$H-NMR (CDCl3, 500 MHz): δ 5.70 (s, 2H), 2.39-2.33 (m, 2H), 1.69-1.61 (m, 2H), 1.33-1.28 (m, 4H), 0.90-0.88 (t, J=7, 3H).

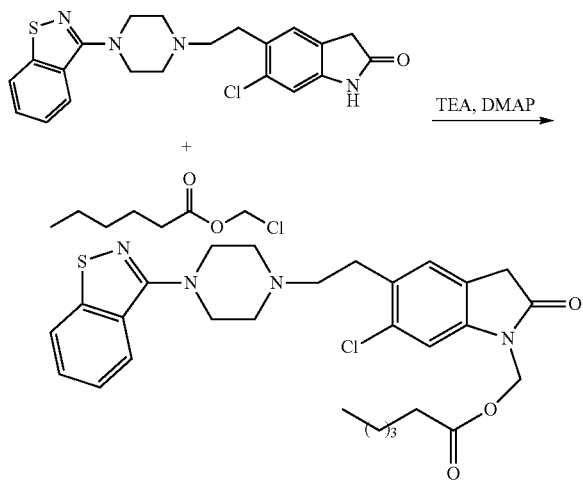

Step 3

Chloromethyl hexanoate (3.18 g, 19.0 mmol) in dichloromethane (6 mL) was added to a suspension of Ziprasidone free base (4.0 g, 9.6 mmol), triethyl amine (4.0 mL, 27 mmol) and 4-dimethylamino pyridine (DMAP, 0.708 g, 5 mmol) in dichloride methane (240 mL) at 25-30° C. The reaction solution was stirred for 24 h at same temperature. The crude mixture was washed with water (100 mL) followed by brine solution (100 mL), upon solvent evaporation under vacuum below 40° C. provided crude title product, Compound 322, which was further purified by silica gel column chromatography. (1.4 g, 27% yield)

$^1$H-NMR (CDCl3, 500 MHz): δ 7.92-7.90 (d, J=7.5, 1H), 7.82-7.80 (d, J=7.5, 1H), 7.48-7.45 (t, J=7.5, 1H), 7.37-7.34 (t, J=7.5, 1H), 7.17 (s, 1H), 7.05 (s, 1H), 5.72 (s, 2H), 3.60-3.55 (m, 6H), 2.98-2.95 (t, J=7.5, 2H), 2.79-2.78 (m, 4H), 2.68-2.65 (t, J=8.5, 2H), 2.35-2.32 (t, J=7.5, 2H), 1.64-1.61 (t, J=7.5, 2H), 1.29-1.25 (m, 4H), 0.88-0.85 (t, J=7, 3H).

Mass (m/z)=541 [M$^+$+1].

(5-(2-(4-(benzo[d]isothiazol-3-yl)piperazin-1-yl) ethyl)-6-chloro-2-oxoindolin-1-yl)methyl dodecanoate (Example 39, Compound 324)

Compound 324 was synthesized in a similar manner to Compound 322, Example 38.

$^1$H-NMR (CDCl3, 500 MHz): δ 7.92-7.90 (d, J=7.5, 1H), 7.82-7.80 (d, J=7.5, 1H), 7.48-7.45 (t, J=7.5, 1H), 7.37-7.34 (t, J=7.5, 1H), 7.17 (s, 1H), 7.05 (s, 1H), 5.72 (s, 2H), 3.60-3.55 (m, 6H), 2.98-2.95 (t, J=8, 2H), 2.79-2.77 (m, 4H), 2.68-2.65 (t, J=8, 2H), 2.34-2.31 (t, J=7, 2H), 1.63-1.60 (m, 2H), 1.24 (s, 16H), 0.89-0.86 (t, J=7, 3H).

Mass (m/z)=625.5 [M$^+$+1].

(5-(2-(4-(benzo[d]isothiazol-3-yl)piperazin-1-yl) ethyl)-6-chloro-2-oxoindolin-1-yl)methyl palmitate (Example 40, Compound 326)

$^1$H-NMR (CDCl$_3$, 500 MHz): δ 7.92-7.90 (d, J=7.5, 1H), 7.82-7.80 (d, J=7.5, 1H), 7.48-7.45 (t, J=7.5, 1H), 7.37-7.34 (t, J=7.5, 1H), 7.17 (s, 1H), 7.05 (s, 1H), 5.72 (s, 2H), 3.60-3.55 (m, 6H), 2.98-2.95 (t, J=8, 2H), 2.79-2.77 (m, 4H), 2.68-2.65 (t, J=8, 2H), 2.34-2.31 (t, J=8, 2H), 1.63-1.56 (m, 2H), 1.25-1.23 (m, 24H), 0.88-0.86 (t, J=7, 2H).

Mass (m/z)=681.5 [M$^+$+1].

(7-[(4-biphenyl-3yl methyl)piperazin-1-yl]-2-oxobenzo[d]oxazol-3(2H)-yl)methyl acetate (Example 41, Compound 416)

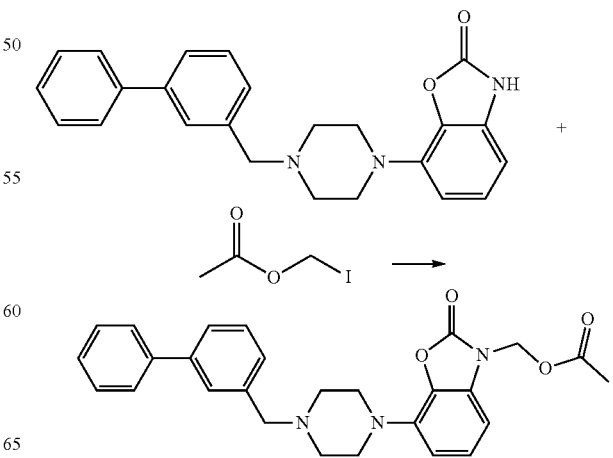

Step 1:

Synthesis of chloromethyl acetate: Acetyl chloride (5 g, 0.06 mol) was added dropwise to a mixture of paraformaldehyde (8.5 g, 0.06 mol) and anhydrous zinc chloride (0.175 g, 0.02 mol) at 0° C. under Argon. The reaction mixture was warmed to room temperature and stirred for 1 hour, then heated to 90° C. for 18 hours. The solid was filtered off washed with dichloromethane, and the filtrate was concentrated under vacuum at 37° C. to provide the desired product (6.6 g, 94% yield). The product was used directly (without purification) in to next step and stored with activated molecular sieves (4° A).

Step 2:

Synthesis of iodomethyl acetate: Sodium iodide (27.6 g, 0.18 mol) was added to a solution of chloromethyl acetate (6.6 g, 0.06 mol) in acetonitrile (66 mL). The reaction flask was covered in aluminum foil to exclude light and stirred at ambient temperature for 15 hours. The reaction mixture was partition between dichloromethane and water, and the aqueous layer was extracted with dichloromethane. The combine organics were washed with aqueous saturated NaHCO₃, 100/aqueous sodium sulfite solution, and brine then dried with sodium sulphate and concentrated to give the product (1.13 g, 12% yield) as a yellow oil.

Step 3:

n-Butyl lithium (1.6 M in hexane; 3.8 mL, 0.007 mol) was added drop wise from a syringe to a stirred solution of bifeprunox (1.46 g, 0.003 mol) in tetrahydrofuran at −78° C. After 1 hour a solution of iodomethyl acetate (1.13 g, 0.005 mol) was added drop-wise at −70° C. The reaction mixture was stirred for 15 hours. The reaction mixture was dumped in a saturated aqueous solution of ammonium chloride and extracted with ethyl acetate. The combined organic layers were washed with 1N solution of NaOH and brine, then dried with sodium sulphate and concentrated under vacuum. Purification by flash chromatography provided compound 416. (0.25 g, 14% yield). ¹H NMR (DMSO, 400 MHz) δ 2.034 (s, 3H), 2.565 (s, 4H), 3.183 (s, 4H), 3.597 (s, 2H), 5.765 (s, 2H), 6.696-6.717 (d, 1H), 6.882-6.901 (d, 1H), 7.091-7.182 (t, 1H), 7.315-7.370 (q, 2H), 7.404-7.473 (m, 3H), 7.515-7.555 (d, 1H), 7.59 (d, 1H), 7.639-7.657 (d, 2H). m/z (M+H) 457.

(7-[(4-biphenyl-3yl methyl)piperazin-1-yl]-2-oxobenzo[d]oxazol-3(2H)-yl)methyl butyrate (Example 42, Compound 417)

Compound 417 was prepared in a similar manner to Example 41 using butanoyl chloride. Purification by flash chromatography provided the desired product (1.25 g, 45% yield). 1H NMR (DMSO, 400 MHz) δ 1.065 (t, 3H), 1.448-1.54 (m, 2H), 2.284-2.320 (t, 2H), 2.564 (s, 4H), 3.184 (s, 4H), 3.597 (s, 2H), 5.787 (s, 2H), 6.694-6.713 (d, 1H), 6.878-6.896 (d, 1H), 7.092-7.133 (t, 1H), 7.315-7.370 (q, 2H), 7.422-7.533 (m, 3H), 7.535-7.555 (d, 1H), 7.639 (d, 1H), 7.657-7.660 (d, 2H). m/z (M+H) 485.

(7-[(4-biphenyl-3yl methyl)piperazin-1-yl]-2-oxobenzo[d]oxazol-3(2H)-yl)methyl hexanoate (Example 43, Compound 413)

Compound 413 was prepared in a similar manner to Example 41 using hexanoyl chloride. Purification by flash chromatography provided the desired product (0.6 g, 60% yield). 1H NMR (DMSO, 400 MHz) δ 0.774 (t, 3H), 1.114-1.187 (m, 4H), 1.433-1.506 (m, 2H), 2.291-2.328 (t, 2H), 2.564 (s, 4H), 3.182 (s, 4H), 3.597 (s, 2H), 5.783 (s, 2H), 6.693-6.713 (d, 1H), 6.870-6.890 (d, 1H), 7.090-7.130 (t, 1H), 7.314-7.351 (q, 2H), 7.422-7.472 (m, 3H), 7.535-7.554 (d, 1H), 7.589 (d, 1H), 7.638-7.656 (d, 2H). m/z (M+H) 513.

(7-[(4-biphenyl-3yl methyl)piperazin-1-yl]-2-oxobenzo[d]oxazol-3(2H)-yl)methyl palmitate (Example 44, Compound 422)

Compound 422 was prepared in a similar manner to Example 41 using palmitoyl chloride. Purification by flash chromatography provided the desired product (0.5 g, 47% yield). 1H NMR (DMSO, 400 MHz) δ 0.819 (t, 3H), 1.127-1.302 (m, 22H), 1.437-1.454 (t, 2H), 2.287-2.305 (t, 2H), 2.564 (s, 4H), 3.182 (s, 4H), 3.596 (s, 2H), 5.784 (s, 2H), 6.688-6.708 (d, 1H), 6.863-6.882 (d, 1H), 7.083-7.124 (t, 1H), 7.331-7.368 (q, 2H), 7.400-7.470 (m, 3H), 7.534-7.553 (d, 1H), 7.587 (d, 1H), 7.635-7.653 (d, 2H). m/z (M+H) 653.

(7-[(4-biphenyl-3yl methyl)piperazin-1-yl]-2-oxobenzo[d]oxazol-3(2H)-yl)methyl decanoate (Example 45, Compound 419)

Compound 419 was prepared in a similar manner to Example 41 using decanoyl chloride. Purification by flash chromatography provided the desired product (0.8 g, 77% yield). 1H NMR (DMSO, 400 MHz) δ 0.795-0.829 (t, 3H), 1.140-1.211 (m, 12H), 1.438-1.471 (t, 2H), 2.288-2.324 (t, 2H), 2.562 (s, 4H), 3.181 (s, 4H), 3.595 (s, 2H), 5.783 (s, 2H), 6.689-6.709 (d, 1H), 6.856-6.884 (d, 1H), 7.083-7.124 (t, 1H), 7.311-7.367 (q, 2H), 7.400-7.470 (m, 3H), 7.533-7.552 (d, 1H), 7.587 (d, 1H), 7.635-7.653 (d, 2H). m/z (M+H) 569.

(7-[(4-biphenyl-3yl methyl)piperazin-1-yl]-2-oxobenzo[d]oxazol-3(2H)-yl)methyl isobutyrate (Example 46, Compound 414)

Compound 414 was prepared in a similar manner to Example 41 using isobutyryl chloride. Purification by flash chromatography provided the desired product (0.3 g, 15% yield). 1H NMR (DMSO, 400 MHz) δ 1.027-1.044 (d, 6H), 2.478-2.553 (m, 1H), 2.562 (s, 4H), 3.185 (s, 4H), 3.597 (s, 2H), 5.785 (s, 2H), 6.692-6.713 (d, 1H), 6.873-6.892 (d, 1H), 7.093-7.134 (t, 1H), 7.315-7.369 (q, 2H), 7.403-7.472 (m, 3H), 7.533-7.555 (d, 1H), 7.590 (d, 1H), 7.657-7.660 (d, 2H). m/z (M+H) 485.

(7-(4-(4-(2,3-dichlorophenyl)piperazin-1-yl)butoxy-2-oxoquinolin-1(2H)-yl)methyl butyrate (Example 47, Compound 151)

(7-(4-(4-(2,3-dichlorophenyl)piperazin-1-yl)butoxy)-2-oxo-3,4-dihydroquinolin-1(2H)-yl)methyl butyrate (Compound 2) was prepared as described in Example 16, supra.

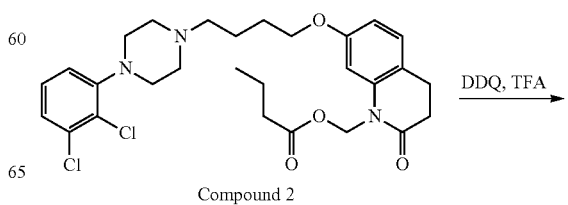

Compound 2

-continued

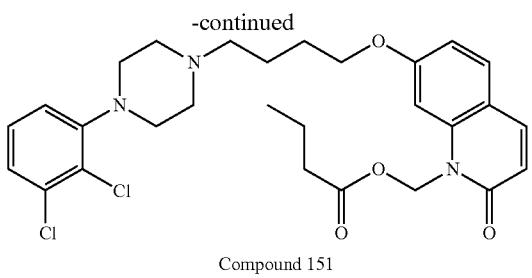

Compound 151

To a stirred solution of (7-(4-(4-(2,3-dichlorophenyl)piperazin-1-yl)butoxy)-2-oxo-3,4-dihydroquinolin-1(2H)-yl) methyl butyrate (3.26 g, 5.94 mmol) in THF (100 mL) was added TFA (2.74 mL, 35.63 mmol) followed by 2,3-dichloro-5,6-dicyanobenzoquinone (DDQ; 7.01 g, 30.88 mmol) in THF (40 mL). The reaction was stirred at room temperature over the weekend. The reaction was quenched with water (100 mL) and then poured into water (600 mL) and dichloromethane (100 mL). Solid NaHCO$_3$ (100 g) was added and the mixture stirred for approximately 30 minutes. Dichloromethane (200 mL) was added and the mixture filtered. The collected filtrate was transferred to a separating funnel and the layers separated. The aqueous layer was extracted with dichloromethane (2×100 mL) and the combined organics washed with water (3×100 mL), brine (100 mL) and dried over MgSO$_4$. After filtration, the volatiles were removed. The crude material was purified by silica chromatography eluting 0-4% Methanol/(1:1 ethyl acetate/dichloromethane). The oil was recrystallized from methanol to give Compound 151. (2.03 g, 3.72 mmol, 63% yield). $^1$H-NMR (300 MHz, CDCl$_3$) δ 7.63 (1H, d), 7.45 (1H, d), 7.19-7.06 (2H, m), 6.99-6.90 (1H, m), 6.88-6.78 (2H, m), 6.52 (1H, d), 6.33 (2H, s), 4.06 (2H, t), 3.17-2.99 (4H, bs), 2.74-2.43 (6H, m), 2.35 (2H, t), 1.94-1.54 (6H, m), 0.93 (3H, t).

The Following Compounds were Synthesized in a Similar Manner to Example 47 from their Corresponding 3.4 Dihydro Precursors:

(7-(4-(4-(2,3-dichlorophenyl)piperazin-1-yl)butoxy)-2-oxoquinolin-1(2H)-yl)methyl palmitate (Example 48, Compound 159)

Compound 159 was synthesized in a similar manner to Example 47 from Compound 10. 2.04 g. $^1$H-NMR (400 MHz, CDCl$_3$) δ 7.62 (1H, d), 7.44 (1H, d), 7.18-7.10 (2H, m), 6.98-6.91 (1H, m), 6.87-6.80 (2H, m), 6.52 (1H, d), 6.32 (2H, s), 4.05 (2H, t), 3.15-2.99 (4H, bs), 2.74-2.44 (6H, m), 2.35 (2H, t), 1.92-1.83 (2H, m), 1.80-1.68 (2H, m) 1.66-1.55 (2H, m), 1.32-1.14 (24H, m), 0.87 (3H, t).

(7-(4-(4-(2,3-dichlorophenyl)piperazin-1-yl)butoxy)-2-oxoquinolin-1(2H)-yl)methyl laurate (Example 49, Compound 156)

Compound 156 was synthesized in a similar manner to Example 47 from Compound 7. 1.37 g. $^1$H-NMR (400 MHz, CDCl$_3$) δ 7.62 (1H, d), 7.43 (1H, d), 7.17-7.10 (2H, m), 6.96-6.92 (1H, m), 6.87-6.80 (2H, m), 6.51 (1H, d), 6.33 (2H, s), 4.06 (2H, t), 3.12-3.01 (4H, bs), 2.71-2.59 (4H, bs), 2.50 (2H, t), 2.35 (2H, t), 1.92-1.83 (2H, m), 1.78-1.69 (2H, m) 1.66-1.55 (2H, m), 1.32-1.16 (16H, m), 0.86 (3H, t).

(7-(4-(4-(2,3-dichlorophenyl)piperazin-1-yl)butoxy)-2-oxoquinolin-1(2H)-yl)methyl stearate (Example 50, Compound 160)

Compound 160 was synthesized in a similar manner to Example 47 from Compound 11. 1.38 g $^1$H-NMR (400 MHz, CDCl$_3$) δ 7.62 (1H, d), 7.44 (1H, d), 7.17-7.11 (2H, m), 6.97-6.92 (1, m), 6.87-6.79 (2H, m), 6.51 (1H, d), 6.32 (2H, s), 4.05 (2H, t), 3.13-3.00 (4H, bs), 2.73-2.58 (4H, bs), 2.50 (2H, t), 2.35 (2H, t), 1.92-1.83 (2H, m), 1.79-1.69 (2H, m) 1.66-1.55 (2H, m), 1.32-1.14 (28H, m), 0.87 (3H, t).

(7-(4-(4-(2,3-dichlorophenyl)piperazin-1-yl)butoxy)-2-oxoquinolin-1(2H)-yl)methyl acetate (Example 51, Compound 150)

Compound 150 was synthesized in a similar manner to Example 47 from Compound 1. 1.61 g $^1$H-NMR (300 MHz, CDCl$_3$) δ 7.63 (1H, d), 7.45 (1H, d), 7.18-7.11 (2H, m), 6.98-6.92 (1H, m), 6.90-6.80 (2H, m), 6.52 (1H, d), 6.32 (2H, s), 4.07 (2H, t), 3.14-3.01 (4, bs), 2.73-2.59 (4H, bs), 2.51 (2H, t), 2.12 (3H, s), 1.95-1.82 (2H, m), 1.82-1.68 (2H, m).

(7-(4-(4-(2,3-dichlorophenyl)piperazin-1-yl)butoxy)-2-oxoquinolin-1(2H-yl)methyl 2,2-dimethylbutanoate (Example 52, Compound 165)

Compound 165 was synthesized in a similar manner to Example 47 from Compound 16. 1.02 g $^1$H-NMR (400 MHz, CDCl$_3$) δ 7.61 (1H, d), 7.43 (1H, d), 7.17-7.10 (2H, m), 6.97-6.92 (1H, m), 6.83-6.79 (2H, m), 6.51 (1H, d), 6.31 (2H, s), 4.05 (2H, t), 3.12-3.02 (4H, bs), 2.71-2.60 (4H, bs), 2.50 (2, t), 1.92-1.83 (2, m), 1.78-1.68 (2H, m) 1.55 (2H, q), 1.15 (6H, s), 0.81 (3H, t).

(2-(N-(1-(1-(4-fluorobenzyl)-1H-benzo[d]imidazol-2-yl)piperidin-4-yl)-N-methylamino)-6-oxopyrimidin-1(6H)-yl)methyl octanoate (Example 53, Compound 704)

Step 1:

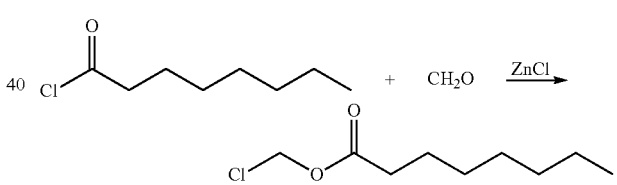

Octanoyl chloride (10 g, 0.06 mol) was added drop wise to a mixture of paraformaldehyde (8.07 g, 0.06 mol) and anhydrous zinc chloride (0.163 g, 0.0012 mol) at 0° C. under Argon. After the addition was completed, the reaction mixture was stirred at 25° C. for 1 hour, and then heated to 90° C. for 16 hours. The solid was filtered off and washed with dichloromethane. The filtrate was concentrated in vacuo at 37° C. to provide the desired chloromethyl octanoate (9.5 g, 84% yield), which was used directly (without purification) in the next step. This product was stored over activated molecular sieves (4 OA) to keep it dry.

Step 2:

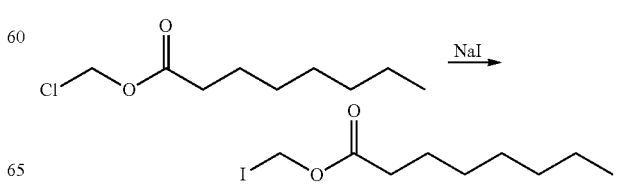

Sodium iodide (21.7 g, 0.1449 mol) was added to a solution of chloromethyl octanoate (9.5 g, 0.0483 mol) in of acetonitrile (100 ml). The flask was covered in aluminum foil to protect from light and stirred at 25° C. for 16 hours. The reaction mixture was partitioned between dichloromethane and water the aqueous layer was further extracted with dichloromethane. The combined organic extracts were washed with aqueous saturated $NaHCO_3$, 10% aqueous sodium sulfite solution and brine, and finally dried with sodium sulphate and concentrated in vacuo to provide the product (8.4 g, 71% yield) as a yellow oil. This product was taken into the next step without further purification.

Step 3:

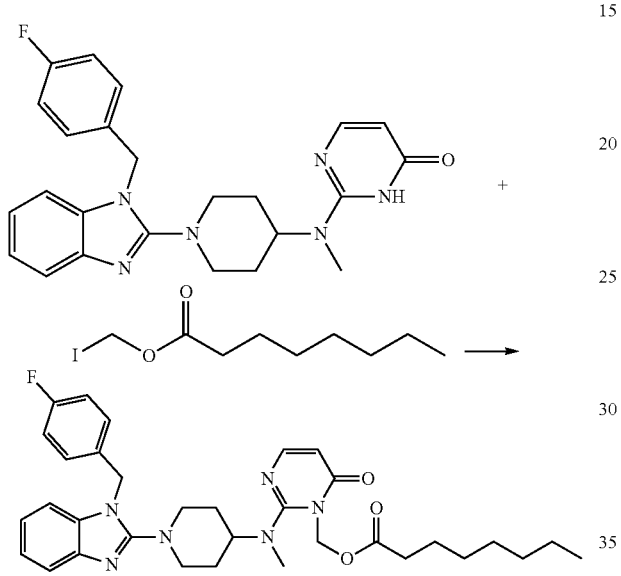

and then dried with sodium sulphate and concentrated in vacuo. Flash chromatography provided the desired product (0.45 g, 17% yield).

$^1$H NMR (DMSO, 400 MHz) δ 0.815 (t, 3H), 1.117-1.235 (m, 10H), 1.474-1.491 (t, 2H), 1.638-1.665 (d, 2H), 1.992-2.010 (m, 2H), 2.292-2.230 (t, 2H), 2.992 (s, 3H), 3.027-3.088 (t, 2H), 3.55-3.62 (t, 2H), 4.625 (s, 1H) 5.311 (s, 2H), 6.040 (s, 2H), 6.110-6.124 (d, 1H), 7.014-7.076 (m, 2H), 7.148-7.253 (m, 5H), 7.442-7.460 (d, 1H), 8.187-8.201 (d, 1H). m/z (M$^+$H) 589.

(2-(N-(1-(1-(4-fluorobenzyl)-1H-benzo[d]imidazol-2-yl)piperidin-4-yl)-N-methylamino-6-oxopyrimidin-1(6H)-yl)methyl laurate (Example 54, Compound 706)

Compound 706 was synthesized using a similar procedure as Example 53 using lauroyl chloride.

$^1$H NMR (DMSO, 400 MHz) δ 0.791-0.826 (t, 3H), 1.134-1.210 (m, 16H), 1.446 (t, 2H), 1.642-1.925 (d, 2H), 1.956-2.008 (m, 2H), 2.266-2.301 (t, 2H), 2.968 (s, 3H), 3.003-3.063 (t, 2H), 3.31-3.62 (t, 2H), 4.625 (s, 1H) 5.286 (s, 2H), 6.015 (s, 2H), 6.085-6.099 (d, 1H), 7.015-7.072 (m, 2H), 7.122-7.215 (m, 5H), 7.418-7.436 (d, 1H), 8.159-8.172 (d, 1H). m/z (M$^+$H) 645.5.

(5-(4-(2-(5-ethylpyridin-2-yl)ethoxy)benzyl)-2,4-dioxothiazolidin-3-yl)methyl hexanoate (Example 55, Compound 1003)

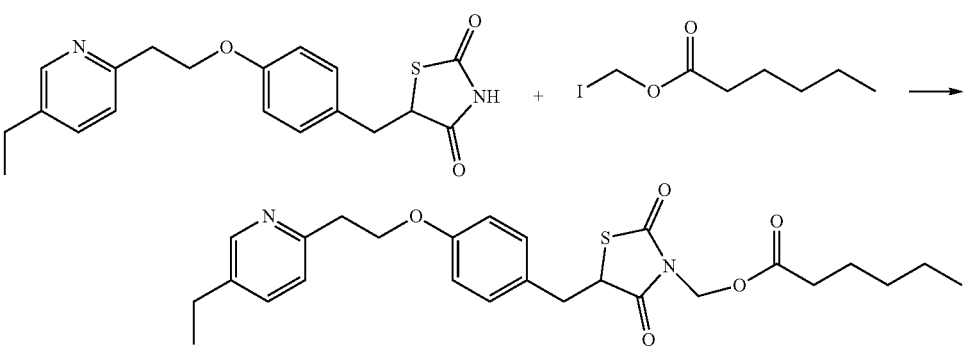

n-Butyl lithium (1.5 M in hexane; 14.6 ml, 0.0042 mol) was added drop wise to a stirred solution of 2-(N-(1-(1-(4-fluorobenzyl)-1H-benzo[d]imidazol-2-yl)piperidin-4-yl)-N-methylamino)pyrimidin-4(3H)-one (Mizolastine, 14.3 g, 0.00696 mol) in tetrahydrofuran (50 ml) at −78° C. After 1 hour the reaction mixture was treated drop-wise with a iodomethyl octanoate (2.5 g, 0.0231 mol) at −70° C. The reaction mixture was stirred at 25° C. for 16 hours. The reaction mixture was poured into ammonium chloride solution and extracted with ethyl acetate. The combined organic was washed with aqueous sodium hydroxide (1N) and brine, Step 1:
Chloromethyl hexanoate was synthesized from hexanoyl chloride in a similar process as described above in Example 53, step 1.

Step 2:
Iodomethyl hexanoate was synthesized from chloromethyl hexanoate in a similar process as described above in Example 53, step 2.

Step 3:
A solution of Pioglitazone (3.0 g, 0.0084 mol) in dimethyl formamide was treated with dry $K_2CO_3$ (3.48 g, 0.0252) at 25° C. After 40 minutes a solution of Iodomethyl hexanoate (4.29 g, 0.0168 mol) was added drop-wise. The reaction mixture was stirred for 15 hours, then dumped into water and extracted with ethyl acetate. The combined organic layers were dried with sodium sulphate and concentrated under vacuum. The product was purified by flash chromatography to obtain the desired product (1.9 g, 44% yield).

$^1$H NMR (CDCl$_3$, 400 MHz) δ 0.86-0.90 (t, 3H), 1.22-1.29 (m, 8H), 1.58-1.62 (t, 2H), 2.27-2.31 (t, 2H), 2.62-2.64 (d, 2H), 3.04-3.099 (q, 1H), 3.21-3.25 (t, 2H), 3.452-3.497 (q, 1H), 4.30-4.34 (t, 2H), 4.46-4.48 (d, 1H), 5.513-5.51 (d, 2H), 6.81-6.85 (t, 2H), 7.09-7.11 (d, 2H), 7.18-7.20 (d, 1H), 7.46-7.48 (q, 1H), 8.38-8.39 (d, 1H) m/z (M$^+$H) 485.

(5-(4-(2-(5-ethylpyridin-2-yl)ethoxy)benzyl)-2,4-dioxothiazolidin-3-yl)methyl laurate (Example 56, Compound 1006)

Compound 1006 was synthesized using a similar procedure as Example 55 using lauroyl chloride.

$^1$H NMR (CDCl$_3$, 400 MHz) δ 0.802-0.836 (t, 3H), 1.133-1.171 (t, 4H), 1.197-1.235 (d, 15H), 1.308 (s, 1H), 1.419-1.452 (t, 2H), 2.172-254 (q, 2H), 2.533-2.590 (q, 2H), 3.044-3.118 (m, 3H), 4.251-4.284 (t, 2H), 4.97-5.005 (q, 1H), 5.345-5.413 (q, 2H), 6.82-6.841 (d, 2H), 7.09-7.11 (d, 2H), 7.23-7.25 (d, 1H), 7.53-7.55 (q, 1H), 8.33-8.34 (d, 1H) m/z (M$^+$H) 569.

(5-(4-(2-(5-ethylpyridin-2-yl)ethoxy)benzyl)-2,4-dioxothiazolidin-3-yl)methyl palmitoate (Example 57, Compound 1008)

Compound 1008 was synthesized using a similar procedure as Example 55 using palmitoyl chloride.

$^1$H NMR (CDCl$_3$, 400 MHz) δ 0.870 (s, 3H), 1.23-1.26 (t, 27H), 1.57-1.61 (t, 2H), 2.27-2.31 (t, 2H), 2.61.265 (t, 2H), 3.06-310 (t, 1H), 3.22-3.25 (t, 2H), 3.45-3.46 (d, 1H), 4.31-4.34 (t, 2H), 4.45-4.49 (q, 1H), 5.487-5.541 (q, 2H), 6.83-6.85 (d, 2H), 7.09-7.11 (d, 2H), 7.19-7.26 (t, 1H), 7.47-7.49 (q, 1H), 8.393-8.397 (d, 1H) m/z (M$^+$H) 625.

(5-(4-(2-(5-ethylpyridin-2-yl)ethoxy)benzyl)-2,4-dioxothiazolidin-3-yl)methyl stearoate (Example 58, Compound 1009)

Compound 1009 was synthesized using a similar procedure as Example 55 using stearoyl chloride.

$^1$H NMR (CDCl$_3$, 400 MHz) δ 0.874-0.894 (t, 3H), 1.222-1.260 (t, 30H), 1.570-1.603 (d, 1H), 2.27-2.31 (t, 2H), 2.609-2.266 (q, 2H), 3.04-3.10 (q, 1H), 3.20-3.24 (t, 2H), 3.46-3.50 (q, 1H), 4.302-4.335 (t, 2H), 4.453-4.487 (q, 1H), 5.488-5.552 (q, 2H), 6.83-6.86 (d, 2H), 7.09-7.11 (d, 2H), 7.17-7.19 (d, 1H), 7.44-7.47 (d, 1H), 8.386-8.391 (d, 1H) m/z (M$^+$H) 653.

(5-(4-(2-(5-ethylpyridin-2-yl)ethoxy)benzyl)-2,4-dioxothiazolidin-3-yl)methyl myristoate (Example 59, Compound 1007)

Compound 1007 was synthesized using a similar procedure as Example 55 using myristoyl chloride.

$^1$H NMR (CDCl$_3$, 400 MHz) δ 0.854-0.887 (t, 3H), 1.226-1.262 (t, 24H), 1.57-1.604 (t, 2H), 2.27-2.308 (t, 2H), 2.609-2.265 (t, 2H), 3.035-3.094 (q, 1H), 3.223-3.256 (t, 2H), 3.456-3.500 (q, 1H), 4.307-4.340 (t, 2H), 4.463-4.487 (t, 1H), 5.487-5.540 (q, 2H), 6.832-6.852 (d, 2H), 7.092-7.114 (d, 2H), 7.198-7.217 (d, 1H), 7.475-7.491 (d, 1H), 8.393-8.397 (d, 1H) m/z (M$^+$H) 596.

(5-(4-(2-(5-ethylpyridin-2-yl)ethoxy)benzyl)-2,4-dioxothiazolidin-3-yl)methyl butyrate (Example 60, Compound 1002)

Compound 1002 was synthesized using a similar procedure as Example 55 using butyroyl chloride.

$^1$H NMR (CDCl$_3$, 400 MHz) δ 0.798-0.835 (t, 3H), 1.133-1.212 (q, 4H), 1.417-1.509 (m, 2H), 2.210-2.246 (t, 2H), 2.482-2.2591 (q, 2H), 3.047-3.118 (q, 3H), 4.253-4.286 (t, 2H), 4.983-5.016 (q, 1H), 5.353-5.415 (q, 2H), 6.824-6.845 (d, 2H), 7.097-7.118 (d, 2H), 7.239-7.258 (d, 1H), 7.538-7.563 (d, 1H), 8.340-8.365 (d, 1H) m/z (M$^+$H) 458.

(5-(4-(2-(5-ethylpyridin-2-yl)ethoxy)benzyl)-2,4-dioxothiazolidin-3-yl)methyl cyclohexanecarboxylate (Example 60, Compound 1015)

Compound 1015 was synthesized using a similar procedure as Example 55 using cyclohexanecarbonyl chloride.

$^1$H NMR (CDCl$_3$, 400 MHz) δ 1.181-1.293 (m, 7H), 1.359-1.449 (m, 2H), 2.624 (s, 1H), 1.714-1.738 (t, 2H), 1.843-1.874 (q, 2H), 2.244-2.319 (m, 1H), 2.607-2.664 (q, 2H), 3.049-3.107 (q, 1H), 3.22-3.253 (t, 2H), 3.340-3.485 (q, 1H), 5.481-5.534 (q, 2H), 6.831-6.853 (d, 2H), 7.091-7.113 (d, 2H), 7.193-7.213 (d, 1H), 7.465-7.590 (q, 1H), 8.392-8.396 (d, 1H) m/z (M$^+$H) 497.

General Scheme for Synthesis

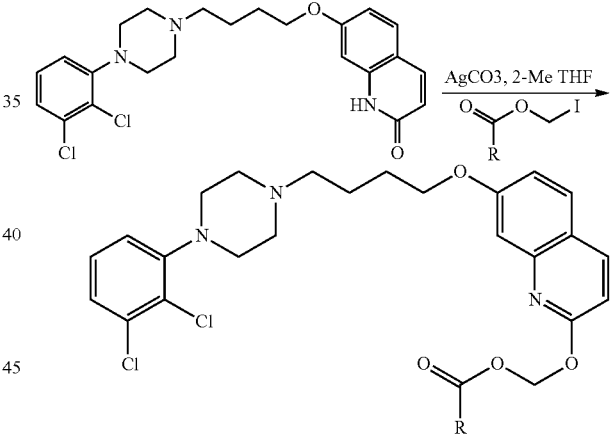

((7-(4-(4-(2,3-dichlorophenyl)piperazin-1-yl)butoxy)quinolin-2-yl)oxy)methyl hexyl carbonate (Example 61, Compound 1240)

To a solution of dehydro-Aripiprazole (1.5 g, 3.36 mmol) in 2-methyltetrahydrofuran (30 mL) was added silver carbonate (1.853 g, 6.72 mmol) and hexyl iodomethyl carbonate (2.021 g, 7.05 mmol) in 2-methyltetrahydrfuran (4 mL) at room temperature. The reaction was stirred for 4.5 days. The reaction was quenched with H$_2$O (30 mL) and filtered through celite. The reaction was extracted with ethyl acetate (3×20 mL), washed with brine (20 mL), dried over MgSO$_4$ and concentrated. The product was purified by column chromatography on silica eluting with 1:1 ethyl acetate to dichloromethane to 2% MeOH in 1:1 ethyl acetate to dichloromethane to provide Compound-1240 (1.08 g) as a yellow oil.

¹H-NMR (300 MHz, CDCl₃) δ 7.96 (1H, d), 7.60 (1H, d), 7.21 (1H, m), 7.14 (2H, m), 7.03 (1H, dd), 6.94 (1H, m), 6.81 (1H, d), 6.26 (2H, s), 4.18 (2H, m), 4.12 (2H, t), 3.09 (4H, m), 2.68 (4H, m), 2.53 (2H, m), 1.91 (2H, m), 1.78 (2H, m), 1.63 (2H, m), 1.28 (6H, m), 0.86 (3H, t). [M+H]⁺=604.2

((7-(4-(4-(2,3-dichlorophenyl)piperazin-1-yl)butoxy)quinolin-2-yl)oxy)methyl octanoate (Example 62, Compound 1206)

To a solution of dehydro-Aripiprazole (1.0 g, 2.24 mmol) in 2-methyltetrahydrofuran (25 mL) was added silver carbonate (0.864 g, 3.13 mmol) and iodomethyl octanoate (0.764 g, 2.68 mmol) at room temperature. The reaction was stirred for 5 days. The reaction was quenched with H₂O (30 mL) and filtered through celite. The reaction was extracted with ethyl acetate (3×20 mL), washed with 5% w/v sodium sulfite solution (15 mL), brine (20 mL), dried over MgSO₄ and concentrated. The product was purified by column chromatography on silica eluting with 0-70% ethyl acetate in heptane to provide Compound 1206 (0.602 g) as a pale orange oil.

¹H-NMR (300 MHz, CDCl₃) δ 7.95 (1H, d), 7.60 (1H, d), 7.21 (1H, m), 7.14 (2H, m), 7.07 (1H, dd), 6.95 (1H, m), 6.79 (1H, d), 6.24 (2H, s), 4.12 (2H, m), 3.09 (4H, m), 2.68 (4H, m), 2.54 (2H, m), 2.36 (2H, t), 1.90 (2H, m), 1.77 (2H, m), 1.61 (4H, m), 1.23 (6H, m), 0.83 (3H, t). [M+H]⁺=602.2.

((7-(4-(4-(2,3-dichlorophenyl)piperazin-1-yl)butoxy)quinolin-2-yl)oxy)methyl dodecanoate (Example 63. Compound 1208)

The experimental procedure was carried out in the same manner as for Compound-1206 in Example 62, to give 1208 (0.738 g) as a yellow oil.

¹H-NMR (300 MHz, CDCl₃) δ 7.95 (1H, d), 7.60 (1H, d), 7.20 (1H, d), 7.14 (2H, m), 7.05 (1H, dd), 6.95 (1H, m), 6.80 (1H, d), 6.24 (2H, s), 4.13 (2H, m), 3.09 (4H, m), 2.68 (4H, m), 2.54 (2H, m), 2.36 (2H, t), 1.93 (2H, m), 1.80 (2H, m), 1.60 (4H, m), 1.23 (14H, m), 0.86 (3H, t). [M+H]⁺=658.4.

((7-(4-(4-(2,3-dichlorophenyl)piperazin-1-yl)butoxy)quinolin-2-yl)oxy)methy butyrate (Example 64, Compound 1202)

The experimental procedure was carried out in the same manner as for Compound-1206 in Example 62, to give 1202 (0.695 g) as a yellow oil.

¹H-NMR (300 MHz, CDCl₃) δ 7.95 (1H, d), 7.61 (1H, d), 7.20 (1H, d), 7.14 (2H, m), 7.04 (1H, dd), 6.96 (1H, m), 6.79 (1H, d), 6.25 (2H, s), 4.13 (2H, m), 3.09 (4H, m), 2.69 (4H, m), 2.54 (2H, m), 2.35 (2H, t), 1.91 (2H, m), 1.78 (2H, m), 1.66 (2H, m), 0.94 (3H, t). [M+H]⁺=546.1.

Example 65: ((7-(4-((4-(2,3-dichlorophenyl)piperazin-1-yl)butoxy)quinolin-2-yl)oxy)methyl 2,2-dimethyltetradecanoate (Compound 1213) and (7-(4-(4-(2,3-dichlorophenyl)piperazin-1-yl)butoxy)-2-oxoquinolin-1(2H)-yl)methyl 2,2-dimethyltetradecanoate (Compound 255)

The experimental procedure was carried out in the same manner as for Compound-1206 in Example 62 to give both Compound-255 and Compound-1212. Compound-1213 was isolated (0.586 g) as a yellow oil, and Compound-255 was isolated (0.156 g) as a yellow oil. Compound-1213:
¹H-NMR (300 MHz, CDCl₃) δ 7.93 (1H, d), 7.59 (1H, d), 7.16 (3H, m), 7.03 (1H, dd), 6.97 (1H, m), 6.78 (1H, d), 6.22 (2H, s), 4.12 (2H, m), 3.10 (4H, m), 2.73 (4H, m), 2.57 (2H, t), 1.91 (2H, m), 1.80 (2H, m), 1.46 (2H, d), 1.01-1.33 (26H, m), 0.87 (3H, t). [M+H]⁺=714.3.

Compound-255: ¹H-NMR (300 MHz, CDCl₃) δ 7.60 (1H, d), 7.42 (1H, d), 7.15 (2H, m), 6.96 (1H, m), 6.82 (2H, m), 6.51 (1H, d), 6.32 (2H, s), 4.04 (2H, t), 3.07 (4H, m), 2.66 (4H, m), 2.49 (2H, m), 1.87 (2H, m), 1.76 (2H, m), 1.45 (2H, m), 1.01-1.36 (26H, m), 0.87 (3H, t). [M+H]⁺=714.3.

((7-(4-(4-(2,3-dichlorophenyl)piperazin-1-yl)butoxy)quinolin-2-yl)oxy)methyl diethylcarbamate (Example 66, Compound 1247)

The experimental procedure was carried out in the same manner as for Compound-1206 in Example 62. The reaction was incomplete after 5 days at room temperature. The reaction was heated to 60° C. for two days before following the same work-up and purification procedures as in Example-62 to give Compound-1247 (0.053 g) as a yellow oil.

¹H-NMR (300 MHz, CDCl₃) δ7.94 (1H, d), 7.60 (1H, d), 7.20 (1H, m), 7.15 (2H, m), 7.04 (1H, dd), 6.95 (1H, m), 6.81 (1H, d), 6.24 (2H, s), 4.11 (2H, m), 3.28 (4H, m), 3.09 (4H, m), 2.70 (4H, m), 2.54 (2H, m), 1.90 (2H, m), 1.78 (2H, m), 1.13 (3H, q), 1.03 (3H, q). [M+H]⁺=575.2.

((7-(4-(4-(2,3-dichlorophenyl)piperazin-1-yl)butoxy)quinolin-2-yl)oxy)methyl pivalate (Example 67. Compound 1215)

The experimental procedure was carried out in the same manner as for Compound-1206 in Example-62 to give Compound 1215 (0.555 g) as a yellow oil.

¹H-NMR (300 MHz, CDCl₃) δ 7.95 (1H, d), 7.60 (1H, d), 7.15 (3H, m), 7.05 (1H, dd), 6.97 (1H, m), 6.79 (1H, d), 6.22 (2H, s), 4.12 (2H, m), 3.10 (4H, m), 2.68 (4H, m), 2.54 (2H, m), 1.91 (2H, m), 1.78 (2H, m), 1.19 (9H, s). [M+H]⁺=560.1.

Example 68: Pharmacokinetic Evaluation in Rats

Pharmacokinetic Evaluation of Prodrugs in Rats Following Intramuscular Injection Animals:

Male Sprague-Dawley rats (Charles River Laboratories, Wilmington, Mass.) were obtained. Approximately 24 rats were used in each study. Rats were approximately 350-375 g at time of arrival. Rats were housed 2 per cage with ad libitum chow and water. Environmental conditions in the housing room: 64-67 OF, 30% to 70% relative humidity, and 12:12-h light:dark cycle. All experiments were approved by the institutional animal care and use committee.

Pharmacokinetics Study:

Rats were dosed IM by means of a 25 gauge, ⅝ inch needle with 1 cc syringe 0.3 mL suspension was withdrawn from the vial containing the test compound (see Table E). The mouse was injected in the muscles of the hind limb after anesthesia with isoflourane. Blood samples were collected via a lateral tail vein after brief anesthesia with Isoflurane. A 27½-G needle and 1 cc syringe without an anticoagulant was used for the blood collection. Approximately 350 μL of whole blood was collected at each sampling time-point of 6 hours, 24 hours and 2, 5, 7, 9, 12, 14, 21, 28, 35 days after administration. Once collected, whole blood was immediately transferred to tubes containing K2 EDTA, inverted 10-15 times and immediately placed on ice. The tubes were centrifuged for 2 minutes at >14,000 g's (11500 RPMs using Eppendorf Centrifuge 5417C, F45-30-11 rotor) at room temperature to separate plasma. Plasma samples were transferred to labeled plain tubes (MICROTAINER®) and stored frozen at <−70° C.

Data Analysis:

Drug concentrations in plasma samples were analyzed by liquid chromatography-mass spectroscopy using appropriate parameters for each compound. Half-life, volume of distribution, clearance, maximal concentration, and AUC were calculated by using WinNonlin Version 5.2_software (Pharsight, St. Louis, Mo.).

Results and Discussion:

The Results are shown in Table J. As shown in Table J, each of the compounds tested provides a plasma concentration that is extended as compared to the parent drug when administered alone.

TABLE J

| API Form used (Compound No.) | Excipients | Dose **(mg/kg) | $AUC_{0-14}$ (ng*day/mL) | $AUC_{0-T}$ (ng*day/mL) |
|---|---|---|---|---|
| 82 | solution in ethyl oleate | 57 | 204 | NC |
| 2 | Recrystallized crystalline suspension in 1% HPMC in PBS + 0.2% Tween 20 | 67 | 1016.9 | 1139.8 |
| 81 | solution in ethyl oleate | 56 | 584 | NC |
| 48 | Milled crystalline suspension in 1% HPMC in PBS + 0.2% Tween 20. Measured and diluted to correct concentration* | 70.00 | 2238 | 2264.6 |
| 5 | Ethyl oleate emulsion in water with DPPC, Glycerol and NCOH | 67 | 1728.6 | 1742 |
| 6 | solution in ethyl oleate | 67 | 67 | 327 |
| 6 | Oil emulsion in water with DPPC and Glycerol | 67 | 1490.3 | 1678.1 |
| 47 | Milled crystalline suspension in 1% HPMC | 100.0 | 113 | 176 |
| 85 | Milled crystalline suspension in 1% HPMC in PBS + 0.2% Tween 20. Measured and diluted to correct concentration | 67 | 1233.9 | 1348 |
| 1 | Crystalline material suspended in 1% HPMC | 56.7 | 1673 | 1938 |
| 7 | Recrystallized crystalline suspension in 1% EIPMC in PBS + 0.2% Tween 20 | 67 | 512.0 | 1169.5 |
| 32 | Milled crystalline suspension in 1% HPMC in PBS + 0.2% Tween 20. Measured and diluted to correct concentration* | 67 | 1334.4 | 1486 |
| 8 | Milled crystalline suspension in 1% HPMC in PBS + 0.2% Tween 20 | 24 | 580.3 | 666.1 |
| 49 | Milled crystalline suspension in 1% HPMC | 73.3 | 152 | 199.7 |
| 34 | Milled crystalline suspension in 1% HPMC in PBS + 0.2% Tween 20. Measured and diluted to correct concentration* | 43.33 | 2050 | 2095.8 |

TABLE J-continued

| API Form used (Compound No.) | Excipients | Dose **(mg/kg) | $AUC_{0-14}$ (ng*day/mL) | $AUC_{0-T}$ (ng*day/mL) |
|---|---|---|---|---|
| 79 | Prodrug solution in ethyl oleate | 67 | 954 | NC |
| 79 | Recrystallized crystalline suspension in 1% HPMC in PBS + 0.2% Tween 20 | 67 | 907.4 | 940 |
| 31 | Recrystallized crystalline suspension in 1% HPMC in PBS + 0.2% Tween 20 | 67 | 819.0 | 997 |
| 10 | Recrystallized crystalline suspension in 1% HPMC in PBS + 0.2% Tween 20 | 67 | 302 | 786.6 |
| 4 | Recrystallized crystalline suspension in 1% HPMC in PBS + 0.2% Tween 20 | 67 | 1455.4 | 1678 |
| 1002 | Crystalline material in 2% CMC, 0.2% Tween 20, PBS buffer 302 mOsm/Kg, pH 6.7 | 67 | 5350 | 5972 |
| 1008 | Crystalline material in 2% CMC, 0.2% Tween 20, PBS buffer 302 mOsm/Kg, pH 6.7 | 67 | 5000 | 6763 |

Example 69: Pharmacokinetic Study for Pioglitazone, Compounds 1002 and 1008

Figure 10:
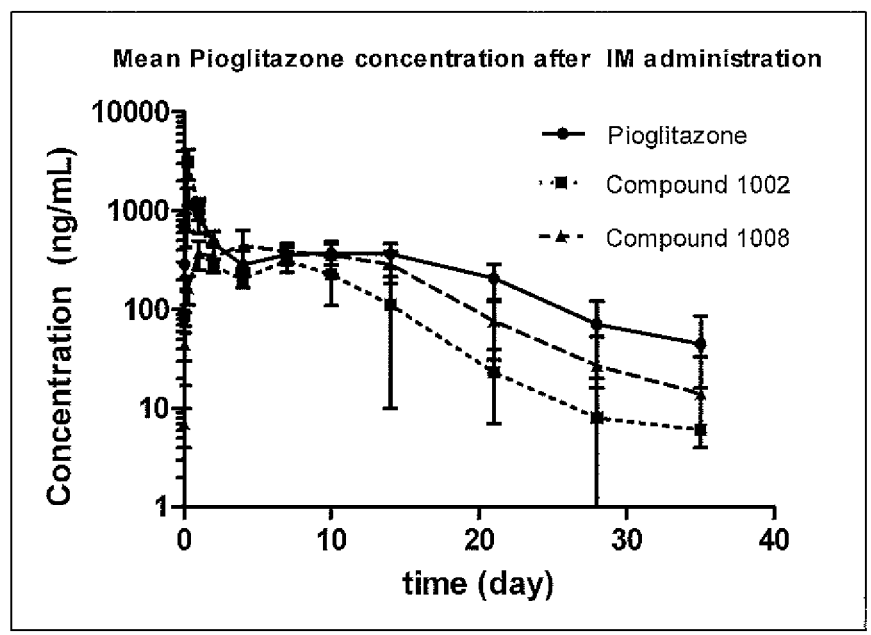
FIG. 10: Pharmacokinetic profile of pioglitazone, Compound-1002 and Compound-1008 after intravenous administration (20 mg pioglitazone equivalent) to rats.

PK profile of compounds 1002 and 1008 was compared to pioglitazone using a similar model as described above. 20 mg of pioglitazone or 20 mg equivilant of pioglitazone prodrug was administered intramuscularly. The results are tabulated in Table J, supra. FIG. 10 shows the PK profile and comparison with pioglitazone.

Example 70—Pharmacodynamic Studies Using an Amphetamine-Induced Locomotion Model Introduction:

Prodrugs of the invention useful in the treatment of schizophrenia and bipolar disorder show predictive validity in rodent models of hyperlocomotion. D-Amphetamine-induced locomotion is postulated to mimic the dopaminergic hyperactivity which forms the basis for the "dopamine hypothesis" of schizophrenia. The AMPH-induced hyperactivity model provides a simple, initial screen of antipsychotic compound efficacy. See, Fell et al., *Journal of Pharmacology and Experimental Therapeutics* (2008) 326:209-217. Amphetamine induced hyperactivity was used to screen various doses of orally administered (PO) prodrug formulations of aripiprazole to measure pharmacodynamic efficacy in an acute hyperlocomotion paradigm. The hypothesis of the study is that PO administration of aripiprazole prodrug formulations, which result in plasma concentrations of ~100-200 ng/ml, will produce a significant attenuation of AMPH-induced locomotion.

General behavior and activity can be measured in experimental animals (typically rats and mice) in order to assess psychomotor stimulant properties, anxiogenic/anxiolytic or sedative properties of a drug. As such, open-field studies can provide insight into the behavioral effects of test compounds. Certain prodrugs of the present invention are useful in the treatment of schizophrenia and bipolar disorder. Aripiprazole is a parent lactam containing drug from which some of the prodrugs of the invention are derived that is useful in the treatment of schizophrenia and bipolar disorder. Such aripiprazole prodrugs of the invention show predictive validity in rodent models of hyperlocomotion. D-Amphetamine-induced locomotion is postulated to mimic the dopaminergic hyperactivity which forms the basis for the "dopamine hypothesis" of schizophrenia. Likewise, glutamate NMDA receptor antagonist (MK-801, PCP, etc.) induced locomotion is postulated to mimic the NMDA hypoactivity hypothesis of schizophrenia (Fell et al., supra). These tests of drug-induced hyperactivity provide simple, initial screens of antipsychotic compound efficacy. Amphetamine induced hyperactivity will be used to screen various prodrugs of aripiprazole, administered PO in oil solutions, to measure pharmacodynamic efficacy. The results of the D-AMPH induced locomotion done in this study will be compared to the historical results of subcutaneous (S.C.) aripiprazole administration on D-AMPH. The hypothesis of the study is that PO exposure to aripiprazole prodrugs, which results in aripiprazole concentrations of 100-200 ng/ml at locomotor testing, will display efficacy in in-vivo measures of antipsychotic efficacy.

Materials: Experimental Animals:

12, Sprague Dawley rats were purchased from Charles River Laboratory. The rats were approximately 90 days old, and weighed in the range of 350-275 grams upon receipt from the supplier. One rat was placed in a cage and allowed to acclimate for about 1 week. The rats were provided with food and water ad libitum.

Dosing Solution of D-Amphetamine (D-AMPH):

D-AMPH was purchased from Sigma Aldrich. D-amphetamine HCl was prepared in 0.9% saline to a concentration of 1.5 mg/ml. D-Amphetamine was given I.P. per body weight at a dose of 1 ml/kg (=1.5 mg/kg). Salt form correction was not used in accordance with historical literature. D-Amphetamine was prepared fresh from solid form 30 min. prior to each test period.

Dosing Solutions of Prodrug Derivatives of Aripiprazole:

TABLE K

| Study Group | Formulation (Route) | Dose mg/rat | Dose volume mL | N |
|---|---|---|---|---|
| A | Compound-7 oral oil Solution (PO) | 7.5 | 1.5 | 4 |
| B | Compound-4 oral oil Solution (PO) | 20 | 1.5 | 4 |
| C | Compound-4 oral oil Solution (PO) | 10 | 1.5 | 4 |
| D | Compound-7 oral oil Solution (PO) | 10 | 1.5 | 4 |
| E | Compound-4 oral oil Solution (PO) | 0.66 | 1.5 | 4 |
| F | Compound-7 oral oil Solution (PO) | 20 | 1.5 | 4 |
| G | Saline (PO) | 0 | 1.5 | 4 |

Behavior Box:

The behavior chambers were purchased from Med Associates, Inc. of St. Albans, Vt., Model ENV-515. Software for measuring animal movement is provided with the behavior chamber by the supplier.

Methods:

Following 1 week habituation to the animal facility, the activity assessments commenced. The animals were initially acclimated to the behavior box for about 15 minutes before they were removed from the box and injected PO with 1.5 ml of an aripiprazole prodrug compound of the invention, at concentrations which produce PK levels of 100-200 ng/ml approximately 1 hour after administration. After an additional 15 minutes the animals were placed back in the behavior box for an additional 30 minute drug-baseline test session. The mice were then administered by IP injection, D-AMPH (1.5 mg/kg) followed by a 60 minute experimental behavioral measurement period. The parameters that were measured were a) total distance measured (primary measure), b) total number of ambulatory moves (second measure), c) total number of vertical moves (secondary measure) and d) time spent immobile (secondary measure).

Blood Sampling:

Tail vein blood was taken on experiment days immediately following locomotor activity measurements (2-hours post-prodrug administration) and again the following day a time-point corresponding to 22 hours post-prodrug administration. Blood samples were collected via a lateral tail vein after anesthesia with Isoflurane. A 27½ G syringe without an anticoagulant was used for the blood collection, and the whole blood transferred to pre-chilled (wet ice) tubes containing K2 EDTA. 0.5 ml of blood per animal was collected per time point. The tubes were inverted 15-20 times and immediately returned to the wet ice until being centrifuged for 2 minutes ≥14,000 g to separate plasma. The plasma samples prepared in this manner were transferred to labeled plain tubes (MICROTAINER®) and stored frozen at <−70° C.

Behavioral Data Acquisition:

Behavioral data was captured electronically by the software package associated with the behavior chambers. Data was transformed and analyzed via GRAPHPAD PRISM® 5 software (GraphPad Software, Inc., La Jolla, Calif.). The data was analyzed using a 2-way repeated measures ANOVA.

Figure 6:
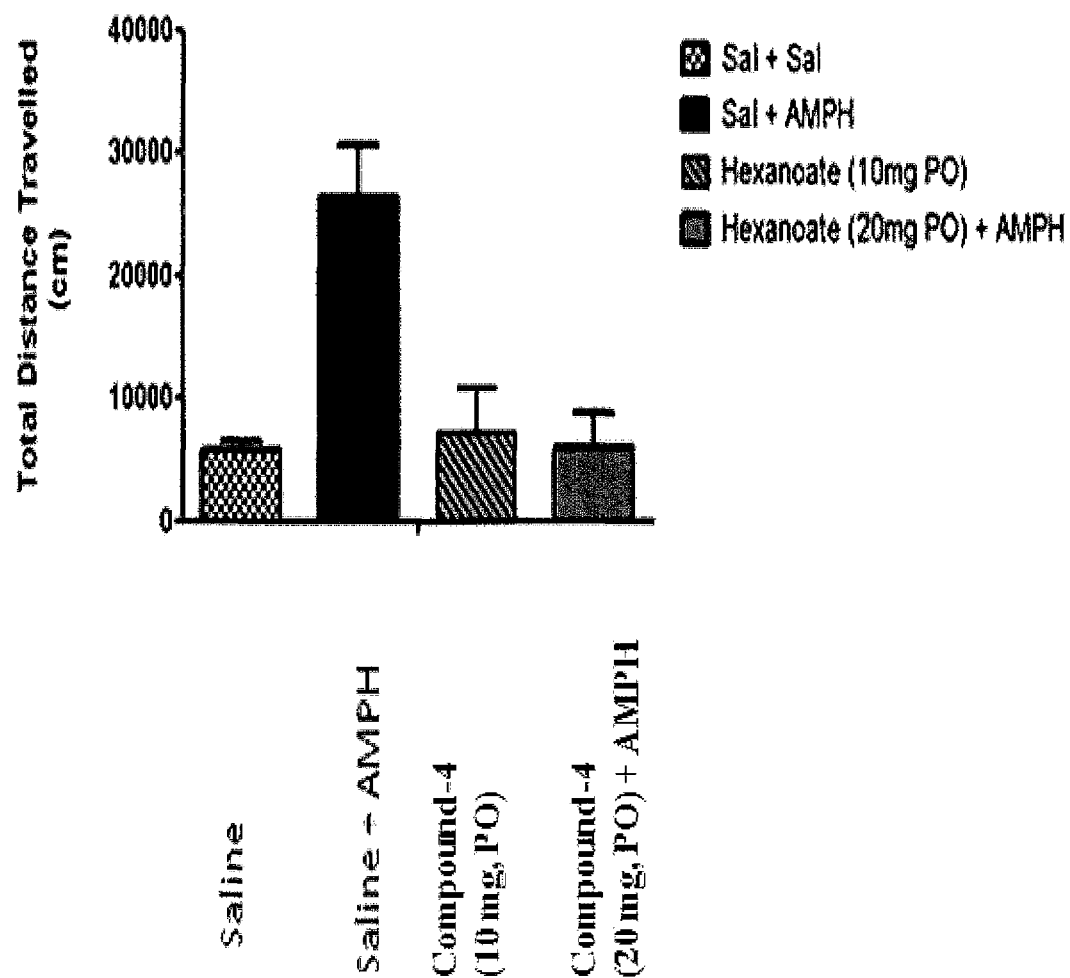
FIG. 6: Pharmacodynamic (PD) study of compound-4 in AMPH induced locomotion model.
Figure 7:
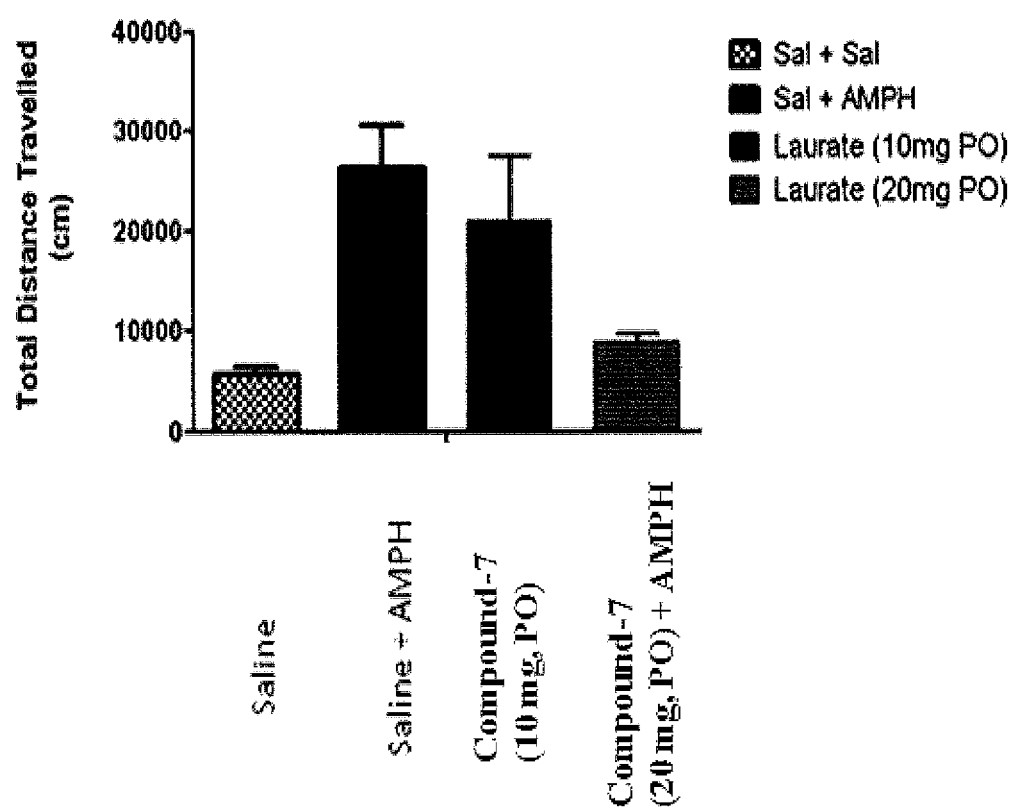
FIG. 7: Pharmacodynamic (PD) study of compound-7 in AMPH induced locomotion model.
Figure 8:
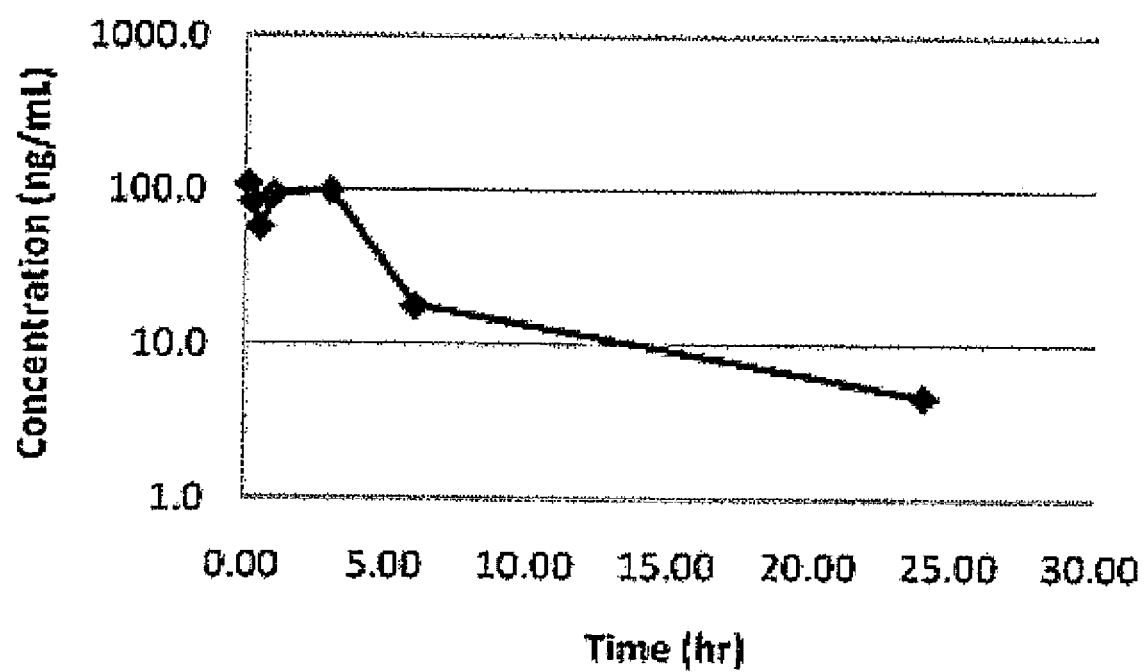
FIG. 8: Plasma concentration of aripiprazole after intravenous administration of (0.5 mg/Kg) compound 7 to rats.
Figure 9:
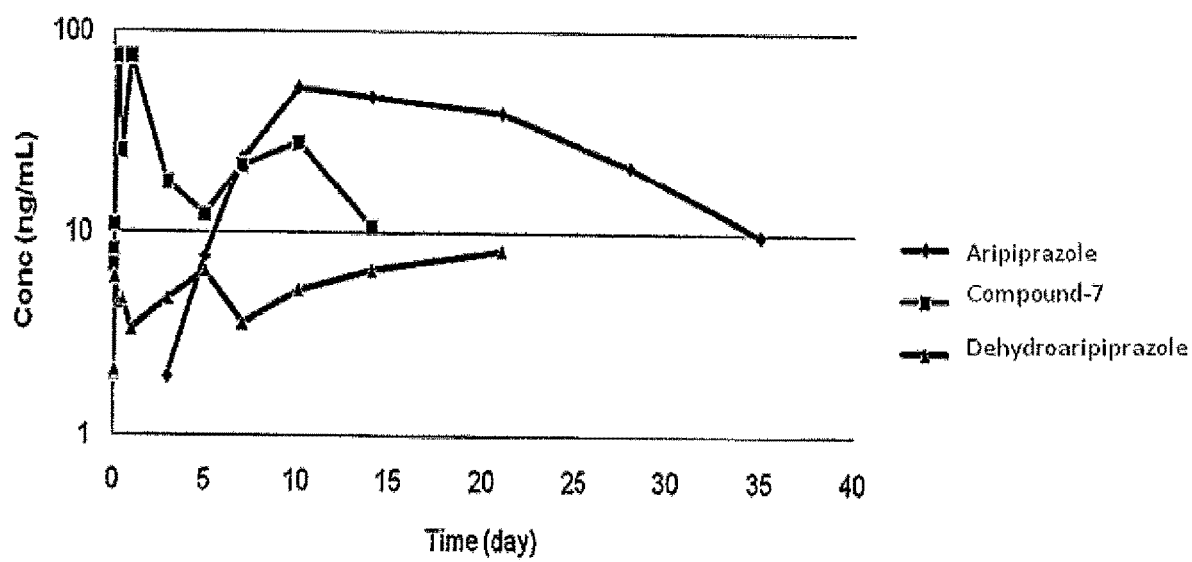
FIG. 9: Plasma concentration of aripiprazole, dehydroaripiprazole and compound 7 after intramuscular administration of 30 mg/kg of compound 7 to dogs.

Results and Discussion:

The results are shown in FIGS. 6 and 7. The results indicate that orally administered D-AMPH caused a significant increase in the total distance traveled by the mice as compared to mice who were administered only saline. The results also indicate that aripiprazole prodrug compound 4 of the invention significantly inhibited the increases in distance traveled caused by D-AMPH. The inhibition of distance travelled by compound 4 did not appear to be dose dependent. Likewise, aripiprazole prodrug compounds 7 and 47 did appear to significantly inhibit increases in distance traveled caused by D-AMPH at the higher dose of 20 mg. This data indicates that in accordance with the invention, the prodrug compounds are cleaved in vivo to release the parent drug (aripiprazole in this example) to provide the expected pharmacological effects on the animal.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the formula XIJ or formula XIIJ:

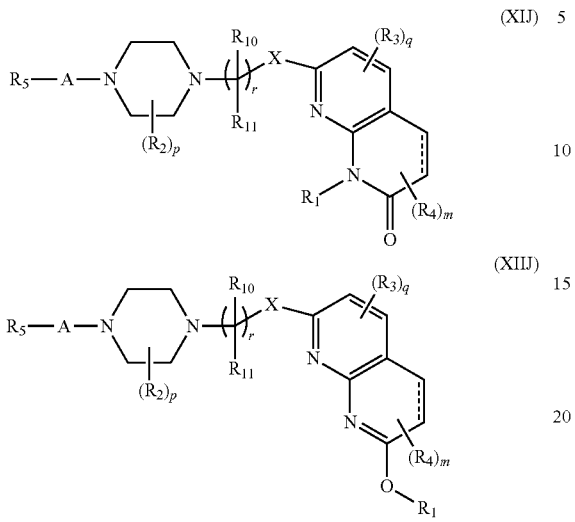

wherein,

X is —S— or —O—;

$R_1$ is selected from —C($R_A$)($R_B$)—O$R_{20}$, —C($R_A$)($R_B$)—OC(O)O$R_{20}$, —C($R_A$)($R_B$)—OC(O)$R_{20}$, —C($R_A$)($R_B$)—OC(O)NR$_{20}$R$_{21}$, —(C($R_A$)($R_B$))—OPO$_3$MY, —(C($R_A$)($R_B$))—OP(O)(O$R_{20}$)(O$R_{21}$), —[C($R_A$)($R_B$)O]$_z$—R$_{20}$, —[C($R_A$)($R_B$)O]$_z$—C(O)OR$_{20}$, —[C($R_A$)($R_B$)O]$_z$—C(O)R$_{20}$, —[C($R_A$)($R_B$)O]$_z$—C(O)OR$_{20}$, —[C($R_A$)($R_B$)O]$_z$—C(O)NR$_{20}$R$_{21}$, —[C($R_A$)($R_B$)O]$_z$—OPO$_3$MY, —[C($R_A$)($R_B$)O]$_z$—P(O)$_2$(OR$_{20}$)M, and —[C($R_A$)($R_B$)]$_z$—P(O)(OR$_{20}$)(OR$_{21}$);

$R_2$ is selected from the group consisting of absent, hydrogen, halogen, —OR$_{10}$, —SR$_{10}$, —NR$_{10}$R$_{11}$—, aliphatic, aryl, and heterocyclyl;

each $R_{10}$ and $R_{11}$ is independently selected from the group consisting of absent, hydrogen, halogen, aliphatic, and aryl;

alternatively, two $R_{10}$ and $R_{11}$ together with the atoms to which they are attached and any intervening atoms may form an additional 3, 4, 5, 6 or 7 membered ring;

A is selected from the group consisting of absent, alkyl, alkenyl, alkynyl, —S—, —O—, —S(O)—, —S(O)$_2$—, —S[C(R$_{30}$)(R$_{31}$)]$_u$—, —S(O)[C(R$_{30}$)(R$_{31}$)]$_u$—, —S(O)$_2$[C(R$_{30}$)(R$_{31}$)]$_u$—, —O[C(R$_{30}$)(R$_{31}$)]$_u$—, —N(R$_{30}$)—, —N(R$_{30}$)[C(R$_{31}$)(R$_{32}$)]$_u$—, —[C(R$_{30}$)(R$_{31}$)]$_u$—, —C(O)[C(R$_{30}$)(R$_{31}$)]$_u$—;

each $R_3$, $R_4$, $R_5$, $R_{30}$, $R_{31}$, and $R_{32}$ is independently selected from the group consisting of absent, hydrogen, halogen, —OR$_{10}$, —SR$_{10}$, —NR$_{10}$R$_{11}$—, —C(O)R$_{10}$, aliphatic, aryl and heterocyclyl;

alternatively, two $R_3$ groups together or two $R_4$ groups together or one $R_3$ group with one $R_4$ group together forms a ring;

each $R_A$ and $R_B$ is independently selected from the group consisting of hydrogen, halogen, aliphatic, and aryl;

each $R_{20}$ and $R_{21}$ is independently selected from the group consisting of hydrogen, aliphatic, and aryl;

Y and M are the same or different and each is a monovalent cation; or M and Y together is a divalent cation;

r is 0, 1, 2, 3, 4, 5, 6, 7, 8, 9, 10 or 11;

m and q are independently 0, 1, or 2;

p is 0, 1, 2 or 3;

z is 2 or 3; and u is independently 1, 2, 3, 4, 5, 6 or 7.

2. The compound of claim 1, wherein the compound of Formula XIJ or Formula XIIJ is a compound of Formula XIK or Formula XIIK:

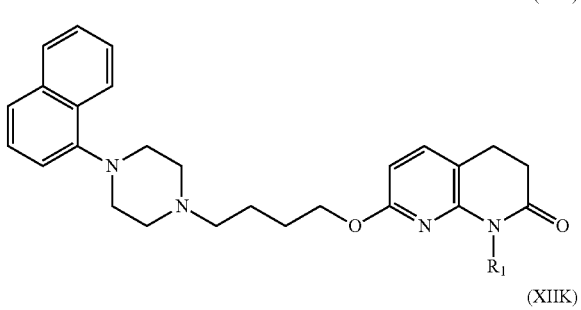

3. The compound of claim 1, wherein $R_5$ is selected from the group consisting of

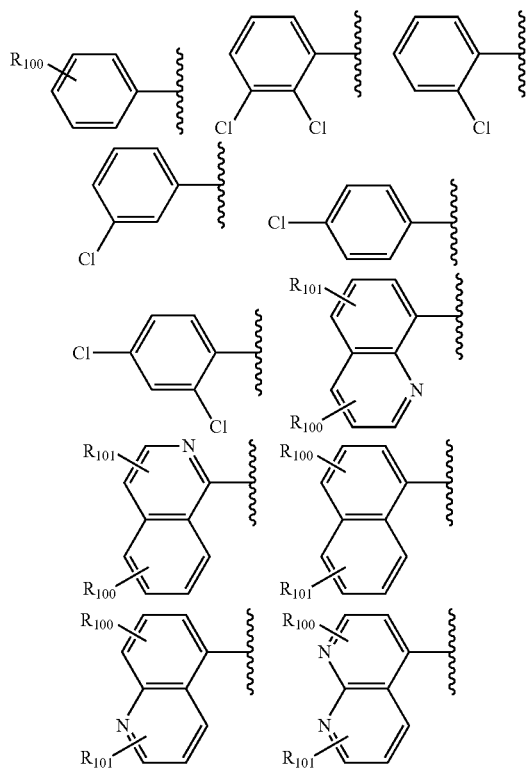

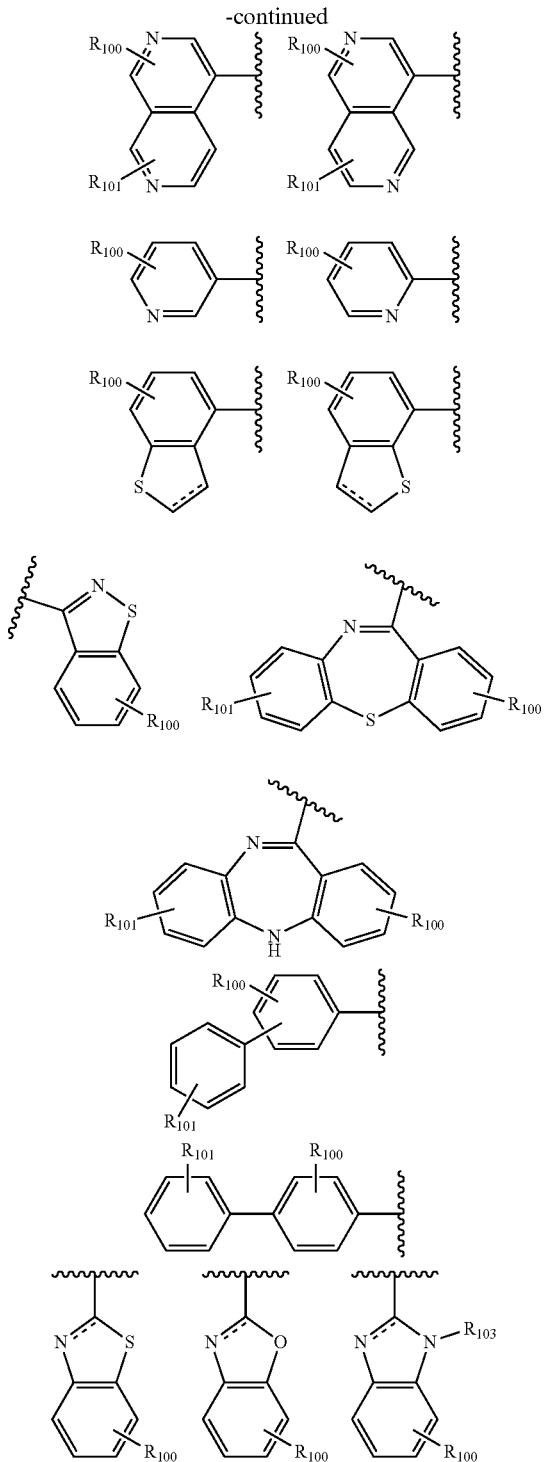
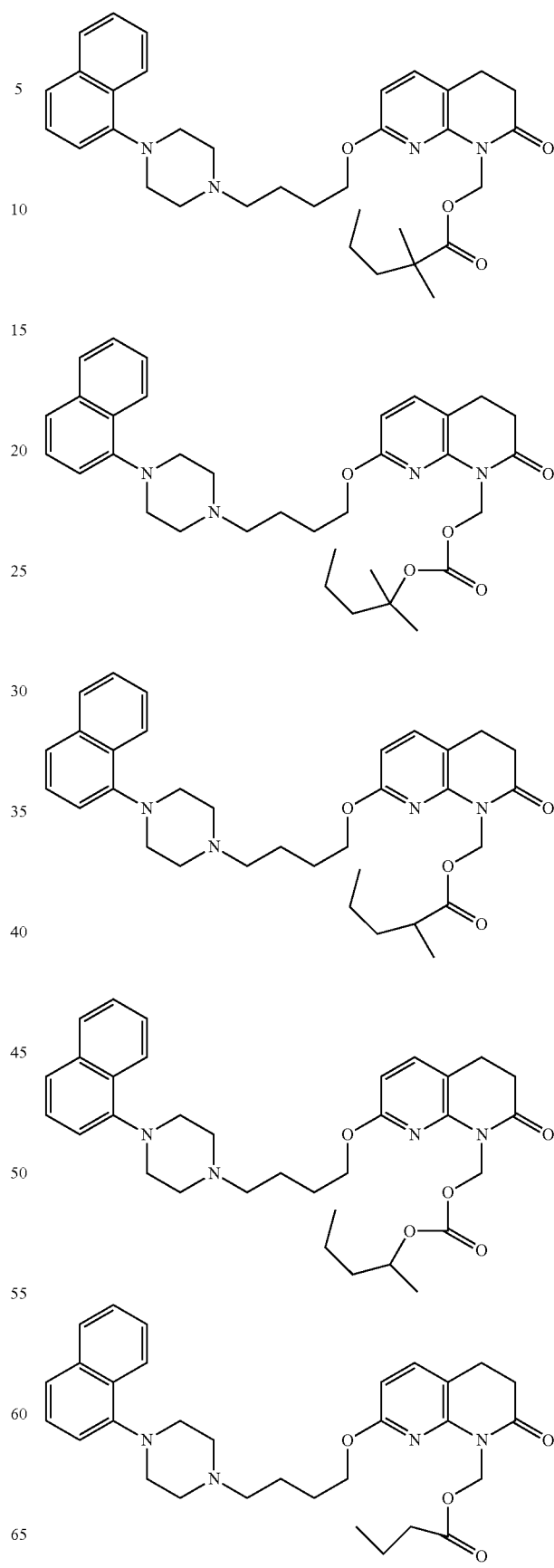
wherein
R₁₀₀ and R₁₀₁, each represent 1 to 4 substituents independently selected from the group consisting of hydrogen, halogen, $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ alkylamino, and $C_6$-$C_8$ aryl.
4. The compound of claim 1, wherein the compound of Formula XIJ or Formula XIIJ is selected from the group consisting of

463
-continued
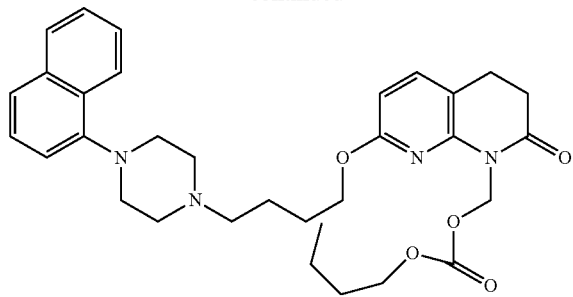
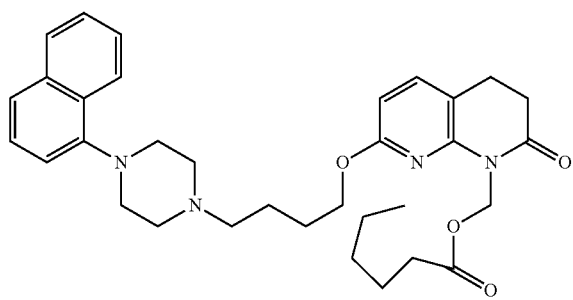
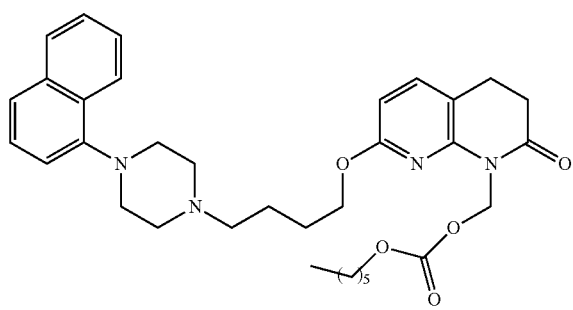
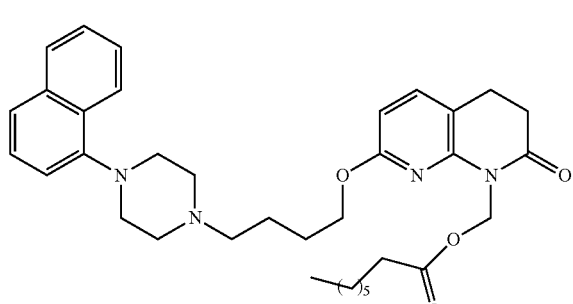
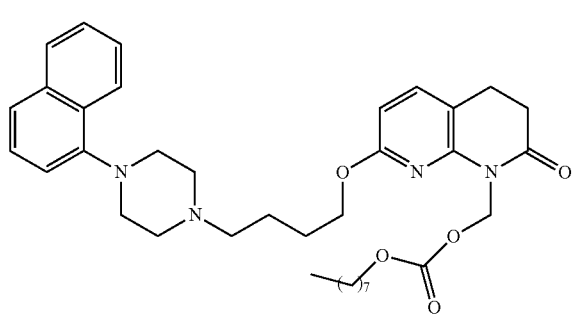
464
-continued
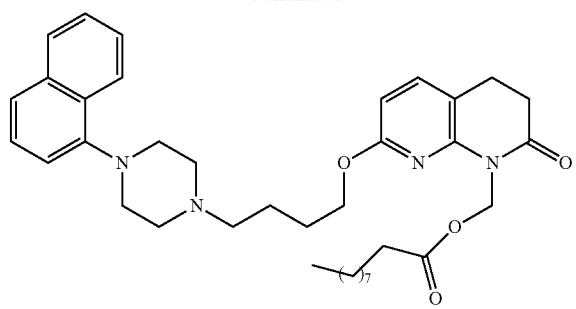
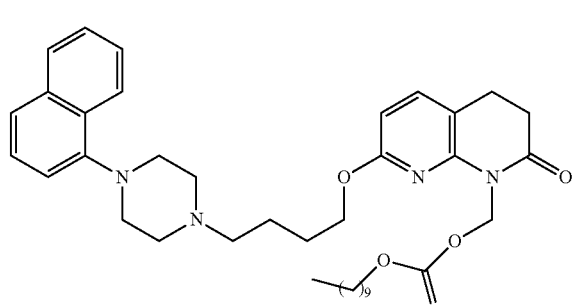
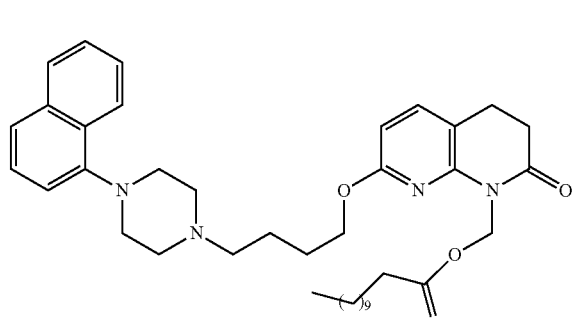
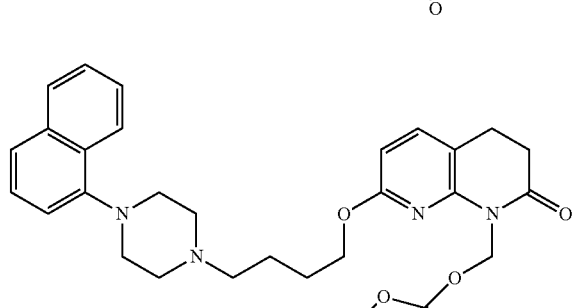
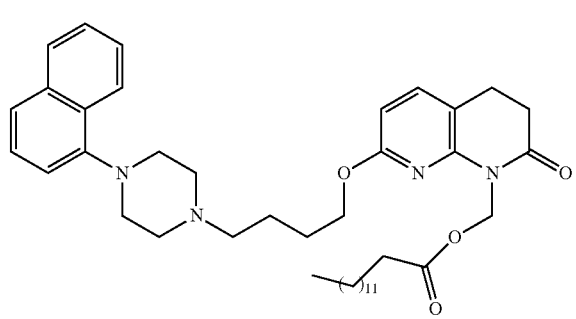

465
-continued
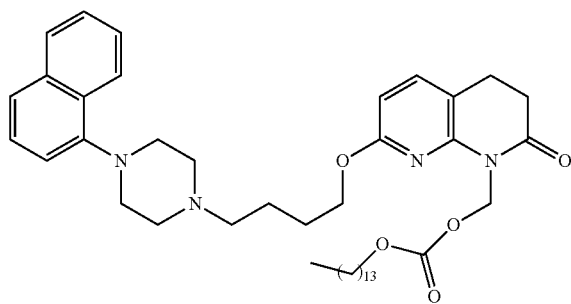
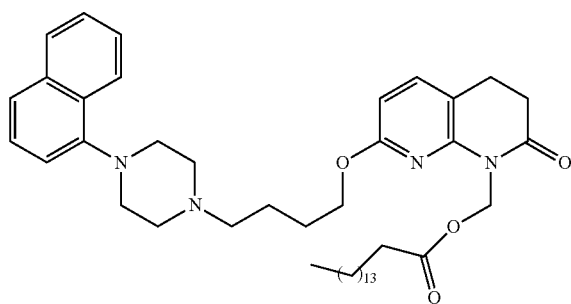
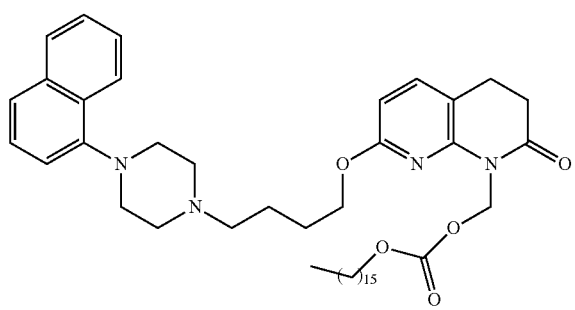
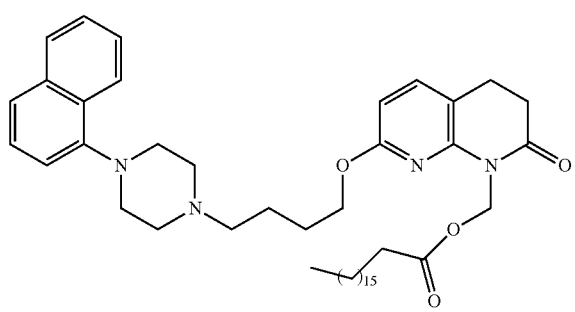
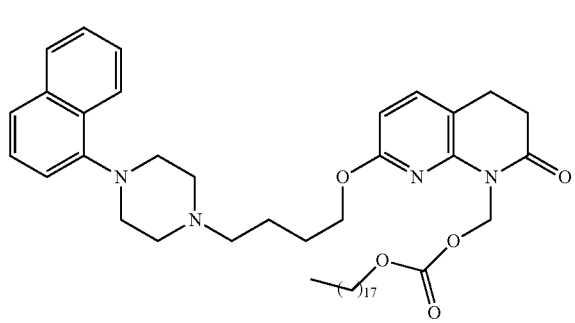
466
-continued
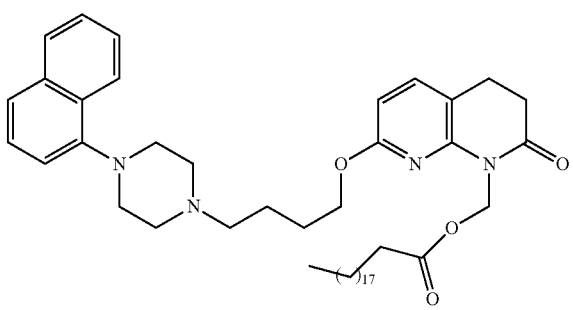
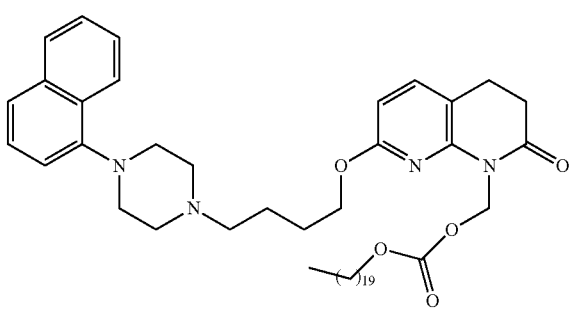
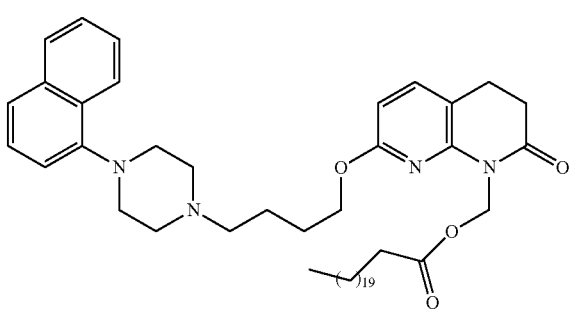
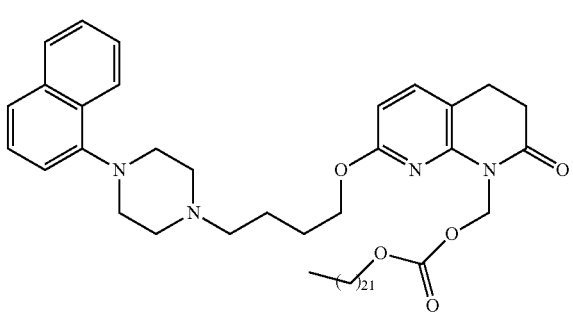
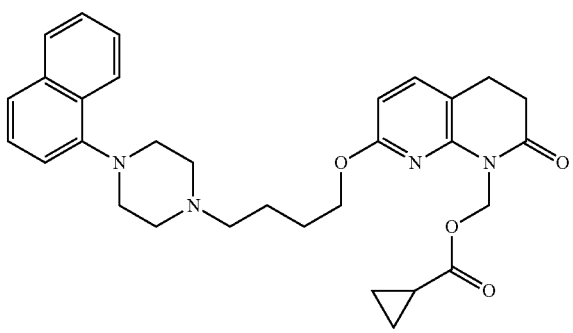

467
-continued
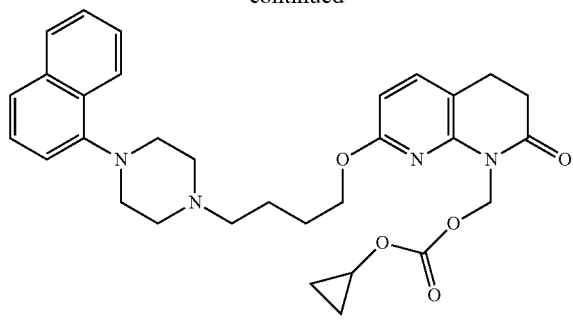
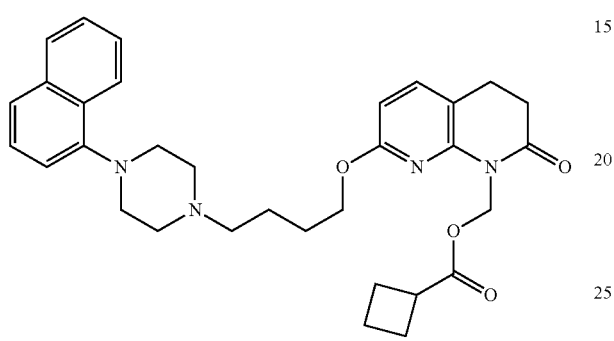
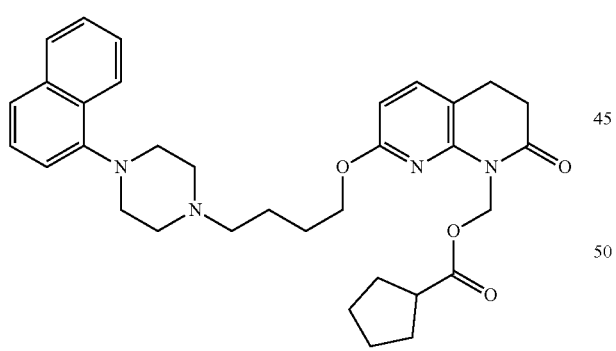
468
-continued
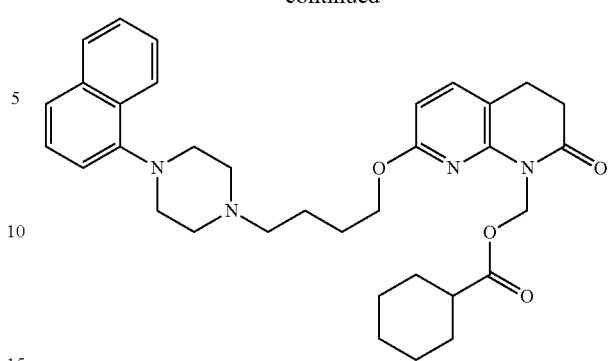
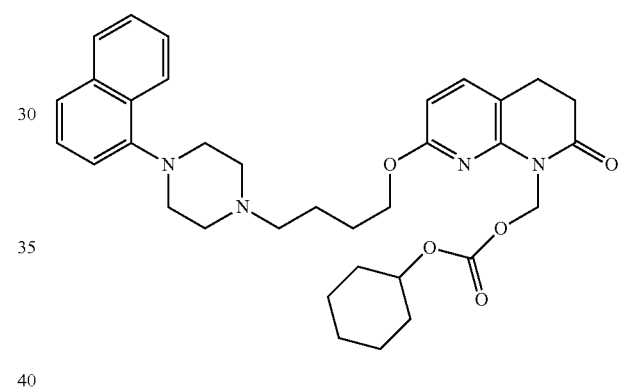
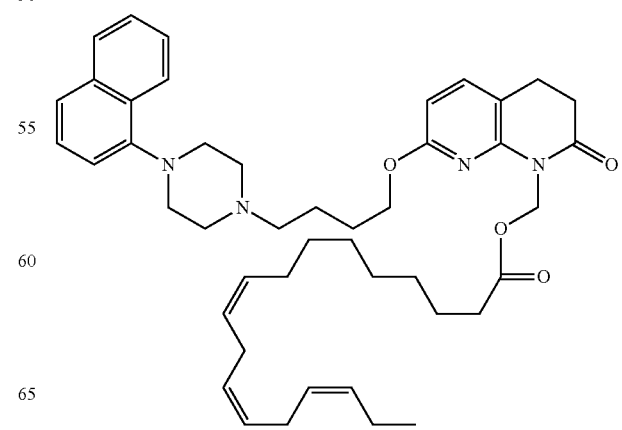

469
-continued
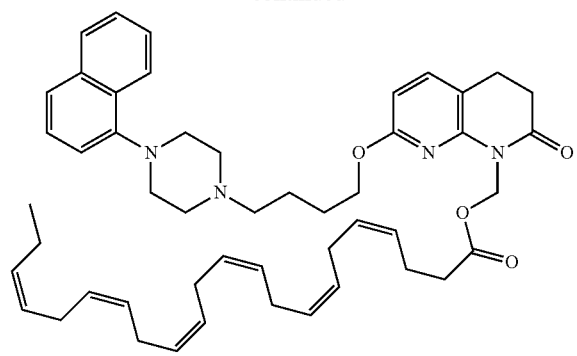
470
-continued
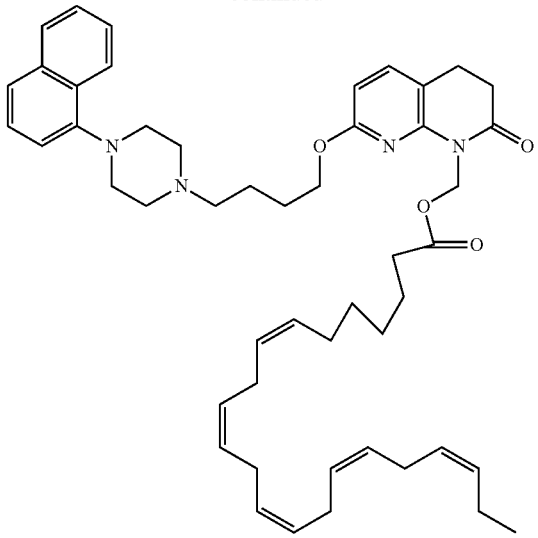
or a pharmaceutically acceptable salt thereof.
5. A pharmaceutical composition comprising the compound of claim 1 and a pharmaceutically acceptable carrier.
* * * * *